(12) United States Patent
Chang et al.

(10) Patent No.: US 9,359,443 B2
(45) Date of Patent: *Jun. 7, 2016

(54) COMBINATION THERAPY WITH ANTI-CD74 AND ANTI-CD20 ANTIBODIES PROVIDES ENHANCED TOXICITY TO B-CELL DISEASES

(71) Applicant: IBC Pharmaceuticals, Inc., Morris Plains, NJ (US)

(72) Inventors: Chien-Hsing Chang, Downingtown, PA (US); David M. Goldenberg, Mendham, NJ (US); Edmund A. Rossi, Woodland Park, NJ (US)

(73) Assignee: IBC Pharmaceuticals, Inc., Morris Plains, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/520,596

(22) Filed: Oct. 22, 2014

(65) Prior Publication Data

US 2015/0037283 A1 Feb. 5, 2015

Related U.S. Application Data

(60) Division of application No. 13/904,534, filed on May 29, 2013, now Pat. No. 8,906,378, which is a division of application No. 13/209,954, filed on Aug. 15, 2011, now Pat. No. 8,475,794, which is a continuation-in-part of application No. 13/086,786, filed on Apr. 14, 2011, now Pat. No. 8,349,332, said application No. 13/209,954 is a continuation-in-part of application No. 13/036,820, filed on Feb. 28, 2011, now Pat. No. 8,883,160, and a continuation-in-part of application No. 13/021,302, filed on Feb. 4, 2011, now Pat. No. 8,246,960, which is a division of application No. 12/417,917, filed on Apr. 3, 2009, now Pat. No. 7,906,121, which is a division of application No. 11/478,021, filed on Jun. 29, 2006, now Pat. No. 7,534,866, which is a continuation-in-part of application No. 11/389,358, filed on Mar. 24, 2006, now Pat. No. 7,550,143, and a continuation-in-part of application No. 11/391,584, filed on Mar. 28, 2006, now Pat. No. 7,521,056, said application No. 13/209,954 is a continuation-in-part of application No.

(Continued)

(51) Int. Cl.
| | | |
|---|---|---|
| C07K 16/28 | (2006.01) | |
| A61K 47/48 | (2006.01) | |
| A61K 39/395 | (2006.01) | |
| A61K 38/19 | (2006.01) | |
| A61K 51/10 | (2006.01) | |
| C07K 14/47 | (2006.01) | |
| A61K 38/21 | (2006.01) | |

(52) U.S. Cl.
CPC ............ *C07K 16/2896* (2013.01); *A61K 38/212* (2013.01); *A61K 39/39541* (2013.01); *A61K 47/487* (2013.01); *A61K 47/48384* (2013.01); *A61K 47/48415* (2013.01); *A61K 47/48561* (2013.01); *A61K 47/48569* (2013.01); *A61K 51/1027* (2013.01); *A61K 51/1045* (2013.01); *C07K 14/47* (2013.01); *C07K 16/2803* (2013.01); *C07K 16/2833* (2013.01); *C07K 16/2887* (2013.01); *C07K 2317/55* (2013.01); *C07K 2317/565* (2013.01); *C07K 2317/732* (2013.01); *C07K 2317/734* (2013.01); *C07K 2319/30* (2013.01); *C07K 2319/55* (2013.01); *C07K 2319/70* (2013.01)

(58) Field of Classification Search
CPC ........... A61K 2039/505; A61K 39/395; A61K 45/06; A61K 47/48746; A61K 51/055; C07K 16/28; C07K 16/2833; C07K 16/2887; C07K 2319/00; C07K 2317/72; C07K 2317/73; C07K 2317/734; C07K 2317/732; C07K 2317/35; C07K 14/52; C07K 14/70596; C07K 16/2803; C07K 16/2896; C07K 16/468; C07K 2317/31; C07K 2317/55; C07K 2317/92; C07K 2319/30; C07K 2317/70

See application file for complete search history.

(56) References Cited

U.S. PATENT DOCUMENTS

| 4,036,945 A | 7/1977 | Haber |
| 4,046,722 A | 9/1977 | Rowland |

(Continued)

FOREIGN PATENT DOCUMENTS

| EP | 0332865 | 9/1989 |
| EP | 0510949 | 10/1992 |

(Continued)

OTHER PUBLICATIONS

Magdelaine-Beuzelin et al., Pharmacogenetics and Genomics 19: 383-387, 2009.*

(Continued)

*Primary Examiner* — Phuong Huynh
(74) *Attorney, Agent, or Firm* — Richard A. Nakashima

(57) ABSTRACT

Disclosed are compositions and methods comprising combinations of anti-CD74 and anti-CD20 antibodies or antigen-binding fragments thereof. The antibody combination may also be used with a therapeutic agent that is attached to antibody or fragment thereof or separately administered. The therapeutic agent may be an immunomodulator, a cytokine, a toxin or other known therapeutic agent. Preferably, the anti-CD74 and anti-CD20 antibody or fragment are part of a DNL complex. More preferably, combination therapy with the anti-CD74 and anti-CD20 antibody or fragment is more effective than either antibody alone, or the combination of unconjugated antibodies. Administration of combination induces apoptosis of target cells in diseases in which CD74 is overexpressed, such as solid tumors, B-cell lymphomas or leukemias, autoimmune disease, immune dysfunction disease or diabetes. Preferably, the target cells are B cells.

4 Claims, 15 Drawing Sheets

Related U.S. Application Data

13/012,977, filed on Jan. 25, 2011, now Pat. No. 8,282,934, which is a division of application No. 12/418,877, filed on Apr. 6, 2009, now Pat. No. 7,906,118, which is a continuation-in-part of application No. 12/396,965, filed on Mar. 3, 2009, now Pat. No. 7,871,622, which is a division of application No. 11/391,584, filed on Mar. 28, 2006, now Pat. No. 7,521,056, said application No. 12/418,877 is a continuation-in-part of application No. 12/396,605, filed on Mar. 3, 2009, now Pat. No. 7,858,070, which is a division of application No. 11/633,729, filed on Dec. 5, 2006, now Pat. No. 7,527,787, said application No. 12/418,877 is a continuation-in-part of application No. 11/389,358, filed on Mar. 24, 2006, now Pat. No. 7,550,143, and a continuation-in-part of application No. 11/478,021, filed on Jun. 29, 2006, now Pat. No. 7,534,866, and a continuation-in-part of application No. 11/745,692, filed on May 8, 2007, now Pat. No. 8,333,971, and a continuation-in-part of application No. 11/925,408, filed on Oct. 26, 2007, now Pat. No. 7,666,400, said application No. 13/209,954 is a continuation-in-part of application No. 13/010,993, filed on Jan. 21, 2011, which is a division of application No. 12/544,476, filed on Aug. 20, 2009, now Pat. No. 7,901,680, which is a continuation-in-part of application No. 12/396,605, filed on Mar. 3, 2009, now Pat. No. 7,858,070, which is a division of application No. 11/633,729, filed on Dec. 5, 2006, now Pat. No. 7,527,787, which is a continuation-in-part of application No. 11/389,358, filed on Mar. 24, 2006, now Pat. No. 7,550,143, and a continuation-in-part of application No. 11/391,584, filed on Mar. 28, 2006, now Pat. No. 7,521,056, and a continuation-in-part of application No. 11/478,021, filed on Jun. 29, 2006, now Pat. No. 7,534,866, said application No. 13/209,954 is a continuation-in-part of application No. 13/004,349, filed on Jan. 11, 2011, now abandoned, and a continuation-in-part of application No. 12/968,936, filed on Dec. 15, 2010, now Pat. No. 8,906,377, which is a division of application No. 12/396,965, filed on Mar. 3, 2009, now Pat. No. 7,871,622, which is a division of application No. 11/391,584, filed on Mar. 28, 2006, now Pat. No. 7,521,056, said application No. 13/209,954 is a continuation-in-part of application No. 12/964,021, filed on Dec. 9, 2010, now Pat. No. 8,491,914, and a continuation-in-part of application No. 12/949,536, filed on Nov. 18, 2010, now Pat. No. 8,211,440, which is a division of application No. 12/396,605, filed on Mar. 3, 2009, now Pat. No. 7,858,070, which is a division of application No. 11/633,729, filed on Dec. 5, 2006, now Pat. No. 7,527,787, said application No. 13/209,954 is a continuation-in-part of application No. 12/915,515, filed on Oct. 29, 2010, now abandoned, and a continuation-in-part of application No. 12/871,345, filed on Aug. 30, 2010, now Pat. No. 8,551,480, and a continuation-in-part of application No. 12/869,823, filed on Aug. 27, 2010, and a continuation-in-part of application No. 12/754,740, filed on Apr. 6, 2010, now Pat. No. 8,562,988, and a continuation-in-part of application No. 12/752,649, filed on Apr. 1, 2010, now Pat. No. 8,034,352, and a continuation-in-part of application No. 12/731,781, filed on Mar. 25, 2010, now Pat. No. 8,003,111, and a continuation-in-part of application No. 13/150,613, filed on Jun. 1, 2011, now Pat. No. 8,277,817, which is a division of application No. 12/644,146, filed on Dec. 22, 2009, now Pat. No. 7,981,398, which is a division of application No. 11/925,408, filed on Oct. 26, 2007, now Pat. No. 7,666,400, said application No. 13/209,954 is a continuation of application No. 12/468,589, filed on May 19, 2009, now Pat. No. 8,163,291, which is a division of application No. 11/389,358, filed on Mar. 24, 2006, now Pat. No. 7,550,143.

(60) Provisional application No. 61/374,751, filed on Aug. 18, 2010, provisional application No. 61/374,772, filed on Aug. 18, 2010, provisional application No. 61/508,871, filed on Jul. 18, 2011, provisional application No. 61/324,111, filed on Apr. 14, 2010, provisional application No. 60/782,332, filed on Mar. 14, 2006, provisional application No. 60/728,292, filed on Oct. 19, 2005, provisional application No. 60/751,196, filed on Dec. 16, 2005, provisional application No. 60/668,603, filed on Apr. 6, 2005, provisional application No. 60/864,530, filed on Nov. 6, 2006, provisional application No. 61/043,932, filed on Apr. 10, 2008, provisional application No. 61/104,916, filed on Oct. 13, 2008, provisional application No. 61/119,542, filed on Dec. 3, 2008, provisional application No. 61/090,487, filed on Aug. 20, 2008, provisional application No. 61/293,846, filed on Jan. 11, 2010, provisional application No. 61/323,001, filed on Apr. 12, 2010, provisional application No. 61/374,449, filed on Aug. 17, 2010, provisional application No. 61/267,877, filed on Dec. 9, 2009, provisional application No. 61/302,682, filed on Feb. 9, 2010, provisional application No. 61/414,592, filed on Nov. 17, 2010, provisional application No. 61/258,369, filed on Nov. 5, 2009, provisional application No. 61/258,729, filed on Nov. 6, 2009, provisional application No. 61/378,059, filed on Aug. 30, 2010, provisional application No. 61/238,473, filed on Aug. 31, 2009, provisional application No. 61/266,305, filed on Dec. 3, 2009, provisional application No. 61/316,996, filed on Mar. 24, 2010, provisional application No. 61/323,960, filed on Apr. 14, 2010, provisional application No. 61/238,424, filed on Aug. 31, 2009, provisional application No. 61/168,290, filed on Apr. 10, 2009, provisional application No. 61/168,657, filed on Apr. 13, 2009, provisional application No. 61/168,668, filed on Apr. 13, 2009, provisional application No. 61/163,666, filed on Mar. 26, 2009.

(56) References Cited

U.S. PATENT DOCUMENTS

| | | |
|---|---|---|
| 4,331,647 A | 5/1982 | Goldenberg |
| 4,699,784 A | 10/1987 | Shih et al. |
| 4,704,692 A | 11/1987 | Ladner |
| 4,816,567 A | 3/1989 | Cabilly et al. |
| 4,824,659 A | 4/1989 | Hawthorne |
| 4,868,109 A | 9/1989 | Lansdorp |
| 4,916,213 A | 4/1990 | Scannon et al. |
| 4,918,163 A | 4/1990 | Young |
| 4,925,922 A | 5/1990 | Byers et al. |
| 4,932,412 A | 6/1990 | Goldenberg |
| 4,946,778 A | 8/1990 | Ladner et al. |
| 5,057,313 A | 10/1991 | Shih et al. |
| 5,106,955 A | 4/1992 | Endo et al. |
| 5,134,075 A | 7/1992 | Hellstrom et al. |
| 5,171,665 A | 12/1992 | Hellstrom et al. |
| 5,196,337 A | 3/1993 | Ochi et al. |
| 5,204,095 A | 4/1993 | Goodall et al. |

(56) References Cited

U.S. PATENT DOCUMENTS

| | | |
|---|---|---|
| 5,229,275 A | 7/1993 | Goroff |
| 5,443,953 A | 8/1995 | Hansen et al. |
| 5,484,892 A | 1/1996 | Tedder et al. |
| 5,525,338 A | 6/1996 | Goldenberg |
| 5,530,101 A | 6/1996 | Queen et al. |
| 5,565,215 A | 10/1996 | Gref et al. |
| 5,567,610 A | 10/1996 | Borrebaeck et al. |
| 5,593,676 A | 1/1997 | Bhat et al. |
| 5,618,920 A | 4/1997 | Robinson et al. |
| 5,620,708 A | 4/1997 | Amkraut et al. |
| 5,633,425 A | 5/1997 | Lonberg et al. |
| 5,686,072 A | 11/1997 | Uhr et al. |
| 5,693,762 A | 12/1997 | Queen et al. |
| 5,698,178 A | 12/1997 | Goldenberg |
| 5,702,727 A | 12/1997 | Amkraut et al. |
| 5,716,595 A | 2/1998 | Goldenberg |
| 5,734,033 A | 3/1998 | Reed |
| 5,736,119 A | 4/1998 | Goldenberg et al. |
| 5,736,137 A | 4/1998 | Anderson et al. |
| 5,770,198 A | 6/1998 | Coller et al. |
| 5,776,456 A | 7/1998 | Anderson et al. |
| 5,789,554 A | 8/1998 | Leung et al. |
| 5,792,845 A | 8/1998 | O'Reilly et al. |
| 5,795,967 A | 8/1998 | Aggarwal et al. |
| 5,798,554 A | 8/1998 | Grimaldi et al. |
| 5,827,690 A | 10/1998 | Meade et al. |
| 5,874,540 A | 2/1999 | Hansen et al. |
| 5,922,302 A | 7/1999 | Goldenberg et al. |
| 6,051,228 A | 4/2000 | Aruffo et al. |
| 6,051,230 A | 4/2000 | Thorpe et al. |
| 6,077,499 A | 6/2000 | Griffiths et al. |
| 6,096,289 A | 8/2000 | Goldenberg |
| 6,165,440 A | 12/2000 | Esenaliev |
| 6,183,744 B1 | 2/2001 | Goldenberg |
| 6,187,287 B1 | 2/2001 | Leung et al. |
| 6,254,868 B1 | 7/2001 | Leung et al. |
| 6,261,537 B1 | 7/2001 | Klaveness et al. |
| 6,306,393 B1 | 10/2001 | Goldenberg |
| 6,331,175 B1 | 12/2001 | Goldenberg |
| 6,379,698 B1 | 4/2002 | Leamon |
| 6,387,350 B2 | 5/2002 | Goldenberg |
| 6,395,276 B1 | 5/2002 | Rybak et al. |
| 6,524,854 B1 | 2/2003 | Monia et al. |
| 6,530,944 B2 | 3/2003 | West et al. |
| 6,562,318 B1 | 5/2003 | Filler |
| 6,617,135 B1 | 9/2003 | Gillies et al. |
| 6,653,104 B2 | 11/2003 | Goldenberg |
| 6,897,044 B1 | 5/2005 | Braslawsky et al. |
| 7,060,506 B2 | 6/2006 | Craig |
| 7,074,403 B1 | 7/2006 | Goldenberg et al. |
| 7,151,164 B2 | 12/2006 | Hansen et al. |
| 7,312,318 B2 | 12/2007 | Hansen et al. |
| 7,321,026 B2 | 1/2008 | Leung |
| 7,338,659 B2 | 3/2008 | Leung |
| 7,387,779 B2 | 6/2008 | Kalluri |
| 7,432,342 B2 | 10/2008 | Braun et al. |
| 7,521,056 B2 | 4/2009 | Chang et al. |
| 7,527,787 B2 | 5/2009 | Chang et al. |
| 7,534,866 B2 | 5/2009 | Chang et al. |
| 7,541,440 B2 | 6/2009 | Goldenberg et al. |
| 7,550,143 B2 | 6/2009 | Goldenberg et al. |
| 7,591,994 B2 | 9/2009 | Govindan et al. |
| 7,666,400 B2 | 2/2010 | Chang et al. |
| 7,772,373 B2 | 8/2010 | Hansen et al. |
| 7,829,064 B2 | 11/2010 | Griffiths et al. |
| 7,858,070 B2 | 12/2010 | Chang et al. |
| 7,871,622 B2 | 1/2011 | Chang et al. |
| 7,901,680 B2 | 3/2011 | Chang et al. |
| 7,906,118 B2 | 3/2011 | Chang et al. |
| 7,906,121 B2 | 3/2011 | Chang et al. |
| 7,919,087 B2 | 4/2011 | Hansen et al. |
| 7,931,903 B2 | 4/2011 | Hansen et al. |
| 7,981,398 B2 | 7/2011 | Chang et al. |
| 8,003,111 B2 | 8/2011 | Chang et al. |
| 8,034,352 B2 | 10/2011 | Chang et al. |
| 8,158,129 B2 | 4/2012 | Chang et al. |
| 8,163,291 B2 | 4/2012 | Chang et al. |
| 8,211,440 B2 | 7/2012 | Chang et al. |
| 8,246,960 B2 | 8/2012 | Chang et al. |
| 8,277,817 B2 | 10/2012 | Chang et al. |
| 8,282,934 B2 | 10/2012 | Chang et al. |
| 8,349,332 B2 | 1/2013 | Chang et al. |
| 8,435,540 B2 | 5/2013 | Chang et al. |
| 8,475,794 B2 | 7/2013 | Chang et al. |
| 8,481,041 B2 | 7/2013 | Chang et al. |
| 8,491,914 B2 | 7/2013 | Chang et al. |
| 8,551,480 B2 | 10/2013 | Chang et al. |
| 8,562,988 B2 | 10/2013 | Chang et al. |
| 8,597,659 B2 | 12/2013 | Chang et al. |
| 2002/0004587 A1 | 1/2002 | Miller et al. |
| 2002/0009427 A1 | 1/2002 | Wolin et al. |
| 2002/0009444 A1 | 1/2002 | Grillo-Lopez |
| 2002/0018749 A1 | 2/2002 | Hudson et al. |
| 2003/0198956 A1 | 10/2003 | Makowski et al. |
| 2003/0219433 A1* | 11/2003 | Hansen et al. ............. 424/141.1 |
| 2003/0232420 A1 | 12/2003 | Braun et al. |
| 2004/0018587 A1 | 1/2004 | Makowski et al. |
| 2004/0076683 A1 | 4/2004 | Hoarau et al. |
| 2005/0003403 A1 | 1/2005 | Rossi et al. |
| 2006/0210475 A1 | 9/2006 | Goldenberg et al. |
| 2007/0020259 A1 | 1/2007 | Hansen et al. |
| 2007/0140966 A1 | 6/2007 | Chang et al. |
| 2009/0060862 A1 | 3/2009 | Chang et al. |
| 2009/0111143 A1 | 4/2009 | Goldenberg et al. |
| 2009/0246214 A1 | 10/2009 | Goldenberg et al. |
| 2010/0015048 A1 | 1/2010 | Hansen et al. |
| 2010/0068137 A1 | 3/2010 | Chang et al. |
| 2010/0104589 A1 | 4/2010 | Govindan et al. |
| 2010/0196266 A1 | 8/2010 | Goldenberg et al. |
| 2010/0266496 A1 | 10/2010 | Hansen et al. |
| 2010/0284906 A1 | 11/2010 | Hansen et al. |
| 2011/0020273 A1 | 1/2011 | Chang et al. |
| 2011/0064754 A1 | 3/2011 | Taylor et al. |
| 2011/0070155 A1 | 3/2011 | Griffiths et al. |
| 2011/0158905 A1 | 6/2011 | Goldenberg et al. |
| 2011/0189083 A1 | 8/2011 | Chang et al. |
| 2011/0195023 A1 | 8/2011 | Hansen et al. |
| 2011/0244546 A1 | 10/2011 | Hansen et al. |
| 2012/0093769 A1 | 4/2012 | Chang et al. |
| 2012/0196346 A1 | 8/2012 | Chang et al. |
| 2012/0276100 A1 | 11/2012 | Chang et al. |
| 2012/0276608 A1 | 11/2012 | Chang et al. |
| 2013/0078183 A1 | 3/2013 | Chang et al. |
| 2013/0109073 A1 | 5/2013 | Chang et al. |
| 2013/0164816 A1 | 6/2013 | Chang et al. |
| 2013/0177532 A1 | 7/2013 | Chang et al. |
| 2013/0217091 A1 | 8/2013 | Chang et al. |
| 2013/0295005 A1 | 11/2013 | Chang et al. |

FOREIGN PATENT DOCUMENTS

| | | |
|---|---|---|
| WO | 88/04936 | 7/1988 |
| WO | 91/13974 | 9/1991 |
| WO | 92/07466 | 5/1992 |
| WO | 94/11026 | 5/1994 |
| WO | 94/27638 | 12/1994 |
| WO | 9509917 | 4/1995 |
| WO | 96/04925 | 2/1996 |
| WO | 98/42378 | 10/1998 |
| WO | 98/50435 | 11/1998 |
| WO | 99/02567 | 1/1999 |
| WO | 99/54440 | 10/1999 |
| WO | 00/29584 | 5/2000 |
| WO | 0044788 | 8/2000 |
| WO | 00/63403 | 10/2000 |
| WO | 00/67795 | 11/2000 |
| WO | 00/68248 | 11/2000 |
| WO | 00/74718 | 12/2000 |
| WO | 02/056910 | 7/2002 |
| WO | 03/002607 | 1/2003 |
| WO | 03074567 | 9/2003 |
| WO | WO03/074567 * | 9/2003 |
| WO | 2004094613 | 11/2004 |
| WO | 2006/107617 | 10/2006 |

(56) References Cited

FOREIGN PATENT DOCUMENTS

| WO | 2006/107786 | 10/2006 |
|---|---|---|
| WO | 2007046893 | 4/2007 |
| WO | 2007/075270 | 7/2007 |
| WO | 2007134037 | 11/2007 |
| WO | 2008/033413 | 3/2008 |
| WO | 2009126558 | 10/2009 |

OTHER PUBLICATIONS

Golay et al., Archives of Biochemistry and Biophysics 526: 146-153, 2012.*
Colman et al., Research in Immunology (145(1):33-35, 1994.*
Lederman et al., Molecular Immunology 28:1171-1181, 1991.*
Stancovski et al., PNAS, 88: 8691-8695, 1991.*
Hay et al., Nature Biotechnology 32(1): 40-51, Jan. 2014.*
US 6,558,648, 05/2003, Griffiths et al. (withdrawn).
Bagshawe et al., "Developments with targeted enzymes in cancer therapy", Curr. Opin. Immunol. 11(5):579-83 (1999).
Bally et al. (Eds.), "Controlling the Drug Delivery Attributes of Lipid-Based Drug Formulations", Journal of Liposome Research, 1998, vol. 8, No. 3, pp. 299-335.
Beers et al., The Merck Manual of Diagnosis and Therapy, Ch. 180, p. 1474-1476; 17th Ed., Whitehouse Station, NJ, Merck Research Labs (1999).
Bendas et al., "Immunoliposomes: a promising approach to targeting cancer therapy", BioDrugs 15(4):215-24 (2001).
Bendig, M., "Humanization of Rodent Monoclonal Antibodies by CDR Grafting", Academic Press Inc., New York, NY, vol. 8, (1995), pp. 83-93.
Bird et al., "Single chain antibody variable regions", Trends Biotechnol. 9(4):132-7 (1991).
Bom et al., "The highly lipophilic DNA topoisomerase I inhibitor DB-67 displays elevated lactone levels in human blood and potent anticancer activity", J. Control Release 74(1-3):325-33 (2001).
Breen et al., "Non-Hodgkin's B cell lymphoma in persons with acquired immunodeficiency syndrome is associated with increased serum levels of IL10, or the IL10 promoter -592 C/C genotype", Clin. Immunol. 109(2):119-29 (2003).
Burgess et al., "Possible dissociation of the heparin-binding and mitogenic activities of heparin-binding (acidic fibroblast) growth factor-1 from its receptor-binding activities by site-directed mutagenesis of a single lysine residue", J. Cell Biol. 111:2129-2138 (1990).
Carter et al., "Humanization of an anti-p185HER2 antibody for human cancer therapy", Proc. Natl. Acad. Sci. USA 89(10):4285-9 (1992).
Chen et al., "Differential Effects of Milatuzumab on Human Antigen-Presenting Cells in Comparison to Malignant B Cells", 2009 ASH Annual Meeting Abstracts, vol. 114(22)1073; Abstr # 2744 (Nov. 20, 2009).
Cochlovius et al., "Cure of Burkitt's lymphoma in severe combined immunodeficiency mice by T cells, tetravalent CD3 × CD19 tandem diabody, and CD28 costimulation", Cancer Res. 60(16):4336-41 (2000).
Coligan et al., (Eds.), Current Protocols in Immunology, vol. 1, pp. 2.5.1-2.6.7; pp. 2.7.1.-2.7.12; pp. 2.8.1-2.8.10; pp. 2.9.1-2.9.3; pp. 2.10.-2.10.4; John Wiley & Sons, Inc., 1991.
Colman, P., "Effects of amino acid sequence changes on antibody-antigen interactions", Res. Immunol. 1994, 145:33-36.
Coloma et al., "Design and production of novel tetravalent bispecific antibodies", Nat. Biotechnol. 15(2):159-63 (1997).
Constantinides et al., "Formulation development and antitumor activity of a filter-sterilizable emulsion of paclitaxel", Pharm. Res. 17(2):175-82 (2000).
Courtenay-Luck, N. S., "Genetic manipulation of monoclonal antibodies", Monoclonal Antibodies: Production, Engineering and Clinical Application, p. 166-179, Ritter et al. (Eds.), Cambridge University Press (1995).

Fitzgerald et al., "Improved tumour targeting by disulphide stabilized diabodies expressed in Pichia pastoris", Protein Eng. 10(10):1221-5 (1997).
Flavell et al., "Systemic therapy with 3BIT, a triple combination cocktail of anti-CD19, -CD22, and -CD38-saporin immunotoxins, is curative of human B-cell lymphoma in severe combined immunodeficient mice", Cancer Res. 57:4824-9 (1997).
Freedman et al., "Non-Hodgkin's Lymphomas", Cancer Medicine, 3rd Ed., vol. 2, p. 2028-2068, Holland et al., (Eds.), Lea & Febiger (1993).
French et al., "Response of B-cell lymphoma to a combination of bispecific antibodies and saporin", Leuk. Res. 20(7):607-17 (1996).
Ghetie et al., "Evaluation of ricin A chain-containing immunotoxins directed against CD19 and CD22 antigens on normal and malignant human B-cells as potential reagents for in vivo therapy", Cancer Res. 48(9):2610-7 (1988).
Ghetie et al., "Homodimers but not monomers of Rituxan (chimeric anti-CD20) induce apoptosis in human B-lymphoma cells and synergize with a chemotherapeutic agent and an immunotoxin", Blood. Mar. 1, 2001;97(5):1392-8.
Gold et al., "Expression of CD74 in pancreatic and colorectal carcinomas as a basis for milatuzumab immunotherapy", Abstract #5485; Proceeding of the American Association for Cancer Research, vol. 50, p. 1322-1323; Apr. 2009.
Goldenberg, D. M. "Future role of radiolabeled monoclonal antibodies in oncological diagnosis and therapy", Semin. Nucl. Med. 19(4):332-9 (1989).
Goldenberg et al., "Targeting, dosimetry, and radioimmunotherapy of B-cell lymphomas with iodine-131-labeled LL2 monoclonal antibody", J Clin Oncol. Apr. 1991;9(4):548-64.
Goldenberg, D. M. "Radiolabeled antibodies", Science & Medicine, 1(1):64 (Apr. 1994).
Goldenberg, D. M. "New Developments in Monoclonal Antibodies for Cancer Detection and Therapy", CA Cancer J. Clin. 44(1):43-64 (1994).
Gondo et al., "HLA class II antigen associated invariant chain gene expression in malignant lymphoma", Br. J. Haematol. 67(4):413-7 (1987).
Goto et al. "A novel membrane antigen selectively expressed on terminally differentiated human B cells", Blood 84 (6):1922-30 (1994).
Green et al., "Antigen-specific human monoclonal antibodies from mice engineered with human Ig heavy and light chain YACs", Nature Genetics 7:13-21 (1994).
Greenwood et al., "Effector functions of matched sets of recombinant human IgG subclass antibodies", Protein Engineering of Antibody Molecules for Prophylactic and Therapeutic Applications in Man, Clark (Ed.), p. 89; p. 97; Academic Titles (1993).
Griffiths et al., "Cure of SCID Mice Bearing Human B-Lymphoma Xenografts by an Anti-CD74 Antibody-Anthracycline Drug Conjugate", vol. 9, 6567-6571, Dec. 15, 2003.
Hansen et al., "Internalization and catabolism of radiolabelled antibodies to the MHC class-II invariant chain by B-cell lymphomas", Biochem. J. 1996, 320:293-300.
Hasan et al., "Laser-induced selective cytotoxicity using monoclonal antibody-chromophore conjugates", Prog. Clin. Biol. Res. 288:471-7 (1989).
Hekman et al. "Initial experience with treatment of human B cell lymphoma with anti-CD19 monoclonal antibody", Cancer Immunol. Immunother. 1991;32(6):364-72.
Hess et al., "Specificity of effector T lymphocytes in autologous graft-versus-host disease: role of the major histocompatibility complex class II invariant chain peptide", Blood 89(6):2203-9 (1997).
Hong et al., "pH-sensitive, serum-stable and long-circulating liposomes as a new drug delivery system", J. Pharm. Pharmacol. 54(1):51-8 (2002).
Hua et al., "Immunoreactivity for LN2 and LN3 distinguishes small cell carcinomas from non-small cell carcinomas in the lung", Hum. Pathol. 29(12):1441-6 (1998).
Huse et al., "Generation of a Large Combinatorial Library of the Immunoglobulin Repertoire in Phage Lambda", Science 246:1275-1281 (1989).

(56) References Cited

OTHER PUBLICATIONS

Ibragimova et al., "Stability of the beta-sheet of the WW domain: A molecular dynamics simulation study", Biophys. J. 77(4):2191-8 (1999).
Johnson et al., "Human antibody engineering", Current Opin. Struct. Biol. 3:564-571 (1993).
Jones et al., "Replacing the complementarity-determining regions in a human antibody with those from a mouse" Nature 321(6069):522-5 (1986).
Juweid et al., "99Tcm-LL1: a potential new bone marrow imaging agent", Nucl. Med. Commun. 18(2):142-8 (1997).
Juweid et al., "Treatment of non-Hodgkin's lymphoma with radiolabeled murine, chimeric, or humanized LL2, an anti-CD22 monoclonal antibody", Cancer Res. 55(23 Suppl):5899s-5907s (1995).
Kaminski et al., "Radioimmunotherapy of B-cell lymphoma with [131I]anti-B1 (anti-CD20) antibody", N. Engl. J. Med. 329(7):459-65 (1993).
Kiesel et al., "Removal of cells from a malignant B-cell line from bone marrow with immunomagnetic beads and with complement and immunoglobulin switch variant mediated cytolysis", Leuk. Res. 11(12):1119-25 (1987).
Kirpotin et al., "Sterically stabilized anti-HER2 immunoliposomes: design and targeting to human breast cancer cells in vitro", Biochemistry 36(1):66-75 (1997).
Kohler et al., "Continuous cultures of fused cells secreting antibody of predefined specificity", Nature 256:495-7 (1975).
Kolata, G., "Clinical promise with new hormones", Science 236:517-519 (1987).
Patti et al., "High-dose cyclophosphamide, etoposide and BCNU (CVB) with autologous stem cell rescue in malignant lymphomas", Eur J Haematol. Jul. 1993;51(1):18-24.
Press et al., "Monoclonal antibody 1F5 (anti-CD20) serotherapy of human B cell lymphomas", Blood. Feb. 1987;69(2):584-91.
Press et al., "Treatment of refractory non-Hodgkin's lymphoma with radiolabeled MB-1 (anti-CD37) antibody", J Clin Oncol. Aug. 1989;7(8):1027-38.
Press et al., "Prospects for the management of non-Hodgkin's lymphomas with monoclonal antibodies and immunoconjugates", Cancer J. Sci. Am. 4(Suppl 2):S19-26 (1998).
Price, K. M., "Production and characterization of synthetic peptide-derived antibodies", Monoclonal Antibodies: Production, Engineering and Clinical Application, Ritter et al., (Eds.), pp. 60-84, Cambridge University Press (1995).
Protheroe et al., "Remission of inflammatory arthropathy in association with anti-CD20 therapy for non-Hodgkin's lymphoma", Rheumatology (Oxford) 38(11):1150-2 (1999).
Qu et al., "Carbohydrates engineered at antibody constant domains can be used for site-specific conjugation of drugs and chelates", J. Immunol. Methods 213(2):131-44 (1998).
Qu et al., "Internalization and cytotoxic effects of a humanized anti-CD74 antibody, LL1", Proc Am Assoc Cancer Res 2002;43:255, Abstract # 1269.
Raag et al., "Single-chain Fvs", FASEB J. 9(1):73-80 (1995).
Renner et al., "Monoclonal antibodies in the treatment of non-Hodgkin's lymphoma: recent results and future prospects", Leukemia 11(Suppl 2):S55-9 (1997).
Riechmann et al., "Reshaping human antibodies for therapy", Nature 332(6162):323-7 (1988).
Robinson et al., "Chimeric mouse-human anti-carcinoma antibodies that mediate different anti-tumor cell biological activities", Hum Antibodies Hybridomas. Apr. 1991;2(2):84-93.
Rowan et al., "Cross-linking of the CAMPATH-1 antigen (CD52) mediates growth inhibition in human B- and T-lymphoma cell lines, and subsequent emergence of CD52-deficient cells", Immunology 95(3):427-36 (1998).
Rudikoff et al., "Single amino acid substitution altering antigen-binding specificity", Proc. Natl. Acad. Sci. USA 79(6):1979-83 (1982).
Ryser et al., "Conjugation of methotrexate to poly(L-lysine) increases drug transport and overcomes drug resistance in cultured cells", Proc. Natl. Acad. Sci. USA 75(8):3867-70 (1978).
Saltzman et al., "Transport rates of proteins in porous materials with known microgeometry", Biophys. J. 55(1):163-71 (1989).
Sambrook et al., "Molecular Cloning", a Laboratory Manual, 2nd Edition, 1989, Cold Spring harbor Laboratory Press, USA.
Sandhu, J. S., "Protein engineering of antibodies", Crit. Rev. Biotechnol. 12(5-6):437-62 (1992).
Sanger et al., "DNA sequencing with chain-terminating inhibitors", Proc Natl Acad Sci U S A. Dec. 1977;74(12):5463-7.
Schlom, J. "Monoclonal Antibodies: They're More and Less Than You Think", Molecular Foundations of Oncology, Broader, S. (Ed.), pp. 95-134 (1991).
Shan et al., "Signaling events involved in anti-CD20-induced apoptosis of malignant human B cells", Cancer Immunol Immunother. Mar. 2000;48(12):673-83.
Sherwood et al., "Controlled antibody delivery systems", Biotechnology 10(11):1446-9 (1992).
Shih et al., "Site-specific linkage of methotrexate to monoclonal antibodies using an intermediate carrier", Int J Cancer 41(6):832-9 (1988).
Shih et al., "A fluorouridine-anti-CEA immunoconjugate is therapeutically effective in a human colonic cancer xenograft model", Int. J. Cancer 46(6):1101-6 (1990).
Shih et al., "Internalization and intracellular processing of an anti-B-cell lymphoma monoclonal antibody, LL2", Int J Cancer 56(4):538-45 (1994).
Shih et al., "Localization of an antibody to CD74 (MHC class II invariant chain) to human B cell lymphoma xenografts in nude mice", Cancer Immunol. Immunother. 49(4-5):208-16 (2000).
Shopes, B., "A genetically engineered human IgG mutant with enhanced cytolytic activity", J Immunol. May 1, 1992;148(9):2918-22.
Singer et al., "Optimal humanization of 1B4, an anti-CD18 murine monoclonal antibody, is achieved by correct choice of human V-region framework sequences", J. Immunol. 150(7):2844-57 (1993).
Stein et al., "Epitope specificity of the anti-(B cell lymphoma) monoclonal antibody, LL2", Cancer Immunol. Immunother. 37(5):293-8 (1993).
Straubinger et al., "Endocytosis and intracellular fate of liposomes using pyranine as a probe", Biochemistry 29(20):4929-39 (1990).
Tatsuta et al., "Diagnosis of gastric cancers with fluorescein-labeled monoclonal antibodies to carcinoembryonic antigen", Lasers Surg. Med. 9(4):422-6 (1989).
Taylor et al., "A transgenic mouse that expresses a diversity of human sequence heavy and light chain immunoglobulins", Nucleic Acids Res. 20(23):6287-95 (1992).
Taylor et al., "Human immunoglobulin transgenes undergo rearrangement, somatic mutation and class switching in mice that lack endogenous IgM", Int Immunol. Apr. 1994;6(4):579-91.
Tempest et al., "Reshaping a human monoclonal antibody to inhibit human respiratory syncytial virus infection in vivo", Biotechnology 9(3):266-71 (1991).
Theocharis et al., "Characterization of in vivo mutated T cell clones from patients with systemic lupus erythematosus", Clin. Immunol. Immunopathol. 74(2):135-42 (1995).
Thorpe et al., "Monoclonal antibodies: clinical and regulatory issues", Trends Biotechnol. 11(2):40-2 (1993).
Torchilin et al., "The antibody-linked chelating polymers for nuclear therapy and diagnostics", Crit. Rev. Ther. Drug Carrier Syst. 7(4):275-308 (1991).
Torchilin et al., "Immunomicelles: targeted pharmaceutical carriers for poorly soluble drugs", Proc. Natl. Acad. Sci. USA 100(10):6039-44 (2003).
Upeslacis et al., "Modification of Antibodies by Chemical Methods," Monoclonal Antibodies: Principles and Applications, Birch et al. (eds.), pp. 187-230 (Wiley-Liss, Inc., 1995).
Van Den Bergh, H., "Light and porphyrins in cancer therapy", Chem. Britain 22:430 (1986).
Vaughan et al., "Human antibodies with sub-nanomolar affinities isolated from a large non-immunized phage display library", Nat. Biotechnol. 14(3):309-14 (1996).

(56) References Cited

OTHER PUBLICATIONS

Verhoeyen et al., "Reshaping human antibodies: grafting an antilysozyme activity", Science 239(4847):1534-6 (1988).
Vuist et al., "Potentiation by interleukin 2 of Burkitt's lymphoma therapy with anti-pan B (anti-CD19) monoclonal antibodies in a mouse xenotransplantation model", Cancer Res. 49(14):3783-8 (1989).
Ward et al., "Genetic Manipulation and Expression of Antibodies," Monoclonal Antibodies: Principles and Applications, Birch et al., (eds.), pp. 137-185 (Wiley-Liss, Inc. 1995).
Werner et al., "Appropriate mammalian expression systems for biopharmaceuticals", Arzneimittelforschung. Aug. 1998;48(8):870-80.
West et al., "Applications of nanotechnology to biotechnology commentary", Curr Opin Biotechnol. 11(2):215-7 (2000).
Wong, S. Chemistry of Protein Conjugation and Cross-Linking, CRC Press, Inc. (1991).
Wrobel et al., "Fusion of cationic liposomes with mammalian cells occurs after endocytosis", Biochim. Biophys. Acta. 1235(2):296-304 (1995).
Xu et al., "Systemic tumor-targeted gene delivery by anti-transferrin receptor scFv-immunoliposomes", Mol. Cancer Ther. 1(5):337-46 (2002).
Yu et al., "Peptide-antibody conjugates for tumour therapy: a MHC-class-II-restricted tetanus toxin peptide coupled to an anti-Ig light chain antibody can induce cytotoxic lysis of a human B-cell lymphoma by specific CD4 T cells", Int. J. Cancer 56(2):244-8 (1994).
Cardillo et al., "Targeting both IGF-1R and mTOR synergistically inhibits growth of renal cell carcinoma in vitro", BMC Cancer. Apr. 1, 2013;13:170.
Chang et al., "A new method to produce monoPEGylated dimeric cytokines shown with human interferon-α2b", Bioconjug Chem. Oct. 21, 2009;20(10):1899-907.
Chang et al., "A novel class of anti-HIV agents with multiple copies of enfuvirtide enhances inhibition of viral replication and cellular transmission in vitro", PLoS One. 2012;7(7):e41235.
Chang et al., "Evaluation of a novel hexavalent humanized anti-IGF-1R antibody and its bivalent parental IgG in diverse cancer cell lines", PLoS One. 2012;7(8):e44235.
Goldenberg et al., "Cancer Imaging and Therapy with Bispecific Antibody Pretargeting", Update Cancer Ther. Mar. 2007; 2(1):19-31.
Govindan et al., "Designing immunoconjugates for cancer therapy", Expert Opin Biol Ther. Jul. 2012;12(7):873-90.
Liu et al., "Trop-2-targeting tetrakis-ranpirnase has potent antitumor activity against triple-negative breast cancer", Mol Cancer Mar. 10, 2014;13:53.
Perry et al., "Murine models of systemic lupus erythematosus", J Biomed Biotechnol. 2011;2011:271694.
Rossi et al., "CD20-targeted tetrameric interferon-alpha, a novel and potent immunocytokine for the therapy of B-cell lymphomas", Blood. Oct. 29, 2009;114(18)3864-71.
Rossi et al., "Hexavalent bispecific antibodies represent a new class of anticancer therapeutics: 1. Properties of anti-CD20/CD22 antibodies in lymphoma", Blood. Jun. 11, 2009;113(24):6161-71.
Rossi et al., "The dock-and-lock method combines recombinant engineering with site-specific covalent conjugation to generate multifunctional structures", Bioconjug Chem. Mar. 21, 2012;23(3):309-23.
Rossi et al., "Complex and defined biostructures with the dock-and-lock method", Trends Pharmacol Sci. Sep. 2012;33(9):474-81.
Rossi et al., "Optimization of multivalent bispecific antibodies and immunocytokines with improved in vivo properties", Bioconjug Chem. Jan. 16, 2013;24(1):63-71.
Rossi et al., "A new class of bispecific antibodies to redirect T cells for cancer immunotherapy", MAbs. Mar.-Apr. 2014;6(2):381-91.
Sharkey et al., "Improved cancer therapy and molecular imaging with multivalent, multispecific antibodies", Cancer Biother Radiopharm. Feb. 2010;25(1):1-12.

Alinari et al., "FTY720 increases CD74 expression and sensitizes mantle cell lymphoma cells to milatuzumab-mediated cell death", Blood. Oct. 31, 2011. [Epub ahead of print].
Ansel et al. (Eds.), "Pharmaceutical Dosage Forms and Drug Delivery Systems", 5th Edition, Lippincott Williams & Wilkins, 1990.
Appelbaum, F., "Radiolabeled monoclonal antibodies in the treatment of non-Hodgkin's lymphoma", Hematol. Oncol. Clin. North Am. Oct. 1991;5(5):1013-25.
Ausubel et al. (Eds.), "Current Protocols in Molecular Biology", vol. 1, Unit 8, John Wiley & Sons, Inc., 1994.
Baines et al., "Purification of Immunoglobulin G (IgG)", Methods in Molecular Biology, 1992, vol. 10, p. 79-104.
Barnes et al., "Advances in animal cell recombinant protein production: GS-NS0 expression system", Cytotechnology Feb. 2000:32(2):109-23.
Berkova et al., "Milatuzumab—a promising new immunotherapeutic agent", Expert Opin Investig Drugs. Jan. 2010;19(1):141-9.
Binsky et al., "IL-8 secreted in a macrophage migration-inhibitory factor- and CD74-dependent manner regulates B cell chronic lymphocytic leukemia survival", Proc Natl Acad Sci U S A. Aug. 14, 2007;104(33):13408-13.
Binsky et al., "TAp63 regulates VLA-4 expression and chronic lymphocytic leukemia cell migration to the bone marrow in a CD74-dependent manner", J Immunol. May 1, 2010;184(9):4761-9.
Burton et al., "CD74 is expressed by multiple myeloma and is a promising target for therapy", Clin Cancer Res. Oct. 1, 2004;10(19):6606-11.
Caron et al., "Engineered humanized dimeric forms of IgG are more effective antibodies", J. Exp. Med. Oct. 1, 1992;176(4):1191-5.
Chang et al., "Effective therapy of human lymphoma xenografts with a novel recombinant ribonuclease/anti-CD74 humanized IgG4 antibody immunotoxin", Blood. Dec. 15, 2005;106(13):4308-14.
Colman et al., "Production of therapeutic proteins in the milk of transgenic livestock", Biochem. Soc. Symp. 1998;63:141-7.
Devesa et al., "Cancer incidence and mortality trends among whites in the United States, 1947-84", J. Natl. Cancer Inst. Oct. 1987;79(4):701-70.
Eary et al., "Imaging and treatment of B-cell lymphoma", J. Nucl. Med. Aug. 1990;31(8):1257-68.
Eisenberg et al., "The therapeutic potential of anti-CD20 what do B-cells do?", Clin. Immunol. Dec. 2005;117(3):207-13.
Foon et al., "Chronic lymphocytic leukemia: new insights into biology and therapy", Ann. Intern. Med. Oct. 1, 1990;113(7):525-39.
Freedman, A., "Immunobiology of chronic lymphocytic leukemia", Hematol. Oncol. Clin. North Am. Apr. 1990;4(2):405-29.
Gennaro, A.R., Remington: 19th Edition, 1995, Mack Publishing Co.
Ghetie et al., "Homodimerization of tumor-reactive monoclonal antibodies markedly increases their ability to induce growth arrest or apoptosis of tumor cells", Proc. Natl. Acad. Sci. USA Jul. 8, 1997;94(14):7509-14.
Gilles et al., "High-level expression of chimeric antibodies using adapted cDNA variable region cassettes", J. Immunol. Methods Dec. 20, 1989;125(1-2):191-202.
Gold et al., "Enhanced expression of CD74 in gastrointestinal cancers and benign tissues", Int J Clin Exp Pathol. Nov. 23, 2010;4(1):1-12.
Goldenberg et al., "Horizontal transmission and retention of malignancy, as well as functional human genes, after spontaneous fusion of human glioblastoma and hamster host cells In Vivo", Int J Cancer. Jul. 1, 2012;131(1):49-58.
Goodman et al., The Pharmacological Basis of Therapeutics, 5th Edition, 1975, MacMillan Publishing Co., Inc, USA.
Goodman et al., "New perspectives on the approach to chronic lymphocytic leukemia", Leuk. Lymphoma Jun. 1996;22(1-2):1-10.
Gopal et al., "Clinical applications of anti-CD20 antibodies", J. Lab. Clin. Med. Nov. 1999;134(5):445-50.
Gorman et al., "B cell depletion in autoimmune disease", Arthritis Res. Ther. 2003;5 Suppl 4:S17-21.
Govindan et al., "Radionuclides linked to a CD74 antibody as therapeutic agents for B-cell lymphoma: comparison of Auger electron emitters with beta-particle emitters", J Nucl Med. Dec. 2000;41(12):2089-97.

(56) References Cited

OTHER PUBLICATIONS

Griffiths et al., "Cytotoxicity with Auger electron-emitting radionuclides delivered by antibodies", Int J Cancer. Jun. 11, 1999;81(6):985-92.
Hertlein et al., "Milatuzumab immunoliposomes induce cell death in CLL by promoting accumulation of CD74 on the surface of B cells", Blood. Oct. 7, 2010;116(14):2554-2558.
Jori et al., (Eds.), Photodynamic Therapy of Tumours and Other Diseases, Libreria Progetto (1985).
Kazkaz et al., "Anti B cell therapy (rituximab) in the treatment of autoimmune diseases", Curr. Opin. Pharmacol. Aug. 2004;4(4):398-402.
Liu et al., "Production of a mouse-human chimeric monoclonal antibody to CD20 with potent Fc-dependent biologic activity", J. Immunol. Nov. 15, 1987;139(10):3521-6.
Losman et al., "Generation of a high-producing clone of a humanized anti-B-cell lymphoma monoclonal antibody (hLL2)", Cancer Dec. 15, 1997;80(12 Suppl):2660-6.
Maloney et al., "Newer treatments for non-Hodgkin's lymphoma: monoclonal antibodies", Oncology (Williston Park) Oct. 1998;12(10 Suppl 8):63-76.
Mark et al., "Milatuzumab: a promising new agent for the treatment of lymphoid malignancies", Expert Opin Investig Drugs. Jan. 2009;18(1):99-104.
Michel et al., "Therapy of small subcutaneous B-lymphoma xenografts with antibodies conjugated to radionuclides emitting low-energy electrons", Clin Cancer Res. Jan. 15, 2005;11(2 Pt 1):777-86.
Michel et al., "177Lu-antibody conjugates for single-cell kill of B-lymphoma cells in vitro and for therapy of micrometastases in vivo", Nucl Med Biol. Apr. 2005;32(3):269-78.
Ong et al., "Cell surface expression and metabolism of major histocompatibility complex class II invariant chain (CD74) by diverse cell lines", Immunology. Oct. 1999;98(2):296-302.
Ong et al., "Single-cell cytotoxicity with radiolabeled antibodies", Clin Cancer Res. Jan. 2001;7(1):192-201.
Paul, W., Fundamental Immunology, 3rd Edition, pp. 292-295 (1993).
Sapra et al., "Anti-CD74 antibody-doxorubicin conjugate, IMMU-110, in a human multiple myeloma xenograft and in monkeys", Clin Cancer Res. Jul. 15, 2005;11(14):5257-64.
Shachar et al., The secret second life of an innocent chaperone: the story of CD74 and B cell/chronic lymphocytic leukemia cell survival, Leuk Lymphoma. Aug. 2011;52(8):1446-54.
Shan et al., "Characterization of scFv-Ig constructs generated from the anti-CD20 mAb 1F5 using linker peptides of varying lengths", J. Immunol. Jun. 1, 1999;162(11):6589-95.
Sharkey et al., "Pretargeted versus directly targeted radioimmunotherapy combined with anti-CD20 antibody consolidation therapy of non-Hodgkin lymphoma, J Nucl Med. Mar. 2009;50(3):444-53.
Stein et al., "Antiproliferative activity of a humanized anti-CD74 monoclonal antibody, hLL1, on B-cell malignancies", Blood. Dec. 1, 2004;104(12):3705-11.
Stein et al., "CD74: a new candidate target for the immunotherapy of B-cell neoplasms", Clin Cancer Res. Sep. 15, 2007;13(18 Pt 2):5556s-5563s.
Stein et al., "Combining milatuzumab with bortezomib, doxorubicin, or dexamethasone improves responses in multiple myeloma cell lines", Clin Cancer Res. Apr. 15, 2009;15(8):2808-17.
Stein et al., "Therapy of B-cell malignancies by anti-HLA-DR humanized monoclonal antibody, IMMU-114, is mediated through hyperactivation of ERK and JNK MAP kinase signaling pathways", Blood. Jun. 24, 2010;115(25):5180-90.
Tesch et al., "Treatment of patients with malignant lymphomas with monoclonal antibodies", Bone Marrow Transplant May 2000;25 Suppl 2:S50-3.
Abbas et al., Cellular and Molecular Immunology, W.B. Saunders Comp. 1991, p. 43.

Alto et al., "Bioinformatic design of A-kinase anchoring protein-in silico: a potent and selective peptide antagonist of type II protein kinase A anchoring" Proc. Natl. Acad. Sci USA Apr. 15, 2003; 100(8):4445-50.
Backer et al., "Self-Assembled "Dock and Lock" System for Linking Payloads to Targeting Proteins" Bioconjugate Chem., 2006, 17(4):912-919.
Baillie et al., "Compartmentalisation of phospodiesterases and protein kinase A: opposites attract", FEBS Letters 2005; 579:3264-3270.
Banky et al., "Dimerization/Docking Domain of the Type Iα Regulatory Subunit of cAMP-dependent Protein Kinase", J. Biol. Chem. 273:35048-55, 1998.
Basu et al., "Structure-Function Engineering of Interferon-β-1b for Improving Stability, Solubility, Potency, Immunogenicity, and Pharmacokinetic Properties by Site-Selective Mono-PEGylation", Bioconjugate Chem. 2006; 17:618-630.
Belardelli et al., "Interferon-alpha in tumor immunity and immunotherapy" Cytokine Growth Factor Rev. 13(2):119-134 (2002).
Belardelli et al., "International Meeting on Cancer Vaccines: How Can We Enhance Efficacy of Therapeutic Vaccines?" Cancer Res. 64:6827-6830 (2004).
Belardelli et al., "The neglected role of type I interferon in the T-cell response: implications for its clinical use" Immunol. Today 17(8):369-72 (1996).
Biron et al., "Natural killer cells in antiviral defense: function and regulation by innate cytokines" Annu. Rev. Immunol. 17:189-220 (1999).
Brunda et al., "Modulation of Murine Natural Killer Cell Activity in Vitro and in Vivo by Recombinant Human Interferons" Cancer Res. 44:597-601 (1984).
Burns-Hamuro et al., "Distinct interaction modes of an AKAP bound to two regulatory subunit isoforms of protein kinase a revealed by amide hydrogen/deuterium exchange" Protein Science (2005), 14:2982-2992.
Carr et al., "Interaction of the Regulatory Subunit (RII) of cAMP-dependent Protein Kinase with RII-anchoring Proteins Occurs through an Amphipathic Helix Binding Motif", J. Biol. Chem. 266:14188-92 (1991).
Carr et al., "Identification of Sperm-specific Proteins That Interact with A-kinase Anchoring Proteins in a Manner Similar to the Type II Regulatory Subunit of PKA" J. Biol. Chem. 276(20):17332-17338 (2001).
Carrero et al., "Lymphocytes are detrimental during the early innate immune response against Listeria monocytogenes" J. Exp. Med. 203(4):933-940 (2006).
Chang et al., "The Dock and Lock Method: A Novel Platform Technology for Building Multivalent, Multifunctional Structures of Defined Composition with Retained Bioactivity" Clin. Cancer Res. Sep. 15, 2007;13(18 Suppl), pp. 5586-5591.
Chmura et al., "Antibodies with infinite affinity" Proc. Natl. Acad. Sci. USA 98(15):8480-8484 (2001).
Colledge et al., "AKAPs: from structure to function", Trends Cell Biol. 6:216-21 (1999).
Corbin et al., "Regulation of Adenosine 3',5'-Monophosphate-dependent Protein Kinase", J. Biol. Chem. 248:1813-21 (1973).
Dhalluin et al., "Structural and Biophysical Characterization of the 40 kDa PEG-Interferon-α2a and Its Individual Positional Isomers" Bioconjugate Chem. 2005;16:504-517.
Dodart et al., "Immunotherapy for Alzheimer's Disease: will vaccination work?" Trends Mol. Med. 9(3):85-87 (2003).
Doherty et al., "Site-Specific PEGylation of Engineered Cysteine Analogues of Recombinant Human Granulocyte-Macrophage Colony-Stimulating Factor", Bioconjugate Chem. 2005;16:1291-1298.
Ferrantini et al., "IFN-α1 Gene Expression into a Metastatic Murine Adenocarcinoma (TS/A) Results in CD8+ T Cell-Mediated Tumor Rejection and Development of Antitumor Immunity" J. Immunol. 153:4604-15 (1994).
Ferrantini et al., "Interferon-α and cancer: Mechanisms of action and new perspectives of clinical use" Biochimie 89: 884-893 (2007).

(56) References Cited

OTHER PUBLICATIONS

Gillies et al., "High-level expression of chimeric antibodies using adapted cDNA variable region cassettes", J. Immunol. Methods 125 (1989) 191-202.
Glennie et al., "Mechanisms of killing by anti-CD20 monoclonal antibodies" Mol. Immunol. 44:3823-3837 (2007).
Gold et al., "A Novel Bispecific, Trivalent Antibody Construct for Targeting Pancreatic Carcinoma", Cancer Res. 68:4819-26, 2008.
Gold et al., "Molecular Basis of AKAP Specificity for PKA Regulatory Subunits" Mol. Cell Nov. 3, 2006;24(3):383-95.
Goldenberg et al., "Multifunctional Antibodies by the Dock-and-Lock Method for Improved Cancer Imaging and Therapy by Pretargeting", J. Nucl. Med. 49:158-63, 2008.
Goldenberg et al., "Properties and structure-function relationships of veltuzumab (hA20), a humanized anti-CD20 monoclonal antibody" Blood 113:1062-70 (2009).
Goodson et al., "Site-Directed PEGylation of Recombinant Interleukin-2 at its Glycosylation Site", Nat. Biotechnology Apr. 1990;8(4):343-6.
Grace et al., "Site of Pegylation and Polyethylene Glycol Molecule Size Attenuate Interferon-60 Antiviral and Antiproliferative Activities through the JAK/STAT Signaling Pathway" J. Biol. Chem. 2005;280(8):6327-6336.
Grimley et al., "Prolonged STAT1 Activation Related to the Growth Arrest of Malignant Lymphoma Cells by Interferon-α" Blood 91(8):3017-27 (1998).
Gutterman et al., "Leukocyte Interferon-Induced Tumor Regression in Human Metastatic Breast Cancer, Multiple Myeloma, and Malignant Lymphoma" Ann. Intern. Med. 93(3):399-406 (1980).
Gutterman et al., "Cytokine therapeutics: Lessons from interferon α" Proc. Natl. Acad. Sci. USA 91:1198-205 (1994).
Harris et al., "Effect of pegylation on pharmaceuticals" Nat. Rev. Drug. Discov. 2:214-221 (2003).
Hausken et al. "Mutational Analysis of the A-Kinase Anchoring Protein (AKAP)-binding Site on RII", J. Biol. Chem. 271:29016-22 (1996).
Hodneland et al., "Selective immobilization of proteins to self-assembled monolayers presenting active site-directed capture ligands", Proc. Natl. Acd. Sci. USA 2002; 99:5048-5052.
Huang et al., "Targeting IFN-α to B Cell Lymphoma by a Tumor-Specific Antibody Elicits Potent Antitumor Activities" J. Immunol. 179:6881-88 (2007).
Hundsrucker et al., "High-affinity AKAP7δ-protein kinase A interaction yields novel protein kinase A-anchoring disruptor peptides" Biochem. J. (2006) 396, 297-306.
Kimby et al., "Long-term molecular remissions in patients with indolent lymphoma treated with rituximab as a single agent or in combination with interferon alpha-2a: A randomized phase II study from the Nordic Lymphoma Group" Leuk. Lymphoma 49(1):102-112 (2008).
Kinderman et al., "A Dynamic Mechanism for AKAP Binding to RII Isoforms of cAMP-Dependent Protein Kinase" Mol. Cell 24(3):397-408 (2006).
Kinstler et al., "Characterization and Stability of N-terminally PEGylated rhG-CSF" Pharm. Res. 1996;13(7):996-1002.
Kramer et al., "Cell and virus sensitivity studies with recombinant human alpha interferons" J. Interferon. Res. 3(4):425-35 (1983).
Le Bon et al., "Type I Interferons Potently Enhance Humoral Immunity and Can Promote Isotype Switching by Stimulating Dendritic Cells In Vivo" Immunity 14:461-470 (2001).
Lee et al., "Solid-Phase PEGylation of Recombinant Interferon α-2a for Site-Specific Modification: Process Performance, Characterization, and in Vitro Bioactivity" Bioconjugate Chem. 2007; 18:1728-34.
Lohmann et al., "High-affinity binding of the regulatory subunit (RII) of cAMP-dependent protein kinase to microtubule-associated and other cellular proteins", Proc. Natl. Acad. Sci. USA 81:6723-27 (1984).
Luft et al., "Type I IFNs Enhance the Terminal Differentiation of Dendritic Cells" J. Immunol. 161:1947-1953 (1998).
Mason, Anthony J., "Functional Analysis of the Cysteine Residues of Activin A", Mol. Endocrinol. 8:325-32, 1994.
Matarrese et al., "Type I Interferon Gene Transfer Sensitizes Melanoma Cells to Apoptosis via a Target Activity on Mitochondrial Function" Am. J. Pathol. 2002, 160(4):1507-1520.
Burton et al., "Expression of CD74 by AML blasts and cell lines, and enhanced in vitro cytotoxicity of anti-CD74 antibody after interferon-gamma (IFN-γ) treatment", 2010 ASCO Annual Meeting, J. Clin. Oncol. 28:15s, 2010 (Suppl., Abstr 6576).
Foran et al., "Treatment of mantle-cell lymphoma with Rituximab (chimeric monoclonal anti-CD20 antibody): analysis of factors associated with response", Ann Oncol. 2000;11 Suppl 1:117-21.
Gupta et al., "Multiple signaling pathways induced by hexavalent, monospecific, anti-CD20 and hexavalent, bispecific, anti-CD20/CD22 humanized antibodies correlate with enhanced toxicity to B-cell lymphomas and leukemias", Blood. Oct. 28, 2010;116(17):3258-67.
Henry et al., "A prostate-specific membrane antigen-targeted monoclonal antibody-chemotherapeutic conjugate designed for the treatment of prostate cancer", Cancer Res. Nov. 1, 2004;64(21):7995-8001.
Jefferis et al., "Human immunoglobulin allotypes: possible implications for immunogenicity", MAbs 1(4):1-7 (2009).
Jubala et al., "CD20 expression in normal canine B cells and in canine non-Hodgkin lymphoma", Vet Pathol. Jul. 2005;42(4):468-76.
Magdelaine-Beuzelin et al., "IgG1 heavy chain-coding gene polymorphism (G1m allotypes) and development of antibodies-to-infliximab", Pharmacogenet Genomics. May 2009;19(5):383-7.
Mecchia et al., "Type I consensus interferon (CIFN) gene transfer into human melanoma cells up-regulates p53 and enhances cisplatin-induced apoptosis: implications for new therapeutic strategies with IFN-alpha", Gene Ther. (2000) 7,167-179.
Meissner et al., "Citta versus IFN-gamma induced MHC class II expression in head and neck cancer cells", Arch Dermatol Res. Feb. 2009;301(2):189-93.
Newlon et al., "A Novel Mechanism of PKA Anchoring Revealed by Solution Structures of Anchoring Complexes", EMBO J. 2001; 20:1651-1662.
Newlon et al., "The molecular basis for protein kinase A anchoring revealed by solution NMR", Nature Struct. Biol. 1999; 3:222-227.
Ngo et al., "Computational Complexity, Protein Structure Prediction, and the Levinthal Paradox", The Protein Folding Problem and Tertiary Structure Prediction, Ch. 14, pp. 492-495, (Mertz & Le Grand, Eds.), Birkhauser Boston, 1994.
Osborn et al., "Pharmacokinetic and Pharmacodynamic Studies of a Human Serum Albumin-Interferon-α Fusion Protein in Cynomolgus Monkeys", J. Pharmacol. Exp. Ther. 303(2):540-548 (2002).
Oyen et al., "Human testis cDNA for the regulatory subunit RIIα of cAMP-dependent protein kinase encodes an alternate amino-terminal region", FEBS Letters 246:57-64, 1989.
Ozzello et al., "Conjugation of interferon alpha to a humanized monoclonal antibody (HuBrE-3vI) enhances the selective localization and antitumor effects of interferon in breast cancer xenografts", Breast Cancer Res. Treat. 48: 135-147 (1998).
Paquette et al., "Interferon-α and granulocyte-macrophage colony-stimulating factor differentiate peripheral blood monocytes into potent antigen-presenting cells", J. Leukoc. Biol. 64:358-367; 1998.
Pelham et al., "Interferon-α conjugation to human osteogenic sarcoma monoclonal antibody 791T/36", Cancer Immunol. Immunother. 1983;15(3):210-216.
Pepinsky et al., "Improved Pharmacokinetic Properties of a Polyethylene Glycol-Modified Form of Interferon-β-1a with Preserved in Vitro Bioactivity", Pharmacol. Exp. Ther. 2001; 297(3):1059-1066.
Pilling et al., "Interferon-β mediates stromal cell rescue of T cells from apoptosis", Eur. J. Immunol. 29:1041-1050 (1999).
Rabjohn et al., "Molecular Cloning and Epitope Analysis of the Peanut Allergen Ara h 3", J. Clinical Investigation 103(4):535-542 (1999).
Raefsky et al., "Studies of Interferon as a regulator of hematopoietic cells proliferation", J. Immunol. 135(4):2507-2512 (1985).
Riemer et al., "Matching of trastuzumab (Herceptin) epitope mimics onto the surface of Her-2/neu—a new method of epitope definition", Mol Immunol. May 2005;42(9):1121-4.

(56) References Cited

OTHER PUBLICATIONS

Rose et al., "Structural basis of dimerization, coactivator recognition and MODY3 mutations in HNF-1α", Nature Struct. Biol. 2000; 7:744-748.
Rosendahl et al., "A Long-Acting, Highly Potent Interferon α-2 Conjugate Created Using Site-Specific PEGylation", Bioconjugate Chem. 2005;16:200-207.
Rossi et al., "Novel Designs of Multivalent Anti-CD20 Humanized Antibodies as Improved Lymphoma Therapeutics", Cancer Res. 68:8384-92, 2008.
Rossi et al., "Stably tethered multifunctional structures of defined composition made by the dock and lock method for use in cancer targeting" Proc. Natl. Acad. Sci. Epub Apr. 24, 2006, vol. 103, No. 18, pp. 6841-6846.
Rustandi et al., "The Ca2+-Dependent Interaction of S100B(ββ)with a Peptide Derived from p53", Biochemistry 1998; 37: 1951-1960.
Sabaawy et al., "Enhancement of 5-fluorouracil cytotoxicity on human colon cancer cells by retrovirus-mediated interferon-α gene transfer", Int. J. Oncol. Jun. 1999; 14(6):1143-51.
Salles et al., "Rituximab combined with chemotherapy and interferon in follicular lymphoma patients: results of the GELA-GOELAMS FL2000 study", Blood 2008; 112:4824-4831.
Santini et al., "Type I Interferon as a Powerful Adjuvant for Monocyte-derived Dendritic Cell Development and Activity In Vivo and in Hu-PBL-SCID Mice", J. Exp. Med. 191(10):1777-1788 (2000).
Scott et al., "Type II Regulatory Subunit Dimerization Determines the Subcellular Localization of the cAMP-dependent Protein Kinase", J. Biol. Chem. 265:21561-66 (1990).
Scott et al., "Cyclic nucleotide-dependent protein kinases", Pharmacol. Ther. 1991;50(1):123-45.
Seffernick et al., "Melamine Deaminase and Atrazine Chlorohydrolase: 98 Percent Identical but Functionally Different", J. Bacteriol. 183(8):2405-2410 (2001).
Sharkey et al., "Improved Therapeutic Results by Pretargeted Radioimmunotherapy of Non-Hodgkin's Lymphoma with a New Recombinant, Trivalent, Anti-CD20, Bispecific Antibody", Cancer Res. 68:5282-90, 2008.
Sharkey et al., "Metastatic Human Colonic Carcinoma: Molecular Imaging with Pretargeted SPECT and PET in a Mouse Model", Radiology 246:497-507, 2008.
Sidky et al., "Inhibition of Angiogenesis by Interferons: Effects on Tumor- and Lymphocyte-induced Vascular Responses", Cancer Res. 47:5155-5161, Oct. 1, 1987.
Stein et al., "Characterization of a New Humanized Anti-CD20 Monoclonal Antibody, IMMU-106, and Its Use in Combination with the Humanized Anti-CD22 Antibody, Epratuzumab, for the Therapy of Non-Hodgkin's Lymphoma", Clin. Cancer Res. vol. 10, 2868-2878, Apr. 15, 2004.
Stein et al., "Characterization of a humanized IgG4 anti—HLA-DR monoclonal antibody that lacks effector cell functions but retains direct antilymphoma activity and increases the potency of rituximab", Blood 2006;108:2736-2744.
Stokka et al., "Characterization of A-kinase-anchoring disruption using a solution-based assay", Biochem. J. (2006) 400, 493-499.
Stryer et al., "Levels of Structure in Protein Architecture", Biochemistry, 3rd Ed., pp. 31-33, W.H. Freeman & Co., New York, 1988.
Takaoka et al., "Integration of interferon-60 /β signalling to p53 responses in tumour suppression and antiviral defence", Nature Jul. 31, 2003;424(6948):516-23.
Taylor, S., "cAMP-dependent Protein Kinase", J. Biol. Chem. 1989;264(15):8443-8446.
Tol et al., "Chemotherapy, bevacizumab, and cetuximab in metastatic colorectal cancer", N Engl J Med. Feb. 5, 2009;360(6):563-72.
Walsh et al., "An Adenosine 3', 5'-Monophosphate-dependant Protein Kinase from Rabbit Skeletal Muscle", J. Biol. Chem. 243(13):3763-3774 (1968).
Weck et al., "Comparison of the Antiviral Activities of Various Cloned Human Interferon-α Subtypes in Mammalian Cell Cultures", J. Gen. Virol. (1981), 57, 233-237.

Winkler et al., "Changing the Antigen Binding Specificity by Single Point Mutations of an Anti-p24 (HIV-1) Antibody", J. Immunol. 165:4505-14, 2000.
Witkowski et al., "Conversion of a β-Ketoacyl Synthase to a Malonyl Decarboxylase by Replacement of the Active-Site Site Cysteine with Glutamine", Biochemistry 38(36):11643-50 (1999).
Wong et al., "AKAP Signalling Complexes: Focal Points in Space and Time", Nat. Rev. Mol. Cell Biol. 12:959-70 (2004).
Yu et al., "Interaction between bevacizumab and murine VEGF-A: a reassessment", Invest Ophthalmol Vis Sci. Feb. 2008;49(2):522-7.
Zhu et al., "Inhibition of tumor growth and metastasis by targeting tumor-associated angiogenesis with antagonists to the receptors of vascular endothelial growth factor", Invest. New Drugs 17:195-212, 1999.
Koning et al., "Selective transfer of a lipophilic prodrug of 5-fluorodeoxyuridine from immunoliposomes to colon cancer cells", Biochim. Biophys. Acta. 1420(1-2):153-67 (1999).
Kratz et al., "Drug-polymer conjugates containing acid-cleavable bonds", Crit. Rev. Ther. Drug Carrier Syst. 16(3):245-88 (1999).
Kreitman et al., "Pseudomonas exotoxin-based immunotoxins containing the antibody LL2 or LL2-Fab' induce regression of subcutaneous human B-cell lymphoma in mice", Cancer Res. 53(4):819-25 (1993).
Larrick et al., "PCR Amplification of Antibody Genes", Methods: A Companion to methods in Enzymology 2 (2):106-110 (1991).
Lazar et al.,"Transforming growth factor alpha: mutation of aspartic acid 47 and leucine 48 results in different biological activities", Mol. Cell. Biol. 8(3):1247-1252 (1988).
Leonard et al., "Epratuzumab, a new Anti-CD22, humanized, monoclonal antibody for the therapy of non-Hodgkin's lymphoma (NHL): phase I/II trial results", Blood 94:92a-93a, Abstract # 404, (1999).
Leung et al., "Chimerization of LL2, a Rapidly Internalizing Antibody Specific for B Cell Lymphoma", Hybridoma 13(6):469-476 (1994).
Leung et al., "Engineering a Unique Glycosylation Site for Site-Specific Conjugation of Haptens to Antibody Fragments", J. Immunol. 154:5919-5926 (1995).
Leung et al., "Construction and characterization of a humanized, internalizing, b-cell (CD22)-specific, leukemia/lymphma antibody, LL2", Mol. Immunol. 32(17/18):1413-1427 (1995).
Levine et al., "IgM antibody-related polyneuropathies: B-cell depletion chemotherapy using Rituximab", Neurology 52(8):1701-4 (1999).
Li et al., "The epitope specificity and tissue reactivity of four murine monoclonal anti-CD22 antibodies", Cell Immunol. 118(1):85-99 (1989).
Lonberg et al., "Antigen-specific human antibodies from mice comprising four distinct genetic modifications", Nature 368:856-9 (1994).
Longo, D. L., "Immunotherapy for non-Hodgkin's lymphoma", Curr. Opin. Oncol. 8(5):353-9 (1996).
Lopez De Menezes et al., "In vitro and in vivo targeting of immunoliposomal doxorubicin to human B-cell lymphoma", Cancer Res. 58(15):3320-30 (1998).
Lopez De Menezes et al., "Cellular Trafficking and Cytotoxicity of Anti-Cd19-Targeted Liposomal Doxorubicin in B Lymphoma Cells", J. Liposome Research 1999, vol. 9, No. 2 , pp. 199-228.
Lundberg, B., "Preparation of drug-carrier emulsions stabilized with phosphatidylcholine-surfactant mixtures", J. Pharm. Sci. 83(1):72-5 (1994).
Lundberg, B., "The solubilization of lipophilic derivatives of podophyllotoxins in sub-micron sized lipid emulsions and their cytotoxic activity against cancer cells in culture", Int. J. Pharm. 109:73-81 (1994).
Lundberg et al., "Submicron lipid emulsions containing amphipathic polyethylene glycol for use as drug-carriers with prolonged circulation time", Int. J. Pharm. 134:119-127 (1996).
Lundberg et al., A submicron lipid emulsion coated with amphipathic polyethylene glycol for parenteral administration of paclitaxel (Taxol), J Pharm Pharmacol. 49:16-21 (1997).

(56) References Cited

OTHER PUBLICATIONS

Lundberg et al., "Biologically active camptothecin derivatives for incorporation into liposome bilayers and lipid emulsions", Anticancer Drug Des. 13(5):453-61 (1998).
Lundberg et al., "Conjugation of an anti-B-cell lymphoma monoclonal antibody, LL2, to long-circulating drug-carrier lipid emulsions", J. Pharm. Pharmacol. 51(10):1099-105 (1999).
Lundberg et al., "Specific binding of sterically stabilized anti-B-cell immunoliposomes and cytotoxicity of entrapped doxorubicin", Int. J. Pharm. 205(1-2):101-8 (2000).
Lundberg et al., "Cellular association and cytotoxicity of anti-CD74-targeted lipid drug-carriers in B lymphoma cells", J. Control. Release 94(1):155-61 (2004).
Mack et al., "A small bispecific antibody construct expressed as a functional single-chain molecule with high tumor cell cytotoxicity", Proc. Natl. Acad. Sci. USA 92:7021-7025 (1995).
Maloney et al., "Phase I clinical trial using escalating single-dose infusion of chimeric anti-CD20 monoclonal antibody (IDEC-C2B8) in patients with recurrent B-cell lymphoma", Blood 84(8):2457-66 (1994).
Maranhao et al., "Association of carmustine with a lipid emulsion: in vitro, in vivo and preliminary studies in cancer patients", Cancer Chemother. Pharmacol. 49(6):487-98 (2002).
McCafferty et al., "Phage antibodies: filamentous phage displaying antibody variable domains", Nature 348:552-553 (1990).
Mendez et al., "Functional transplant of megabase human immunoglobulin loci recapitulates human antibody response in mice", Nature Genetics 15:146-156 (1997).
Mew et al., "Photoimmunotherapy: treatment of animal tumors with tumor-specific monoclonal antibodyhematoporphyrin conjugates", J. Immunol. 130(3):1473-7 (1983).
Mew et al., "Ability of Specific Monoclonal Antibodies and Conventional Antisera Conjugated to Hematoporphyrin to Label and Kill Selected Cell Lines Subsequent to Light Activation", Cancer Res. 45:4380-4386 (1985).
Moase et al., "Anti-MUC-1 immunoliposomal doxorubicin in the treatment of murine models of metastatic breast cancer", Biochim. Biophys. Acta. 1510(1-2):43-55 (2001).
Moller et al., "CD74", J. Biol. Regul. Homeost. Agents 14(4):299-301 (2000).
Mosmann, T., "Rapid colorimetric assay for cellular growth and survival: application to proliferation and cytotoxicity assays", J. Immunol. Methods 65(1-2):55-63 (1983).
Nagel et al., "HLXB9 activates IL6 in Hodgkin lymphoma cell lines and is regulated by PI3K signalling involving E2F3", Leukemia 19(5):841-6 (2005).
Nakagawa et al., "Clinical trial of intrathecal administration of 5-fluoro-2'-deoxyuridine for treatment of meningeal dissemination of malignant tumors", J. Neurooncol. 45(2):175-83 (1999).
Nisonoff et al., "Separation of Univalent Fragments from the Bivalent Rabbit Antibody Molecule by Reduction of Disulfide Bonds", Arch. Biochem. Biophys. 89:230-244 (1960).
Ochakovskaya et al., Therapy of Disseminated B-Cell Lymphoma Xenografts in Severe Combined Immunodeficient Mice with an Anti-CD74 Antibody Conjugated with (111)Indium, (67)Gallium, or (90)Yttrium, Clin. Cancer Res. 7(6):1505-1510 (2001).
Orlandi et al., "Cloning immunoglobulin variable domains for expression by the polymerase chain reaction", Proc. Natl. Acad. Sci. USA 86:3833-3837 (1989).
Oseroff et al., "Antibody-targeted photolysis: Selective photodestruction of human T-cell leukemia cells using monoclonal antibody-chlorin e6 conjugates", Proc. Natl. Acad. Sci. USA 83:8744-8748 (1986).
Oseroff et al., "Strategies for selective cancer photochemotherapy: antibody-targeted and selective carcinoma cell photolysis", Photochem. Potobiol. 46(1):83-96 (1987).
Oster et al., "Erythropoietin for the Treatment of Anemia of Malignancy Associated with Neoplastic Bone Marrow Infiltration", J. Clin. Oncol. 8(6):956-962 (1990).
Pastan et al., "Immunotoxins", Cell 47:641-648 (1986).
Patti et al., "High-dose cyclophosphamide, etoposide and BCNU (CVB) with autologous stem cell rescue in malignant lymphomas", Eur. J. Haematol. 51(1):18-24 (1993).
Pawlak-Byczkowska et al., "Two new monoclonal antibodies, EPB-1 and EPB-2, reactive with human lymphoma", Cancer Res. 49(16):4568-77 (1989).
Pelegrin et al., "Antibody-Fluorescein Conjugates for Photoimmunodiagnosis of Human Colon Carcinoma in Nude Mice", Cancer 67:2529-2537 (1991).
Perkins et al., "Novel therapeutic nano-particles (lipocores): trapping poorly water soluble compounds", Int. J. Pharm. 200(1):27-39 (2000).
Pirker et al., "Characterization of immunotoxins active against ovarian cancer cell lines", J. Clin. Invest. 76(3):1261-7 (1985).
Porter et al., "The Hydrolysis of Rabbit γ-Globulin and Antibodies with Crystalline Papain", Biochem. J. 73(1):119-127 (1959).
Press et al., "Radiolabeled-antibody therapy of B-cell lymphoma with autologous bone marrow support", N. Engl. J. Med. 329(17):1219-24 (1993).
Press et al., "Phase II trial of 131I-B1 (anti-CD20) antibody therapy with autologous stem cell transplantation for relapsed B cell lymphomas", Lancet 346:336-40 (1995).
Martin et al., "Phase I study of the anti-CD74 monoclonal antibody milatuzumab (hLL1) in patients with previously treated B-cell lymphomas", Leuk Lymphoma. May 2015 12:1-6.

* cited by examiner

COMBINATION THERAPY WITH ANTI-CD74 AND ANTI-CD20 ANTIBODIES PROVIDES ENHANCED TOXICITY TO B-CELL DISEASES

CROSS-REFERENCE TO RELATED APPLICATIONS

This application is a divisional of U.S. patent application Ser. No. 13/904,534, filed May 29, 2014, which was a divisional of U.S. patent application Ser. No. 13/209,954, filed Aug. 15, 2011 (now U.S. Pat. No. 8,475,794), which claimed the benefit under 35 U.S.C. 119(e) of provisional U.S. Patent Application Ser. Nos. 61/374,751, filed Aug. 18, 2010; 61/374,772, filed Aug. 18, 2010; and 61/508,871, filed Jul. 18, 2011. Ser. No. 13/904,534 was a continuation-in-part of U.S. patent application Ser. No. 13/086,786, filed Apr. 14, 2011; Ser. No. 13/036,820, filed Feb. 28, 2011; Ser. No. 13/021,302, filed Feb. 4, 2011, (which was a divisional of U.S. Pat. No. 7,906,121; which was a divisional of U.S. Pat. No. 7,534,866); Ser. No. 13/012,977, filed Jan. 25, 2011, (which was a divisional of U.S. Pat. No. 7,906,118); Ser. No. 13/010,993, filed Jan. 21, 2011, (which was a divisional of U.S. Pat. No. 7,901,680); Ser. No. 13/004,349, filed Jan. 11, 2011; Ser. No. 12/968,936, filed Dec. 15, 2010, (which was a divisional of U.S. Pat. No. 7,871,622; which was a divisional of U.S. Pat. No. 7,521,056); Ser. No. 12/964,021, filed Dec. 9, 2010; Ser. No. 12/949,536, filed Nov. 18, 2010, (which was a divisional of U.S. Pat. No. 7,858,070; which was a divisional of U.S. Pat. No. 7,527,787); Ser. No. 12/915,515, filed Oct. 29, 2010; Ser. No. 12/871,345, filed Aug. 30, 2010; Ser. No. 12/869,823, filed Aug. 27, 2010; Ser. No. 12/754,740, filed Apr. 6, 2010; Ser. No. 12/752,649, filed Apr. 1, 2010; Ser. No. 12/731,781, filed Mar. 25, 2010; Ser. No. 13/150,613, filed Jun. 1, 2011, (which was a divisional of U.S. Pat. No. 7,981,398; which was a divisional of U.S. Pat. No. 7,666,400); and Ser. No. 12/468,589, filed May 19, 2009, (which was a divisional of U.S. Pat. No. 7,550,143). Those applications claimed the benefit under 35 U.S.C. 119(e) of provisional U.S. Patent Applications 61/414,592, filed Nov. 17, 2010; 61/378,059, filed Aug. 30, 2010; 61/374,449, filed Aug. 17, 2010; 61/324,111, filed Apr. 14, 2010; 61/323,001, filed Apr. 12, 2010; 61/323,960, filed Apr. 14, 2010; 61/316,996, filed Mar. 24, 2010; 61/302,682, filed Feb. 9, 2010; 61/293,846, filed Jan. 11, 2010; 61/267,877, filed Dec. 9, 2009; 61/266,305, filed Dec. 3, 2009; 61/258,729, filed Nov. 6, 2009; 61/258,369, filed Nov. 5, 2009; 61/238,424, filed Aug. 31, 2009; 61/238,473, filed Aug. 31, 2009; 61/168,668, filed Apr. 13, 2009; 61/168,657, filed Apr. 13, 2009; 61/168,290, filed Apr. 10, 2009; 61/163,666, filed Mar. 26, 2009; 61/119,542, filed Dec. 3, 2008; 61/104,916, filed Oct. 13, 2008; 61/090,487, filed Aug. 20, 2008; 61/043,932, filed Apr. 10, 2008; 60/864,530, filed Nov. 6, 2006; 60/782,332, filed Mar. 14, 2006; 60/751,196, filed Dec. 16, 2005; 60/728,292, filed Oct. 19, 2005; 60/668,603, filed Apr. 6, 2005.

SEQUENCE LISTING

The instant application contains a Sequence Listing which has been submitted in ASCII format via EFS-Web and is hereby incorporated by reference in its entirety. Said ASCII copy, created on Aug. 15, 2011, is named IMM331US.txt and is 64,529 bytes in size.

FIELD OF THE INVENTION

The present invention concerns compositions and methods of use of combination therapy using at least one anti-CD74 antibody or antigen-binding fragment thereof and at least one other therapeutic agent. In preferred embodiments, the other therapeutic agent may be another antibody or fragment thereof against the same or a different target antigen, including but not limited to CD19, CD20, CD21, CD22, CD23, CD37, CD40, CD40L, CD52, CD80, IL-6, CXCR4 or HLA-DR. In other embodiments, the other therapeutic agent may be an immunomodulator, a cytotoxic agent, a drug, a toxin, an anti-angiogenic agent, a proapoptotic agent or a radionuclide. In more preferred embodiments, the anti-CD74 antibody or fragment may be administered in combination with another antibody or therapeutic agent as part of a dock-and-lock (DNL) complex, as described in detail below. Alternatively, the anti-CD74 and other therapeutic agent may be administered together or separately, with the other therapeutic agent administered before, concurrently with or after the anti-CD74 antibody. In most preferred embodiments, the combination of anti-CD74 antibody and second antibody or other therapeutic agent is significantly more efficacious for treating a disease than either agent administered alone or the sum of effects of the two agents administered separately. The combination may be highly effective for treating a disease in which CD74 is overexpressed in target cells, such as B cell lymphoma or leukemia (e.g., mantle cell lymphoma, multiple myeloma, Hodgkin's lymphoma, non-Hodgkin's lymphoma, diffuse large B cell lymphoma, Burkitt lymphoma, follicular lymphoma, acute lymphocytic leukemia, chronic lymphocytic leukemia, and hairy cell leukemia), solid tumors (e.g., glioblastoma, gastric cancer, bladder cancer, prostate cancer, thymic cancer, colorectal cancer, lung cancer, renal cancer, pancreatic cancer and breast cancer), autoimmune disease, immune dysfunction disease (e.g., graft-versus-host disease, organ transplant rejection), type-1 or type-2 diabetes.

BACKGROUND

To address the clinical concerns of immunogenicity and suboptimal pharmacokinetics, cancer therapy with monoclonal antibodies has evolved from murine to chimeric, humanized, and fully human constructs. Parallel to these improvements have been continuing efforts to develop more effective forms of antibodies, which to date include different antibody isotypes, single-chain antibody fragments with monomeric or multimeric binding moieties, specific mutations in the Fc region to modulate effector function or circulating half-life, and bispecific antibodies of numerous designs that vary in valency, structure, and constituents (Chames et al., Br J Pharmacol 2009, 157:220-233).

Because signaling pathway redundancies can result in lack of response to a single antibody, diverse strategies to use combination therapy with antibodies that bind to different epitopes or different antigens on the same target cell have been proposed. Combinations such as anti-CD20 and anti-CD22 (Stein et al., Clin Cancer Res 2004, 10:2868-2878), anti-CD20 and anti-HLA-DR (Tobin et al., Leuk Lymphoma 2007, 48:944-956), anti-CD20 and anti-TRAIL-R1 (Maddipatla et al., Clin Cancer Res 2007, 13:4556-4564), anti-IGF-1R and anti-EGFR (Goetsche et al., Int J Cancer 2005, 113:316-328), anti-IGF-1R and anti-VEGF (Shang et al., Mol Cancer Ther 2008, 7:2599-2608), or trastuzumab and pertuzumab that target different regions of human EGFR2 (Nahta et al., Cancer Res 2004, 64:2343-2346) have been evaluated preclinically, showing enhanced or synergistic antitumor activity in vitro and in vivo.

The first clinical evidence of an apparent advantage of combining two antibodies against different cancer cell antigens involved the administration of rituximab (chimeric anti- CD20) and epratuzumab (humanized anti-CD22 antibody) in patients with non-Hodgkin lymphoma (NHL). The combination was found to enhance anti-lymphoma efficacy without a commensurate increase in toxicity, based on 3 independent clinical trials (Leonard et al., J Clin Oncol 2005, 23:5044-5051; Strauss et al., J Clin Oncol 2006, 24:3880-86; Leonard and Goldenberg, Oncogene 2007, 26:3704-13). Although these results are promising, a need exists in the field for more effective antibody-based combination therapies.

SUMMARY

The present invention concerns improved compositions and methods of use of combination therapy with at least one anti-CD74 antibody or fragment thereof and a second antibody or fragment thereof or other therapeutic agent. In preferred embodiments, the combination is a trivalent, tetravalent or hexavalent construct made by the dock-and-lock (DNL) technique (see, e.g., U.S. Pat. Nos. 7,521,056; 7,527,787; 7,534,866; 7,550,143; 7,666,400; 7,858,070; 7,871,622; 7,901,680; 7,906,118 and 7,906,121, the Examples section of each of which is incorporated herein by reference.) The DNL technique takes advantage of the specific, high-affinity binding interaction between a dimerization and docking domain (DDD) sequence from the regulatory subunit of human cAMP-dependent protein kinase (PKA), such as human PKA RIα, RIβ, RIIα or RIIβ, and an anchor domain (AD) sequence from any of a variety of AKAP proteins. The DDD and AD peptides may be attached to any protein, peptide or other molecule.

Because the DDD sequences spontaneously dimerize and bind to the AD sequence, the DNL technique allows the formation of complexes between any selected molecules that may be attached to DDD or AD sequences. Although the standard DNL complex comprises a trimer with two DDD-linked molecules attached to one AD-linked molecule, variations in complex structure allow the formation of dimers, trimers, tetramers, pentamers, hexamers and other multimers. In some embodiments, the DNL complex may comprise two or more antibodies, antibody fragments or fusion proteins which bind to the same antigenic determinant or to two or more different antigens. The DNL complex may also comprise one or more other effectors, such as a cytokine, toxin or PEG moiety.

In preferred embodiments, hexavalent DNL constructs comprise an IgG molecule covalently attached to two copies of an AD moiety, which binds to four Fab fragments, each covalently attached to a DDD moiety. The hexavalent DNL construct therefore comprises six Fab moieties attached to an Fc moiety. By formation of disulfide bonds between the AD and DDD subunits, the entire DNL complex is highly stable under in vivo conditions and each Fab moiety retains the binding specificity and affinity of the parent antibody. In alternative embodiments, the hexavalent DNL construct may comprise 6 anti-CD74 Fabs; 4 anti-CD74 and 2 anti-CD20 Fabs; 2 anti-CD20 and 4 anti-CD74 Fabs; 4 anti-CD74 and 2 anti-CD22 Fabs; 2 anti-CD74 and 4 anti-CD22 Fabs; or other combinations of anti-CD74 with a second antibody, attached to an Fc moiety. The skilled artisan will realize that the constructs are not so limited, and DNL constructs comprising combinations of anti-CD74 antibody with antibodies against other known antigens, such as CD19, CD21, CD23, CD37, CD40, CD40L, CD52, CD80 IL-6, CXCR4, or HLA-DR may also be used. Previous studies have shown that such hexavalent constructs have distinct properties compared with their parental counterparts, including enhanced anti-lymphoma activity in vitro and comparable efficacy in vivo, despite showing shorter circulating half-lives (Rossi et al., Blood 2009, 113:6161-6171; Rossi et al., Cancer Res 2008, 68:8384-8392).

Although in preferred embodiments, the combination therapy with anti-CD74 antibody or fragment thereof and second antibody or other therapeutic agent may involve a DNL complex, in alternative embodiments the combination therapy may involve an anti-CD74 antibody or fragment thereof used in combination with a second antibody or fragment thereof or another therapeutic agent. The skilled artisan will be aware of many therapeutic agents of use for treatment of cancer, autoimmune disease or other B cell associated diseases that may be used in combination with an anti-CD74 antibody, such as the hLL1 antibody.

Many examples of anti-CD74 antibodies are known in the art and any such known antibody or fragment thereof may be utilized. In a preferred embodiment, the anti-CD74 antibody is an hLL1 antibody (also known as milatuzumab) that comprises the light chain complementarity-determining region (CDR) sequences CDR1 (RSSQSLVHRNGNTYLH; SEQ ID NO:1), CDR2 (TVSNRFS; SEQ ID NO:2), and CDR3 (SQSSHVPPT; SEQ ID NO:3) and the heavy chain variable region CDR sequences CDR1 (NYGVN; SEQ ID NO:4), CDR2 (WINPNTGEPTFDDDFKG; SEQ ID NO:5), and CDR3 (SRGKNEAWFAY; SEQ ID NO:6). A humanized LL1 (hLL1) anti-CD74 antibody suitable for use is disclosed in U.S. Pat. No. 7,312,318, incorporated herein by reference from Col. 35, line 1 through Col. 42, line 27 and FIG. 1 through FIG. 4. However, in alternative embodiments, other known and/or commercially available anti-CD74 antibodies may be utilized, such as LS-B1963, LS-B2594, LS-B1859, LS-B2598, LS-05525, LS-C44929, etc. (LSBio, Seattle, Wash.); LN2 (BIOLEGEND®, San Diego, Calif.); PIN.1, SPM523, LN3, CerCLIP.1 (ABCAM®, Cambridge, Mass.); At14/19, Bu45 (SEROTEC®, Raleigh, N.C.); 1D1 (ABNOVA®, Taipei City, Taiwan); 5-329 (EBIOSCIENCE®, San Diego, Calif.); and any other antagonistic anti-CD74 antibody known in the art.

The anti-CD74 antibody may be selected such that it competes with or blocks binding to CD74 of an LL1 antibody comprising the light chain CDR sequences CDR1 (RSSQSLVHRNGNTYLH; SEQ ID NO:1), CDR2 (TVSNRFS; SEQ ID NO:2), and CDR3 (SQSSHVPPT; SEQ ID NO:3) and the heavy chain variable region CDR sequences CDR1 (NYGVN; SEQ ID NO:4), CDR2 (WINPNTGEPTFDDDFKG; SEQ ID NO:5), and CDR3 (SRGKNEAWFAY; SEQ ID NO:6). Alternatively, the anti-CD74 antibody may bind to the same epitope of CD74 as an LL1 antibody.

Many examples of anti-CD20 antibodies are known in the art and any such known antibody or fragment thereof may be utilized. In a preferred embodiment, the anti-CD20 antibody is an hA20 antibody (also known as veltuzumab) that comprises the light chain complementarity-determining region (CDR) sequences CDR1 (RASSSVSYIH; SEQ ID NO:7), CDR2 (ATSNLAS; SEQ ID NO:8), and CDR3 (QQWTSNPPT; SEQ ID NO:9) and the heavy chain variable region CDR sequences CDR1 (SYNMH; SEQ ID NO:10), CDR2 (AIYPGNGDTSYNQKFKG; SEQ ID NO:11), and CDR3 (STYYGGDWYFDV; SEQ ID NO:12).

A humanized anti-CD20 antibody suitable for use is disclosed in U.S. Pat. No. 7,435,803, incorporated herein by reference from Col. 36, line 4 through Col. 46, line 52 and FIGS. 1, 2, 4, 5 and 7. However, in alternative embodiments, other known and/or commercially available anti-CD20 antibodies may be utilized, such as rituximab; ofatumumab; ibritumomab; tositumomab; ocrelizumab; GA101; BCX-301; DXL 625; L26, B-Ly1, MEM-97, LT20, 2H7, AT80, B-H20

(ABCAM®, Cambridge, Mass.); HI20a, HI47, 13.6E12 (ABBIOTEC®, San Diego, Calif.); 4f11, 5c11, 7d1 (ABD SEROTEC®, Raleigh, N.C.) and any other anti-CD20 antibody known in the art.

The anti-CD20 antibody may be selected such that it competes with or blocks binding to CD20 of an hA20 antibody comprising the light chain complementarity-determining region (CDR) sequences CDR1 (RASSSVSYIH; SEQ ID NO:7), CDR2 (ATSNLAS; SEQ ID NO:8), and CDR3 (QQWTSNPPT; SEQ ID NO:9) and the heavy chain variable region CDR sequences CDR1 (SYNMH; SEQ ID NO:10), CDR2 (AIYPGNGDTSYNQKFKG; SEQ ID NO:11), and CDR3 (STYYGGDWYFDV; SEQ ID NO:12). Alternatively, the anti-CD20 antibody may bind to the same epitope of CD20 as a hA20 antibody.

Many examples of anti-CD22 antibodies are also known in the art and any such known antibody or fragment thereof may be utilized. In a preferred embodiment, the anti-CD22 antibody is an hLL2 antibody (also known as epratuzumab) that comprises the light chain CDR sequences CDR1 (KSSQSVLYSANHKYLA, SEQ ID NO:13), CDR2 (WASTRES, SEQ ID NO:14), and CDR3 (HQYLSSWTF, SEQ ID NO:15) and the heavy chain CDR sequences CDR1 (SYWLH, SEQ ID NO:16), CDR2 (YINPRNDYTEYNQNFKD, SEQ ID NO:17), and CDR3 (RDITTFY, SEQ ID NO:18). A humanized LL2 anti-CD22 antibody suitable for use is disclosed in U.S. Pat. No. 6,187,287, incorporated herein by reference from Col. 11, line 40 through Col. 20, line 38 and FIGS. 1, 4 and 5. However, in alternative embodiments, other known and/or commercially available anti-CD22 antibodies may be utilized, such as 1F5; HIB22 (ABBIOTEC®, San Diego, Calif.); FPC1, LT22, MEM-1, RFB4 (ABCAM®, Cambridge, Mass.); bu59, fpc1, mc64-12 (ABD SEROTEC®, Raleigh, N.C.); IS7 (ABNOVA®, Taipei City, Taiwan) and any other anti-CD22 antibody known in the art.

The anti-CD22 antibody may be selected such that it competes with or blocks binding to CD22 of an LL2 antibody comprising the light chain CDR sequences CDR1 (KSSQSVLYSANHKYLA, SEQ ID NO:13), CDR2 (WASTRES, SEQ ID NO:14), and CDR3 (HQYLSSWTF, SEQ ID NO:15) and the heavy chain CDR sequences CDR1 (SYWLH, SEQ ID NO:16), CDR2 (YINPRNDYTEYNQNFKD, SEQ ID NO:17), and CDR3 (RDITTFY, SEQ ID NO:18). Alternatively, the anti-CD22 antibody may bind to the same epitope of CD22 as an LL2 antibody.

Many examples of anti-HLA-DR antibodies are also known in the art and any such known antibody or fragment thereof may be utilized. In a preferred embodiment, the anti-HLA-DR antibody is an hL243 antibody (also known as IMMU-114) that comprises the heavy chain CDR sequences CDR1 (NYGMN, SEQ ID NO:19), CDR2 (WINTYTREPTYADDFKG, SEQ ID NO:20), and CDR3 (DITAVVPTGFDY, SEQ ID NO:21) and the light chain CDR sequences CDR1 (RASENIYSNLA, SEQ ID NO:22), CDR2 (AASNLAD, SEQ ID NO:23), and CDR3 (QHFWTTPWA, SEQ ID NO:24). A humanized L243 anti-HLA-DR antibody suitable for use is disclosed in U.S. Pat. No. 7,612,180, incorporated herein by reference from Col. 46, line 45 through Col. 60, line 50 and FIG. 1 through FIG. 6. However, in alternative embodiments, other known and/or commercially available anti-HLA-DR antibodies may be utilized, such as 1D10 (apolizumab) (Kostelny et al., 2001, Int J Cancer 93:556-65); MS-GPC-1, MS-GPC-6, MS-GPC-8, MS-GPC-10, etc. (U.S. Pat. No. 7,521,047); Lym-1, TAL 8.1, 520B, ML11C11, SPM289, MEM-267, TAL 15.1, TAL 1B5, G-7, 4D12, Bra30 (Santa Cruz Biotechnology, Inc., Santa Cruz, Calif.); TAL 16.1, TU36, C120 (ABCAM®, Cambridge, Mass.); and any other anti-HLA-DR antibody known in the art.

The anti-HLA-DR antibody may be selected such that it competes with or blocks binding to HLA-DR of an L243 antibody comprising the heavy chain CDR sequences CDR1 (NYGMN, SEQ ID NO:19), CDR2 (WINTYTREPTYADDFKG, SEQ ID NO:20), and CDR3 (DITAVVPTGFDY, SEQ ID NO:21) and the light chain CDR sequences CDR1 (RASENIYSNLA, SEQ ID NO:22), CDR2 (AASNLAD, SEQ ID NO:23), and CDR3 (QHFWTTPWA, SEQ ID NO:24). Alternatively, the anti-HLA-DR antibody may bind to the same epitope of HLA-DR as an L243 antibody.

The anti-CD74 and/or other antibodies or fragments thereof may be used as naked antibodies, alone or in combination with one or more therapeutic agents. Alternatively, the antibodies or fragments may be utilized as immunoconjugates, attached to one or more therapeutic agents. (For methods of making immunoconjugates, see, e.g., U.S. Pat. Nos. 4,699,784; 4,824,659; 5,525,338; 5,677,427; 5,697,902; 5,716,595; 6,071,490; 6,187,284; 6,306,393; 6,548,275; 6,653,104; 6,962,702; 7,033,572; 7,147,856; and 7,259,240, the Examples section of each incorporated herein by reference.) Therapeutic agents may be selected from the group consisting of a radionuclide, a cytotoxin, a chemotherapeutic agent, a drug, a pro-drug, a toxin, an enzyme, an immunomodulator, an anti-angiogenic agent, a pro-apoptotic agent, a cytokine, a hormone, an oligonucleotide molecule (e.g., an antisense molecule or a gene) or a second antibody or fragment thereof.

The therapeutic agent may be selected from the group consisting of aplidin, azaribine, anastrozole, azacytidine, bleomycin, bortezomib, bryostatin-1, busulfan, calicheamycin, camptothecin, 10-hydroxycamptothecin, carmustine, celebrex, chlorambucil, cisplatin, irinotecan (CPT-11), SN-38, carboplatin, cladribine, cyclophosphamide, cytarabine, dacarbazine, docetaxel, dactinomycin, daunomycin glucuronide, daunorubicin, dexamethasone, diethylstilbestrol, doxorubicin, doxorubicin glucuronide, epirubicin glucuronide, ethinyl estradiol, estramustine, etoposide, etoposide glucuronide, etoposide phosphate, floxuridine (FUdR), 3',5'-O-dioleoyl-FudR (FUdR-dO), fludarabine, flutamide, fluorouracil, fluoxymesterone, gemcitabine, hydroxyprogesterone caproate, hydroxyurea, idarubicin, ifosfamide, L-asparaginase, leucovorin, lomustine, mechlorethamine, medroprogesterone acetate, megestrol acetate, melphalan, mercaptopurine, 6-mercaptopurine, methotrexate, mitoxantrone, mithramycin, mitomycin, mitotane, phenyl butyrate, prednisone, procarbazine, paclitaxel, pentostatin, PSI-341, semustine streptozocin, tamoxifen, taxanes, taxol, testosterone propionate, thalidomide, thioguanine, thiotepa, teniposide, topotecan, uracil mustard, velcade, vinblastine, vinorelbine, vincristine, ricin, abrin, ribonuclease, onconase, rapLR1, DNase I, Staphylococcal enterotoxin-A, pokeweed antiviral protein, gelonin, diphtheria toxin, *Pseudomonas* exotoxin, and *Pseudomonas* endotoxin.

The therapeutic agent may comprise a radionuclide selected from the group consisting of $^{103m}$Rh, $^{103}$Ru, $^{105}$Rh, $^{105}$Ru, $^{107}$Hg, $^{109}$Pd, $^{109}$Pt, $^{111}$Ag, $^{111}$In, $^{113m}$In, $^{119}$Sb, $^{11}$C, $^{121m}$Te, $^{122m}$Te, $^{125}$I, $^{125m}$Te, $^{126}$I, $^{131}$I, $^{133}$I, $^{13}$N, $^{142}$Pr, $^{143}$Pr, $^{149}$Pm, $^{152}$Dy, $^{153}$Sm, $^{15}$O, $^{161}$Ho, $^{161}$Tb, $^{165}$Tm, $^{166}$Dy, $^{166}$Ho, $^{167}$Tm, $^{168}$Tm, $^{169}$Er, $^{169}$Yb, $^{177}$Lu, $^{186}$Re, $^{188}$Re, $^{189m}$Os, $^{189}$Re, $^{192}$Ir, $^{194}$Ir, $^{197}$Pt, $^{198}$Au, $^{199}$Au, $^{201}$Tl, $^{203}$Hg, $^{211}$At, $^{211}$Bi, $^{211}$Pb, $^{212}$Bi, $^{212}$Pb, $^{213}$Bi, $^{215}$Po, $^{217}$At, $^{219}$Rn, $^{221}$Fr, $^{223}$Ra, $^{224}$Ac, $^{225}$Ac, $^{225}$Fm, $^{32}$P, $^{33}$P, $^{47}$Sc, $^{51}$Cr, $^{57}$Co, $^{58}$Co, $^{59}$Fe, $^{62}$Cu, $^{67}$Cu, $^{67}$Ga, $^{75}$Br, $^{75}$Se, $^{76}$Br, $^{77}$As, $^{77}$Br, $^{80m}$Br, $^{89}$Sr, $^{90}$Y, $^{95}$Ru, $^{97}$Ru, $^{99}$Mo and $^{99m}$Tc.

The therapeutic agent may be an enzyme selected from the group consisting of malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase.

An immunomodulator of use may be selected from the group consisting of a cytokine, a stem cell growth factor, a lymphotoxin, a hematopoietic factor, a colony stimulating factor (CSF), an interferon (IFN), erythropoietin, thrombopoietin and combinations thereof. Exemplary immunomodulators may include IL-1, IL-2, IL-3, IL-6, IL-10, IL-12, IL-18, IL-21, interferon-α, interferon-β, interferon-γ, G-CSF, GM-CSF, and mixtures thereof.

Exemplary anti-angiogenic agents may include angiostatin, endostatin, baculostatin, canstatin, maspin, anti-VEGF binding molecules, anti-placental growth factor binding molecules, or anti-vascular growth factor binding molecules.

In certain embodiments, the antibody or fragment may comprise one or more chelating moieties, such as NOTA, DOTA, DTPA, TETA, Tscg-Cys, or Tsca-Cys. In certain embodiments, the chelating moiety may form a complex with a therapeutic or diagnostic cation, such as Group II, Group III, Group IV, Group V, transition, lanthanide or actinide metal cations, Tc, Re, Bi, Cu, As, Ag, Au, At, or Pb.

In some embodiments, the antibody or fragment thereof may be a human, chimeric, or humanized antibody or fragment thereof. A humanized antibody or fragment thereof may comprise the complementarity-determining regions (CDRs) of a murine antibody and the constant and framework (FR) region sequences of a human antibody, which may be substituted with at least one amino acid from corresponding FRs of a murine antibody. A chimeric antibody or fragment thereof may include the light and heavy chain variable regions of a murine antibody, attached to human antibody constant regions. The antibody or fragment thereof may include human constant regions of IgG1, IgG2a, IgG3, or IgG4.

Exemplary known antibodies of use include, but are not limited to, hR1 (anti-IGF-1R), hPAM4 (anti-mucin), hA20 (anti-CD20), hA19 (anti-CD 19), hIMMU31 (anti-AFP), hLL1 (anti-CD74), hLL2 (anti-CD22), hMu-9 (anti-CSAp), hL243 (anti-HLA-DR), hMN-14 (anti-CEACAM5), hMN-15 (anti-CEACAM6), 29H2 (anti-CEACAM1, ABCAM®), hRS7 (anti-EGP-1—also known as Trop-2), elsilimomab (anti-IL-6), ALD518 (anti-IL-6), alemtuzumab (anti-CD52), daclizumab (anti-CD25), galiximab (anti-CD80), adalimumab (anti-TNF-α), infliximab (anti-TNF-α), lucatumumab (anti-CD40), ofatumumab (anti-CD20) and hMN-3 (anti-CEACAM6). Antibodies against antigens of use include anti-CXCR4 (e.g., U.S. Pat. Nos. 7,138,496; 7,682,611; 7,521,045; 7,892,546) and IL-6 (e.g., U.S. Pat. Nos. 7,919,095; 7,935,340; 7,955,597), the Examples section of each cited patent incorporated herein by reference.

Although in preferred embodiments that antibodies or fragments thereof incorporated into the hexavalent constructs bind to CD74 and/or CD20, in alternative embodiments antibodies or fragments may bind to one or more target antigens selected from the group consisting of carbonic anhydrase IX, alpha-fetoprotein, α-actinin-4, A3, antigen specific for A33 antibody, ART-4, B7, Ba 733, BAGE, BrE3-antigen, CA125, CAMEL, CAP-1, CASP-8/m, CCCL19, CCCL21, CD1, CD1a, CD2, CD3, CD4, CD5, CD8, CD11A, CD14, CD15, CD16, CD18, CD19, CD20, CD21, CD22, CD23, CD25, CD29, CD30, CD32b, CD33, CD37, CD38, CD40, CD40L, CD45, CD46, CD52, CD54, CD55, CD59, CD64, CD66a-e, CD67, CD70, CD74, CD79a, CD80, CD83, CD95, CD126, CD132, CD133, CD138, CD147, CD154, CDC27, CDK-4/m, CDKN2A, CXCR4, colon-specific antigen-p (CSAp), CEA (CEACAM5), CEACAM1, CEACAM6, c-met, DAM, EGFR, EGFRvIII, EGP-1, EGP-2, ELF2-M, Ep-CAM, Flt-1, Flt-3, folate receptor, G250 antigen, GAGE, gp100, GROB, HLA-DR, HM1.24, human chorionic gonadotropin (HCG) and its subunits, HER2/neu, HMGB-1, hypoxia inducible factor (HIF-1), HSP70-2M, HST-2, Ia, IGF-1R, IFN-γ, IFN-α, IFN-β, IL-2, IL-4R, IL-6R, IL-13R, IL-15R, IL-17R, IL-18R, IL-6, IL-8, IL-12, IL-15, IL-17, IL-18, IL-23, IL-25, insulin-like growth factor-1 (IGF-1), KC4-antigen, KS-1-antigen, KS1-4, Le-Y, LDR/FUT, macrophage migration inhibitory factor (MIF), MAGE, MAGE-3, MART-1, MART-2, NY-ESO-1, TRAG-3, mCRP, MCP-1, MIP-1A, MIP-1B, MIF, MUC1, MUC2, MUC3, MUC4, MUC5, MUM-1/2, MUM-3, NCA66, NCA95, NCA90, antigen specific for PAM-4 antibody, placental growth factor, p53, PLAGL2, prostatic acid phosphatase, PSA, PRAME, PSMA, PlGF, IGF, IGF-1R, IL-6, RS5, RANTES, T101, SAGE, S100, survivin, survivin-2B, TAC, TAG-72, tenascin, TRAIL receptors, TNF-α, Tn antigen, Thomson-Friedenreich antigens, tumor necrosis antigens, VEGFR, ED-B fibronectin, WT-1, 17-1A-antigen, complement factors C3, C3a, C3b, C5a, C5, an angiogenesis marker, bcl-2, bcl-6, Kras, cMET, an oncogene marker and an oncogene product (see, e.g., Sensi et al., Clin Cancer Res 2006, 12:5023-32; Parmiani et al., J Immunol 2007, 178:1975-79; Novellino et al. Cancer Immunol Immunother 2005, 54:187-207). Reports on tumor associated antigens include Mizukami et al., (2005, Nature Med. 11:992-97); Hatfield et al., (2005, Curr. Cancer Drug Targets 5:229-48); Vallbohmer et al. (2005, J. Clin. Oncol. 23:3536-44); and Ren et al. (2005, Ann. Surg. 242:55-63).

Also disclosed is a method for treating and/or diagnosing a disease or disorder that includes administering to a patient a therapeutic and/or diagnostic composition that includes any of the aforementioned antibodies or fragments thereof. Typically, the composition is administered to the patient intravenously, intramuscularly or subcutaneously at a dose of 20-5000 mg. In preferred embodiments, the disease or disorder is a solid tumor that overexpresses CD74, a B-cell lymphoma or leukemia, an immune dysregulation disease, an autoimmune disease, organ-graft rejection or graft-versus-host disease. Exemplary malignancies that may be treated using the claimed methods and compositions include, but are not limited to, glioblastoma, gastric cancer, bladder cancer, prostate cancer, thymic cancer, colorectal cancer, lung cancer, renal cancer, pancreatic cancer, breast cancer, indolent forms of B-cell lymphomas, aggressive forms of B-cell lymphomas, acute lymphocytic leukemia, chronic lymphocytic leukemia, Hodgkin's lymphoma, non-Hodgkin's lymphoma, mantle cell lymphoma, diffuse large B-cell lymphoma, follicular lymphoma, marginal zone lymphoma, Burkitt's lymphoma and multiple myeloma.

Exemplary autoimmune diseases include acute immune thrombocytopenia, chronic immune thrombocytopenia, dermatomyositis, Sydenham's chorea, myasthenia gravis, systemic lupus erythematosus, lupus nephritis, rheumatic fever, polyglandular syndromes, bullous pemphigoid, pemphigus vulgaris, diabetes mellitus (e.g., juvenile diabetes), Henoch-Schonlein purpura, post-streptococcal nephritis, erythema nodosum, Takayasu's arteritis, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitis obliterans, Sjogren's syndrome, primary biliary cirrhosis, Hashimoto's thyroiditis, thyrotoxicosis, scleroderma, chronic active hepatitis, polymyositis/dermatomyositis, polychondritis, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, psoriasis, or fibrosing alveolitis.

BRIEF DESCRIPTION OF THE DRAWINGS

The following Figures are provided to illustrate exemplary, but non-limiting, preferred embodiments of the invention.

DETAILED DESCRIPTION

Definitions

Figure 1A:
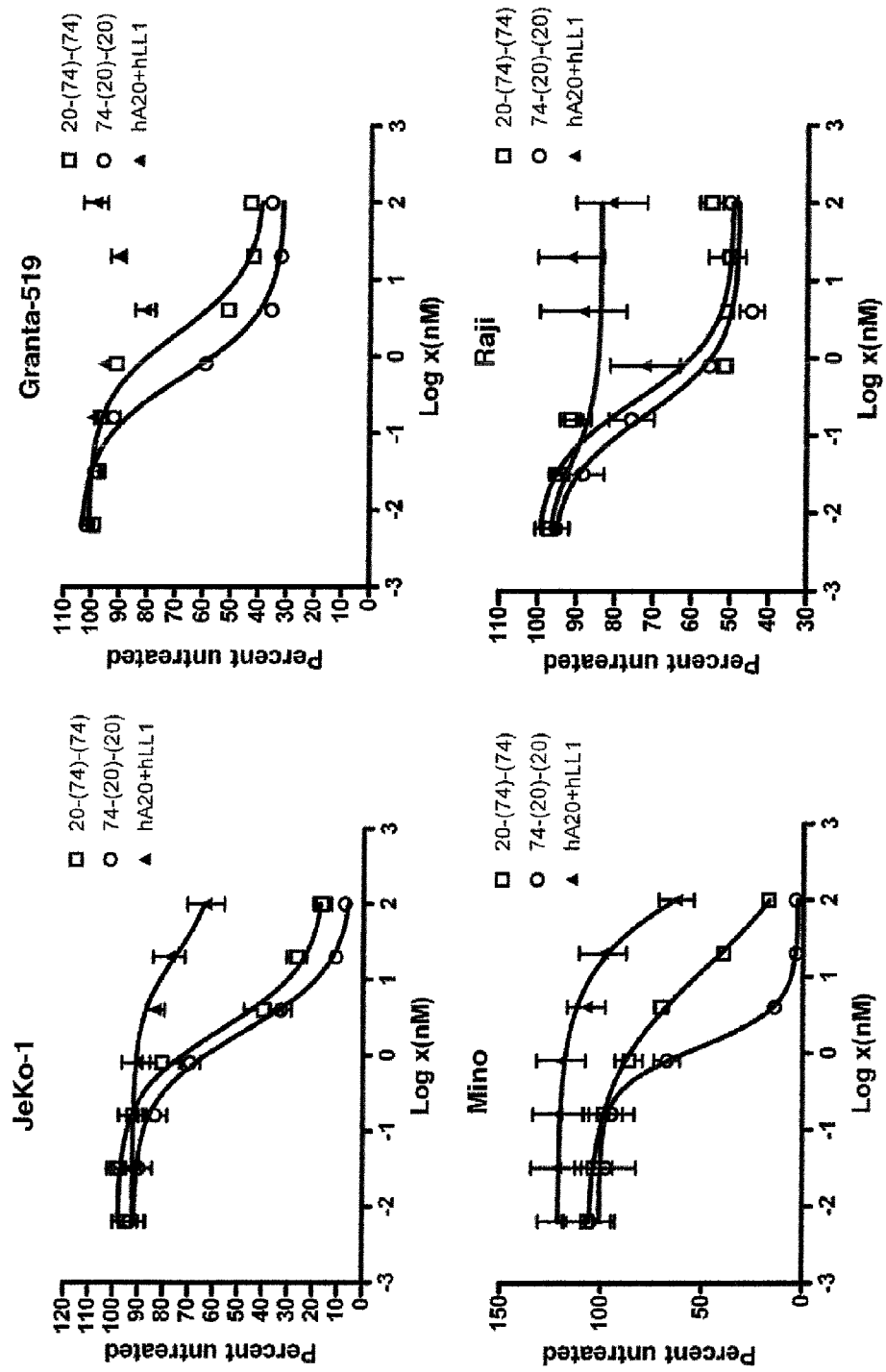
FIG. 1A. Direct cytotoxicity induced by anti-CD20/CD74 HexAbs in NHL cell lines as determined by the MTS assay. JeKo-1, Granta-519, Mino, and Raji ($5 \times 10^4$ cells per well in 48-well plate) treated with indicated concentrations of antibodies for 4 days.

As used herein, the terms "a", "an" and "the" may refer to either the singular or plural, unless the context otherwise makes clear that only the singular is meant.

An "antibody" refers to a full-length (i.e., naturally occurring or formed by normal immunoglobulin gene fragment recombinatorial processes) immunoglobulin molecule (e.g., an IgG antibody) or an immunologically active (i.e., antigen-binding) portion of an immunoglobulin molecule, like an antibody fragment.

An "antibody fragment" is a portion of an antibody such as F(ab')$_2$, F(ab)$_2$, Fab', Fab, Fv, scFv, single domain antibodies (DABs or VHHs) and the like, including half-molecules of IgG4 (van der Neut Kolfschoten et al. (Science 2007; 317(14 September):1554-1557). Regardless of structure, an antibody fragment binds with the same antigen that is recognized by the intact antibody. For example, an anti-CD74 antibody fragment binds with an epitope of CD74. The term "antibody fragment" also includes isolated fragments consisting of the variable regions, such as the "Fv" fragments consisting of the variable regions of the heavy and light chains and recombinant single chain polypeptide molecules in which light and heavy chain variable regions are connected by a peptide linker ("scFv proteins"). As used herein, the term "antibody fragment" does not include fragments such as Fc fragments that do not contain antigen-binding sites.

A "chimeric antibody" is a recombinant protein that contains the variable domains including the complementarity determining regions (CDRs) of an antibody derived from one species, preferably a rodent antibody, while the constant domains of the antibody molecule are derived from those of a human antibody. For veterinary applications, the constant domains of the chimeric antibody may be derived from that of other species, such as a cat or dog.

A "humanized antibody" is a recombinant protein in which the CDRs from an antibody from one species; e.g., a rodent antibody, are transferred from the heavy and light variable chains of the rodent antibody into human heavy and light variable domains. Additional FR amino acid substitutions from the parent, e.g. murine, antibody may be made. The constant domains of the antibody molecule are derived from those of a human antibody.

A "human antibody" is, for example, an antibody obtained from transgenic mice that have been genetically engineered to produce human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., Nature Genet. 7:13 (1994), Lonberg et al., Nature 368:856 (1994), and Taylor et al., Int. Immun. 6:579 (1994). A fully human antibody also can be constructed by genetic or chromosomal transfection methods, as well as phage display technology, all of which are known in the art. (See, e.g., McCafferty et al., Nature 348:552-553 (1990) for the production of human antibodies and fragments thereof in vitro, from immunoglobulin variable domain gene repertoires from unimmunized donors). In this technique, antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell. Phage display can be performed in a variety of formats, for their review, see, e.g. Johnson and Chiswell, Current Opinion in Structural Biology 3:5564-571 (1993). Human antibodies may also be generated by in vitro activated B cells. (See, U.S. Pat. Nos. 5,567,610 and 5,229,275).

A "therapeutic agent" is an atom, molecule, or compound that is useful in the treatment of a disease. Examples of therapeutic agents include but are not limited to antibodies, antibody fragments, drugs, toxins, enzymes, nucleases, hormones, immunomodulators, antisense oligonucleotides, chelators, boron compounds, photoactive agents, dyes and radioisotopes.

A "diagnostic agent" is an atom, molecule, or compound that is useful in diagnosing a disease. Useful diagnostic agents include, but are not limited to, radioisotopes, dyes, contrast agents, fluorescent compounds or molecules and enhancing agents (e.g., paramagnetic ions). Preferably, the diagnostic agents are selected from the group consisting of radioisotopes, enhancing agents, and fluorescent compounds.

An "immunoconjugate" is a conjugate of an antibody, antibody fragment, antibody fusion protein, bispecific antibody or multispecific antibody with an atom, molecule, or a higher-ordered structure (e.g., with a carrier, a therapeutic agent, or a diagnostic agent). A "naked antibody" is an antibody that is not conjugated to any other agent.

As used herein, the term "antibody fusion protein" is a recombinantly produced antigen-binding molecule in which an antibody or antibody fragment is covalently linked to another protein or peptide, such as the same or different antibody or antibody fragment or a DDD or AD peptide. The fusion protein may comprise a single antibody component, a multivalent or multispecific combination of different antibody components or multiple copies of the same antibody component. The fusion protein may additionally comprise an antibody or an antibody fragment and a therapeutic agent. Examples of therapeutic agents suitable for such fusion proteins include immunomodulators and toxins. One preferred toxin comprises a ribonuclease (RNase), preferably a recombinant RNase.

A "multispecific antibody" is an antibody that can bind simultaneously to at least two targets that are of different structure, e.g., two different antigens, two different epitopes on the same antigen, or a hapten and/or an antigen or epitope. A "multivalent antibody" is an antibody that can bind simultaneously to at least two targets that are of the same or different structure. Valency indicates how many binding arms or sites the antibody has to a single antigen or epitope; i.e., monovalent, bivalent, trivalent or multivalent. The multivalency of the antibody means that it can take advantage of multiple interactions in binding to an antigen, thus increasing the avidity of binding to the antigen. Specificity indicates how many antigens or epitopes an antibody is able to bind; i.e., monospecific, bispecific, trispecific, multispecific. Using these definitions, a natural antibody, e.g., an IgG, is bivalent because it has two binding arms but is monospecific because it binds to one epitope. Multispecific, multivalent antibodies are constructs that have more than one binding site of different specificity. For example, a diabody, where one binding site reacts with one antigen and the other with another antigen.

A "bispecific antibody" is an antibody that can bind simultaneously to two targets which are of different structure.

CD74

CD74 (also known as invariant chain or Ii) is a transmembrane glycoprotein that associates with MHC class II α and β chains and directs transport of αβIi complexes to endosomes and lysosomes. CD74 functions as a molecular chaperone in the processing of exogenous peptides for antigen presentation via MHC class II. More recently, CD74 has been identified as the endogenous receptor for MIF (macrophage migration inhibitory factor), a key regulatory molecule that promotes cell survival and inhibits apoptosis by activation of the Akt pathway (Lue et al., Oncogene 207, 26:5046-59). As such, the interaction of CD74 and MIF is thought to play a significant role in tumorigenesis and tumor progression (Id.)

CD74 is overexpressed in a variety of disease states, including many solid and hematopoietic tumors (Stein et al., Clin Cancer Res 2007, 13:5556s-63s; Gold et al., Int J Clin Exp Pathol 2011, 4:1-12). Milatuzumab (hLL1), a humanized anti-CD74 antibody, is rapidly internalized into CD74 expressing cells and has been used to target therapeutic agents to tumor cells, with excellent therapeutic effects (see, e.g., Griffiths et al., Clin Cancer Res 2003, 9:6567-71; Ochaskovskaya et al., Clin Cancer Res 2001, 7:1505-10). However, naked milatuzumab has also been shown to be cytotoxic in the presence of cross-linking antibodies (e.g., U.S. Pat. No. 7,312,318). Combinations of milatuzumab with other therapeutic agents show enhanced cytotoxicity and improved therapeutic response in multiple myeloma cell lines (Stein et al., Clin Cancer Res 2009, 15:2808-17).

Milatuzumab has been reported to be efficacious for a wide range of hematopoietic malignancies, including non-Hodgkin's lymphoma, Burkitt lymphoma, follicular lymphoma, multiple myeloma, chronic lymphocytic leukemia and mantle cell lymphoma (Stein et al., Clin Cancer Res 2007, 13:5556s-63s; Berkova et al., Expert Opin. Invest. Drugs 2010, 19:141-49). Since CD74 is also over-expressed in a number of solid tumors, use of milatuzumab or other anti-CD74 antibodies for therapy of colorectal carcinoma, pancreatic carcinoma, gastric carcinoma, non-small cell lung carcinoma, glioblastoma, thymic carcinoma, pancreatic cancer, breast cancer, bladder cancer and prostate cancer has also been suggested (Gold et al., Int J Clin Exp Pathol 2011, 4:1-12; Berkova et al., Expert Opin. Invest. Drugs 2010, 19:141-49). Therapy directed to CD74 has been indicated in autoimmune or immune dysfunction diseases, such as systemic lupus erythematosus and rheumatoid arthritis (Lapter et al., Immunology 2011, 1327-95; Morand and Leech, Front Biosci 2005, 10:12-22). Combination therapy, such as with anti-CD74/anti-CD20 antibodies, has been reported to show improved efficacy in mantle cell lymphoma (Alinari et al., Blood 2011, 117:4530-41).

The skilled artisan will realize that these therapeutic effects are not limited to milatuzumab, but may also be seen with other anti-CD74 antibodies, particularly those that compete with milatuzumab for binding or that bind to the same epitope of CD74 as milatuzumab.

Dock-and-Lock (DNL)

In preferred embodiments, multivalent monospecific or bispecific antibodies may be produced using the dock-and-lock (DNL) technology (see, e.g., U.S. Pat. Nos. 7,521,056; 7,550,143; 7,534,866; 7,527,787 and 7,666,400; the Examples section of each of which is incorporated herein by reference). The DNL method exploits specific protein/protein interactions that occur between the regulatory (R) subunits of cAMP-dependent protein kinase (PKA) and the anchoring domain (AD) of A-kinase anchoring proteins (AKAPs) (Baillie et al., FEBS Letters. 2005; 579: 3264. Wong and Scott, Nat. Rev. Mol. Cell Biol. 2004; 5: 959). PKA, which plays a central role in one of the best studied signal transduction pathways triggered by the binding of the second messenger cAMP to the R subunits, was first isolated from rabbit skeletal muscle in 1968 (Walsh et al., J. Biol. Chem. 1968; 243:3763). The structure of the holoenzyme consists of two catalytic subunits held in an inactive form by the R subunits (Taylor, J. Biol. Chem. 1989; 264:8443). Isozymes of PKA are found with two types of R subunits (RI and RII), and each type has α and β isoforms (Scott, Pharmacol. Ther. 1991; 50:123). Thus, there are four types of PKA regulatory subunits—RIα, RIβ, RIIα and RIIβ. The R subunits have been isolated only as stable dimers and the dimerization domain has been shown to consist of the first 44 amino-terminal residues (Newlon et al., Nat. Struct. Biol. 1999; 6:222). Binding of cAMP to the R subunits leads to the release of active catalytic subunits for a broad spectrum of serine/threonine kinase activities, which are oriented toward selected substrates through the compartmentalization of PKA via its docking with AKAPs (Scott et al., J. Biol. Chem. 1990; 265; 21561).

Since the first AKAP, microtubule-associated protein-2, was characterized in 1984 (Lohmann et al., Proc. Natl. Acad. Sci USA. 1984; 81:6723), more than 50 AKAPs that localize to various sub-cellular sites, including plasma membrane, actin cytoskeleton, nucleus, mitochondria, and endoplasmic reticulum, have been identified with diverse structures in species ranging from yeast to humans (Wong and Scott, Nat. Rev. Mol. Cell Biol. 2004; 5:959). The AD of AKAPs for PKA is an amphipathic helix of 14-18 residues (Carr et al., J. Biol. Chem. 1991; 266:14188). The amino acid sequences of the AD are quite varied among individual AKAPs, with the binding affinities reported for RII dimers ranging from 2 to 90 nM (Alto et al., Proc. Natl. Acad. Sci. USA. 2003; 100:4445). AKAPs will only bind to dimeric R subunits. For human RIIα, the AD binds to a hydrophobic surface formed by the 23 amino-terminal residues (Colledge and Scott, Trends Cell Biol. 1999; 6:216). Thus, the dimerization domain and AKAP binding domain of human RIIα are both located within the same N-terminal 44 amino acid sequence (Newlon et al., Nat. Struct. Biol. 1999; 6:222; Newlon et al., EMBO J. 2001; 20:1651), which is termed the DDD herein.

We have developed a platform technology to utilize the DDD of human PKA regulatory subunit and the AD of AKAP as an excellent pair of linker modules for docking any two entities, referred to hereafter as A and B, into a noncovalent complex, which could be further locked into a stably tethered structure through the introduction of cysteine residues into both the DDD and AD at strategic positions to facilitate the formation of disulfide bonds. The general methodology of the "dock-and-lock" approach is as follows. Entity A is constructed by linking a DDD sequence to a precursor of A, resulting in a first component hereafter referred to as a. Because the DDD sequence would effect the spontaneous formation of a dimer, A would thus be composed of $a_2$. Entity B is constructed by linking an AD sequence to a precursor of B, resulting in a second component hereafter referred to as b. The dimeric motif of DDD contained in $a_2$ will create a docking site for binding to the AD sequence contained in b, thus facilitating a ready association of $a_2$ and b to form a binary, trimeric complex composed of $a_2b$. This binding event is made irreversible with a subsequent reaction to covalently secure the two entities via disulfide bridges, which occurs very efficiently based on the principle of effective local concentration because the initial binding interactions should bring the reactive thiol groups placed onto both the DDD and AD into proximity (Chmura et al., Proc. Natl. Acad. Sci. USA. 2001; 98:8480) to ligate site-specifically. Using various combinations of linkers, adaptor modules and precursors, a wide variety of DNL constructs of different stoichiometry may be produced and used, including but not limited to dimeric, trimeric, tetrameric, pentameric and hexameric DNL constructs (see, e.g., U.S. Pat. Nos. 7,550,143; 7,521, 056; 7,534,866; 7,527,787 and 7,666,400.)

By attaching the DDD and AD away from the functional groups of the two precursors, such site-specific ligations are also expected to preserve the original activities of the two precursors. This approach is modular in nature and potentially can be applied to link, site-specifically and covalently, a wide range of substances, including peptides, proteins, antibodies, antibody fragments, and other effector moieties with a wide range of activities. Utilizing the fusion protein method of constructing AD and DDD conjugated effectors described in the Examples below, virtually any protein or peptide may be incorporated into a DNL construct. However, the technique is not limiting and other methods of conjugation may be utilized.

A variety of methods are known for making fusion proteins, including nucleic acid synthesis, hybridization and/or amplification to produce a synthetic double-stranded nucleic acid encoding a fusion protein of interest. Such double-stranded nucleic acids may be inserted into expression vectors for fusion protein production by standard molecular biology techniques (see, e.g. Sambrook et al., Molecular Cloning, A laboratory manual, $2^{nd}$ Ed, 1989). In such preferred embodiments, the AD and/or DDD moiety may be attached to either the N-terminal or C-terminal end of an effector protein or peptide. However, the skilled artisan will realize that the site of attachment of an AD or DDD moiety to an effector moiety may vary, depending on the chemical nature of the effector moiety and the part(s) of the effector moiety involved in its physiological activity. Site-specific attachment of a variety of effector moieties may be performed using techniques known in the art, such as the use of bivalent cross-linking reagents and/or other chemical conjugation techniques.

The skilled artisan will realize that the DNL technique may be utilized to produce complexes comprising multiple copies of the same anti-CD74 or anti-CD20 antibodies, or to attach one or more anti-CD74 antibodies to one or more anti-CD20 antibodies or an antibody against a different target antigen expressed by B-cells. Alternatively, the DNL technique may be used to attach antibodies to different effector moieties, such as toxins, cytokines, carrier proteins for siRNA and other known effectors.

Structure-Function Relationships in AD and DDD Moieties

For different types of DNL constructs, different AD or DDD sequences may be utilized. Exemplary DDD and AD sequences are provided below.

```
DDD1
                                          (SEQ ID NO: 25)
SHIQIPPGLTELLQGYTVEVLRQQPPDLVEFAVEYFTRLREARA

DDD2
                                          (SEQ ID NO: 26)
CGHIQIPPGLTELLQGYTVEVLRQQPPDLVEFAVEYFTRLREARA

AD1
                                          (SEQ ID NO: 27)
QIEYLAKQIVDNAIQQA

AD2
                                          (SEQ ID NO: 28)
CGQIEYLAKQIVDNAIQQAGC
```

The skilled artisan will realize that DDD1 and DDD2 are based on the DDD sequence of the human RIIα isoform of protein kinase A. However, in alternative embodiments, the DDD and AD moieties may be based on the DDD sequence of the human RIα form of protein kinase A and a corresponding AKAP sequence, as exemplified in DDD3, DDD3C and AD3 below.

```
DDD3
                                          (SEQ ID NO: 29)
SLRECELYVQKHNIQALLKDSIVQLCTARPERPMAFLREYFERLEKEEAK

DDD3C
                                          (SEQ ID NO: 30)
MSCGGSLRECELYVQKHNIQALLKDSIVQLCTARPERPMAFLREYFERLE
KEEAK

AD3
                                          (SEQ ID NO: 31)
CGFEELAWKIAKMIWSDVFQQGC
```

In other alternative embodiments, other sequence variants of AD and/or DDD moieties may be utilized in construction of the DNL complexes. For example, there are only four variants of human PKA DDD sequences, corresponding to the DDD moieties of PKA RIα, RIIα, RIβ and RIIβ. The RIIα DDD sequence is the basis of DDD1 and DDD2 disclosed above. The four human PKA DDD sequences are shown below. The DDD sequence represents residues 1-44 of RIIα, 1-44 of RIIβ, 12-61 of RIα and 13-66 of RIβ. (Note that the sequence of DDD1 is modified slightly from the human PKA RIIα DDD moiety.)

```
PKA RIα
                                          (SEQ ID NO: 32)
SLRECELYVQKHNIQALLKDVSIVQLCTARPERPMAFLREYFEKLEKEE
AK

PKA RIβ
                                          (SEQ ID NO: 33)
SLKGCELYVQLHGIQQVLKDCIVHLCISKPERPMKFLREHFEKLEKEEN
RQILA

PKA RIIα
                                          (SEQ ID NO: 34)
SHIQIPPGLTELLQGYTVEVGQQPPDLVDFAVEYFTRLREARRQ

PKA RIIβ
                                          (SEQ ID NO: 35)
SIEIPAGLTELLQGFTVEVLRHQPADLLEFALQHFTRLQQENER
```

The structure-function relationships of the AD and DDD domains have been the subject of investigation. (See, e.g., Burns-Hamuro et al., 2005, Protein Sci 14:2982-92; Carr et al., 2001, J Biol Chem 276:17332-38; Alto et al., 2003, Proc Natl Acad Sci USA 100:4445-50; Hundsrucker et al., 2006, Biochem J 396:297-306; Stokka et al., 2006, Biochem J 400: 493-99; Gold et al., 2006, Mol Cell 24:383-95; Kinderman et al., 2006, Mol Cell 24:397-408, the entire text of each of which is incorporated herein by reference.)

For example, Kinderman et al. (2006, Mol Cell 24:397-408) examined the crystal structure of the AD-DDD binding interaction and concluded that the human DDD sequence contained a number of conserved amino acid residues that were important in either dimer formation or AKAP binding, underlined in SEQ ID NO:25 below. (See FIG. 1 of Kinderman et al., 2006, incorporated herein by reference.) The skilled artisan will realize that in designing sequence variants of the DDD sequence, one would desirably avoid changing any of the underlined residues, while conservative amino acid substitutions might be made for residues that are less critical for dimerization and AKAP binding.

```
                                          (SEQ ID NO: 25)
SHIQIPPGLTELLQGYTVEVLRQQPPDLVEFAVEYFTRLREARA
```

As discussed in more detail below, conservative amino acid substitutions have been characterized for each of the twenty common L-amino acids. Thus, based on the data of Kinderman (2006) and conservative amino acid substitutions, potential alternative DDD sequences based on SEQ ID NO:25 are shown in Table 1. In devising Table 1, only highly conservative amino acid substitutions were considered. For example, charged residues were only substituted for residues of the same charge, residues with small side chains were substituted with residues of similar size, hydroxyl side chains were only substituted with other hydroxyls, etc. Because of the unique effect of proline on amino acid secondary structure, no other residues were substituted for proline. Even with such conservative substitutions, there are over twenty million possible alternative sequences for the 44 residue peptide (2×3×2×2× 2×2×2×2×2×2×2×2×2×2×2×4×2×2×2×2×2×4×2×4). A limited number of such potential alternative DDD moiety sequences are shown in SEQ ID NO:36 to SEQ ID NO:55 below. The skilled artisan will realize that an almost unlimited number of alternative species within the genus of DDD moieties can be constructed by standard techniques, for example using a commercial peptide synthesizer or well known site-directed mutagenesis techniques. The effect of the amino acid substitutions on AD moiety binding may also be readily determined by standard binding assays, for example as disclosed in Alto et al. (2003, Proc Natl Acad Sci USA 100:4445-50).

TABLE 1

Conservative Amino Acid Substitutions in DDD1 (SEQ ID NO: 25). Consensus sequence disclosed as SEQ ID NO: 141.

| S | H | I | Q | I | P | P | G | L | T | E | L | L | Q | G | Y | T | V | E | V | L | R |
|---|---|---|---|---|---|---|---|---|---|---|---|---|---|---|---|---|---|---|---|---|---|
| T | K<br>R | | N | | | | A | | S | D | | | N | A | | S | | D | | | K |
| Q | Q | P | P | D | L | V | E | F | A | V | E | Y | F | T | R | L | R | E | A | R | A |
| N | N | | | E | | | D | | L<br>I<br>V | | D | | | S | K | | K | D | L<br>I<br>V | K | L<br>I<br>V |

```
                                    (SEQ ID NO: 36)
THIQIPPGLTELLQGYTVEVLRQQPPDLVEFAVEYFTRLREARA (SEQ ID NO: 37)
SKIQIPPGLTELLQGYTVEVLRQQPPDLVEFAVEYFTRLREARA (SEQ ID NO: 38)
SRIQIPPGLTELLQGYTVEVLRQQPPDLVEFAVEYFTRLREARA (SEQ ID NO: 39)
SHINIPPGLTELLQGYTVEVLRQQPPDLVEFAVEYFTRLREARA (SEQ ID NO: 40)
SHIQIPPALTELLQGYTVEVLRQQPPDLVEFAVEYFTRLREARA (SEQ ID NO: 41)
SHIQIPPGLSELLQGYTVEVLRQQPPDLVEFAVEYFTRLREARA (SEQ ID NO: 42)
SHIQIPPGLTDLLQGYTVEVLRQQPPDLVEFAVEYFTRLREARA (SEQ ID NO: 43)
SHIQIPPGLTELLNGYTVEVLRQQPPDLVEFAVEYFTRLREARA (SEQ ID NO: 44)
SHIQIPPGLTELLQAYTVEVLRQQPPDLVEFAVEYFTRLREARA (SEQ ID NO: 45)
SHIQIPPGLTELLQGYSVEVLRQQPPDLVEFAVEYFTRLREARA (SEQ ID NO: 46)
SHIQIPPGLTELLQGYTVDVLRQQPPDLVEFAVEYFTRLREARA (SEQ ID NO: 47)
SHIQIPPGLTELLQGYTVEVLKQQPPDLVEFAVEYFTRLREARA (SEQ ID NO: 48)
SHIQIPPGLTELLQGYTVEVLRNQPPDLVEFAVEYFTRLREARA (SEQ ID NO: 49)
SHIQIPPGLTELLQGYTVEVLRQNPPDLVEFAVEYFTRLREARA (SEQ ID NO: 50)
SHIQIPPGLTELLQGYTVEVLRQQPPELVEFAVEYFTRLREARA (SEQ ID NO: 51)
SHIQIPPGLTELLQGYTVEVLRQQPPDLVDFAVEYFTRLREARA
```

-continued

```
                                    (SEQ ID NO: 52)
SHIQIPPGLTELLQGYTVEVLRQQPPDLVEFLVEYFTRLREARA (SEQ ID NO: 53)
SHIQIPPGLTELLQGYTVEVLRQQPPDLVEFIVEYFTRLREARA (SEQ ID NO: 54)
SHIQIPPGLTELLQGYTVEVLRQQPPDLVEFVVEYFTRLREARA (SEQ ID NO: 55)
SHIQIPPGLTELLQGYTVEVLRQQPPDLVEFAVDYFTRLREARA
```

Alto et al. (2003, Proc Natl Acad Sci USA 100:4445-50) performed a bioinformatic analysis of the AD sequence of various AKAP proteins to design an RII selective AD sequence called AKAP-IS (SEQ ID NO:27), with a binding constant for DDD of 0.4 nM. The AKAP-IS sequence was designed as a peptide antagonist of AKAP binding to PKA. Residues in the AKAP-IS sequence where substitutions tended to decrease binding to DDD are underlined in SEQ ID NO:27 below. The skilled artisan will realize that in designing sequence variants of the AD sequence, one would desirably avoid changing any of the underlined residues, while conservative amino acid substitutions might be made for residues that are less critical for DDD binding. Table 2 shows potential conservative amino acid substitutions in the sequence of AKAP-IS (AD1, SEQ ID NO:27), similar to that shown for DDD1 (SEQ ID NO:25) in Table 1 above.

Even with such conservative substitutions, there are over thirty-five thousand possible alternative sequences for the 17 residue AD1 (SEQ ID NO:27) peptide sequence (2×3×2×4×3×2×2×2×2×2×2×4). A limited number of such potential alternative AD moiety sequences are shown in SEQ ID NO:56 to SEQ ID NO:73 below. Again, a very large number of species within the genus of possible AD moiety sequences could be made, tested and used by the skilled artisan, based on the data of Alto et al. (2003). It is noted that FIG. 2 of Alto (2003) shows an even large number of potential amino acid substitutions that may be made, while retaining binding activity to DDD moieties, based on actual binding experiments.

```
AKAP-IS
                                    (SEQ ID NO: 27)
QIEYLAKQIVDNAIQQA
```

TABLE 2

Conservative Amino Acid Substitutions in AD1 (SEQ ID NO: 27). Consensus sequence disclosed as SEQ ID NO: 142.

| Q | I | E | Y | L | A | K | Q | I | V | D | N | A | I | Q | Q | A |
|---|---|---|---|---|---|---|---|---|---|---|---|---|---|---|---|---|
| N | L<br>V | D | F<br>T<br>S | I<br>V | | R | N | | | E | Q | | | N | N | L<br>I<br>V |

```
NIEYLAKQIVDNAIQQA       (SEQ ID NO: 56)
QLEYLAKQIVDNAIQQA       (SEQ ID NO: 57)
QVEYLAKQIVDNAIQQA       (SEQ ID NO: 58)
QIDYLAKQIVDNAIQQA       (SEQ ID NO: 59)
QIEFLAKQIVDNAIQQA       (SEQ ID NO: 60)
QIETLAKQIVDNAIQQA       (SEQ ID NO: 61)
QIESLAKQIVDNAIQQA       (SEQ ID NO: 62)
QIEYIAKQIVDNAIQQA       (SEQ ID NO: 63)
QIEYVAKQIVDNAIQQA       (SEQ ID NO: 64)
QIEYLARQIVDNAIQQA       (SEQ ID NO: 65)
QIEYLAKNIVDNAIQQA       (SEQ ID NO: 66)
QIEYLAKQIVENAIQQA       (SEQ ID NO: 67)
QIEYLAKQIVDQAIQQA       (SEQ ID NO: 68)
QIEYLAKQIVDNAINQA       (SEQ ID NO: 69)
QIEYLAKQIVDNAIQNA       (SEQ ID NO: 70)
QIEYLAKQIVDNAIQQL       (SEQ ID NO: 71)
QIEYLAKQIVDNAIQQI       (SEQ ID NO: 72)
QIEYLAKQIVDNAIQQV       (SEQ ID NO: 73)
```

Gold et al. (2006, Mol Cell 24:383-95) utilized crystallography and peptide screening to develop a SuperAKAP-IS sequence (SEQ ID NO:74), exhibiting a five order of magnitude higher selectivity for the RII isoform of PKA compared with the R1 isoform. Underlined residues indicate the positions of amino acid substitutions, relative to the AKAP-IS sequence, which increased binding to the DDD moiety of RIIα. In this sequence, the N-terminal Q residue is numbered as residue number 4 and the C-terminal A residue is residue number 20. Residues where substitutions could be made to affect the affinity for RIIα were residues 8, 11, 15, 16, 18, 19 and 20 (Gold et al., 2006). It is contemplated that in certain alternative embodiments, the SuperAKAP-IS sequence may be substituted for the AKAP-IS AD moiety sequence to prepare DNL constructs. Other alternative sequences that might be substituted for the AKAP-IS AD sequence are shown in SEQ ID NO:75-77. Substitutions relative to the AKAP-IS sequence are underlined. It is anticipated that, as with the AD2 sequence shown in SEQ ID NO:28, the AD moiety may also include the additional N-terminal residues cysteine and glycine and C-terminal residues glycine and cysteine.

```
SuperAKAP-IS
                        (SEQ ID NO: 74)
QIEYVAKQIVDYAIHQA

Alternative AKAP sequences
                        (SEQ ID NO: 75)
QIEYKAKQIVDHAIHQA (SEQ ID NO: 76)
QIEYHAKQIVDHAIHQA (SEQ ID NO: 77)
QIEYVAKQIVDHAIHQA
```

FIG. 2 of Gold et al. disclosed additional DDD-binding sequences from a variety of AKAP proteins, shown below.

```
RII-Specific AKAPs
AKAP-KL
                        (SEQ ID NO: 78)
PLEYQAGLLVQNAIQQAI

AKAP79
                        (SEQ ID NO: 79)
LLIETASSLVKNAIQLSI

AKAP-Lbc
                        (SEQ ID NO: 80)
LIEEAASRIVDAVIEQVK

RI-Specific AKAPs
AKAPce
                        (SEQ ID NO: 81)
ALYQFADRFSELVISEAL

RIAD
                        (SEQ ID NO: 82)
LEQVANQLADQIIKEAT

PV38
                        (SEQ ID NO: 83)
FEELAWKIAKMIWSDVF

Dual-Specificity AKAPs
AKAP7
                        (SEQ ID NO: 84)
ELVRLSKRLVENAVLKAV

MAP2D
                        (SEQ ID NO: 85)
TAEEVSARIVQVVTAEAV

DAKAP1
                        (SEQ ID NO: 86)
QIKQAAFQLISQVILEAT

DAKAP2
                        (SEQ ID NO: 87)
LAWKIAKMIVSDVMQQ
```

Stokka et al. (2006, Biochem J 400:493-99) also developed peptide competitors of AKAP binding to PKA, shown in SEQ ID NO:88-09. The peptide antagonists were designated as Ht31 (SEQ ID NO:88), RIAD (SEQ ID NO:89) and PV-38 (SEQ ID NO:90). The Ht-31 peptide exhibited a greater affinity for the RII isoform of PKA, while the RIAD and PV-38 showed higher affinity for R1.

```
Ht31
                        (SEQ ID NO: 88)
DLIEEAASRIVDAVIEQVKAAGAY

RIAD
                        (SEQ ID NO: 89)
LEQYANQLADQIIKEATE

PV-38
                        (SEQ ID NO: 90)
FEELAWKIAKMIWSDVFQQC
```

Hundsrucker et al. (2006, Biochem J 396:297-306) developed still other peptide competitors for AKAP binding to PKA, with a binding constant as low as 0.4 nM to the DDD of the RII form of PKA. The sequences of various AKAP antagonistic peptides are provided in Table 1 of Hundsrucker et al., reproduced in Table 3 below. AKAPIS represents a synthetic RII subunit-binding peptide. All other peptides are derived from the RII-binding domains of the indicated AKAPs.

TABLE 3

AKAP Peptide sequences

| Name | Peptide Sequence |
|---|---|
| AKAPIS | QIEYLAKQIVDNAIQQA (SEQ ID NO: 27) |
| AKAPIS-P | QIEYLAKQIPDNAIQQA (SEQ ID NO: 91) |
| Ht31 | KGADLIEEAASRIVDAVIEQVKAAG (SEQ ID NO: 92) |
| Ht31-P | KGADLIEEAASRIPDAPIEQVKAAG (SEQ ID NO: 93) |
| AKAP7δ-wt-pep | PEDAELVRLSKRLVENAVLKAVQQY (SEQ ID NO: 94) |
| AKAP7δ-L304T-pep | PEDAELVRTSKRLVENAVLKAVQQY (SEQ ID NO: 95) |
| AKAP7δ-L308D-pep | PEDAELVRLSKRDVENAVLKAVQQY (SEQ ID NO: 96) |
| AKAP7δ-P-pep | PEDAELVRLSKRLPENAVLKAVQQY (SEQ ID NO: 97) |
| AKAP7δ-PP-pep | PEDAELVRLSKRLPENAPLKAVQQY (SEQ ID NO: 98) |
| AKAP7δ-L314E-pep | PEDAELVRLSKRLVENAVEKAVQQY (SEQ ID NO: 99) |
| AKAP1-pep | EEGLDRNEEIKRAAFQIISQVISEA (SEQ ID NO: 100) |
| AKAP2-pep | LVDDPLEYQAGLLVQNAIQQAIAEQ (SEQ ID NO: 101) |
| AKAP5-pep | QYETLLIETASSLVKNAIQLSIEQL (SEQ ID NO: 102) |
| AKAP9-pep | LEKQYQEQLEEEVAKVIVSMSIAFA (SEQ ID NO: 103) |
| AKAP10-pep | NTDEAQEELAWKIAKMIVSDIMQQA (SEQ ID NO: 104) |
| AKAP11-pep | VNLDKKAVLAEKIVAEAIEKAEREL (SEQ ID NO: 105) |
| AKAP12-pep | NGILELETKSSKLVQNIIQTAVDQF (SEQ ID NO: 106) |
| AKAP14-pep | TQDKNYEDELTQVALALVEDVINYA (SEQ ID NO: 107) |
| Rab32-pep | ETSAKDNINIEEAARFLVEKILVNH (SEQ ID NO: 108) |

Residues that were highly conserved among the AD domains of different AKAP proteins are indicated below by underlining with reference to the AKAP IS sequence (SEQ ID NO:27). The residues are the same as observed by Alto et al. (2003), with the addition of the C-terminal alanine residue. (See FIG. 4 of Hundsrucker et al. (2006), incorporated herein by reference.) The sequences of peptide antagonists with particularly high affinities for the R11 DDD sequence were those of AKAP-IS, AKAP7δ-wt-pep, AKAP7δ-L304T-pep and AKAP7δ-L308D-pep.

```
                    AKAP-IS
                                  (SEQ ID NO: 27)
             QIEYLAKQIVDNAIQQA
```

Can et al. (2001, J Biol Chem 276:17332-38) examined the degree of sequence homology between different AKAP-binding DDD sequences from human and non-human proteins and identified residues in the DDD sequences that appeared to be the most highly conserved among different DDD moieties. These are indicated below by underlining with reference to the human PKA RIIα DDD sequence of SEQ ID NO:25. Residues that were particularly conserved are further indicated by italics. The residues overlap with, but are not identical to those suggested by Kinderman et al. (2006) to be important for binding to AKAP proteins. The skilled artisan will realize that in designing sequence variants of DDD, it would be most preferred to avoid changing the most conserved residues (italicized), and it would be preferred to also avoid changing the conserved residues (underlined), while conservative amino acid substitutions may be considered for residues that are neither underlined nor italicized.

```
                                              (SEQ ID NO: 25)
    SHIQIPPGLTELLQGYTVEVLRQQPPDLVEFAVEYFTRLREARA
```

A modified set of conservative amino acid substitutions for the DDD1 (SEQ ID NO:25) sequence, based on the data of Carr et al. (2001) is shown in Table 4. Even with this reduced set of substituted sequences, there are over 65,000 possible alternative DDD moiety sequences that may be produced, tested and used by the skilled artisan without undue experimentation. The skilled artisan could readily derive such alternative DDD amino acid sequences as disclosed above for Table 1 and Table 2.

TABLE 4

Conservative Amino Acid Substitutions in DDD1 (SEQ ID NO: 25).
Consensus sequence disclosed as SEQ ID NO: 143.

| S | H | I | Q | I | P | P | G | L | T | E | L | L | Q | G | Y | T | V | E | V | L | R |
|---|---|---|---|---|---|---|---|---|---|---|---|---|---|---|---|---|---|---|---|---|---|
| T |   | N |   |   |   |   |   | S |   |   |   |   |   |   |   |   | I |   |   |   |   |
|   |   |   |   |   |   |   |   |   |   |   |   |   |   |   |   |   | L |   |   |   |   |
|   |   |   |   |   |   |   |   |   |   |   |   |   |   |   |   |   | A |   |   |   |   |

| Q | Q | P | P | D | L | V | E | F | A | V | E | Y | F | T | R | L | R | E | A | R | A |
|---|---|---|---|---|---|---|---|---|---|---|---|---|---|---|---|---|---|---|---|---|---|
| N |   |   |   |   |   | I | D |   |   |   |   | S | K |   | K |   |   | L |   | L |   |
|   |   |   |   |   |   | L |   |   |   |   |   |   |   |   |   |   |   | I |   | I |   |
|   |   |   |   |   |   | A |   |   |   |   |   |   |   |   |   |   |   | V |   | V |   |

The skilled artisan will realize that these and other amino acid substitutions in the DDD or AD amino acid sequences may be utilized to produce alternative species within the genus of AD or DDD moieties, using techniques that are standard in the field and only routine experimentation.

Amino Acid Substitutions

In various embodiments, the disclosed methods and compositions may involve production and use of proteins or peptides with one or more substituted amino acid residues. For example, the DDD and/or AD sequences used to make DNL constructs may be modified as discussed above.

The skilled artisan will be aware that, in general, amino acid substitutions typically involve the replacement of an amino acid with another amino acid of relatively similar properties (i.e., conservative amino acid substitutions). The properties of the various amino acids and effect of amino acid substitution on protein structure and function have been the subject of extensive study and knowledge in the art.

For example, the hydropathic index of amino acids may be considered (Kyte & Doolittle, 1982, J. Mol. Biol., 157:105-132). The relative hydropathic character of the amino acid contributes to the secondary structure of the resultant protein, which in turn defines the interaction of the protein with other molecules. Each amino acid has been assigned a hydropathic index on the basis of its hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making conservative substitutions, the use of amino acids whose hydropathic indices are within ±2 is preferred, within ±1 are more preferred, and within ±0.5 are even more preferred.

Amino acid substitution may also take into account the hydrophilicity of the amino acid residue (e.g., U.S. Pat. No. 4,554,101). Hydrophilicity values have been assigned to amino acid residues: arginine (+3.0); lysine (+3.0); aspartate (+3.0); glutamate (+3.0); serine (+0.3); asparagine (+0.2); glutamine (+0.2); glycine (0); threonine (−0.4); proline (−0.5+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). Replacement of amino acids with others of similar hydrophilicity is preferred.

Other considerations include the size of the amino acid side chain. For example, it would generally not be preferred to replace an amino acid with a compact side chain, such as glycine or serine, with an amino acid with a bulky side chain, e.g., tryptophan or tyrosine. The effect of various amino acid residues on protein secondary structure is also a consideration. Through empirical study, the effect of different amino acid residues on the tendency of protein domains to adopt an alpha-helical, beta-sheet or reverse turn secondary structure has been determined and is known in the art (see, e.g., Chou & Fasman, 1974, Biochemistry, 13:222-245; 1978, Ann. Rev. Biochem., 47: 251-276; 1979, Biophys. J., 26:367-384).

Based on such considerations and extensive empirical study, tables of conservative amino acid substitutions have been constructed and are known in the art. For example: arginine and lysine; glutamate and aspartate; serine and threonine; glutamine and asparagine; and valine, leucine and isoleucine. Alternatively: Ala (A) leu, ile, val; Arg (R) gln, asn, lys; Asn (N) his, asp, lys, arg, gln; Asp (D) asn, glu; Cys (C) ala, ser; Gln (Q) glu, asn; Glu (E) gln, asp; Gly (G) ala; His (H) asn, gln, lys, arg; Ile (I) val, met, ala, phe, leu; Leu (L) val, met, ala, phe, ile; Lys (K) gln, asn, arg; Met (M) phe, ile, leu; Phe (F) leu, val, ile, ala, tyr; Pro (P) ala; Ser (S), thr; Thr (T) ser; Trp (W) phe, tyr; Tyr (Y) trp, phe, thr, ser; Val (V) ile, leu, met, phe, ala.

Other considerations for amino acid substitutions include whether or not the residue is located in the interior of a protein or is solvent exposed. For interior residues, conservative substitutions would include: Asp and Asn; Ser and Thr; Ser and Ala; Thr and Ala; Ala and Gly; Ile and Val; Val and Leu; Leu and Ile; Leu and Met; Phe and Tyr; Tyr and Trp. (See, e.g., PROWL website at rockefeller.edu) For solvent exposed residues, conservative substitutions would include: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Ile and Val; Phe and Tyr. (Id.) Various matrices have been constructed to assist in selection of amino acid substitutions, such as the PAM250 scoring matrix, Dayhoff matrix, Grantham matrix, McLachlan matrix, Doolittle matrix, Henikoff matrix, Miyata matrix, Fitch matrix, Jones matrix, Rao matrix, Levin matrix and Risler matrix (Idem.)

In determining amino acid substitutions, one may also consider the existence of intermolecular or intramolecular bonds, such as formation of ionic bonds (salt bridges) between positively charged residues (e.g., His, Arg, Lys) and negatively charged residues (e.g., Asp, Glu) or disulfide bonds between nearby cysteine residues.

Methods of substituting any amino acid for any other amino acid in an encoded protein sequence are well known and a matter of routine experimentation for the skilled artisan, for example by the technique of site-directed mutagenesis or by synthesis and assembly of oligonucleotides encoding an amino acid substitution and splicing into an expression vector construct.

Preparation of Antibodies

The complexes described herein may comprise one or more monoclonal antibodies or fragments thereof. Rodent monoclonal antibodies to specific antigens may be obtained by methods known to those skilled in the art. (See, e.g., Kohler and Milstein, Nature 256: 495 (1975), and Coligan et al. (eds.), CURRENT PROTOCOLS IN IMMUNOLOGY, VOL. 1, pages 2.5.1-2.6.7 (John Wiley & Sons 1991)).

General techniques for cloning murine immunoglobulin variable domains have been disclosed, for example, by the publication of Orlandi et al., Proc. Nat'l Acad. Sci. USA 86: 3833 (1989). Techniques for constructing chimeric antibodies are well known to those of skill in the art. As an example, Leung et al., Hybridoma 13:469 (1994), disclose how they produced an LL2 chimera by combining DNA sequences encoding the $V_k$ and $V_H$ domains of LL2 monoclonal antibody, an anti-CD22 antibody, with respective human and IgG$_1$ constant region domains. This publication also provides the nucleotide sequences of the LL2 light and heavy chain variable regions, $V_k$ and $V_H$, respectively. Techniques for producing humanized antibodies are disclosed, for example, by Jones et al., Nature 321: 522 (1986), Riechmann et al., Nature 332: 323 (1988), Verhoeyen et al., Science 239: 1534 (1988), Carter et al., Proc. Nat'l Acad. Sci. USA 89: 4285 (1992), Sandhu, Crit. Rev. Biotech. 12: 437 (1992), and Singer et al., J. Immun. 150: 2844 (1993).

A chimeric antibody is a recombinant protein that contains the variable domains including the CDRs derived from one species of animal, such as a rodent antibody, while the remainder of the antibody molecule; i.e., the constant domains, is derived from a human antibody. Accordingly, a chimeric monoclonal antibody can also be humanized by replacing the sequences of the murine FR in the variable domains of the chimeric antibody with one or more different human FR. Specifically, mouse CDRs are transferred from heavy and light variable chains of the mouse immunoglobulin into the corresponding variable domains of a human antibody. As simply transferring mouse CDRs into human FRs often results in a reduction or even loss of antibody affinity, additional modification might be required in order to restore the original affinity of the murine antibody. This can be accomplished by the replacement of one or more some human residues in the FR regions with their murine counterparts to obtain an antibody that possesses good binding affinity to its epitope. (See, e.g., Tempest et al., Biotechnology 9:266 (1991) and Verhoeyen et al., Science 239: 1534 (1988)).

A fully human antibody can be obtained from a transgenic non-human animal. (See, e.g., Mendez et al., Nature Genetics, 15: 146-156, 1997; U.S. Pat. No. 5,633,425.) Methods for producing fully human antibodies using either combinatorial approaches or transgenic animals transformed with human immunoglobulin loci are known in the art (e.g., Mancini et al., 2004, *New Microbiol.* 27:315-28; Conrad and Scheller, 2005, *Comb. Chem. High Throughput Screen.* 8:117-26; Brekke and Loset, 2003, *Curr. Opin. Pharmacol.* 3:544-50; each incorporated herein by reference). Such fully human antibodies are expected to exhibit even fewer side effects than chimeric or humanized antibodies and to function in vivo as essentially endogenous human antibodies. In certain embodiments, the claimed methods and procedures may utilize human antibodies produced by such techniques.

In one alternative, the phage display technique may be used to generate human antibodies (e.g., Dantas-Barbosa et al., 2005, *Genet. Mol. Res.* 4:126-40, incorporated herein by reference). Human antibodies may be generated from normal humans or from humans that exhibit a particular disease state, such as a hematopoietic cancer (Dantas-Barbosa et al., 2005). The advantage to constructing human antibodies from a diseased individual is that the circulating antibody repertoire may be biased towards antibodies against disease-associated antigens.

In one non-limiting example of this methodology, Dantas-Barbosa et al. (2005) constructed a phage display library of human Fab antibody fragments from osteosarcoma patients. Generally, total RNA was obtained from circulating blood lymphocytes (Id.) Recombinant Fab were cloned from the μ, γ and κ chain antibody repertoires and inserted into a phage display library (Id.) RNAs were converted to cDNAs and used to make Fab cDNA libraries using specific primers against the heavy and light chain immunoglobulin sequences (Marks et al., 1991, *J. Mol. Biol.* 222:581-97). Library construction was performed according to Andris-Widhopf et al. (2000, In: *Phage Display Laboratory Manual*, Barbas et al. (eds), 1$^{st}$ edition, Cold Spring Harbor Laboratory Press, Cold Spring Harbor, N.Y. pp. 9.1 to 9.22, incorporated herein by reference). The final Fab fragments were digested with restriction endonucleases and inserted into the bacteriophage genome to make the phage display library. Such libraries may be screened by standard phage display methods. The skilled artisan will realize that this technique is exemplary only and any known method for making and screening human antibodies or antibody fragments by phage display may be utilized.

In another alternative, transgenic animals that have been genetically engineered to produce human antibodies may be used to generate antibodies against essentially any immunogenic target, using standard immunization protocols as discussed above. Methods for obtaining human antibodies from transgenic mice are described by Green et al., Nature Genet. 7:13 (1994), Lonberg et al., Nature 368:856 (1994), and Taylor et al., Int. Immun. 6:579 (1994). A non-limiting example of such a system is the XENOMOUSE® (e.g., Green et al., 1999, *J. Immunol. Methods* 231:11-23, incorporated herein by reference) from Abgenix (Fremont, Calif.). In the XENOMOUSE® and similar animals, the mouse antibody genes have been inactivated and replaced by functional human antibody genes, while the remainder of the mouse immune system remains intact.

The XENOMOUSE® was transformed with germline-configured YACs (yeast artificial chromosomes) that contained portions of the human IgH and Ig kappa loci, including the majority of the variable region sequences, along accessory genes and regulatory sequences. The human variable region repertoire may be used to generate antibody producing B cells, which may be processed into hybridomas by known techniques. A XENOMOUSE® immunized with a target antigen will produce human antibodies by the normal immune response, which may be harvested and/or produced by standard techniques discussed above. A variety of strains of XENOMOUSE® are available, each of which is capable of producing a different class of antibody. Transgenically produced human antibodies have been shown to have therapeutic potential, while retaining the pharmacokinetic properties of normal human antibodies (Green et al., 1999). The skilled artisan will realize that the claimed compositions and methods are not limited to use of the XENOMOUSE® system but may utilize any transgenic animal that has been genetically engineered to produce human antibodies.

Antibody Cloning and Production

Various techniques, such as production of chimeric or humanized antibodies, may involve procedures of antibody cloning and construction. The antigen-binding Vκ (variable light chain) and $V_H$ (variable heavy chain) sequences for an antibody of interest may be obtained by a variety of molecular cloning procedures, such as RT-PCR, 5'-RACE, and cDNA library screening. The V genes of an antibody from a cell that expresses a murine antibody can be cloned by PCR amplification and sequenced. To confirm their authenticity, the cloned $V_L$ and $V_H$ genes can be expressed in cell culture as a chimeric Ab as described by Orlandi et al., (*Proc. Natl. Acad. Sci., USA*, 86: 3833 (1989)). Based on the V gene sequences, a humanized antibody can then be designed and constructed as described by Leung et al. (*Mol. Immunol.*, 32: 1413 (1995)).

cDNA can be prepared from any known hybridoma line or transfected cell line producing a murine antibody by general molecular cloning techniques (Sambrook et al., Molecular Cloning, A laboratory manual, $2^{nd}$ Ed (1989)). The Vκ sequence for the antibody may be amplified using the primers VK1BACK and VK1FOR (Orlandi et al., 1989) or the extended primer set described by Leung et al. (*BioTechniques*, 15: 286 (1993)). The $V_H$ sequences can be amplified using the primer pair VH1BACK/VH1FOR (Orlandi et al., 1989) or the primers annealing to the constant region of murine IgG described by Leung et al. (Hybridoma, 13:469 (1994)). Humanized V genes can be constructed by a combination of long oligonucleotide template syntheses and PCR amplification as described by Leung et al. (*Mol. Immunol.*, 32: 1413 (1995)).

PCR products for Vκ can be subcloned into a staging vector, such as a pBR327-based staging vector, VKpBR, that contains an Ig promoter, a signal peptide sequence and convenient restriction sites. PCR products for $V_H$ can be subcloned into a similar staging vector, such as the pBluescript-based VHpBS. Expression cassettes containing the Vκ and $V_H$ sequences together with the promoter and signal peptide sequences can be excised from VKpBR and VHpBS and ligated into appropriate expression vectors, such as pKh and pG1g, respectively (Leung et al., Hybridoma, 13:469 (1994)). The expression vectors can be co-transfected into an appropriate cell and supernatant fluids monitored for production of a chimeric, humanized or human antibody. Alternatively, the Vκ and $V_H$ expression cassettes can be excised and subcloned into a single expression vector, such as pdHL2, as described by Gillies et al. (*J. Immunol. Methods* 125:191 (1989) and also shown in Losman et al., *Cancer,* 80:2660 (1997)).

In an alternative embodiment, expression vectors may be transfected into host cells that have been pre-adapted for transfection, growth and expression in serum-free medium. Exemplary cell lines that may be used include the Sp/EEE, Sp/ESF and Sp/ESF-X cell lines (see, e.g., U.S. Pat. Nos. 7,531,327; 7,537,930 and 7,608,425; the Examples section of each of which is incorporated herein by reference). These exemplary cell lines are based on the Sp2/0 myeloma cell line, transfected with a mutant Bcl-EEE gene, exposed to methotrexate to amplify transfected gene sequences and pre-adapted to serum-free cell line for protein expression.

Antibody Allotypes

Immunogenicity of therapeutic antibodies is associated with increased risk of infusion reactions and decreased duration of therapeutic response (Baert et al., 2003, N Engl J Med 348:602-08). The extent to which therapeutic antibodies induce an immune response in the host may be determined in part by the allotype of the antibody (Stickler et al., 2011, Genes and Immunity 12:213-21). Antibody allotype is related to amino acid sequence variations at specific locations in the constant region sequences of the antibody. The allotypes of IgG antibodies containing a heavy chain γ-type constant region are designated as Gm allotypes (1976, J Immunol 117:1056-59).

For the common IgG1 human antibodies, the most prevalent allotype is G1m1 (Stickler et al., 2011, Genes and Immunity 12:213-21). However, the G1m3 allotype also occurs frequently in Caucasians (Id.). It has been reported that G1m1 antibodies contain allotypic sequences that tend to induce an immune response when administered to non-G1m1 (nG1m1) recipients, such as G1m3 patients (Id.). Non-G1m1 allotype antibodies are not as immunogenic when administered to G1m1 patients (Id.).

The human G1m1 allotype comprises the amino acids D12 (Kabat position 356) and L14 (Kabat position 358) in the CH3 sequence of the heavy chain IgG1. The nG1m1 allotype comprises the amino acids E12 and M14 at the same locations. Both G1m1 and nG1m1 allotypes comprise an E13 residue in between the two variable sites and the allotypes are sometimes referred to as DEL and EEM allotypes. A non-limiting example of the heavy chain constant region sequence for an nG1m1 (G1 m3) allotype antibody is shown in Example 1 below for the exemplary antibody veltuzumab (SEQ ID NO:144).

With regard to therapeutic antibodies, veltuzumab (G1m3) and rituximab (G1m17,1) are, respectively, humanized and chimeric IgG1 antibodies against CD20, of use for therapy of a wide variety of hematological malignancies and/or autoimmune diseases. Table 5 compares the allotype sequences of the heavy chain constant region sequences of rituximab vs. veltuzumab. The light chain constant region sequences of the two antibodies are identical. As shown in Table 5, rituximab (G1m17,1) is a DEL allotype IgG1, with an additional sequence variation at Kabat position 214 (heavy chain CH1) of lysine in rituximab vs. arginine in veltuzumab. It has been reported that veltuzumab is less immunogenic in subjects than rituximab (see, e.g., Morchhauser et al., 2009, J Clin Oncol 27:3346-53; Goldenberg et al., 2009, Blood 113:1062-70; Robak & Robak, 2011, BioDrugs 25:13-25), an effect that has been attributed to the difference between humanized and chimeric antibodies. However, the difference in allotypes between the EEM and DEL allotypes likely also accounts for the lower immunogenicity of veltuzumab.

TABLE 5

Allotypes of Rituximab vs. Veltuzumab

| | Complete allotype | Heavy chain position and associated allotypes | | | | | | |
|---|---|---|---|---|---|---|---|---|
| | | 214 (allotype) | | 356/358 (allotype) | | 431 (allotype) | | |
| Rituximab | G1m17,1 | K | 17 | D/L | 1 | A | — | |
| Veltuzumab | G1m3 | R | 3 | E/M | — | A | — | |

In order to reduce the immunogenicity of therapeutic antibodies in individuals of nG1m1 genotype, it is desirable to select the allotype of the antibody to correspond to the EEM allotype, with a glutamate residue at Kabat position 356, a methionine at Kabat position 358, and preferably an arginine residue at Kabat position 214. Surprisingly, it was found that repeated subcutaneous administration of G1m3 antibodies over a long period of time did not result in a significant immune response.

Known Antibodies

In various embodiments, the claimed methods and compositions may utilize any of a variety of antibodies known in the art. Antibodies of use may be commercially obtained from a number of known sources. For example, a variety of antibody secreting hybridoma lines are available from the American Type Culture Collection (ATCC, Manassas, Va.). A large number of antibodies against various disease targets have been deposited at the ATCC and/or have published variable region sequences and are available for use in the claimed methods and compositions. See, e.g., U.S. Pat. Nos. 7,312, 318; 7,282,567; 7,151,164; 7,074,403; 7,060,802; 7,056,509; 7,049,060; 7,045,132; 7,041,803; 7,041,802; 7,041,293; 7,038,018; 7,037,498; 7,012,133; 7,001,598; 6,998,468; 6,994,976; 6,994,852; 6,989,241; 6,974,863; 6,965,018; 6,964,854; 6,962,981; 6,962,813; 6,956,107; 6,951,924; 6,949,244; 6,946,129; 6,943,020; 6,939,547; 6,921,645; 6,921,645; 6,921,533; 6,919,433; 6,919,078; 6,916,475; 6,905,681; 6,899,879; 6,893,625; 6,887,468; 6,887,466; 6,884,594; 6,881,405; 6,878,812; 6,875,580; 6,872,568; 6,867,006; 6,864,062; 6,861,511; 6,861,227; 6,861,226; 6,838,282; 6,835,549; 6,835,370; 6,824,780; 6,824,778; 6,812,206; 6,793,924; 6,783,758; 6,770,450; 6,767,711; 6,764,688; 6,764,681; 6,764,679; 6,743,898; 6,733,981; 6,730,307; 6,720,155; 6,716,966; 6,709,653; 6,693,176; 6,692,908; 6,689,607; 6,689,362; 6,689,355; 6,682,737; 6,682,736; 6,682,734; 6,673,344; 6,653,104; 6,652,852; 6,635,482; 6,630,144; 6,610,833; 6,610,294; 6,605,441; 6,605,279; 6,596,852; 6,592,868; 6,576,745; 6,572,856; 6,566,076; 6,562,618; 6,545,130; 6,544,749; 6,534,058; 6,528,625; 6,528,269; 6,521,227; 6,518,404; 6,511,665; 6,491,915; 6,488,930; 6,482,598; 6,482,408; 6,479,247; 6,468,531; 6,468,529; 6,465,173; 6,461,823; 6,458,356; 6,455,044; 6,455,040, 6,451,310; 6,444,206, 6,441,143; 6,432,404; 6,432,402; 6,419,928; 6,413,726; 6,406,694; 6,403,770; 6,403,091; 6,395,276; 6,395,274; 6,387,350; 6,383,759; 6,383,484; 6,376,654; 6,372,215; 6,359,126; 6,355,481; 6,355,444; 6,355,245; 6,355,244; 6,346,246; 6,344,198; 6,340,571; 6,340,459; 6,331,175; 6,306,393; 6,254,868; 6,187,287; 6,183,744; 6,129,914; 6,120,767; 6,096,289; 6,077,499; 5,922,302; 5,874,540; 5,814,440; 5,798,229; 5,789,554; 5,776,456; 5,736,119; 5,716,595;

5,677,136; 5,587,459; 5,443,953, 5,525,338, the Examples section of each of which is incorporated herein by reference. These are exemplary only and a wide variety of other antibodies and their hybridomas are known in the art. The skilled artisan will realize that antibody sequences or antibody-secreting hybridomas against almost any disease-associated antigen may be obtained by a simple search of the ATCC, NCBI and/or USPTO databases for antibodies against a selected disease-associated target of interest. The antigen binding domains of the cloned antibodies may be amplified, excised, ligated into an expression vector, transfected into an adapted host cell and used for protein production, using standard techniques well known in the art.

Exemplary known antibodies that may be of use for therapy of cancer or autoimmune disease within the scope of the claimed methods and compositions include, but are not limited to, LL1 (anti-CD74), LL2 and RFB4 (anti-CD22), RS7 (anti-epithelial glycoprotein-1 (EGP-1)), PAM4 and KC4 (both anti-mucin), MN-14 (anti-carcinoembryonic antigen (CEA or CEACAM5, also known as CD66e)), Mu-9 (anti-colon-specific antigen-p), Immu-31 (an anti-alpha-fetoprotein), TAG-72 (e.g., CC49), Tn, J591 or HuJ591 (anti-PSMA (prostate-specific membrane antigen)), AB-PG1-XG1-026 (anti-PSMA dimer), D2/B (anti-PSMA), G250 (an anti-carbonic anhydrase IX MAb), hL243 (anti-HLA-DR), R1 (anti-IGF-1R), A20 (anti-CD20), A19 (anti-CD19), MN-3 or MN-15 (anti-CEACAM6), alemtuzumab (anti-CD52), bevacizumab (anti-VEGF), cetuximab (anti-EGFR), gemtuzumab (anti-CD33), ibritumomab tiuxetan (anti-CD20); panitumumab (anti-EGFR); rituximab (anti-CD20); tositumomab (anti-CD20); GA101 (anti-CD20); and trastuzumab (anti-ErbB2). Such antibodies are known in the art (e.g., U.S. Pat. Nos. 5,686,072; 5,874,540; 6,107,090; 6,183,744; 6,306, 393; 6,653,104; 6,730,300; 6,899,864; 6,926,893; 6,962,702; 7,074,403; 7,230,084; 7,238,785; 7,238,786; 7,256,004; 7,282,567; 7,300,655; 7,312,318; 7,585,491; 7,612,180; 7,642,239; and U.S. Patent Application Publ. No. 20040202666 (now abandoned); 20050271671; and 20060193865; the Examples section of each incorporated herein by reference.)

Specific known antibodies of use include, but are not limited to, hPAM4 (U.S. Pat. No. 7,282,567), hA20 (U.S. Pat. No. 7,251,164), hA19 (U.S. Pat. No. 7,109,304), hIMMU31 (U.S. Pat. No. 7,300,655), hLL1 (U.S. Pat. No. 7,312,318,), hLL2 (U.S. Pat. No. 7,074,403), hMu-9 (U.S. Pat. No. 7,387, 773), hL243 (U.S. Pat. No. 7,612,180), hMN-14 (U.S. Pat. No. 6,676,924), hMN-15 (U.S. Pat. No. 7,541,440), hR1 (U.S. patent application Ser. No. 12/689,336), hRS7 (U.S. Pat. No. 7,238,785), hMN-3 (U.S. Pat. No. 7,541,440), 15B8 (anti-CD40, U.S. Pat. No. 7,820,170), AB-PG1-XG1-026 (U.S. patent application Ser. No. 11/983,372, deposited as ATCC PTA-4405 and PTA-4406) and D2/B (WO 2009/ 130575). Other known antibodies are disclosed, for example, in U.S. Pat. Nos. 5,686,072; 5,874,540; 6,107,090; 6,183, 744; 6,306,393; 6,653,104; 6,730.300; 6,899,864; 6,926,893; 6,962,702; 7,074,403; 7,230,084; 7,238,785; 7,238,786; 7,256,004; 7,282,567; 7,300,655; 7,312,318; 7,585,491; 7,612,180; 7,642,239; and U.S. Patent Application Publ. No. 20040202666 (now abandoned); 20050271671; and 20060193865. The text of each recited patent or application is incorporated herein by reference with respect to the Figures and Examples sections.

Anti-TNF-α antibodies are known in the art and may be of use to treat immune diseases, such as autoimmune disease, immune dysfunction (e.g., graft-versus-host disease, organ transplant rejection) or diabetes. Known antibodies against TNF-α include the human antibody CDP571 (Ofei et al., 2011, Diabetes 45:881-85); murine antibodies MTNFAI, M2TNFAI, M3TNFAI, M3TNFABI, M302B and M303 (Thermo Scientific, Rockford, Ill.); infliximab (Centocor, Malvern, Pa.); certolizumab pegol (UCB, Brussels, Belgium); and adalimumab (Abbott, Abbott Park, Ill.). These and many other known anti-TNF-α antibodies may be used in the claimed methods and compositions. Other antibodies of use for therapy of immune dysregulatory or autoimmune disease include, but are not limited to, anti-B-cell antibodies such as veltuzumab, epratuzumab, milatuzumab or hL243; tocilizumab (anti-IL-6 receptor); basiliximab (anti-CD25); daclizumab (anti-CD25); efalizumab (anti-CD11a); GA101 (anti-CD20; Glycart Roche); muromonab-CD3 (anti-CD3 receptor); Benlysta (Human Genome Sciences); anti-CD40L (UCB, Brussels, Belgium); natalizumab (anti-α4 integrin) and omalizumab (anti-IgE).

Type-1 and Type-2 diabetes may be treated using known antibodies against B-cell antigens, such as CD22 (epratuzumab), CD74 (milatuzumab), CD19 (hA19), CD20 (veltuzumab) or HLA-DR (hL243) (see, e.g., Winer et al., 2011, Nature Med 17:610-18). Anti-CD3 antibodies also have been proposed for therapy of type 1 diabetes (Cernea et al., 2010, Diabetes Metab Rev 26:602-05).

Macrophage migration inhibitory factor (MIF) is an important regulator of innate and adaptive immunity and apoptosis. It has been reported that CD74 is the endogenous receptor for MIF (Leng et al., 2003, J Exp Med 197:1467-76). The therapeutic effect of antagonistic anti-CD74 antibodies on MIF-mediated intracellular pathways may be of use for treatment of a broad range of disease states, such as cancers of the bladder, prostate, breast, lung, colon and chronic lymphocytic leukemia (e.g., Meyer-Siegler et al., 2004, BMC Cancer 12:34; Shachar & Haran, 2011, Leuk Lymphoma 52:1446- 54); autoimmune diseases such as rheumatoid arthritis and systemic lupus erythematosus (Morand & Leech, 2005, Front Biosci 10:12-22; Shachar & Haran, 2011, Leuk Lymphoma 52:1446-54); kidney diseases such as renal allograft rejection (Lan, 2008, Nephron Exp Nephrol. 109:e79-83); and numerous inflammatory diseases (Meyer-Siegler et al., 2009, Mediators Inflamm epub Mar. 22, 2009; Takahashi et al., 2009, Respir Res 10:33; Milatuzumab (hLL1) is an exemplary anti-CD74 antibody of therapeutic use for treatment of MIF-mediated diseases.

Antibody Fragments

Antibody fragments which recognize specific epitopes can be generated by known techniques. The antibody fragments are antigen binding portions of an antibody, such as F(ab)$_2$, Fab', Fab, Fv, scFv and the like. Other antibody fragments include, but are not limited to, F(ab')$_2$ fragments which can be produced by pepsin digestion of the antibody molecule and Fab' fragments which can be generated by reducing disulfide bridges of the F(ab')$_2$ fragments. Alternatively, Fab' expression libraries can be constructed (Huse et al., 1989, Science, 246:1274-1281) to allow rapid and easy identification of monoclonal Fab' fragments with the desired specificity.

A single chain Fv molecule (scFv) comprises a VL domain and a VH domain. The VL and VH domains associate to form a target binding site. These two domains are further covalently linked by a peptide linker (L). Methods for making scFv molecules and designing suitable peptide linkers are disclosed in U.S. Pat. No. 4,704,692, U.S. Pat. No. 4,946,778, R. Raag and M. Whitlow, "Single Chain Fvs." FASEB Vol 9:73-80 (1995) and R. E. Bird and B. W. Walker, "Single Chain Antibody Variable Regions," TIBTECH, Vol 9: 132- 137 (1991).

An antibody fragment can be prepared by known methods, for example, as disclosed by Goldenberg, U.S. Pat. Nos.

4,036,945 and 4,331,647 and references contained therein. Also, see Nisonoff et al., Arch Biochem. Biophys. 89: 230 (1960); Porter, Biochem. J. 73: 119 (1959), Edelman et al., in METHODS IN ENZYMOLOGY VOL. 1, page 422 (Academic Press 1967), and Coligan at pages 2.8.1-2.8.10 and 2.10.-2.10.4.

A single complementarity-determining region (CDR) is a segment of the variable region of an antibody that is complementary in structure to the epitope to which the antibody binds and is more variable than the rest of the variable region. Accordingly, a CDR is sometimes referred to as hypervariable region. A variable region comprises three CDRs. CDR peptides can be obtained by constructing genes encoding the CDR of an antibody of interest. Such genes are prepared, for example, by using the polymerase chain reaction to synthesize the variable region from RNA of antibody-producing cells. (See, e.g., Larrick et al., Methods: A Companion to Methods in Enzymology 2: 106 (1991); Courtenay-Luck, "Genetic Manipulation of Monoclonal Antibodies," in MONOCLONAL ANTIBODIES: PRODUCTION, ENGINEERING AND CLINICAL APPLICATION, Ritter et al. (eds.), pages 166-179 (Cambridge University Press 1995); and Ward et al., "Genetic Manipulation and Expression of Antibodies," in MONOCLONAL ANTIBODIES: PRINCIPLES AND APPLICATIONS, Birch et al., (eds.), pages 137-185 (Wiley-Liss, Inc. 1995).

Another form of an antibody fragment is a single-domain antibody (dAb), sometimes referred to as a single chain antibody. Techniques for producing single-domain antibodies are well known in the art (see, e.g., Cossins et al., Protein Expression and Purification, 2007, 51:253-59; Shuntao et al., Molec Immunol 2006, 43:1912-19; Tanha et al., J. Biol. Chem. 2001, 276:24774-780). Single domain antibodies may be obtained, for example, from camels, alpacas or llamas by standard immunization techniques. (See, e.g., Muyldermans et al., TIBS 26:230-235, 2001; Yau et al., J Immunol Methods 281: 161-75, 2003; Maass et al., J Immunol Methods 324:13-25, 2007). They can have potent antigen-binding capacity and can interact with novel epitopes that are inaccessible to conventional $V_H$-$V_L$ pairs. (Muyldermans et al., 2001). Alpaca serum IgG contains about 50% camelid heavy chain only IgG antibodies (HCAbs) (Maass et al., 2007). Alpacas may be immunized with known antigens, such as TNF-α, and single domain antibodies can be isolated that bind to and neutralize the target antigen (Maass et al., 2007). PCR primers that amplify virtually all alpaca antibody coding sequences have been identified and may be used to construct single domain phage display libraries, which can be used for antibody fragment isolation by standard biopanning techniques well known in the art (Maass et al., 2007).

In certain embodiments, the sequences of antibodies or antibody fragments, such as the Fc portions of antibodies, may be varied to optimize their physiological characteristics, such as the half-life in serum. Methods of substituting amino acid sequences in proteins are widely known in the art, such as by site-directed mutagenesis (e.g. Sambrook et al., Molecular Cloning, A laboratory manual, $2^{nd}$ Ed, 1989). In preferred embodiments, the variation may involve the addition or removal of one or more glycosylation sites in the Fc sequence (e.g., U.S. Pat. No. 6,254,868, the Examples section of which is incorporated herein by reference). In other preferred embodiments, specific amino acid substitutions in the Fc sequence may be made (e.g., Hornick et al., 2000, J Nucl Med 41:355-62; Hinton et al., 2006, J Immunol 176:346-56; Petkova et al. 2006, Int Immunol 18:1759-69; U.S. Pat. No. 7,217,797).

Multispecific and Multivalent Antibodies

Various embodiments may concern use of multispecific and/or multivalent antibodies. For example, an anti-CD74 antibody or fragment thereof and an anti-CD20 antibody or fragment thereof may be joined together by means such as the dock-and-lock technique described above. Other combinations of antibodies or fragments thereof may be utilized. For example, the anti-CD74 antibody could be combined with another antibody against a different epitope of the same antigen, or alternatively with an antibody against another antigen, such as CD4, CD5, CD8, CD14, CD15, CD19, CD20, CD21, CD22, CD23, CD25, CD33, CD37, CD38, CD40, CD40L, CD46, CD52, CD54, CD74, CD80, CD126, CD138, B7, HM1.24, HLA-DR, an angiogenesis factor, tenascin, VEGF, PlGF, ED-B fibronectin, an oncogene, an oncogene product, NCA 66a-d, necrosis antigens, Ii (HLA-DR invariant chain), IL-2, T101, TAC, IL-6, MUC-1, TRAIL-R1 (DR4) or TRAIL-R2 (DR5).

Methods for producing bispecific antibodies include engineered recombinant antibodies which have additional cysteine residues so that they crosslink more strongly than the more common immunoglobulin isotypes. (See, e.g., FitzGerald et al, Protein Eng 10:1221-1225, 1997). Another approach is to engineer recombinant fusion proteins linking two or more different single-chain antibody or antibody fragment segments with the needed dual specificities. (See, e.g., Coloma et al., Nature Biotech. 15:159-163, 1997). A variety of bispecific antibodies can be produced using molecular engineering. In one form, the bispecific antibody may consist of, for example, a scFv with a single binding site for one antigen and a Fab fragment with a single binding site for a second antigen. In another form, the bispecific antibody may consist of, for example, an IgG with two binding sites for one antigen and two scFv with two binding sites for a second antigen.

Immunoconjugates

In certain embodiments, an antibody or antibody fragment may be directly attached to one or more therapeutic agents to form an immunoconjugate. Therapeutic agents may be attached, for example to reduced SH groups and/or to carbohydrate side chains. A therapeutic agent can be attached at the hinge region of a reduced antibody component via disulfide bond formation. Alternatively, such agents can be attached using a heterobifunctional cross-linker, such as N-succinyl 3-(2-pyridyldithio)propionate (SPDP). Yu et al., Int. J. Cancer 56: 244 (1994). General techniques for such conjugation are well-known in the art. See, for example, Wong, CHEMISTRY OF PROTEIN CONJUGATION AND CROSS-LINKING (CRC Press 1991); Upeslacis et al., "Modification of Antibodies by Chemical Methods," in MONOCLONAL ANTIBODIES: PRINCIPLES AND APPLICATIONS, Birch et al. (eds.), pages 187-230 (Wiley-Liss, Inc. 1995); Price, "Production and Characterization of Synthetic Peptide-Derived Antibodies," in MONOCLONAL ANTIBODIES: PRODUCTION, ENGINEERING AND CLINICAL APPLICATION, Ritter et al. (eds.), pages 60-84 (Cambridge University Press 1995). Alternatively, the therapeutic agent can be conjugated via a carbohydrate moiety in the Fc region of the antibody.

Methods for conjugating functional groups to antibodies via an antibody carbohydrate moiety are well-known to those of skill in the art. See, for example, Shih et al., Int. J. Cancer 41: 832 (1988); Shih et al., Int. J. Cancer 46: 1101 (1990); and Shih et al., U.S. Pat. No. 5,057,313, the Examples section of which is incorporated herein by reference. The general method involves reacting an antibody having an oxidized carbohydrate portion with a carrier polymer that has at least one free amine function. This reaction results in an initial Schiff base (imine) linkage, which can be stabilized by reduction to a secondary amine to form the final conjugate.

The Fc region may be absent if the antibody component of the immunoconjugate is an antibody fragment. However, it is possible to introduce a carbohydrate moiety into the light chain variable region of a full length antibody or antibody fragment. See, for example, Leung et al., *J. Immunol.* 154: 5919 (1995); U.S. Pat. Nos. 5,443,953 and 6,254,868, the Examples section of which is incorporated herein by reference. The engineered carbohydrate moiety is used to attach the therapeutic or diagnostic agent.

An alternative method for attaching therapeutic agents to an antibody or fragment involves use of click chemistry reactions. The click chemistry approach was originally conceived as a method to rapidly generate complex substances by joining small subunits together in a modular fashion. (See, e.g., Kolb et al., 2004, Angew Chem Int Ed 40:3004-31; Evans, 2007, Aust J Chem 60:384-95.) Various forms of click chemistry reaction are known in the art, such as the Huisgen 1,3-dipolar cycloaddition copper catalyzed reaction (Tornoe et al., 2002, J Organic Chem 67:3057-64), which is often referred to as the "click reaction." Other alternatives include cycloaddition reactions such as the Diels-Alder, nucleophilic substitution reactions (especially to small strained rings like epoxy and aziridine compounds), carbonyl chemistry formation of urea compounds and reactions involving carbon-carbon double bonds, such as alkynes in thiol-yne reactions.

The azide alkyne Huisgen cycloaddition reaction uses a copper catalyst in the presence of a reducing agent to catalyze the reaction of a terminal alkyne group attached to a first molecule. In the presence of a second molecule comprising an azide moiety, the azide reacts with the activated alkyne to form a 1,4-disubstituted 1,2,3-triazole. The copper catalyzed reaction occurs at room temperature and is sufficiently specific that purification of the reaction product is often not required. (Rostovstev et al., 2002, Angew Chem Int Ed 41:2596; Tornoe et al., 2002, J Org Chem 67:3057.) The azide and alkyne functional groups are largely inert towards biomolecules in aqueous medium, allowing the reaction to occur in complex solutions. The triazole formed is chemically stable and is not subject to enzymatic cleavage, making the click chemistry product highly stable in biological systems. Although the copper catalyst is toxic to living cells, the copper-based click chemistry reaction may be used in vitro for immunoconjugate formation.

A copper-free click reaction has been proposed for covalent modification of biomolecules. (See, e.g., Agard et al., 2004, J Am Chem Soc 126:15046-47.) The copper-free reaction uses ring strain in place of the copper catalyst to promote a [3+2] azide-alkyne cycloaddition reaction (Id.) For example, cyclooctyne is an 8-carbon ring structure comprising an internal alkyne bond. The closed ring structure induces a substantial bond angle deformation of the acetylene, which is highly reactive with azide groups to form a triazole. Thus, cyclooctyne derivatives may be used for copper-free click reactions (Id.)

Another type of copper-free click reaction was reported by Ning et al. (2010, Angew Chem Int Ed 49:3065-68), involving strain-promoted alkyne-nitrone cycloaddition. To address the slow rate of the original cyclooctyne reaction, electron-withdrawing groups are attached adjacent to the triple bond (Id.) Examples of such substituted cyclooctynes include difluorinated cyclooctynes, 4-dibenzocyclooctynol and azacyclooctyne (Id.) An alternative copper-free reaction involved strain-promoted akyne-nitrone cycloaddition to give N-alkylated isoxazolines (Id.) The reaction was reported to have exceptionally fast reaction kinetics and was used in a one-pot three-step protocol for site-specific modification of peptides and proteins (Id.) Nitrones were prepared by the condensation of appropriate aldehydes with N-methylhydroxylamine and the cycloaddition reaction took place in a mixture of acetonitrile and water (Id.) These and other known click chemistry reactions may be used to attach therapeutic agents to antibodies in vitro.

The specificity of the click chemistry reaction may be used as a substitute for the antibody-hapten binding interaction used in pretargeting with bispecific antibodies. In this alternative embodiment, the specific reactivity of e.g., cyclooctyne moieties for azide moieties or alkyne moieties for nitrone moieties may be used in an in vivo cycloaddition reaction. An antibody, antibody fragment or antibody-based complex is activated by incorporation of a substituted cyclooctyne, an azide or a nitrone moiety. A targetable construct is labeled with one or more diagnostic or therapeutic agents and a complementary reactive moiety. I.e., where the antibody comprises a cyclooctyne, the targetable construct will comprise an azide; where the antibody comprises a nitrone, the targetable construct will comprise an alkyne, etc. The activated antibody or fragment is administered to a subject and allowed to localize to a targeted cell, tissue or pathogen, as disclosed for pretargeting protocols. The reactive labeled targetable construct is then administered. Because the cyclooctyne, nitrone or azide on the targetable construct is unreactive with endogenous biomolecules and highly reactive with the complementary moiety on the antibody, the specificity of the binding interaction results in the highly specific binding of the targetable construct to the tissue-localized antibody.

Therapeutic Agents

A wide variety of therapeutic reagents can be administered concurrently or sequentially with the subject anti-CD74 antibodies or antibody combinations. For example, drugs, toxins, oligonucleotides, immunomodulators, cytokine or chemokine inhibitors, proapoptotic agents, tyrosine kinase inhibitors, sphingosine inhibitors, hormones, hormone antagonists, enzymes, enzyme inhibitors, radionuclides, angiogenesis inhibitors, other antibodies or fragments thereof, etc. The therapeutic agents recited here are those agents that also are useful for administration separately with an antibody or fragment thereof as described above. Therapeutic agents include, for example, cytotoxic agents such as vinca alkaloids, anthracyclines, gemcitabine, epipodophyllotoxins, taxanes, antimetabolites, alkylating agents, antibiotics, SN-38, COX-2 inhibitors, antimitotics, anti-angiogenic and pro-apoptotic agents, particularly doxorubicin, methotrexate, taxol, CPT-11, camptothecans, proteosome inhibitors, mTOR inhibitors, HDAC inhibitors, tyrosine kinase inhibitors, and others.

Other useful cytotoxic agents include nitrogen mustards, alkyl sulfonates, nitrosoureas, triazenes, folic acid analogs, COX-2 inhibitors, antimetabolites, pyrimidine analogs, purine analogs, platinum coordination complexes, mTOR inhibitors, tyrosine kinase inhibitors, proteosome inhibitors, HDAC inhibitors, camptothecins, hormones, and the like. Suitable cytotoxic agents are described in REMINGTON'S PHARMACEUTICAL SCIENCES, 19th Ed. (Mack Publishing Co. 1995), and in GOODMAN AND GILMAN'S THE PHARMACOLOGICAL BASIS OF THERAPEUTICS, 7th Ed. (MacMillan Publishing Co. 1985), as well as revised editions of these publications.

In a preferred embodiment, conjugates of camptothecins and related compounds, such as SN-38, may be conjugated to an antibody, for example as disclosed in U.S. Pat. No. 7,591, 994, the Examples section of which is incorporated herein by reference.

The therapeutic agent may be selected from the group consisting of aplidin, azaribine, anastrozole, azacytidine, bleomycin, bortezomib, bryostatin-1, busulfan, calicheamycin, camptothecin, 10-hydroxycamptothecin, carmustine, celebrex, chlorambucil, cisplatin, irinotecan (CPT-11), SN-38, carboplatin, cladribine, cyclophosphamide, cytarabine, dacarbazine, docetaxel, dactinomycin, daunomycin glucuronide, daunorubicin, dexamethasone, diethylstilbestrol, doxorubicin, doxorubicin glucuronide, epirubicin glucuronide, ethinyl estradiol, estramustine, etoposide, etoposide glucuronide, etoposide phosphate, floxuridine (FUdR), 3',5'-O-dioleoyl-FudR (FUdR-dO), fludarabine, flutamide, fluorouracil, fluoxymesterone, gemcitabine, hydroxyprogesterone caproate, hydroxyurea, idarubicin, ifosfamide, L-asparaginase, leucovorin, lomustine, mechlorethamine, medroprogesterone acetate, egestrol acetate, melphalan, mercaptopurine, 6-mercaptopurine, methotrexate, mitoxantrone, mithramycin, mitomycin, mitotane, phenyl butyrate, prednisone, procarbazine, paclitaxel, pentostatin, PSI-341, semustine streptozocin, tamoxifen, taxanes, taxol, testosterone propionate, thalidomide, thioguanine, thiotepa, teniposide, topotecan, uracil mustard, velcade, vinblastine, vinorelbine, vincristine, ricin, abrin, ribonuclease, onconase, rapLR1, DNase I, Staphylococcal enterotoxin-A, pokeweed antiviral protein, gelonin, diphtheria toxin, *Pseudomonas* exotoxin, and *Pseudomonas* endotoxin.

A toxin can be of animal, plant or microbial origin. A toxin, such as *Pseudomonas* exotoxin, may also be complexed to or form the therapeutic agent portion of an immunoconjugate. Other toxins include ricin, abrin, ribonuclease (RNase), DNase I, Staphylococcal enterotoxin-A, pokeweed antiviral protein, onconase, gelonin, diphtheria toxin, *Pseudomonas* exotoxin, and *Pseudomonas* endotoxin. See, for example, Pastan et al., Cell 47:641 (1986), Goldenberg, C A—A Cancer Journal for Clinicians 44:43 (1994), Sharkey and Goldenberg, CA—A Cancer Journal for Clinicians 56:226 (2006). Additional toxins suitable for use are known to those of skill in the art and are disclosed in U.S. Pat. No. 6,077,499, the Examples section of which is incorporated herein by reference.

The therapeutic agent may be an enzyme selected from the group consisting of malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase.

As used herein, the term "immunomodulator" includes cytokines, lymphokines, monokines, stem cell growth factors, lymphotoxins, hematopoietic factors, colony stimulating factors (CSF), interferons (IFN), parathyroid hormone, thyroxine, insulin, proinsulin, relaxin, prorelaxin, follicle stimulating hormone (FSH), thyroid stimulating hormone (TSH), luteinizing hormone (LH), hepatic growth factor, prostaglandin, fibroblast growth factor, prolactin, placental lactogen, OB protein, transforming growth factor (TGF), TGF-α, TGF-β, insulin-like growth factor (IGF), erythropoietin, thrombopoietin, tumor necrosis factor (TNF), TNF-α, TNF-β, mullerian-inhibiting substance, mouse gonadotropin-associated peptide, inhibin, activin, vascular endothelial growth factor, integrin, interleukin (IL), granulocyte-colony stimulating factor (G-CSF), granulocyte macrophage-colony stimulating factor (GM-CSF), interferon-α, interferon-β, interferon-γ, S1 factor, IL-1, IL-1cc, IL-2, IL-3, IL-4, IL-5, IL-6, IL-7, IL-8, IL-9, IL-10, IL-11, IL-12, IL-13, IL-14, IL-15, IL-16, IL-17, IL-18 IL-21, IL-23, IL-25, LIF, kit-ligand, FLT-3, angiostatin, thrombospondin, endostatin, and the like.

Exemplary anti-angiogenic agents may include angiostatin, endostatin, vasculostatin, canstatin, maspin, anti-VEGF binding molecules, anti-placental growth factor binding molecules, or anti-vascular growth factor binding molecules.

In certain embodiments, the antibody or complex may comprise one or more chelating moieties, such as NOTA, DOTA, DTPA, TETA, Tscg-Cys, or Tsca-Cys. In certain embodiments, the chelating moiety may form a complex with a therapeutic or diagnostic cation, such as Group II, Group III, Group IV, Group V, transition, lanthanide or actinide metal cations, Tc, Re, Bi, Cu, As, Ag, Au, At, or Pb.

The antibody or fragment thereof may be administered as an immunoconjugate comprising one or more radioactive isotopes useful for treating diseased tissue. Particularly useful therapeutic radionuclides include, but are not limited to $^{111}$In, $^{177}$Lu, $^{212}$Bi, $^{213}$Bi, $^{211}$At, $^{62}$Cu, $^{64}$Cu, $^{67}$Cu, $^{90}$Y, $^{125}$I, $^{131}$I, $^{32}$P, $^{33}$P, $^{47}$Sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{199}$Au, and $^{211}$Pb. The therapeutic radionuclide preferably has a decay energy in the range of 20 to 6,000 keV, preferably in the ranges 60 to 200 keV for an Auger emitter, 100-2,500 keV for a beta emitter and 4,000-6,000 keV for an alpha emitter. Maximum decay energies of useful beta-particle-emitting nuclides are preferably 20-5,000 keV, more preferably 100-4,000 keV and most preferably 500-2,500 keV. Also preferred are radionuclides that substantially decay with Auger-emitting particles. For example, Co-58, Ga-67, Br-80m, Tc-99m, Rh-103m, Pt-109, In-111, Sb-119, I-125, Ho-161, Os-189m and Ir-192. Decay energies of useful beta-particle-emitting nuclides are preferably <1,000 keV, more preferably <100 keV, and most preferably <70 keV. Also preferred are radionuclides that substantially decay with generation of alpha-particles. Such radionuclides include, but are not limited to: Dy-152, At-211, Bi-212, Ra-223, Rn-219, Po-215, Bi-211, Ac-225, Fr-221, At-217, Bi-213 and Fm-255. Decay energies of useful alpha-particle-emitting radionuclides are preferably 2,000-10,000 keV, more preferably 3,000-8,000 keV, and most preferably 4,000-7,000 keV.

Additional potential therapeutic radioisotopes include $^{11}$C, $^{13}$N, $^{15}$O, $^{75}$Br, $^{198}$Au, $^{224}$Ac, $^{126}$I, $^{133}$I, $^{77}$Br, $^{113m}$In, $^{95}$Ru, $^{97}$Ru, $^{103}$Ru, $^{105}$Ru, $^{107}$Hg, $^{203}$Hg, $^{121m}$Te, $^{122m}$Te, $^{125m}$Te, $^{165}$Tm, $^{167}$T, $^{168}$Tm, $^{197}$Pt, $^{109}$Pd, $^{105}$Rh, $^{142}$Pr, $^{143}$Pr, $^{161}$Tb, $^{166}$Ho, $^{199}$Au, $^{57}$Co, $^{58}$Co, $^{51}$Cr, $^{59}$Fe, $^{75}$Se, $^{201}$Tl, $^{225}$Ac, $^{76}$Br, $^{169}$Yb, and the like.

Interference RNA

In certain preferred embodiments the therapeutic agent may be a siRNA or interference RNA species. The siRNA, interference RNA or therapeutic gene may be attached to a carrier moiety that is conjugated to an antibody or fragment thereof. A variety of carrier moieties for siRNA have been reported and any such known carrier may be incorporated into a therapeutic antibody for use. Non-limiting examples of carriers include protamine (Rossi, 2005, Nat Biotech 23:682-84; Song et al., 2005, Nat Biotech 23:709-17); dendrimers such as PAMAM dendrimers (Pan et al., 2007, Cancer Res. 67:8156-8163); polyethylenimine (Schiffelers et al., 2004, Nucl Acids Res 32:e149); polypropyleneimine (Taratula et al., 2009, J Control Release 140:284-93); polylysine (Inoue et al., 2008, J Control Release 126:59-66); histidine-containing reducible polycations (Stevenson et al., 2008, J Control Release 130:46-56); histone H1 protein (Haberland et al., 2009, Mol Biol Rep 26:1083-93); cationic comb-type copolymers (Sato et al., 2007, J Control Release 122:209-16);

polymeric micelles (U.S. Patent Application Publ. No. 20100121043); and chitosan-thiamine pyrophosphate (Rojanarata et al., 2008, Pharm Res 25:2807-14). The skilled artisan will realize that in general, polycationic proteins or polymers are of use as siRNA carriers. The skilled artisan will further realize that siRNA carriers can also be used to carry other oligonucleotide or nucleic acid species, such as antisense oligonucleotides or short DNA genes.

Known siRNA species of potential use include those specific for IKK-gamma (U.S. Pat. No. 7,022,828); VEGF, Flt-1 and Flk-1/KDR (U.S. Pat. No. 7,148,342); Bcl2 and EGFR (U.S. Pat. No. 7,541,453); CDC20 (U.S. Pat. No. 7,550,572); transducin (beta)-like 3 (U.S. Pat. No. 7,576,196); K-ras (U.S. Pat. No. 7,576,197); carbonic anhydrase II (U.S. Pat. No. 7,579,457); complement component 3 (U.S. Pat. No. 7,582,746); interleukin-1 receptor-associated kinase 4 (IRAK4) (U.S. Pat. No. 7,592,443); survivin (U.S. Pat. No. 7,608,7070); superoxide dismutase 1 (U.S. Pat. No. 7,632,938); MET proto-oncogene (U.S. Pat. No. 7,632,939); amyloid beta precursor protein (APP) (U.S. Pat. No. 7,635,771); IGF-1R (U.S. Pat. No. 7,638,621); ICAM1 (U.S. Pat. No. 7,642,349); complement factor B (U.S. Pat. No. 7,696,344); p53 (U.S. Pat. No. 7,781,575), and apolipoprotein B (U.S. Pat. No. 7,795,421), the Examples section of each referenced patent incorporated herein by reference.

Additional siRNA species are available from known commercial sources, such as Sigma-Aldrich (St Louis, Mo.), Invitrogen (Carlsbad, Calif.), Santa Cruz Biotechnology (Santa Cruz, Calif.), Ambion (Austin, Tex.), Dharmacon (Thermo Scientific, Lafayette, Colo.), Promega (Madison, Wis.), Minis Bio (Madison, Wis.) and Qiagen (Valencia, Calif.), among many others. Other publicly available sources of siRNA species include the siRNAdb database at the Stockholm Bioinformatics Centre, the MIT/ICBP siRNA Database, the RNAi Consortium shRNA Library at the Broad Institute, and the Probe database at NCBI. For example, there are 30,852 siRNA species in the NCBI Probe database. The skilled artisan will realize that for any gene of interest, either a siRNA species has already been designed, or one may readily be designed using publicly available software tools. Any such siRNA species may be delivered using the subject antibodies, antibody fragments or antibody complexes.

Exemplary siRNA species known in the art are listed in Table 6. Although siRNA is delivered as a double-stranded molecule, for simplicity only the sense strand sequences are shown in Table 6.

TABLE 6

Exemplary siRNA Sequences

| Target | Sequence | SEQ ID NO |
|---|---|---|
| VEGF R2 | AATGCGGCGGTGGTGACAGTA | SEQ ID NO: 109 |
| VEGF R2 | AAGCTCAGCACACAGAAAGAC | SEQ ID NO: 110 |
| CXCR4 | UAAAAUCUUCCUGCCCACCdTdT | SEQ ID NO: 111 |
| CXCR4 | GGAAGCUGUUGGCUGAAAAdTdT | SEQ ID NO: 112 |
| PPARC1 | AAGACCAGCCUCUUUGCCCAG | SEQ ID NO: 113 |
| Dynamin 2 | GGACCAGGCAGAAAACGAG | SEQ ID NO: 114 |
| Catenin | CUAUCAGGAUGACGCGG | SEQ ID NO: 115 |
| E1A binding protein | UGACACAGGCAGGCUUGACUU | SEQ ID NO: 116 |
| Plasminogen activator | GGTGAAGAAGGGCGTCCAA | SEQ ID NO: 117 |
| K-ras | GATCCGTTGGAGCTGTTGGCGTAGTT CAAGAGACTCGCCAACAGCTCCAACT TTTGGAAA | SEQ ID NO: 118 |
| Sortilin 1 | AGGTGGTGTTAACAGCAGAG | SEQ ID NO: 119 |
| Apolipoprotein E | AAGGTGGAGCAAGCGGTGGAG | SEQ ID NO: 120 |
| Apolipoprotein E | AAGGAGTTGAAGGCCGACAAA | SEQ ID NO: 121 |
| Bcl-X | UAUGGAGCUGCAGAGGAUGdTdT | SEQ ID NO: 122 |
| Raf-1 | TTTGAATATCTGTGCTGAGAACACA GTTCTCAGCACAGATATTCTTTTT | SEQ ID NO: 123 |
| Heat shock transcription factor 2 | AATGAGAAAAGCAAAAGGTGCCCTGTCTC | SEQ ID NO: 124 |
| IGFBP3 | AAUCAUCAUCAAGAAAGGGCA | SEQ ID NO: 125 |
| Thioredoxin | AUGACUGUCAGGAUGUUGCdTdT | SEQ ID NO: 126 |
| CD44 | GAACGAAUCCUGAAGACAUCU | SEQ ID NO: 127 |
| MMP14 | AAGCCTGGCTACAGCAATATGCCTGTCTC | SEQ ID NO: 128 |
| MAPKAPK2 | UGACCAUCACCGAGUUUAUdTdT | SEQ ID NO: 129 |

TABLE 6-continued

Exemplary siRNA Sequences

| Target | Sequence | SEQ ID NO |
|---|---|---|
| FGFR1 | AAGTCGGACGCAACAGAGAAA | SEQ ID NO: 130 |
| ERBB2 | CUACCUUUCUACGGACGUGdTdT | SEQ ID NO: 131 |
| BCL2L1 | CTGCCTAAGGCGGATTTGAAT | SEQ ID NO: 132 |
| ABL1 | TTAUUCCUUCUUCGGGAAGUC | SEQ ID NO: 133 |
| CEACAM1 | AACCTTCTGGAACCCGCCCAC | SEQ ID NO: 134 |
| CD9 | GAGCATCTTCGAGCAAGAA | SEQ ID NO: 135 |
| CD151 | CATGTGGCACCGTTTGCCT | SEQ ID NO: 136 |
| Caspase 8 | AACTACCAGAAAGGTATACCT | SEQ ID NO: 137 |
| BRCA1 | UCACAGUGUCCUUUAUGUAdTdT | SEQ ID NO: 138 |
| p53 | GCAUGAACCGGAGGCCCAUTT | SEQ ID NO: 139 |
| CEACAM6 | CCGGACAGTTCCATGTATA | SEQ ID NO: 140 |

The skilled artisan will realize that Table 6 represents a very small sampling of the total number of siRNA species known in the art, and that any such known siRNA may be utilized in the claimed methods and compositions.

Immunotoxins Comprising Ranpirnase (Rap)

Ribonucleases, in particular, Rap (Lee, Exp Opin Biol Ther 2008; 8:813-27) and its more basic variant, amphinase (Ardelt et al., Curr Pharm Biotechnol 2008:9:215-25), are potential anti-tumor agents (Lee and Raines, Biodrugs 2008; 22:53-8). Rap is a single-chain ribonuclease of 104 amino acids originally isolated from the oocytes of *Rana pipiens*. Rap exhibits cytostatic and cytotoxic effects on a variety of tumor cell lines in vitro, as well as antitumor activity in vivo. The amphibian ribonuclease enters cells via receptor-mediated endocytosis and once internalized into the cytosol, selectively degrades tRNA, resulting in inhibition of protein synthesis and induction of apoptosis.

Rap has completed a randomized Phase Mb clinical trial, which compared the effectiveness of Rap plus doxorubicin with that of doxorubicin alone in patients with unrespectable malignant mesothelioma, with the interim analysis showing that the MST for the combination was 12 months, while that of the monotherapy was 10 months (Mutti and Gaudino, Oncol Rev 2008; 2:61-5). Rap can be administered repeatedly to patients without an untoward immune response, with reversible renal toxicity reported to be dose-limiting (Mikulski et al., J Clin Oncol 2002; 20:274-81; Int J Oncol 1993; 3:57-64).

Conjugation or fusion of Rap to a tumor-targeting antibody or antibody fragment is a promising approach to enhance its potency, as first demonstrated for LL2-onconase (Newton et al., Blood 2001; 97:528-35), a chemical conjugate comprising Rap and a murine anti-CD22 monoclonal antibody (MAb), and subsequently for 2L-Rap-hLL1-γ4P, a fusion protein comprising Rap and a humanized anti-CD74 MAb (Stein et al., Blood 2004; 104:3705-11).

The method used to generate 2L-Rap-hLL1-γ4P allowed us to develop a series of structurally similar immunotoxins, referred to in general as 2L-Rap-X, all of which consist of two Rap molecules, each connected via a flexible linker to the N-terminus of one L chain of an antibody of interest (X). We have also generated another series of immunotoxins of the same design, referred to as 2LRap(Q)-X, by substituting Rap with its non-glycosylation form of Rap, designated as Rap(Q) to denote that the potential glycosylation site at Asn69 is changed to Gln (or Q, single letter code). For both series, we made the IgG as either IgG1(γ1) or IgG4(γ4), and to prevent the formation of IgG4 half molecules (Aalberse and Schuurman, Immunology 2002; 105:9-19), we converted the serine residue in the hinge region (S228) of IgG4 to proline (γ4P). A pyroglutamate residue at the N-terminus of Rap is required for the RNase to be fully functional (Liao et al., Nucleic Acids Res 2003; 31:5247-55).

The skilled artisan will recognize that the cytotoxic RNase moieties suitable for use in the present invention include polypeptides having a native ranpirnase structure and all enzymatically active variants thereof. These molecules advantageously have an N-terminal pyroglutamic acid resides that appears essential for RNase activity and are not substantially inhibited by mammalian RNase inhibitors. Nucleic acid that encodes a native cytotoxic RNase may be prepared by cloning and restriction of appropriate sequences, or using DNA amplification with polymerase chain reaction (PCR). The amino acid sequence of *Rana pipiens* ranpirnase can be obtained from Ardelt et al., J. Biol. Chem., 256: 245 (1991), and cDNA sequences encoding native ranpirnase, or a conservatively modified variation thereof, can be gene-synthesized by methods similar to the en bloc V-gene assembly method used in hLL2 humanization. (Leung et al., Mol. Immunol., 32: 1413, 1995). Methods of making cytotoxic RNase variants are known in the art and are within the skill of the routineer.

As described in the Examples below, Rap conjugates of targeting antibodies may be made using the DNL technology. The DNL Rap-antibody constructs show potent cytotoxic activity that can be targeted to disease-associated cells.

Diagnostic Agents

In various embodiments, the antibodies, antibody fragments or antibody complexes may be conjugated to, or may bind a targetable construct comprising one or more diagnostic agents. Diagnostic agents are preferably selected from the group consisting of a radionuclide, a radiological contrast agent, a paramagnetic ion, a metal, a fluorescent label, a chemiluminescent label, an ultrasound contrast agent and a photoactive agent. Such diagnostic agents are well known and any such known diagnostic agent may be used. Non-limiting examples of diagnostic agents may include a radionuclide such as $^{18}$F, $^{52}$Fe, $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94m}$Te, $^{94}$Tc, $^{99m}$Tc, $^{120}$I, $^{123}$I, $^{124}$I, $^{125}$I, $^{131}$I, $^{154-158}$Gd, $^{32}$P, $^{11}$C, $^{13}$N, $^{15}$O, $^{186}$Re, $^{188}$Re, $^{51}$Mn, $^{52m}$Mn, $^{55}$Co, $^{72}$As, $^{75}$Br, $^{76}$Br, $^{82m}$Rb, $^{86}$Sr, or other gamma-, beta-, or positron-emitters.

Paramagnetic ions of use may include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) or erbium (III). Metal contrast agents may include lanthanum (III), gold (III), lead (II) or bismuth (III).

Ultrasound contrast agents may comprise liposomes, such as gas filled liposomes. Radiopaque diagnostic agents may be selected from compounds, barium compounds, gallium compounds, and thallium compounds. A wide variety of fluorescent labels are known in the art, including but not limited to fluorescein isothiocyanate, rhodamine, phycoerytherin, phycocyanin, allophycocyanin, o-phthaldehyde and fluorescamine. Chemiluminescent labels of use may include luminol, isoluminol, an aromatic acridinium ester, an imidazole, an acridinium salt or an oxalate ester.

Methods of Therapeutic Treatment

The claimed methods and compositions are of use for treating disease states, such as B-cell lymphomas or leukemias, autoimmune disease or immune system dysfunction (e.g., graft-versus-host disease). The methods may comprise administering a therapeutically effective amount of an anti-CD74 antibody or fragment thereof or immunoconjugate, either alone or in combination with one or more other therapeutic agents, administered either concurrently or sequentially. In preferred embodiments, as described in the Examples below, the anti-CD74 antibody or fragment thereof may be administered in the form of a DNL complex in combination with one or more other therapeutic agents, such as a second antibody or fragment thereof.

Multimodal therapies may include therapy with other antibodies, such as antibodies against CD4, CD5, CD8, CD14, CD15, CD19, CD20, CD21, CD22, CD23, CD25, CD33, CD37, CD38, CD40, CD40L, CD46, CD52, CD54, CD74, CD80, CD126, CD138, CXCR4, B7, HM1.24, HLA-DR, an angiogenesis factor, tenascin, VEGF, PlGF, ED-B fibronectin, an oncogene, an oncogene product, NCA 66a-d, necrosis antigens, Ii, IL-2, T101, TAC, IL-6, MUC-1, TRAIL-R1 (DR4) or TRAIL-R2 (DR5) in the form of naked antibodies, fusion proteins, or as immunoconjugates. Various antibodies of use are known to those of skill in the art. See, for example, Ghetie et al., *Cancer Res.* 48:2610 (1988); Hekman et al., *Cancer Immunol. Immunother.* 32:364 (1991); Longo, *Curr. Opin. Oncol.* 8:353 (1996), U.S. Pat. Nos. 5,798,554; 6,187, 287; 6,306,393; 6,676,924; 7,109,304; 7,151,164; 7,230,084; 7,230,085; 7,238,785; 7,238,786; 7,282,567; 7,300,655; 7,312,318; 7,612,180; 7,501,498; the Examples section of each of which is incorporated herein by reference.

In another form of multimodal therapy, subjects may receive therapeutic anti-CD74 antibodies or antibody combinations in conjunction with standard chemotherapy. For example, "CVB" (1.5 g/m$^2$ cyclophosphamide, 200-400 mg/m$^2$ etoposide, and 150-200 mg/m$^2$ carmustine) is a regimen used to treat non-Hodgkin's lymphoma. Patti et al., *Eur. J. Haematol.* 51: 18 (1993). Other suitable combination chemotherapeutic regimens are well-known to those of skill in the art. See, for example, Freedman et al., "Non-Hodgkin's Lymphomas," in CANCER MEDICINE, VOLUME 2, 3rd Edition, Holland et al. (eds.), pages 2028-2068 (Lea & Febiger 1993). As an illustration, first generation chemotherapeutic regimens for treatment of intermediate-grade non-Hodgkin's lymphoma (NHL) include C-MOPP (cyclophosphamide, vincristine, procarbazine and prednisone) and CHOP (cyclophosphamide, doxorubicin, vincristine, and prednisone). A useful second generation chemotherapeutic regimen is m-BACOD (methotrexate, bleomycin, doxorubicin, cyclophosphamide, vincristine, dexamethasone and leucovorin), while a suitable third generation regimen is MACOP-B (methotrexate, doxorubicin, cyclophosphamide, vincristine, prednisone, bleomycin and leucovorin). Additional useful drugs include phenyl butyrate, bendamustine, and bryostatin-1.

Therapeutic antibodies or complexes, such as DNL complexes, can be formulated according to known methods to prepare pharmaceutically useful compositions, whereby the therapeutic antibody complex is combined in a mixture with a pharmaceutically suitable excipient. Sterile phosphate-buffered saline is one example of a pharmaceutically suitable excipient. Other suitable excipients are well-known to those in the art. See, for example, Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The therapeutic antibody complex can be formulated for intravenous administration via, for example, bolus injection or continuous infusion. Preferably, the therapeutic antibody complex is infused over a period of less than about 4 hours, and more preferably, over a period of less than about 3 hours. For example, the first 25-50 mg could be infused within 30 minutes, preferably even 15 min, and the remainder infused over the next 2-3 hrs. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The therapeutic antibody complex may also be administered to a mammal subcutaneously or even by other parenteral routes. Moreover, the administration may be by continuous infusion or by single or multiple boluses. In most preferred embodiments, the therapeutic antibody or combination is administered subcutaneously in a volume of 1, 2 or 3 ml and at a concentration of at least 80 mg/ml, at least 100 mg/ml, at least 125 mg/ml, at least 150 mg/ml, at least 200 mg/ml, at least 250 mg/ml or at least 300 mg/ml. Methods of antibody concentration and subcutaneous formulations are disclosed in provisional U.S. Patent No. 61/509,850, filed Jul. 20, 2011, the Examples section of which (from paragraph 0133, page 48 to paragraph 0195, page 64) is incorporated herein by reference.

More generally, the dosage of an administered therapeutic antibody complex for humans will vary depending upon such factors as the patient's age, weight, height, sex, general medical condition and previous medical history. It may be desirable to provide the recipient with a dosage of therapeutic antibody complex that is in the range of from about 1 mg/kg to 25 mg/kg as a single intravenous infusion, although a lower or higher dosage also may be administered as circumstances dictate. A dosage of 1-20 mg/kg for a 70 kg patient, for example, is 70-1,400 mg, or 41-824 mg/m$^2$ for a 1.7-m patient. The dosage may be repeated as needed, for example, once per week for 4-10 weeks, once per week for 8 weeks, or once per week for 4 weeks. It may also be given less frequently, such as every other week for several months, or monthly or quarterly for many months, as needed in a maintenance therapy.

Alternatively, a therapeutic antibody complex may be administered as one dosage every 2 or 3 weeks, repeated for a total of at least 3 dosages. Or, the therapeutic antibody complex may be administered twice per week for 4-6 weeks. If the dosage is lowered to approximately 200-300 mg/m$^2$ (340 mg per dosage for a 1.7-m patient, or 4.9 mg/kg for a 70 kg patient), it may be administered once or even twice weekly for 4 to 10 weeks. Alternatively, the dosage schedule may be decreased, namely every 2 or 3 weeks for 2-3 months. It has been determined, however, that even higher doses, such as 20 mg/kg once weekly or once every 2-3 weeks can be administered by slow i.v. infusion, for repeated dosing cycles. The dosing schedule can optionally be repeated at other intervals and dosage may be given through various parenteral routes, with appropriate adjustment of the dose and schedule.

Additional pharmaceutical methods may be employed to control the duration of action of the therapeutic immunoconjugate or naked antibody. Control release preparations can be prepared through the use of polymers to complex or adsorb the antibody. For example, biocompatible polymers include matrices of poly(ethylene-co-vinyl acetate) and matrices of a polyanhydride copolymer of a stearic acid dimer and sebacic acid. Sherwood et al., Bio/Technology 10: 1446 (1992). The rate of release of an antibody from such a matrix depends upon the molecular weight of the antibody, the amount of antibody within the matrix, and the size of dispersed particles. Saltzman et al., Biophys. J. 55: 163 (1989); Sherwood et al., supra. Other solid dosage forms are described in Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

Cancer Therapy

In preferred embodiments, the anti-CD74 antibodies, combinations or complexes are of use for therapy of cancer. Examples of cancers include, but are not limited to, carcinoma, lymphoma, glioblastoma, melanoma, sarcoma, and leukemia, myeloma, or lymphoid malignancies. More particular examples of such cancers are noted below and include: squamous cell cancer (e.g., epithelial squamous cell cancer), Ewing sarcoma, Wilms tumor, astrocytomas, lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma multiforme, cervical cancer, ovarian cancer, liver cancer, bladder cancer, hepatoma, hepatocellular carcinoma, neuroendocrine tumors, medullary thyroid cancer, differentiated thyroid carcinoma, breast cancer, ovarian cancer, colon cancer, rectal cancer, endometrial cancer or uterine carcinoma, salivary gland carcinoma, kidney or renal cancer, prostate cancer, vulvar cancer, anal carcinoma, penile carcinoma, as well as head-and-neck cancer. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor).

Other examples of cancers or malignancies include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumors, Exocrine Pancreatic Cancer, Extracranial Germ Cell Tumor, Extragonadal Germ Cell Tumor, Extrahepatic Bile Duct Cancer, Eye Cancer, Female Breast Cancer, Gaucher's Disease, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Polycythemia vera, Parathyroid Cancer, Penile Cancer, Pheochromocytoma, Pituitary Tumor, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's Macroglobulinemia, Wilms' Tumor, and any other hyperproliferative disease, besides neoplasia, located in an organ system listed above.

The methods and compositions described and claimed herein may be used to treat malignant or premalignant conditions and to prevent progression to a neoplastic or malignant state, including but not limited to those disorders described above. Such uses are indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, Basic Pathology, 2d Ed., W. B. Saunders Co., Philadelphia, pp. 68-79 (1976)).

Dysplasia is frequently a forerunner of cancer, and is found mainly in the epithelia. It is the most disorderly form of non-neoplastic cell growth, involving a loss in individual cell uniformity and in the architectural orientation of cells. Dysplasia characteristically occurs where there exists chronic irritation or inflammation. Dysplastic disorders which can be treated include, but are not limited to, anhidrotic ectodermal dysplasia, anterofacial dysplasia, asphyxiating thoracic dysplasia, atriodigital dysplasia, bronchopulmonary dysplasia, cerebral dysplasia, cervical dysplasia, chondroectodermal dysplasia, cleidocranial dysplasia, congenital ectodermal dysplasia, craniodiaphysial dysplasia, craniocarpotarsal dysplasia, craniometaphysial dysplasia, dentin dysplasia, diaphysial dysplasia, ectodermal dysplasia, enamel dysplasia, encephalo-ophthalmic dysplasia, dysplasia epiphysialis hemimelia, dysplasia epiphysialis multiplex, dysplasia epiphysialis punctata, epithelial dysplasia, faciodigitogenital dysplasia, familial fibrous dysplasia of jaws, familial white folded dysplasia, fibromuscular dysplasia, fibrous dysplasia of bone, florid osseous dysplasia, hereditary renal-retinal dysplasia, hidrotic ectodermal dysplasia, hypohidrotic ectodermal dysplasia, lymphopenic thymic dysplasia, mammary dysplasia, mandibulofacial dysplasia, metaphysial dysplasia, Mondini dysplasia, monostotic fibrous dysplasia, mucoepithelial dysplasia, multiple epiphysial dysplasia, oculoauriculovertebral dysplasia, oculodentodigital dysplasia, oculovertebral dysplasia, odontogenic dysplasia, opthalmomandibulomelic dysplasia, periapical cemental dysplasia, polyostotic fibrous dysplasia, pseudoachondroplastic spondyloepiphysial dysplasia, retinal dysplasia, septo-optic dysplasia, spondyloepiphysial dysplasia, and ventriculoradial dysplasia.

Additional pre-neoplastic disorders which can be treated include, but are not limited to, benign dysproliferative disorders (e.g., benign tumors, fibrocystic conditions, tissue hypertrophy, intestinal polyps or adenomas, and esophageal dysplasia), leukoplakia, keratoses, Bowen's disease, Farmer's Skin, solar cheilitis, and solar keratosis.

In preferred embodiments, the method of the invention is used to inhibit growth, progression, and/or metastasis of cancers, in particular those listed above.

Additional hyperproliferative diseases, disorders, and/or conditions include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, emangioblastoma, acoustic neuroma, oligodendroglioma, meningioma, melanoma, neuroblastoma, and retinoblastoma.

Therapy of Autoimmune Disease

The subject anti-CD74 antibodies, combinations or complexes thereof can be used to treat immune dysregulation disease and related autoimmune diseases. Immune diseases may include acute immune thrombocytopenia, Addison's disease, adult respiratory distress syndrome (ARDS), agranulocytosis, allergic conditions, allergic encephalomyelitis, allergic neuritis, amyotrophic lateral sclerosis (ALS), ankylosing spondylitis, antigen-antibody complex mediated diseases, anti-glomerular basement membrane disease, antiphospholipid antibody syndrome, aplastic anemia, arthritis, asthma, atherosclerosis, autoimmune disease of the testis and ovary, autoimmune endocrine diseases, autoimmune myocarditis, autoimmune neutropenia, autoimmune polyendocrinopathies, autoimmune polyglandular syndromes (or polyglandular endocrinopathy syndromes), autoimmune thrombocytopenia, Bechet disease, Berger's disease (IgA nephropathy), bronchiolitis obliterans (non-transplant), bullous pemphigoid, pemphigus vulgaris, Castleman's syndrome, Celiac sprue (gluten enteropathy), central nervous system (CNS) inflammatory disorders, chronic active hepatitis, chronic immune thrombocytopenia dermatomyositis, colitis, conditions involving infiltration of T cells and chronic inflammatory responses, coronary artery disease, Crohn's disease, cryoglobulinemia, dermatitis, dermatomyositis, diabetes mellitus, diseases involving leukocyte diapedesis, eczema, encephalitis, erythema multiforme, erythema nodosum, Factor VIII deficiency, fibrosing alveolitis, giant cell arteritis, glomerulonephritis, Goodpasture's syndrome, graft versus host disease (GVHD), granulomatosis, Grave's disease, Guillain-Barre Syndrome, Hashimoto's thyroiditis, hemophilia A, Henoch-Schonlein purpura, idiopathic hypothyroidism, immune thrombocytopenia (ITP), IgA nephropathy, IgA nephropathy, IgM mediated neuropathy, immune complex nephritis, immune hemolytic anemia including autoimmune hemolytic anemia (AIHA), immune responses associated with acute and delayed hypersensitivity mediated by cytokines and T-lymphocytes, immune-mediated thrombocytopenias, juvenile onset diabetes, juvenile rheumatoid arthritis, Lambert-Eaton Myasthenic Syndrome, large vessel vasculitis, leukocyte adhesion deficiency, leukopenia, lupus nephritis, lymphoid interstitial pneumonitis (HIV), medium vessel vasculitis, membranous nephropathy, meningitis, multiple organ injury syndrome, multiple sclerosis, myasthenia gravis, osteoarthritis, pancytopenia, pemphigoid bullous, pemphigus vulgaris, pernicious anemia, polyarteritis nodosa, polychondritis, polyglandular syndromes, polymyalgia, polymyositis, post-streptococcal nephritis, primary biliary cirrhosis, primary hypothyroidism, psoriasis, psoriatic arthritis, pure red cell aplasia (PRCA), rapidly progressive glomerulonephritis, Reiter's disease, respiratory distress syndrome, responses associated with inflammatory bowel disease, Reynaud's syndrome, rheumatic fever, rheumatoid arthritis, sarcoidosis, scleroderma, Sjogren's syndrome, solid organ transplant rejection, Stevens-Johnson syndrome, stiff-man syndrome, subacute thyroiditis, Sydenham's chorea, systemic lupus erythematosus (SLE), systemic scleroderma and sclerosis, tabes dorsalis, Takayasu's arteritis, thromboangitis obliterans, thrombotic thrombocytopenic purpura (TTP), thyrotoxicosis, toxic epidermal necrolysis, tuberculosis, Type I diabetes, ulcerative colitis, uveitis, vasculitis (including ANCA) and Wegener's granulomatosis.

Type-1 and Type-2 diabetes may be treated using known antibodies against B-cell antigens, such as CD22 (epratuzumab), CD74 (milatuzumab), CD19 (hA19), CD20 (veltuzumab) or HLA-DR (hL243) (see, e.g., Winer et al., 2011, Nature Med 17:610-18). Anti-CD3 antibodies also have been proposed for therapy of type 1 diabetes (Cernea et al., 2010, Diabetes Metab Rev 26:602-05).

Kits

Various embodiments may concern kits containing anti-CD74 antibodies, antibody combinations and/or antibody constructs and/or other components. Such components may include a targetable construct. In alternative embodiments it is contemplated that a targetable construct may be attached to one or more different therapeutic and/or diagnostic agents.

If the composition containing components for administration is not formulated for delivery via the alimentary canal, such as by oral delivery, a device capable of delivering the kit components through some other route may be included. One type of device, for applications such as parenteral delivery, is a syringe that is used to inject the composition into the body of a subject. Inhalation devices may also be used for certain applications.

The kit components may be packaged together or separated into two or more containers. In some embodiments, the containers may be vials that contain sterile, lyophilized formulations of a composition that are suitable for reconstitution. A kit may also contain one or more buffers suitable for reconstitution and/or dilution of other reagents. Other containers that may be used include, but are not limited to, a pouch, tray, box, tube, or the like. Kit components may be packaged and maintained sterilely within the containers. Another component that can be included is instructions to a person using a kit for its use.

EXAMPLES

Various embodiments of the present invention are illustrated by the following examples, without limiting the scope thereof.

Example 1

Preparation of hLL1, hLL2, hA20 and hL243 Antibodies

The hLL1, hLL2, hA20 and hL243 antibodies were prepared as previously described and as summarized below. The constant region sequences of each of the hLL1, hLL2, hA20 and hL243 antibodies are as shown below in SEQ ID NO:144 (heavy chain constant region amino acid sequence); SEQ ID NO:145 (heavy chain constant region DNA sequence); SEQ ID NO:146 (light chain constant region amino acid sequence); and SEQ ID NO:147 (light chain constant region amino acid sequence). Although the constant region sequences are derived from the hLL2 antibody, they are identical in each of hLL1, hLL2, hA20 and hL243. Therefore, each of the hLL1, hLL2, hA20 and hL243 antibodies is a G1m3 allotype antibody.

```
Heavy chain constant region amino acid sequence
(CH1-Hinge-CH2-CH3)
                                          (SEQ ID NO: 144)
ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKRVE
PKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWL
NGKEYKCKVSNKALPAPIEKTISKAKGQPREPQVYTLPPSREEMTKNQVS
LTCLVKGFYPSDIAVEWESNGQPENNYKTTPPVLDSDGSFFLYSKLTVD
KSRWQQGNVFSCSVMHEALHNHYTQKSLSLSPGK Heavy chain constant region DNA sequence
                                          (SEQ ID NO: 145)
GCCTCCACCAAGGGCCCATCGGTCTTCCCCCTGGCACCCTCCTCCAAG
AGCACCTCTGGGGGCACAGCGGCCCTGGGCTGCCTGGTCAAGGACTAC
TTCCCCGAACCGGTGACGGTGTCGTGGAACTCAGGCGCCCTGACCAGC
GGCGTGCACACCTTCCCGGCTGTCCTACAGTCCTCAGGACTCTACTCCC
TCAGCAGCGTGGTGACCGTGCCCTCCAGCAGCTTGGGCACCCAGACCTA
CATCTGCAACGTGAATCACAAGCCCAGCAACACCAAGGTGGACAAGAGA
GTTGAGCCCAAATCTTGTGACAAAACTCACACATGCCCACCGTGCCCAG
CACCTGAACTCCTGGGGGGACCGTCAGTCTTCCTCTTCCCCCCAAAACC
CAAGGACACCCTCATGATCTCCCGGACCCCTGAGGTCACATGCGTGGTG
GTGGACGTGAGCCACGAAGACCCTGAGGTCAAGTTCAACTGGTACGTGGA
CGGCGTGGAGGTGCATAATGCCAAGACAAAGCCGCGGGAGGAGCAGTAC
AACAGCACGTACCGGGTGGTCAGCGTCCTCACCGTCCTGCACCAGGACT
GGCTGAATGGCAAGGAGTACAAGTGCAAGGTCTCCAACAAAGCCCTCCC
AGCCCCCATCGAGAAAACCATCTCCAAAGCCAAAGGGCAGCCCCGAGAA
CCACAGGTGTACACCCTGCCCCCATCCCGGGAGGAGATGACCAAGAAC
CAGGTCAGCCTGACCTGCCTGGTCAAAGGCTTCTATCCCAGCGACATCGC
CGTGGAGTGGGAGAGCAATGGGCAGCCGGAGAACAACTACAAGACCACG
CCTCCCGTGCTGGACTCCGACGGCTCCTTCTTCCTCTATAGCAAGCTCA
CCGTGGACAAGAGCAGGTGGCAGCAGGGGAACGTCTTCTCATGCTCCGTG
ATGCATGAGGCTCTGCACAACCACTACACGCAGAAGAGCCTCTCCCTGT
CTCCGGGTAAA Light chain constant region amino acid sequence
                                          (SEQ ID NO: 146)
TVAAPSVFIFPPSDEQLKSGTASVVCLLNNFYPREAKVQWKVDNALQSGN
SQESVTEQDSKDSTYSLSSTLTLSKADYEKHKVYACEVTHQGLSSPVTK
SFNRGEC Light chain constant region DNA sequence
                                          (SEQ ID NO: 147)
ACTGTGGCTGCACCATCTGTCTTCATCTTCCCGCCATCTGATGAGCAGTT
GAAATCTGGAACTGCCTCTGTTGTGTGCCTGCTGAATAACTTCTATCCCA
GAGAGGCCAAAGTACAGTGGAAGGTGGATAACGCCCTCCAATCGGGTAA
CTCCCAGGAGAGTGTCACAGAGCAGGACAGCAAGGACAGCACCTACAG
CCTCAGCAGCACCCTGACGCTGAGCAAAGCAGACTACGAGAAACACAA
AGTCTACGCCTGCGAAGTCACCCATCAGGGCCTGAGCTCGCCCGTCACA
AAGAGCTTCAACAGGGGAGAGTGT
``` hLL1 Antibody

The hLL1 anti-CD74 antibody was prepared as described in U.S. Pat. No. 7,772,373 (incorporated by reference from Col. 3, line 54 to Col. 5, line 32 and Col. 34, line 15 to Col. 40, line 45, FIGS. 1A, 1B, 2A, 2B, 3A, 3B, 4A, 4B). The variable region sequences of the light and heavy chains of the hLL1 antibody are as described in U.S. Pat. No. 7,772,373 (e.g., FIG. 3 and FIG. 4).

A modified strategy as described by Leung et al. (1994, Hybridoma 13:469-76) was used to construct the VK and VH genes for hLL1 using a combination of long oligonucleotide synthesis and PCR. For the construction of the hLL1 VH domain, two long oligonucleotides, hLL1VHA (176 mer) and hLL1VHB (165-mer) (U.S. Pat. No. 7,772,373) were synthesized on an automated DNA synthesizer. The hLL1VHA sequence represented nt 20 to 195 of the hLL1VH domain. The hLL1 VHB sequence represented the minus strand of the hLL1 VH domain complementary to nt 173 to 337. The 3'-terminal sequences (22 nt residues) of hLL1VHA and B were complementary to each other. Under PCR condition, the 3'-ends of hLL1 VHA and B annealed to form a short double stranded DNA. Each annealed end served as a primer for the transcription of single stranded DNA, resulting in a double strand DNA composed of the nt 20 to 337 of hLL1VH. This DNA was further amplified in the presence of two short oligonucleotides, hLL1VHBACK and hLL1VHFOR (U.S. Pat. No. 7,772,373) to form the full-length hLL1VH. Double-stranded PCR-amplified product for hLL1VH was gel-purified, restriction-digested with PstI and BstEII and cloned into the complementary PstI/BstEII sites of the heavy chain staging vector, VHpBS2.

For constructing the full length DNA of the humanized VK sequence, hLL1VKA (159-mer) and hLL1VKB (169-mer) (U.S. Pat. No. 7,772,373) were synthesized. The hLL1 VKA sequence represented nt 16 to 174 of the hLL1VK domain. The hLL1VKB sequence represented the minus strand of the hLL1VK domain complementary to nt 153 to 321. hLL1VKA and B were amplified by two short oligonucleotides hLL1VKBACK and hLL1VKFOR (U.S. Pat. No. 7,772,373) to form double-stranded DNA. Further amplification produced the full length VK gene (U.S. Pat. No. 7,772,373). Gel-purified PCR products for hLL1VK were restriction-digested with PvuII and BglIII and cloned into the complementary PvuI/BclI sites of the light chain staging vector, VKpBR2.

The final expression vector hLL1pdHL2 was constructed by sequentially subcloning the XbaI-BamHI and XhoI/BamHI fragments of hLL1VK and VH, respectively, into pdHL2. The pdHL2 vector is known in the art (see, e.g., Gillies et al., 1989, J Immunol Methods 125:191). The pdHL2 vector provides expression of both IgG heavy and light chain genes that are independently controlled by two metallothionine promoters and IgH enhancers. Use of pdHL2 as an expression vector for antibody production has been disclosed, for example, in Losman et al., 1999, Clin Cancer Res 5:3101s-05s.

The fragment containing the VK sequence of hLL1, together with the signal peptide sequence, was excised from LL1VKpBR2 by double restriction digestion with XbaI and BamHI. The ~550 bp VK fragment was then subcloned into the XbaI/BamHI site of a mammalian expression vector, pdHL2. The resulting vector was designated as hLL1VKpdHL2. Similarly, the ~750 bp fragment encoding hLL1 VH, together with the signal peptide sequence, was excised from LL1VHpBS2 by XhoI and BamHI digestion and isolated by electrophoresis in an agarose gel. The fragment was subcloned into the XhoI and HindIII site of hLL1VKpdHL2 with the aid of linker comparable to both BamHI and HindIII ends, resulting in the final expression vector, designated as hLL1pdHL2.

Approximately 30 μg of hLL1pdHL2 was linearized by digestion with Sal I and transfected into Sp2/0-Ag14 cells by electroporation. The transfected cells were plated into 96-well plate for 2 days and then selected for MTX resistance. Supernatants from colonies surviving selection were monitored for chimeric antibody secretion by ELISA assay. Positive cell clones were expanded and hLL1 was purified from cell culture supernatant.

hLL2 Antibody

The hLL2 anti-CD22 antibody was prepared as described in U.S. Pat. No. 6,187,287 (incorporated by reference from Col. 3, line 35 to Col. 4, line 34 and Col. 11, line 40 to Col. 20, line 38, FIGS. 1, 4A, 4B, 5A, 5B). The variable region sequences of the light and heavy chains of the hLL2 antibody are as described in U.S. Pat. No. 6,187,287 (e.g., FIG. 1, FIG. 5). The LL2 antibody was deposited on May 27, 2005, with the American Type Culture Collection, Manassas, Va. (ATCC Accession No. PTA-6735), formerly the EPB-2 monoclonal antibody, which was produced against human Raji cells derived from a Burkitt lymphoma. (Pawlak-Byczkowska et al., 1989, Cancer Res. 49:4568.) The cloning, transfection and protein production were performed as described above for the hLL1 antibody.

hA20 Antibody

The hA20 anti-CD20 antibody was prepared as described in U.S. Pat. No. 7,919,273 (incorporated by reference from Col. 7, line 25 to Col. 9, line 4 and Col. 34, line 15 to Col. 72, line 2, FIGS. 1A, 1B, 2A, 2B, 3A, 3B). The variable region sequences of the light and heavy chains of the hA20 antibody are as described in U.S. Pat. No. 7,919,273 (e.g., FIG. 2, FIG. 3). The cloning, transfection and protein production were performed as described above for the hLL1 antibody.

hL243 Antibody

The hL243 anti-HLA-DR antibody was prepared as described in U.S. Pat. No. 7,612,180 (incorporated by reference from Col. 4, line 16 to Col. 6, line 38 and Col. 46, line 50 to Col. 60, line 67, FIGS. 1 to 6). The variable region sequences of the light and heavy chains of the hL243 antibody are as described in U.S. Pat. No. 7,612,180 (e.g., FIG. 3, FIG. 4, FIG. 5, FIG. 6). The cloning, transfection and protein production were performed as described above for the hLL1 antibody.

Other known antibodies, such as hPAM4 (U.S. Pat. No. 7,282,567), hA19 (U.S. Pat. No. 7,109,304), hIMMU31 (U.S. Pat. No. 7,300,655), hMu-9 (U.S. Pat. No. 7,387,773), hMN-14 (U.S. Pat. No. 6,676,924), hMN-15 (U.S. Pat. No. 7,541,440), hR1 (U.S. patent application Ser. No. 12/689,336), hRS7 (U.S. Pat. No. 7,238,785), hMN-3 (U.S. Pat. No. 7,541,440), 15B8 (anti-CD40, U.S. Pat. No. 7,820,170), AB-PG1-XG1-026 (U.S. patent application Ser. No. 11/983,372, deposited as ATCC PTA-4405 and PTA-4406) and D2/B (WO 2009/130575), may be prepared as described above, using the techniques disclosed herein.

Example 2

Preparation of Dock-and-Lock (DNL) Constructs

DDD and AD Fusion Proteins

The DNL technique can be used to make dimers, trimers, tetramers, hexamers, etc. comprising virtually any antibody, antibody fragment, immunomodulator, cytokine, enzyme, peptide, PEG moiety, toxin, xenoantigen or other effector moiety. For certain preferred embodiments, antibodies, cytokines or toxins (such as ranpirnase) may be produced as fusion proteins comprising either a dimerization and docking domain (DDD) or anchoring domain (AD) sequence. Although in preferred embodiments the DDD and AD moieties may be joined to antibodies, antibody fragments, cytokines, toxins or other effector moieties as fusion proteins, the skilled artisan will realize that other methods of conjugation exist, such as chemical cross-linking, click chemistry reaction, etc.

The technique is not limiting and any protein or peptide of use may be produced as an AD or DDD fusion protein for incorporation into a DNL construct. Where chemical cross-linking is utilized, the AD and DDD conjugates may comprise any molecule that may be cross-linked to an AD or DDD sequence using any cross-linking technique known in the art. In certain exemplary embodiments, a dendrimer or other polymeric moiety such as polyethyleneimine or polyethylene glycol (PEG), may be incorporated into a DNL construct, as described in further detail below.

Expression Vectors

The plasmid vector pdHL2 has been used to produce a number of antibodies and antibody-based constructs. See Gillies et al., J Immunol Methods (1989), 125:191-202; Losman et al., Cancer (Phila) (1997), 80:2660-6. The di-cistronic mammalian expression vector directs the synthesis of the heavy and light chains of IgG. The vector sequences are mostly identical for many different IgG-pdHL2 constructs, with the only differences existing in the variable domain ($V_H$ and $V_L$) sequences. Using molecular biology tools known to those skilled in the art, these IgG expression vectors can be converted into Fab-DDD or Fab-AD expression vectors.

To generate Fab-DDD expression vectors, the coding sequences for the hinge, CH2 and CH3 domains of the heavy chain were replaced with a sequence encoding the first 4 residues of the hinge, a 14 residue Gly-Ser linker and a DDD moiety, such as the first 44 residues of human RIIα (referred to as DDD1, SEQ ID NO:25). To generate Fab-AD expression vectors, the sequences for the hinge, CH2 and CH3 domains of IgG were replaced with a sequence encoding the first 4 residues of the hinge, a 15 residue Gly-Ser linker and an AD moiety, such as a 17 residue synthetic AD called AKAP-IS (referred to as AD1, SEQ ID NO:27), which was generated using bioinformatics and peptide array technology and shown to bind RIIα dimers with a very high affinity (0.4 nM). See Alto, et al. Proc. Natl. Acad. Sci., U.S.A (2003), 100:4445-50.

Two shuttle vectors were designed to facilitate the conversion of IgG-pdHL2 vectors to either Fab-DDD1 or Fab-AD1 expression vectors, as described below.

Preparation of CH1

The CH1 domain was amplified by PCR using the pdHL2 plasmid vector as a template. The left PCR primer consisted of the upstream (5') end of the CH1 domain and a SacII restriction endonuclease site, which is 5' of the CH1 coding sequence. The right primer consisted of the sequence coding for the first 4 residues of the hinge followed by four glycines and a serine, with the final two codons (GS) comprising a Bam HI restriction site. The 410 bp PCR amplimer was cloned into the PGEMT® PCR cloning vector (PROMEGA®, Inc.) and clones were screened for inserts in the T7 (5') orientation.

A duplex oligonucleotide was synthesized to code for the amino acid sequence of DDD1 preceded by 11 residues of the linker peptide, with the first two codons comprising a BamHI restriction site. A stop codon and an EagI restriction site are appended to the 3' end. The encoded polypeptide sequence is shown below.

(SEQ ID NO: 148)
GSGGGGSGGGG<u>SHIQIPPGLTELLQGYTVEVLRQQPPDLVEFAVEYFTR</u>
<u>LREARA</u>

Two oligonucleotides, designated RIIA1-44 top and RIIA1-44 bottom, which overlap by 30 base pairs on their 3' ends, were synthesized and combined to comprise the central 154 base pairs of the 174 bp DDD1 sequence. The oligonucleotides were annealed and subjected to a primer extension reaction with Taq polymerase. Following primer extension, the duplex was amplified by PCR. The amplimer was cloned into PGEMT® and screened for inserts in the T7 (5') orientation.

A duplex oligonucleotide was synthesized to code for the amino acid sequence of AD1 preceded by 11 residues of the linker peptide with the first two codons comprising a BamHI restriction site. A stop codon and an EagI restriction site are appended to the 3' end. The encoded polypeptide sequence is shown below.

(SEQ ID NO: 149)
GSGGGGSGGGG<u>SQIEYLAKQIVDNAIQQA</u>

Two complimentary overlapping oligonucleotides encoding the above peptide sequence, designated AKAP-IS Top and AKAP-IS Bottom, were synthesized and annealed. The duplex was amplified by PCR. The amplimer was cloned into the PGEMT® vector and screened for inserts in the T7 (5') orientation.

Ligating DDD1 with CH1

A 190 bp fragment encoding the DDD1 sequence was excised from PGEMT® with BamHI and NotI restriction enzymes and then ligated into the same sites in CH1-PGEMT® to generate the shuttle vector CH1-DDD1-PGEMT®.

Ligating AD1 with CH1

A 110 bp fragment containing the AD1 sequence was excised from PGEMT® with BamHI and NotI and then ligated into the same sites in CH1-PGEMT® to generate the shuttle vector CH1-AD1-PGEMT®.

Cloning CH1-DDD1 or CH1-AD1 into pdHL2-Based Vectors

With this modular design either CH1-DDD1 or CH1-AD1 can be incorporated into any IgG construct in the pdHL2 vector. The entire heavy chain constant domain is replaced with one of the above constructs by removing the SacII/EagI restriction fragment (CH1-CH3) from pdHL2 and replacing it with the SacII/EagI fragment of CH1-DDD1 or CH1-AD1, which is excised from the respective PGEMT® shuttle vector.

Construction of h679-Fd-AD1-pdHL2 h679-Fd-AD1-pdHL2 is an expression vector for production of h679 Fab with AD1 coupled to the carboxyl terminal end of the CH1 domain of the Fd via a flexible Gly/Ser peptide spacer composed of 14 amino acid residues. A pdHL2-based vector containing the variable domains of h679 was converted to h679-Fd-AD1-pdHL2 by replacement of the SacII/EagI fragment with the CH1-AD1 fragment, which was excised from the CH1-AD1-SV3 shuttle vector with SacII and EagI.

Production and Purification of h679-Fab-AD1

The h679-Fd-AD1-pdHL2 vector was linearized by digestion with Sal I restriction endonuclease and transfected into Sp/EEE myeloma cells (U.S. Pat. No. 7,785,880) by electroporation. The di-cistronic expression vector directs the synthesis and secretion of both h679 kappa light chain and h679 Fd-AD1, which combine to form h679 Fab-AD1. Following electroporation, the cells were plated in 96-well tissue culture plates and transfectant clones were selected with 0.05 µM methotrexate (MTX). Clones were screened for protein expression by ELISA using microtiter plates coated with a BSA-IMP260 (HSG) conjugate and detection with HRP-conjugated goat anti-human Fab. BIACORE® analysis using an HSG (IMP239) sensorchip was used to determine the productivity by measuring the initial slope obtained from injection of diluted media samples. The highest producing clone had an initial productivity of approximately 30 mg/L. A total of 230 mg of h679-Fab-AD1 was purified from 4.5 liters of roller bottle culture by single-step IMP291 affinity chromatography. Culture media was concentrated approximately 10-fold by ultrafiltration before loading onto an IMP291-affigel column. The column was washed to baseline with PBS and h679-Fab-AD1 was eluted with 1 M imidazole, 1 mM EDTA, 0.1 M NaAc, pH 4.5. SE-HPLC analysis of the eluate shows a single sharp peak with a retention time consistent with a 50 kDa protein (not shown). Only two bands, which represent the polypeptide constituents of h679-AD1, were evident by reducing SDS-PAGE analysis (not shown).

Construction of C-DDD1-Fd-hMN-14-pdHL2

C-DDD1-Fd-hMN-14-pdHL2 is an expression vector for production of a stable dimer that comprises two copies of a fusion protein C-DDD1-Fab-hMN-14, in which DDD1 is linked to hMN-14 Fab at the carboxyl terminus of CH1 via a flexible peptide spacer. The plasmid vector hMN-14(I)-pdHL2, which has been used to produce hMN-14 IgG, was converted to C-DDD1-Fd-hMN-14-pdHL2 by digestion with SacII and EagI restriction endonucleases to remove the CH1-CH3 domains and insertion of the CH1-DDD1 fragment, which was excised from the CH1-DDD1-SV3 shuttle vector with SacII and EagI.

The same technique has been utilized to produce plasmids for Fab expression of a wide variety of known antibodies, such as hLL1, hLL2, hPAM4, hR1, hRS7, hMN-14, hMN-15, hA19, hA20 and many others. Generally, the antibody variable region coding sequences were present in a pdHL2 expression vector and the expression vector was converted for production of an AD- or DDD-fusion protein as described above. The AD- and DDD-fusion proteins comprising a Fab fragment of any of such antibodies may be combined, in an approximate ratio of two DDD-fusion proteins per one AD-fusion protein, to generate a trimeric DNL construct comprising two Fab fragments of a first antibody and one Fab fragment of a second antibody.

Production and Purification of C-DDD1-Fab-hMN-14

The C-DDD1-Fd-hMN-14-pdHL2 vector was transfected into Sp2/0-derived myeloma cells by electroporation. C-DDD1-Fd-hMN-14-pdHL2 is a di-cistronic expression vector, which directs the synthesis and secretion of both hMN-14 kappa light chain and hMN-14 Fd-DDD1, which combine to form C-DDD1-hMN-14 Fab. The fusion protein forms a stable homodimer via the interaction of the DDD1 domain.

Following electroporation, the cells were plated in 96-well tissue culture plates and transfectant clones were selected with 0.05 µM methotrexate (MTX). Clones were screened for protein expression by ELISA using microtiter plates coated with WI2 (a rat anti-id monoclonal antibody to hMN-14) and detection with HRP-conjugated goat anti-human Fab. The initial productivity of the highest producing C-DDD1-Fab-hMN14 Fab clone was 60 mg/L.

Affinity Purification of C-DDD1-hMN-14 with AD 1-Affigel

The DDD/AD interaction was utilized to affinity purify DDD1-containing constructs. AD 1-C is a peptide that was made synthetically consisting of the AD1 sequence and a carboxyl terminal cysteine residue, which was used to couple the peptide to Affigel following reaction of the sulfhydryl group with chloroacetic anhydride. DDD-containing dimer structures specifically bind to the AD1-C-Affigel resin at neutral pH and can be eluted at low pH (e.g., pH 2.5).

A total of 81 mg of C-DDD1-Fab-hMN-14 was purified from 1.2 liters of roller bottle culture by single-step AD 1-C affinity chromatography. Culture media was concentrated approximately 10-fold by ultrafiltration before loading onto an AD1-C-affigel column. The column was washed to baseline with PBS and C-DDD1-Fab-hMN-14 was eluted with 0.1 M Glycine, pH 2.5. SE-HPLC analysis of the eluate showed a single protein peak with a retention time consistent with a 107 kDa protein (not shown). The purity was also confirmed by reducing SDS-PAGE, showing only two bands of molecular size expected for the two polypeptide constituents of C-DDD1-Fab-hMN-14 (not shown).

The binding activity of C-DDD1-Fab-hMN-14 was determined by SE-HPLC analysis of samples in which the test article was mixed with various amounts of WI2. A sample prepared by mixing WI2 Fab and C-DDD1-Fab-hMN-14 at a molar ratio of 0.75:1 showed three peaks, which were attributed to unbound C-DDD1-Fab-hMN14 (8.71 min), C-DDD1-Fab-hMN-14 bound to one WI2 Fab (7.95 min), and C-DDD1-Fab-hMN14 bound to two WI2 Fabs (7.37 min) (not shown). When a sample containing WI2 Fab and C-DDD1-Fab-hMN-14 at a molar ratio of 4 was analyzed, only a single peak at 7.36 minutes was observed (not shown). These results demonstrated that hMN14-Fab-DDD1 is dimeric and has two active binding sites. Very similar results were obtained when this experiment was repeated with an hMN-14 Fab construct with DDD1 linked to the amino terminal instead of the carboxyl terminal end (not shown).

A competitive ELISA demonstrated that C-DDD1-Fab-hMN-14 binds to CEA with an avidity similar to hMN-14 IgG, and significantly stronger than monovalent hMN-14 Fab (not shown). ELISA plates were coated with a fusion protein containing the epitope (A3B3) of CEA for which hMN-14 is specific.

C-DDD2-Fd-hMN-14-pdHL2

C-DDD2-Fd-hMN-14-pdHL2 is an expression vector for production of C-DDD2-Fab-hMN-14, which possesses a dimerization and docking domain sequence of DDD2 (SEQ ID NO:26) appended to the carboxyl terminus of the Fd of hMN-14 via a 14 amino acid residue Gly/Ser peptide linker. The fusion protein secreted is composed of two identical copies of hMN-14 Fab held together by non-covalent interaction of the DDD2 domains.

The expression vector was engineered as follows. Two overlapping, complimentary oligonucleotides, which comprise the coding sequence for part of the linker peptide and residues 1-13 of DDD2, were made synthetically. The oligonucleotides were annealed and phosphorylated with T4 PNK, resulting in overhangs on the 5' and 3' ends that are compatible for ligation with DNA digested with the restriction endonucleases BamHI and PstI, respectively.

The duplex DNA was ligated with the shuttle vector CH1-DDD1-PGEMT®, which was prepared by digestion with BamHI and PstI, to generate the shuttle vector CH1-DDD2-PGEMT®. A 507 bp fragment was excised from CH1-DDD2-PGEMT® with SacII and EagI and ligated with the IgG expression vector hMN-14(I)-pdHL2, which was prepared by digestion with SacII and EagI. The final expression construct was designated C-DDD2-Fd-hMN-14-pdHL2. Similar techniques have been utilized to generated DDD2-fusion proteins of the Fab fragments of a number of different humanized antibodies.

h679-Fd-AD2-pdHL2 h679-Fab-AD2, was designed to pair to C-DDD2-Fab-hMN-14. h679-Fd-AD2-pdHL2 is an expression vector for the production of h679-Fab-AD2, which possesses an anchoring domain sequence of AD2 (SEQ ID NO:28) appended to the carboxyl terminal end of the CH1 domain via a 14 amino acid residue Gly/Ser peptide linker. AD2 has one cysteine residue preceding and another one following the anchor domain sequence of AD1.

The expression vector was engineered as follows. Two overlapping, complimentary oligonucleotides (AD2 Top and AD2 Bottom), which comprise the coding sequence for AD2 and part of the linker sequence, were made synthetically. The oligonucleotides were annealed and phosphorylated with T4 PNK, resulting in overhangs on the 5' and 3' ends that are compatible for ligation with DNA digested with the restriction endonucleases BamHI and SpeI, respectively.

The duplex DNA was ligated into the shuttle vector CH1-AD1-PGEMT®, which was prepared by digestion with BamHI and SpeI, to generate the shuttle vector CH1-AD2-PGEMT®. A 429 base pair fragment containing CH1 and AD2 coding sequences was excised from the shuttle vector with SacII and EagI restriction enzymes and ligated into h679-pdHL2 vector that prepared by digestion with those same enzymes. The final expression vector is h679-Fd-AD2-pdHL2.

Example 3

Generation of Trimeric DNL Constructs

TF2 DNL Construct

A trimeric DNL construct designated TF2 was obtained by reacting C-DDD2-Fab-hMN-14 with h679-Fab-AD2. A pilot batch of TF2 was generated with >90% yield as follows. Protein L-purified C-DDD2-Fab-hMN-14 (200 mg) was mixed with h679-Fab-AD2 (60 mg) at a 1.4:1 molar ratio. The total protein concentration was 1.5 mg/ml in PBS containing 1 mM EDTA. Subsequent steps involved TCEP reduction, HIC chromatography, DMSO oxidation, and IMP 291 affinity chromatography. Before the addition of TCEP, SE-HPLC did not show any evidence of $a_2b$ formation. Addition of 5 mM TCEP rapidly resulted in the formation of $a_2b$ complex consistent with a 157 kDa protein expected for the binary structure. TF2 was purified to near homogeneity by IMP 291 affinity chromatography (not shown). IMP 291 is a synthetic peptide containing the HSG hapten to which the 679 Fab binds (Rossi et al., 2005, Clin Cancer Res 11:7122s-29s). SE-HPLC analysis of the IMP 291 unbound fraction demonstrated the removal of $a_4$, $a_2$ and free kappa chains from the product (not shown).

The functionality of TF2 was determined by BIACORE® assay. TF2, C-DDD1-hMN-14+h679-AD1 (used as a control sample of noncovalent $a_2b$ complex), or C-DDD2-hMN-14+h679-AD2 (used as a control sample of unreduced $a_2$ and b components) were diluted to 1 µg/ml (total protein) and passed over a sensorchip immobilized with HSG. The response for TF2 was approximately two-fold that of the two control samples, indicating that only the h679-Fab-AD component in the control samples would bind to and remain on the sensorchip. Subsequent injections of WI2 IgG, an anti-idiotype antibody for hMN-14, demonstrated that only TF2 had a DDD-Fab-hMN-14 component that was tightly associated with h679-Fab-AD as indicated by an additional signal response. The additional increase of response units resulting from the binding of WI2 to TF2 immobilized on the sensorchip corresponded to two fully functional binding sites, each contributed by one subunit of C-DDD2-Fab-hMN-14. This was confirmed by the ability of TF2 to bind two Fab fragments of WI2 (not shown).

TF10 DNL Construct

A similar protocol was used to generate a trimeric TF10 DNL construct, comprising two copies of a C-DDD2-Fab-hPAM4 and one copy of C-AD2-Fab-679. The TF10 bispecific ([hPAM4]$_2$×h679) antibody was produced using the method disclosed for production of the (anti CEA)$_2$×anti HSG bsAb TF2, as described above. The TF10 construct bears two humanized PAM4 Fabs and one humanized 679 Fab.

The two fusion proteins (hPAM4-DDD2 and h679-AD2) were expressed independently in stably transfected myeloma cells. The tissue culture supernatant fluids were combined, resulting in a two-fold molar excess of hPAM4-DDD2. The reaction mixture was incubated at room temperature for 24 hours under mild reducing conditions using 1 mM reduced glutathione. Following reduction, the DNL reaction was completed by mild oxidation using 2 mM oxidized glutathione. TF10 was isolated by affinity chromatography using IMP291-affigel resin, which binds with high specificity to the h679 Fab.

Example 4

Production of AD- and DDD-Linked Fab and IgG Fusion Proteins from Multiple Antibodies Using the techniques described in the preceding Examples, the IgG and Fab fusion proteins shown in Table 7 were constructed and incorporated into DNL constructs. The fusion proteins retained the antigen-binding characteristics of the parent antibodies and the DNL constructs exhibited the antigen-binding activities of the incorporated antibodies or antibody fragments.

TABLE 7

| Fusion proteins comprising IgG or Fab | |
|---|---|
| Fusion Protein | Binding Specificity |
| C-AD1-Fab-h679 | HSG |
| C-AD2-Fab-h679 | HSG |
| C-(AD)$_2$-Fab-h679 | HSG |
| C-AD2-Fab-h734 | Indium-DTPA |
| C-AD2-Fab-hA20 | CD20 |
| C-AD2-Fab-hA20L | CD20 |
| C-AD2-Fab-hL243 | HLA-DR |
| C-AD2-Fab-hLL2 | CD22 |
| N-AD2-Fab-hLL2 | CD22 |
| C-AD2-IgG-hMN-14 | CEACAM5 |
| C-AD2-IgG-hR1 | IGF-1R |
| C-AD2-IgG-hRS7 | EGP-1 |
| C-AD2-IgG-hPAM4 | MUC |
| C-AD2-IgG-hLL1 | CD74 |
| C-DDD1-Fab-hMN-14 | CEACAM5 |
| C-DDD2-Fab-hMN-14 | CEACAM5 |
| C-DDD2-Fab-h679 | HSG |
| C-DDD2-Fab-hA19 | CD19 |
| C-DDD2-Fab-hA20 | CD20 |
| C-DDD2-Fab-hAFP | AFP |
| C-DDD2-Fab-hL243 | HLA-DR |
| C-DDD2-Fab-hLL1 | CD74 |
| C-DDD2-Fab-hLL2 | CD22 |
| C-DDD2-Fab-hMN-3 | CEACAM6 |
| C-DDD2-Fab-hMN-15 | CEACAM6 |
| C-DDD2-Fab-hPAM4 | MUC |
| C-DDD2-Fab-hR1 | IGF-1R |
| C-DDD2-Fab-hRS7 | EGP-1 |
| N-DDD2-Fab-hMN-14 | CEACAM5 |

Example 5

Antibody-Dendrimer DNL Complex for siRNA

Cationic polymers, such as polylysine, polyethylenimine, or polyamidoamine (PAMAM)-based dendrimers, form complexes with nucleic acids. However, their potential applications as non-viral vectors for delivering therapeutic genes or siRNAs remain a challenge. One approach to improve selectivity and potency of a dendrimeric nanoparticle may be achieved by conjugation with an antibody that internalizes upon binding to target cells.

We synthesized and characterized a novel immunoconjugate, designated E1-G5/2, which was made by the DNL method to comprise half of a generation 5 (G5) PAMAM dendrimer (G5/2) site-specifically linked to a stabilized dimer of Fab derived from hRS7, a humanized antibody that is rapidly internalized upon binding to the Trop-2 antigen expressed on various solid cancers.

Methods

E1-G5/2 was prepared by combining two self-assembling modules, AD2-G5/2 and hRS7-Fab-DDD2, under mild redox conditions, followed by purification on a Protein L column. To make AD2-G5/2, we derivatized the AD2 peptide with a maleimide group to react with the single thiol generated from reducing a G5 PAMAM with a cystamine core and used reversed-phase HPLC to isolate AD2-G5/2. We produced hRS7-Fab-DDD2 as a fusion protein in myeloma cells, as described in the Examples above.

The molecular size, purity and composition of E1-G5/2 were analyzed by size-exclusion HPLC, SDS-PAGE, and Western blotting. The biological functions of E1-G5/2 were assessed by binding to an anti-idiotype antibody against hRS7, a gel retardation assay, and a DNase protection assay.

Results

E1-G5/2 was shown by size-exclusion HPLC to consist of a major peak (>90%) flanked by several minor peaks (not shown). The three constituents of E1-G5/2 (Fd-DDD2, the light chain, and AD2-G5/2) were detected by reducing SDS-PAGE and confirmed by Western blotting (not shown). Anti-idiotype binding analysis revealed E1-G5/2 contained a population of antibody-dendrimer conjugates of different size, all of which were capable of recognizing the anti-idiotype antibody, thus suggesting structural variability in the size of the purchased G5 dendrimer (not shown). Gel retardation assays showed E1-G5/2 was able to maximally condense plasmid DNA at a charge ratio of 6:1 (+/−), with the resulting dendriplexes completely protecting the complexed DNA from degradation by DNase I (not shown).

Conclusion

The DNL technique can be used to build dendrimer-based nanoparticles that are targetable with antibodies. Such agents have improved properties as carriers of drugs, plasmids or siRNAs for applications in vitro and in vivo. In preferred embodiments, anti-B-cell antibodies, such as anti-CD74 and/or anti-CD20, may be utilized to deliver cytotoxic or cytostatic siRNA species to targeted B-cells for therapy of lymphoma, leukemia, autoimmune or other diseases and conditions.

Example 6

Targeted Delivery of siRNA Using Protamine Linked Antibodies

Summary

RNA interference (RNAi) has been shown to down-regulate the expression of various proteins such as HER2, VEGF, Raf-1, bcl-2, EGFR and numerous others in preclinical studies. Despite the potential of RNAi to silence specific genes, the full therapeutic potential of RNAi remains to be realized due to the lack of an effective delivery system to target cells in vivo.

To address this critical need, we developed novel DNL constructs having multiple copies of human protamine tethered to a tumor-targeting, internalizing hRS7 (anti-Trop-2) antibody for targeted delivery of siRNAs in vivo. A DDD2-L-thP1 module comprising truncated human protamine (thP1, residues 8 to 29 of human protamine 1) was produced, in which the sequences of DDD2 and thP1 were fused respectively to the N- and C-terminal ends of a humanized antibody light chain (not shown). The sequence of the truncated hP1 (thP1) is shown below. Reaction of DDD2-L-thP1 with the antibody hRS7-IgG-AD2 under mild redox conditions, as described in the Examples above, resulted in the formation of an E1-L-thP1 complex (not shown), comprising four copies of thP1 attached to the carboxyl termini of the hRS7 heavy chains.

tHP1
(SEQ ID NO: 150)
RSQSRSRYYRQRQRSRRRRRRS

The purity and molecular integrity of E1-L-thP1 following Protein A purification were determined by size-exclusion HPLC and SDS-PAGE (not shown). In addition, the ability of E1-L-thP1 to bind plasmid DNA or siRNA was demonstrated by the gel shift assay (not shown). E1-L-thP1 was effective at binding short double-stranded oligonucleotides (not shown) and in protecting bound DNA from digestion by nucleases added to the sample or present in serum (not shown).

The ability of the E1-L-thP1 construct to internalize siRNAs into Trop-2-expressing cancer cells was confirmed by fluorescence microscopy using FITC-conjugated siRNA and the human Calu-3 lung cancer cell line (not shown).

Methods

The DNL technique was employed to generate E1-L-thP1. The hRS7 IgG-AD module, constructed as described in the Examples above, was expressed in myeloma cells and purified from the culture supernatant using Protein A affinity chromatography. The DDD2-L-thP1 module was expressed as a fusion protein in myeloma cells and was purified by Protein L affinity chromatography. Since the CH3-AD2-IgG module possesses two AD2 peptides and each can bind to a DDD2 dimer, with each DDD2 monomer attached to a protamine moiety, the resulting E1-L-thP1 conjugate comprises four protamine groups. E1-L-thp1 was formed in nearly quantitative yield from the constituent modules and was purified to near homogeneity (not shown) with Protein A.

DDD2-L-thP1 was purified using Protein L affinity chromatography and assessed by size exclusion HPLC analysis and SDS-PAGE under reducing and nonreducing conditions (data not shown). A major peak was observed at 9.6 min (not shown). SDS-PAGE showed a major band between 30 and 40 kDa in reducing gel and a major band about 60 kDa (indicating a dimeric form of DDD2-L-thP1) in nonreducing gel (not shown). The results of Western blotting confirmed the presence of monomeric DDD2-L-tP1 and dimeric DDD2-L-tP1 on probing with anti-DDD antibodies (not shown).

To prepare the E1-L-thP1, hRS7-IgG-AD2 and DDD2-L-thP1 were combined in approximately equal amounts and reduced glutathione (final concentration 1 mM) was added. Following an overnight incubation at room temperature, oxidized glutathione was added (final concentration 2 mM) and the incubation continued for another 24 h. E1-L-thP1 was purified from the reaction mixture by Protein A column chromatography and eluted with 0.1 M sodium citrate buffer (pH 3.5). The product peak (not shown) was neutralized, concentrated, dialyzed with PBS, filtered, and stored in PBS containing 5% glycerol at 2 to 8° C. The composition of E1-L-thP1 was confirmed by reducing SDS-PAGE (not shown), which showed the presence of all three constituents (AD2-appended heavy chain, DDD2-L-htP1, and light chain).

The ability of DDD2-L-thP1 and E1-L-thP1 to bind DNA was evaluated by gel shift assay. DDD2-L-thP1 retarded the mobility of 500 ng of a linear form of 3-kb DNA fragment in 1% agarose at a molar ratio of 6 or higher (not shown). E1-L-thP1 retarded the mobility of 250 ng of a linear 200-bp DNA duplex in 2% agarose at a molar ratio of 4 or higher (not shown), whereas no such effect was observed for hRS7-IgG-AD2 alone (not shown). The ability of E1-L-thP1 to protect bound DNA from degradation by exogenous DNase and serum nucleases was also demonstrated (not shown).

The ability of E1-L-thP1 to promote internalization of bound siRNA was examined in the Trop-2 expressing ME-180 cervical cell line (not shown). Internalization of the E1-L-thP1 complex was monitored using FITC conjugated goat anti-human antibodies. The cells alone showed no fluorescence (not shown). Addition of FITC-labeled siRNA alone resulted in minimal internalization of the siRNA (not shown). Internalization of E1-L-thP1 alone was observed in 60 minutes at 37° C. (not shown). E1-L-thP1 was able to effectively promote internalization of bound FITC-conjugated siRNA (not shown). E1-L-thP1 (10 µg) was mixed with FITC-siRNA (300 nM) and allowed to form E1-L-thP1-siRNA complexes which were then added to Trop-2-expressing Calu-3 cells. After incubation for 4 h at 37° C. the cells were checked for internalization of siRNA by fluorescence microscopy (not shown).

The ability of E1-L-thP1 to induce apoptosis by internalization of siRNA was examined. E1-L-thP1 (10 µg) was mixed with varying amounts of siRNA (AllStars Cell Death siRNA, Qiagen, Valencia, Calif.). The E1-L-thP1-siRNA complex was added to ME-180 cells. After 72 h of incubation, cells were trypsinized and annexin V staining was performed to evaluate apoptosis. The Cell Death siRNA alone or E1-L-thP1 alone had no effect on apoptosis (not shown). Addition of increasing amounts of E1-L-thP1-siRNA produced a dose-dependent increase in apoptosis (not shown). These results show that E1-L-thP1 could effectively deliver siRNA molecules into the cells and induce apoptosis of target cells.

Conclusions

The DNL technology provides a modular approach to efficiently tether multiple protamine molecules to the anti-Trop-2 hRS7 antibody resulting in the novel molecule E1-L-thP1. SDS-PAGE demonstrated the homogeneity and purity of E1-L-thP1. DNase protection and gel shift assays showed the DNA binding activity of E1-L-thP1. E1-L-thP1 internalized in the cells like the parental hRS7 antibody and was able to effectively internalize siRNA molecules into Trop-2-expressing cells, such as ME-180 and Calu-3.

The skilled artisan will realize that the DNL technique is not limited to any specific antibody or siRNA species. Rather, the same methods and compositions demonstrated herein can be used to make targeted delivery complexes comprising any antibody, any siRNA carrier and any siRNA species. The use of a bivalent IgG in targeted delivery complexes would result in prolonged circulating half-life and higher binding avidity to target cells, resulting in increased uptake and improved efficacy.

Example 7

Ribonuclease Based DNL Immunotoxins Comprising Quadruple Ranpirnase (Rap) Conjugated to B-Cell Targeting Antibodies We applied the DNL method to generate a novel class of immunotoxins, each of which comprises four copies of Rap site-specifically linked to a bivalent IgG. We combined a recombinant Rap-DDD module, produced in *E. coli*, with recombinant, humanized IgG-AD modules, which were produced in myeloma cells and targeted B-cell lymphomas and leukemias via binding to CD20 (hA20, veltuzumab), CD22 (hLL2, epratuzumab) or HLA-DR (hL243, IMMU-114), to generate 20-Rap, 22-Rap and C2-Rap, respectively. For each construct, a dimer of Rap was covalently tethered to the C-terminus of each heavy chain of the respective IgG. A control construct, 14-Rap, was made similarly, using labetuzumab (hMN-14), that binds to an antigen (CEACAM5) not expressed on B-cell lymphomas/leukemias.

Rap-DDD2

(SEQ ID NO: 151)

pQDWLTFQKKHITNTRDVDCDNIMSTNLFHCKDKNTFIYSRPEPVKAICK

GIIASKNVLTTSEFYLSDCNVTSRPCKYKLKKSTNKFCVTCENQAPVHFV

GVGSCGGGGSLECGHIQIPPGLTELLQGYTVEVLRQQPPDLVEFAVEYF

TRLREARAVEHHHHHH

The deduced amino acid sequence of secreted Rap-DDD2 is shown above (SEQ ID NO:151). Rap, underlined; linker, italics; DDD2, bold; pQ, amino-terminal glutamine converted to pyroglutamate. Rap-DDD2 was produced in *E. coli* as inclusion bodies, which were purified by IMAC under denaturing conditions, refolded and then dialyzed into PBS before purification by anion exchange chromatography. SDS-PAGE under reducing conditions resolved a protein band with a Mr appropriate for Rap-DDD2 (18.6 kDa) (not shown). The final yield of purified Rap-DDD2 was 10 mg/L of culture.

The DNL method was employed to rapidly generate a panel of IgG-Rap conjugates. The IgG-AD modules were expressed in myeloma cells and purified from the culture supernatant using Protein A affinity chromatography. The Rap-DDD2 module was produced and mixed with IgG-AD2 to form a DNL complex. Since the CH3-AD2-IgG modules possess two AD2 peptides and each can tether a Rap dimer, the resulting IgG-Rap DNL construct comprises four Rap groups and one IgG. IgG-Rap is formed nearly quantitatively from the constituent modules and purified to near homogeneity with Protein A.

Prior to the DNL reaction, the CH3-AD2-IgG exists as both a monomer, and a disulfide-linked dimer (not shown). Under non-reducing conditions, the IgG-Rap resolves as a cluster of high molecular weight bands of the expected size between those for monomeric and dimeric CH3-AD2-IgG (not shown). Reducing conditions, which reduces the conjugates to their constituent polypeptides, show the purity of the IgG-Rap and the consistency of the DNL method, as only bands representing heavy-chain-AD2 (HC-AD2), kappa light chain and Rap-DDD2 were visualized (not shown). Reversed phase HPLC analysis of 22-Rap (not shown) resolved a single protein peak at 9.10 min eluting between the two peaks of CH3-AD2-IgG-hLL2, representing the monomeric (7.55 min) and the dimeric (8.00 min) forms. The Rap-DDD2 module was isolated as a mixture of dimer and tetramer (reduced to dimer during DNL), which were eluted at 9.30 and 9.55 min, respectively (not shown).

LC/MS analysis of 22-Rap (not shown) showed that both the Rap-DDD2 and HC-AD2 polypeptides have an amino terminal glutamine that is converted to pyroglutamate (pQ) and that 22-Rap has 6 of its 8 constituent polypeptides modified by pQ.

In vitro cytotoxicity was evaluated in three NHL cell lines. Each cell line expresses CD20 at a considerably higher surface density compared to CD22; however, the internalization rate for hLL2 (anti-CD22) is much faster than hA20 (anti-CD20). 14-Rap shares the same structure as 22-Rap and 20-Rap, but its antigen (CEACAM5) is not expressed by the NHL cells. Cells were treated continuously with IgG-Rap as single agents or with combinations of the parental MAbs plus rRap. Both 20-Rap and 22-Rap killed each cell line at concentrations above 1 nM, indicating that their action is cytotoxic as opposed to merely cytostatic (not shown). 20-Rap was the most potent IgG-Rap, suggesting that antigen density may be more important than internalization rate. Similar results were obtained for Daudi and Ramos, where 20-Rap (EC50~0.1 nM) was 3-6-fold more potent than 22-Rap (not shown). The rituximab-resistant mantle cell lymphoma line, Jeko-1, exhibits increased CD20 but decreased CD22, compared to Daudi and Ramos. Importantly, 20-Rap exhibited very potent cytotoxicity ($EC_{50}$~20 pM) in Jeko-1, which was 25-fold more potent than 22-Rap (not shown).

The DNL method provides a modular approach to efficiently tether multiple cytotoxins onto a targeting antibody, resulting in novel immunotoxins that are expected to show higher in vivo potency due to improved pharmacokinetics and targeting specificity. Targeting Rap with a MAb to a cell surface antigen enhanced its tumor-specific cytotoxicity. Antigen density and internalization rate are both critical factors for the observed in vitro potency of IgG-Rap. In vitro results show that CD20-, CD22-, or HLA-DR-targeted IgG-Rap have potent biologic activity for therapy of B-cell lymphomas and leukemias. The skilled artisan will realize that the modular DNL technique may be utilized to produce Rap DNL constructs targeted to CD74.

Example 8

Production and Use of a DNL Construct Comprising Two Different Antibody Moieties and a Cytokine In certain embodiments, trimeric DNL constructs may comprise three different effector moieties, for example two different antibody moieties and a cytokine moiety. We report here the generation and characterization of the first bispecific MAb-IFNα, designated 20-C2-2b, which comprises two copies of IFN-α2b and a stabilized F(ab)$_2$ of hL243 (humanized anti-HLA-DR; IMMU-114) site-specifically linked to veltuzumab (humanized anti-CD20). In vitro, 20-C2-2b inhibited each of four lymphoma and eight myeloma cell lines, and was more effective than monospecific CD20-targeted MAb-IFNα or a mixture comprising the parental antibodies and IFNα in all but one (HLA-DR$^-$/CD20$^-$) myeloma line (not shown), suggesting that 20-C2-2b should be useful in the treatment of various hematopoietic disorders. The 20-C2-2b displayed greater cytotoxicity against KMS12-BM (CD20$^+$/HLA-DR$^+$ myeloma) than monospecific MAb-IFNα that targets only HLA-DR or CD20 (not shown), indicating that all three components in 20-C2-2b can contribute to toxicity. Our findings indicate that a given cell's responsiveness to MAb-IFNα depends on its sensitivity to IFNα and the specific antibodies, as well as the expression and density of the targeted antigens.

Because 20-C2-2b has antibody-dependent cellular cytotoxicity (ADCC), but not CDC, and can target both CD20 and HLA-DR, it is useful for therapy of a broad range of hematopoietic disorders that express either or both antigens.

Antibodies

The abbreviations used in the following discussion are: 20 ($C_H$3-AD2-IgG-v-mab, anti-CD20 IgG DNL module); C2 ($C_H$1-DDD2-Fab-hL243, anti-HLA-DR Fab$_2$ DNL module); 2b (dimeric IFNα2B-DDD2 DNL module); 734 (anti-in-DTPA IgG DNL module used as non-targeting control). The following MAbs were provided by Immunomedics, Inc.: veltuzumab or v-mab (anti-CD20 IgG$_1$), hL243γ4p (Immu-114, anti-HLA-DR IgG$_4$), a murine anti-IFNα MAb, and rat anti-idiotype MAbs to v-mab (WR2) and hL243 (WT).

DNL Constructs

Monospecific MAb-IFNα (20-2b-2b, 734-2b-2b and C2-2b-2b) and the bispecific HexAb (20-C2-C2) were generated by combination of an IgG-AD2-module with DDD2-modules using the DNL method, as described in the preceding Examples. The 734-2b-2b, which comprises tetrameric IFNα2b and MAb h734 [anti-Indium-DTPA IgG$_1$], was used as a non-targeting control MAb-IFNα.

The construction of the mammalian expression vector as well as the subsequent generation of the production clones and the purification of $C_H$3-AD2-IgG-v-mab are disclosed in the preceding Examples. The expressed recombinant fusion protein has the AD2 peptide linked to the carboxyl terminus of the $C_H$3 domain of v-mab via a 15 amino acid long flexible linker peptide. Co-expression of the heavy chain-AD2 and light chain polypeptides results in the formation of an IgG structure equipped with two AD2 peptides. The expression vector was transfected into Sp/ESF cells (an engineered cell line of Sp2/0) by electroporation. The pdHL2 vector contains the gene for dihydrofolate reductase, thus allowing clonal selection, as well as gene amplification with methotrexate (MTX). Stable clones were isolated from 96-well plates selected with media containing 0.2 µM MTX. Clones were screened for $C_H$3-AD2-IgG-vmab productivity via a sandwich ELISA. The module was produced in roller bottle culture with serum-free media.

The DDD-module, IFNα2b-DDD2, was generated as discussed above by recombinant fusion of the DDD2 peptide to the carboxyl terminus of human IFNα2b via an 18 amino acid long flexible linker peptide. As is the case for all DDD-modules, the expressed fusion protein spontaneously forms a stable homodimer.

The $C_H$1-DDD2-Fab-hL243 expression vector was generated from hL243-IgG-pdHL2 vector by excising the sequence for the $C_H$1-Hinge-$C_H$2-$C_H$3 domains with SacII and EagI restriction enzymes and replacing it with a 507 bp sequence encoding $C_H$1-DDD2, which was excised from the C-DDD2-hMN-14-pdHL2 expression vector with the same enzymes. Following transfection of $C_H$1-DDD2-Fab-hL243-pdHL2 into Sp/ESF cells by electroporation, stable, MTX-resistant clones were screened for productivity via a sandwich ELISA using 96-well microtiter plates coated with mouse anti-human kappa chain to capture the fusion protein, which was detected with horseradish peroxidase-conjugated goat anti-human Fab. The module was produced in roller bottle culture.

Roller bottle cultures in serum-free H-SFM media and fed-batch bioreactor production resulted in yields comparable to other IgG-AD2 modules and cytokine-DDD2 modules generated to date. $C_H3$-AD2-IgG-v-mab and IFNα2b-DDD2 were purified from the culture broths by affinity chromatography using MABSELECT™ (GE Healthcare) and HIS-SELECT® HF Nickel Affinity Gel (Sigma), respectively, as described previously (Rossi et al., Blood 2009, 114:3864-71). The culture broth containing the $C_H1$-DDD2-Fab-hL243 module was applied directly to KAPPASE-LECT® affinity gel (GE-Healthcare), which was washed to baseline with PBS and eluted with 0.1 M Glycine, pH 2.5.

The purity of the DNL modules was assessed by SDS-PAGE and SE-HPLC (not shown). Analysis under non-reducing conditions showed that, prior to the DNL reaction, IFNα2b-DDD2 and $C_H1$-DDD2-Fab-hL243 exist as disulfide-linked dimers (not shown). This phenomenon, which is always seen with DDD-modules, is beneficial, as it protects the reactive sulfhydryl groups from irreversible oxidation. In comparison, $C_H3$-AD2-IgG-v-mab (not shown) exists as both a monomer and a disulfide-linked dimer, and is reduced to monomer during the DNL reaction. Reducing SDS-PAGE demonstrated that each module was purified to near homogeneity and identified the component polypeptides comprising each module (not shown).

Generation of 20-C2-2b by DNL

Three DNL modules ($C_H3$-AD2-IgG-v-mab, $C_H1$-DDD2-Fab-hL243, and IFN-α2b-DDD2) were combined in equimolar quantities to generate the bsMAb-IFNα, 20-C2-2b. Following an overnight docking step under mild reducing conditions (1 mM reduced glutathione) at room temperature, oxidized glutathione was added (2 mM) to facilitate disulfide bond formation (locking). The 20-C2-2b was purified to near homogeneity using three sequential affinity chromatography steps, first with Protein A (MABSELECT™), second by IMAC using HIS-SELECT® HF Nickel Affinity Gel, and third by an hL243-anti-idiotype affinity chromatography. Only those DNL constructs comprising each of the 3 desired monomers bound to all three columns.

The skilled artisan will realize that affinity chromatography may be used to purify DNL complexes comprising any combination of effector moieties, so long as ligands for each of the three effector moieties can be obtained and attached to the column material. The selected DNL construct is the one that binds to each of three columns containing the ligand for each of the three effector moieties and can be eluted after washing to remove unbound complexes.

Generation and Characterization of 20-C2-2b

The bispecific MAb-IFNα was generated by combining the IgG-AD2 module, $C_H3$-AD2-IgG-v-mab, with two different dimeric DDD-modules, $C_H1$-DDD2-Fab-hL243 and IFNα2b-DDD2. Due to the random association of either DDD-module with the two AD2 groups, two side-products, 20-C2-C2 and 20-2b-2b are expected to form, in addition to 20-C2-2b.

Non-reducing SDS-PAGE (not shown) resolved 20-C2-2b (~305 kDa) as a cluster of bands positioned between those of 20-C2-C2 (~365 kDa) and 20-2b-2b (255 kDa). Reducing SDS-PAGE resolved the five polypeptides (v-mab HC-AD2, hL243 Fd-DDD2, IFNα2b-DDD2 and co-migrating v-mab and hL243 kappa light chains) comprising 20-C2-2b (not shown). IFNα2b-DDD2 and hL243 Fd-DDD2 are absent in 20-C2-C2 and 20-2b-2b. MABSELECT™ binds to all three of the major species produced in the DNL reaction, but removes any excess IFNα2b-DDD2 and $C_H1$-DDD2-Fab-hL243. The HIS-SELECT® unbound fraction contained mostly 20-C2-C2 (not shown). The unbound fraction from WT affinity chromatography comprised 20-2b-2b (not shown). Each of the samples was subjected to SE-HPLC and immunoreactivity analyses, which corroborated the results and conclusions of the SDS-PAGE analysis.

SE-HPLC analysis of 20-C2-2b resolved a predominant protein peak with a retention time (6.7 min) consistent with its calculated mass and between those of the larger 20-C2-C2 (6.6 min) and smaller 20-2b-2b (6.85 min), as well as some higher molecular weight peaks that likely represent non-covalent dimers formed via self-association of IFNα2b (not shown).

Immunoreactivity assays demonstrated the homogeneity of 20-C2-2b with each molecule containing the three functional groups (not shown). Incubation of 20-C2-2b with an excess of antibodies to any of the three constituent modules resulted in quantitative formation of high molecular weight immune complexes and the disappearance of the 20-C2-2b peak (not shown). The MAb-IFNα showed similar binding avidity to their parental MAbs (not shown).

IFNα Biological Activity

The specific activities for various MAb-IFNα were measured using a cell-based reporter gene assay and compared to peginterferon alfa-2b (not shown). Expectedly, the specific activity of 20-C2-2b (2454 IU/pmol), which has two IFNα2b groups, was significantly lower than those of 20-2b-2b (4447 IU/pmol) or 734-2b-2b (3764 IU/pmol), yet greater than peginterferon alfa-2b (P<0.001) (not shown). The difference between 20-2b-2b and 734-2b-2b was not significant. The specific activity among all agents varies minimally when normalized to IU/pmol of total IFNα. Based on these data, the specific activity of each IFNα2b group of the MAb-IFNα is approximately 30% of recombinant IFNα2b (~4000 IU/pmol).

In the ex-vivo setting, the 20-C2-2b DNL construct depleted lymphoma cells more effectively than normal B cells and had no effect on T cells (not shown). However, it did efficiently eliminate monocytes (not shown). Where v-mab had no effect on monocytes, depletion was observed following treatment with hL243α4p and MAb-IFNα, with 20-2b-2b and 734-2b-2b exhibiting similar toxicity (not shown). Therefore, the predictably higher potency of 20-C2-2b is attributed to the combined actions of anti-HLA-DR and IFNα, which may be augmented by HLA-DR targeting.

The skilled artisan will realize that the approach described here to produce and use bispecific immunocytokine, or other DNL constructs comprising three different effector moieties, may be utilized with any combinations of antibodies, antibody fragments, cytokines or other effectors that may be incorporated into a DNL construct, for example the combination of anti-CD20 and anti-CD22 with IFNα2b.

Example 9

Hexavalent DNL Constructs

The DNL technology described above for formation of trivalent DNL complexes was applied to generate hexavalent IgG-based DNL structures (HIDS). Because of the increased number of binding sites for target antigens, hexavalent constructs are expected to show greater affinity and/or efficacy against target cells. Two types of modules, which were produced as recombinant fusion proteins, were combined to generate a variety of HIDS. Fab-DDD2 modules were as described above. The Fab-DDD2 modules form stable homodimers that bind to AD2-containing modules. To generate HIDS, C-H-AD2-IgG modules were created to pair with the Fab-DDD2 modules.

C-H-AD2-IgG modules have an AD2 peptide fused to the carboxyl terminus (C) of the heavy (H) chain of IgG via a peptide linker. The DNA coding sequences for the linker peptide followed by the AD2 peptide are coupled to the 3' end of the CH3 (heavy chain constant domain 3) coding sequence by standard recombinant DNA methodologies, resulting in a contiguous open reading frame. When the heavy chain-AD2 polypeptide is co-expressed with a light chain polypeptide, an IgG molecule is formed possessing two AD2 peptides, which can therefore bind two Fab-DDD2 dimers. The C-H-AD2-IgG module can be combined with any Fab-DDD2 module to generate a wide variety of hexavalent structures composed of an Fc fragment and six Fab fragments. If the C-H-AD2-IgG module and the Fab-DDD2 module are derived from the same parental monoclonal antibody (MAb) the resulting HIDS is monospecific with 6 binding arms to the same antigen. If the modules are instead derived from two different MAbs then the resulting HIDS are bispecific, with two binding arms for the specificity of the C-H-AD2-IgG module and 4 binding arms for the specificity of the Fab-DDD2 module.

The same technique has been utilized to produce DNL complexes comprising an IgG moiety attached to four effector moieties, such as cytokines. In an exemplary embodiment, an IgG moiety was attached to four copies of interferon-α2b. The antibody-cytokine DNL construct exhibited superior pharmacokinetic properties and/or efficacy compared to PEGylated forms of interferon-α2b.

Creation of C-H-AD2-IgG-pdHL2 Expression Vectors

The pdHL2 mammalian expression vector has been used to mediate the expression of many recombinant IgGs. A plasmid shuttle vector was produced to facilitate the conversion of any IgG-pdHL2 vector into a C-H-AD2-IgG-pdHL2 vector. The gene for the Fc (CH2 and CH3 domains) was amplified using the pdHL2 vector as a template and a pair of primers. The amplimer was cloned in the PGEMT® PCR cloning vector. The Fc insert fragment was excised from PGEMT® with XbaI and BamHI restriction enzymes and ligated with AD2-pdHL2 vector that was prepared by digestion of h679-Fab-AD2-pdHL2 with XbaI and BamHI, to generate the shuttle vector Fc-AD2-pdHL2.

To convert any IgG-pdHL2 expression vector to a C-H-AD2-IgG-pdHL2 expression vector, an 861 bp BsrGI/NdeI restriction fragment is excised from the former and replaced with a 952 bp BsrGI/NdeI restriction fragment excised from the Fc-AD2-pdHL2 vector. BsrGI cuts in the CH3 domain and NdeI cuts downstream (3') of the expression cassette.

Production of C-H-AD2-hLL2 IgG

Epratuzumab, or hLL2 IgG, is a humanized anti-human CD22 MAb. An expression vector for C-H-AD2-hLL2 IgG was generated from hLL2 IgG-pdHL2, as described above, and used to transfect Sp2/0 myeloma cells by electroporation. Following transfection, the cells were plated in 96-well plates and transgenic clones were selected in media containing methotrexate. Clones were screened for C-H-AD2-hLL2 IgG productivity by a sandwich ELISA using 96-well microtiter plates coated with an hLL2-specific anti-idiotype MAb and detection with peroxidase-conjugated anti-human IgG. Clones were expanded to roller bottles for protein production and C-H-AD2-hLL2 IgG was purified from the spent culture media in a single step using Protein-A affinity chromatography. SDS-PAGE analysis demonstrated that the purified C-H-AD2-hLL2-IgG consisted of both monomeric and disulfide-linked dimeric forms of the module (not shown). Protein bands representing these two forms are evident by SDS-PAGE under non-reducing conditions, while under reducing conditions all of the forms are reduced to two bands representing the constituent polypeptides (Heavy chain-AD2 and kappa chain) (not shown). No other contaminating bands were detected.

Production of C-H-AD2-hA20 IgG hA20 IgG is a humanized anti-human CD20 MAb. An expression vector for C-H-AD2-hA20 IgG was generated from hA20 IgG-pdHL2, as described above, and used to transfect Sp2/0 myeloma cells by electroporation. Following transfection, the cells were plated in 96-well plates and transgenic clones were selected in media containing methotrexate. Clones were screened for C-H-AD2-hA20 IgG productivity by a sandwich ELISA using 96-well microtiter plates coated with a hA20-specific anti-idiotype MAb and detection with peroxidase-conjugated anti-human IgG. Clones were expanded to roller bottles for protein production and C-H-AD2-hA20 IgG was purified from the spent culture media in a single step using Protein-A affinity chromatography. SE-HPLC and SDS-PAGE analyses gave very similar results to those obtained for C-H-AD2-hLL2 IgG (not shown).

Example 10

Generation of Hexavalent DNL Constructs

Generation of Hex-hA20

The DNL method was used to create Hex-hA20, a monospecific anti-CD20 HIDS, by combining C-H-AD2-hA20 IgG with hA20-Fab-DDD2. The Hex-hA20 structure contains six anti-CD20 Fab fragments and an Fc fragment, arranged as four Fab fragments and one IgG antibody. Hex-hA20 was made as described below.

A 210% molar equivalent of (hA20-Fab-DDD2)$_2$ was mixed with C-H-AD2-hA20 IgG. This molar ratio was used because two Fab-DDD2 dimers are coupled to each C-H-AD2-hA20 IgG molecule and an additional 10% excess of the former to ensure that the coupling reaction is complete. The mixture was typically made in phosphate buffered saline, pH 7.4 (PBS) with 1 mM EDTA. Then reduced glutathione (GSH) was added to a final concentration of 1 mM and the solution was held at room temperature (16-25° C.) for 1-24 hours. Following reduction, oxidized glutathione (GSSH) was added directly to the reaction mixture to a final concentration of 2 mM and the solution was held at room temperature for 1-24 hours.

After oxidation, the reaction mixture was loaded directly onto a Protein-A affinity chromatography column. The column was washed with PBS and the Hex-hA20 was eluted with 0.1 M glycine, pH 2.5. Since excess hA20-Fab-DDD2 was used in the reaction, there was no unconjugated C-H-AD2-hA20 IgG, or incomplete DNL structures containing only one (hA20-Fab-DDD2)$_2$ moiety. The unconjugated excess hA20-Fab-DDD2 does not bind to the affinity resin. The calculated molecular weight from the deduced amino acid sequences of the constituent polypeptides is 386 kDa. Size exclusion HPLC analysis showed a single protein peak with a retention time consistent with a protein structure of 375-400 kDa (not shown).

Generation of Hex-hLL2

The DNL method was used to create a monospecific anti-CD22 HIDS (Hex-hLL2) by combining C-H-AD2-hLL2 IgG with hLL2-Fab-DDD2. The DNL reaction was accomplished as described above for Hex-hA20. The calculated molecular weight from the deduced amino acid sequences of the constituent polypeptides is 386 kDa. Size exclusion HPLC analysis showed a single protein peak with a retention time consistent with a protein structure of 375-400 kDa (not shown). SDS-PAGE analysis under non-reducing conditions showed a cluster of high molecular weight bands, which were eliminated under reducing conditions to leave only the three expected polypeptide chains: HC-AD2, Fd-DDD2, and the kappa chain (not shown).

Generation of DNL1 and DNL

The DNL method was used to create bispecific HIDS by combining C-H-AD2-hLL2 IgG with either hA20-Fab-DDD2 to obtain DNL1 or hMN-14-DDD2 to obtain DNL1C. DNL1 has four binding arms for CD20 and two for CD22. As hMN-14 is a humanized MAb to carcinoembryonic antigen (CEACAM5), DNL1C has four binding arms for CEACAM5 and two for CD22. The DNL reactions were accomplished as described for Hex-hA20 above. HPLC and SDS-PAGE were consistent with the desired products.

Generation of DNL2 and DNL2C

The DNL method was used to create bispecific HIDS by combining C-H-AD2-hA20 IgG with either hLL2-Fab-DDD2 to obtain DNL2 or hMN-14-DDD2 to obtain DNL2C. DNL2 has four binding arms for CD22 and two for CD20. DNL2C has four binding arms for CEACAM5 and two for CD20. The DNL reactions were accomplished as described for Hex-hA20. HPLC and SDS-PAGE were consistent with the desired products.

Stability in Serum

The stability of DNL1 and DNL2 in human serum was determined using a bispecific ELISA assay. The protein structures were incubated at 10 μg/ml in fresh pooled human sera at 37° C. and 5% $CO_2$ for five days. For day 0 samples, aliquots were frozen in liquid nitrogen immediately after dilution in serum. ELISA plates were coated with an anti-Id to hA20 IgG and bispecific binding was detected with an anti-Id to hLL2 IgG. Both DNL1 and DNL2 were highly stable in serum and maintained complete bispecific binding activity (not shown).

Binding Activity

The HIDS generated as described above retained the binding properties of their parental Fab/IgGs. Competitive ELISAs were used to investigate the binding avidities of the various HIDS using either a rat anti-idiotype MAb to hA20 (WR2) to assess the binding activity of the hA20 components or a rat anti-idiotype MAb to hLL2 (WN) to assess the binding activity of the hLL2 components. To assess hA20 binding, ELISA plates were coated with hA20 IgG and the HIDS were allowed to compete with the immobilized IgG for WR2 binding. To assess hLL2 binding, plates were coated with hLL2 IgG and the HIDS were allowed to compete with the immobilized IgG for WN binding. The relative amount of anti-Id bound to the immobilized IgG was detected using peroxidase-conjugated anti-Rat IgG.

Examining the relative CD20 binding avidities, DNL2, which has two CD20 binding groups, showed a similar binding avidity to hA20 IgG, which also has two CD20-binding arms (not shown). DNL1, which has four CD20-binding groups, had a stronger (~4-fold) relative avidity than DNL2 or hA20 IgG (not shown). Hex-hA20, which has six CD20-binding groups, had an even stronger (~10-fold) relative avidity than hA20 IgG (not shown).

Similar results were observed for CD22 binding. DNL1, which has two CD20 binding groups, showed a similar binding avidity to hLL2 IgG, which also has two CD22-binding arms (not shown). DNL2, which has four CD22-binding groups, had a stronger (>5-fold) relative avidity than DNL1 or hLL2 IgG. Hex-hLL2, which has six CD22-binding groups, had an even stronger (>10-fold) relative avidity than hLL2 IgG (not shown). As both DNL2 and DNL3 contain two hA20 Fabs and four hLL2 Fabs, they showed similar strength in binding to the same anti-id antibody (not shown).

In Vivo Anti-Tumor Activity

The HIDS were shown to have therapeutic efficacy in vivo using a human Burkitt Lymphoma model in mice. Low doses (12 μg) of DNL2 and Hex-hA20 more than doubled the survival times of tumor bearing mice. Treatment with higher doses (60 μg) resulted in long-term survivors.

In Vitro Activity

Some of the HIDS were observed to have potent anti-proliferative activity on lymphoma cell lines. DNL1, DNL2 and Hex-hA20 inhibited cell growth of Daudi Burkitt Lymphoma cells in vitro (not shown). Treatment of the cells with 10 nM concentrations was substantially more effective for the HIDS compared to rituximab (not shown). Using a cell counting assay, the potency of DNL1 and DNL2 was estimated to be more than 100-fold greater than that of rituximab, while the Hex-hA20 was shown to be even more potent (not shown). This was confirmed with an MTS proliferation assay in which dose-response curves were generated for Daudi cells treated with a range of concentrations of the HIDS (not shown). Compared to rituximab, the bispecific HIDS (DNL1 and DNL2) and Hex-hA20 were >100-fold and >10000-fold more potent, respectively.

Dose-response curves for HIDS (DNL1, DNL2, Hex-hA20) versus a parent IgG (hA20 IgG) were compared for three different lymphoma cell lines, using an MTS proliferation assay. In Daudi lymphoma cells, the bispecific structures DNL1 and DNL2 showed >100-fold more potent anti-proliferative activity and Hex-hA20 showed >10,000-fold more potent activity than the parent hA20 IgG (not shown). Hex-hLL2 and the control structures (DNL1-C and DNL2-C) had very little anti-proliferative activity in this assay (not shown).

In Raji lymphoma cells, Hex-hA20 displayed potent anti-proliferative activity, but DNL2 showed only minimal activity compared with hA20 IgG (not shown). In Ramos lymphoma cells, both DNL2 and Hex-hA20 displayed potent anti-proliferative activity, compared with hA20 IgG (not shown). These results show that the increased potency of HIDS relative to the parent IgGs is not limited to particular cell lines, but rather is a general phenomenon for cells displaying the appropriate targets.

CDC and ADCC Activity of Hexavalent DNL Constructs

In vivo, anti-CD20 monoclonal antibodies such as rituximab and hA20 can utilize complement-dependent cytotoxicity (CDC), antibody-dependent cellular cytotoxicity (ADCC) and signal transduction induced growth inhibition/apoptosis for tumor cell killing. The hexavalent DNL structures (DNL1, DNL2, Hex-hA20) were tested for CDC activity using Daudi cells in an in vitro assay. Surprisingly, none of the hexavalent structures that bind CD20 exhibited CDC activity (not shown). The parent hA20 IgG exhibited potent CDC activity (not shown), while as expected the hLL2 antibody against CD22 showed no activity (not shown). The lack of effect of DNL2 and Hex-hA20 was of interest, since they comprise hA20-IgG-Ad2, which showed similar positive CDC activity to hA20 IgG (not shown).

DNL1 was assayed for ADCC activity using freshly isolated peripheral blood mononuclear cells. Both rituximab and hA20 IgG showed potent activity on Daudi cells, while DNL1 did not exhibit any detectable ADCC activity (not shown).

These data suggest that the Fc region may become inaccessible for effector functions (CDC and ADCC) when four additional Fab groups are tethered to its carboxyl termini. Therefore, the hexavalent DNL structures appear to rely only on signal transduction induced growth inhibition/apoptosis for in vivo anti-tumor activity.

Example 11

Combination DNL Constructs Comprising Anti-CD74 Antibodies Show Potent Toxicity Against B Cell Lymphoma Juxtaposing CD20 and CD74 by Bispecific Antibodies Evokes Potent Cytotoxicity in Mantle Cell Lymphoma Abstract We describe the potent growth-inhibitory and apoptotic activities of two bispecific hexavalent antibodies (HexAbs) constructed by the dock-and-lock (DNL) technique from veltuzumab (anti-CD20) and milatuzumab (anti-CD74) in mantle cell lymphoma (MCL) and other lymphoma/leukemia lines, as well as primary patient tumor samples. In vitro, the bispecific HexAbs had different properties and were more potent than their parental antibodies. The juxtaposition of CD20 and CD74 on MCL cells by the HexAbs resulted in homotypic adhesion and triggered intracellular changes that included loss of mitochondrial membrane potential, production of reactive oxygen species, increased phosphorylation of ERKs and JNK, downregulation of pAkt and Bcl-xL, and enlargement of lysosomes, culminating in cell death. The two HexAbs also displayed different potencies in depleting lymphoma cells from whole blood ex vivo, and significantly extended the survival of nude mice bearing MCL xenografts.

Introduction

Mantle cell lymphoma (MCL) is an aggressive subtype of B-cell non-Hodgkin lymphoma (NHL) generally having a poor prognosis. Currently, there is no established standard of care and relapsed MCL remains a major clinical challenge. Thus, there is a need to develop new targeted therapeutics to treat this disease (Diefenbach & O'Connor, 2010, *Curr Opin Oncol.* 22:419-423).

Monoclonal antibodies (MAbs), exemplified by rituximab, are among the treatment options for MCL (Weigert et al., 2009, *Leuk Lymphoma* 50:1937-1950; Zhou et al., 2007, *Am J Hematol* 83:144-149) and have shown encouraging results in MCL (Lenz et al., 2005, *J Clin Oncol* 23:1984-1992; Sachanas et al., 2011, *Leuk Lymphoma* 52:387-93). However, resistance to rituximab therapy remains a problem (Lim et al., 2011, *Blood* July 18, Epub ahead of print) and more effective methods of treatment for MCL are needed.

The combination of two different targeting MAbs to achieve improved efficacy without increased toxicity was shown in NHL patients receiving both rituximab and epratuzumab (humanized anti-CD22 IgG$_1$, also referred to as hLL2) (Leonard et al., 2005, *J Clin Oncol* 23:5044-5051; Strauss et al., 2006, *J Clin Oncol* 24:3880-3886; Leonard et al., 2008, *Cancer* 113:2714-2723). More recently, the potential advantage of targeting both CD20 and CD74 was reported in a preclinical study involving rituximab and milatuzumab (humanized anti-CD74 IgG$_1$, also referred to as hLL1) which, in the presence of a crosslinking antibody, showed improved anti-tumor activity in MCL lines and primary patient samples than either parental antibody alone (Alinari et al., 2011, *Blood* 117:4530-41; Alinari et al., 2008, *Blood* 112:Abstract 886). In principle, combination antibody therapy can be accomplished with a bispecific antibody (bsAb) to avoid the need for administering two different antibodies sequentially, which is time-consuming, expensive, and inconvenient.

The potential of bsAbs as novel therapeutics for cancer and autoimmune disease is being explored with various constructs differing in design, structure, and antigen-binding properties. Depending on the built-in dual specificity, a bsAb may serve to recruit effector cells or effector molecules to target cells, or it may improve the target selectivity by concurrent ligation of two different antigens expressed on the same cell, wherein a multivalent bsAb should also enhance its functional affinity, resulting in increased retention on the bound cells and, likely, a higher potency.

The Dock-and-Lock (DNL) method, described above, is a platform technology that combines genetic engineering with site-specific conjugation to enable self-assembly of two modular components only with each other, resulting in a covalent structure of defined composition with retained bioactivity. We have applied DNL to generate various multivalent, multispecific structures that include mono- and bi-specific HexAbs, each comprising a pair of stabilized dimers of Fab linked to a full IgG at the carboxyl termini of the two heavy chains, thus conferring six Fab-arms and a common Fc entity. To identify these HexAbs, each is assigned a code of X-(Y)-(Y), where X and Y are specific numbers given to differentiate the antibodies, and a designated number enclosed in a parenthesis representing the antibody as a Fab. For example, 20-(74)-(74) designates the bispecific HexAb comprising a divalent anti-CD20 IgG of veltuzumab (also referred to as hA20) and a pair of stabilized dimers of Fab derived from milatuzumab. The designations of various HexAbs relevant to this study, which include 20-(74)-(74), 74-(20)-(20), 74-(74)-(74), 20-(20)-(20), 20-(22)-(22), and 22-(20)-(20), along with their modular components, are provided in Table 8.

TABLE 8

Hexavalent Antibody Designations

| Designation | | CH$_3$-AD2-IgG module | | CH$_1$-DDD2-Fab module | |
|---|---|---|---|---|---|
| Current | Previous | Ab | Ag | Ab | Ag |
| 20-(74)-(74) | N/A | Veltuzumab | CD20 | Milatuzumab | CD74 |
| 74-(20)-(20) | N/A | Milatuzumab | CD74 | Epratuzumab | CD20 |
| 74-(74)-(74) | N/A | Milatuzumab | CD74 | Milatuzumab | CD74 |
| 20-(20)-(20) | 20-20 | Veltuzumab | CD20 | Veltuzumab | CD20 |
| 20-(22)-(22) | 20-22 | Veltuzumab | CD20 | Epratuzumab | CD22 |
| 22-(20)-(20) | 22-20 | Epratuzumab | CD22 | Veltuzumab | CD20 |

In our initial efforts to develop HexAbs from veltuzumab and epratuzumab, we found both 20-(22)-(22) and 22-(20)-(20) induced growth inhibition and apoptosis in Burkitt lymphoma lines (Daudi, Raji and Ramos) in the absence of a crosslinking antibody, which is often required for the parental antibodies to be effective in vitro (Rossi et al., 2008, *Cancer Res* 68:8384-8392; Rossi et al., 2009, *Blood* 113:6161-6171; Gupta et al., 2010, *Blood* 116:3258-3267). Such direct cytotoxicity, however, was not observed in JeKo-1, a MCL line expressing comparable levels of CD20 and CD22 as Daudi NHL.

In the present Example, we describe the generation and characterization of three novel HexAbs, 20-(74)-(74), 74-(20)-(20), and 74-(74)-(74), from veltuzumab (hA20) and milatuzumab (hLL1). Surprisingly, even though mantle cell lymphoma was resistant to anti-CD20/CD22 HexAbs and to the parental anti-CD74 and anti-CD20 antibodies, the HexAbs based on the combination of anti-CD74 and anti-CD20 antibodies were highly cytotoxic in three blastoid MCL lines, JeKo-1, Granta-519 and Mino, as well as in primary tumor cells from patients with MCL or chronic lymphocytic leukemia (CLL). Selective experiments performed to investigate the intracellular events triggered by juxtaposing CD20 and CD74 revealed the prominent roles of actin reorganization and lysosomal membrane permeabilization (LMP) in the mechanisms of cell death.

Methods

Cell Lines, Antibodies, and Reagents—

All cell lines were purchased from ATCC (Manassas, Va.). Humanized antibodies, including veltuzumab, milatuzumab, epratuzumab, labetuzumab (anti-CEACAM5 IgG$_1$, also referred to as hMN-14), and hRS7 (anti-human Trop-2 IgG$_1$), were obtained as described in Example 1. Tositumomab and rituximab were obtained commercially. Phospho-specific antibodies and other commercially available antibodies were acquired from Cell Signaling (Beverly, Mass.) or Santa Cruz Biotechnology (Santa Cruz, Calif.). Cell culture media, supplements, annexin V ALEXA FLUOR® 488 conjugate, tetramethylrhodamine ethyl ester (TMRE), LYSOTRACKER® Red DND-99, CM-H$_2$DCF-DA, DAPI, ALEXA FLUOR® phalloidin, and acridine orange were bought from Invitrogen (Carlsbad, Calif.). One Solution Cell Proliferation assay (MTS) was obtained from Promega (Madison, Wis.). PHOSPHOSAFE™ buffer, latrunculin B, cytochalasin D, bafilomycin A1 and concanamycin A were procured from EMD chemicals (Gibbstown, N.J.). MAGIC RED™ Cathepsin B assay kit was purchased from ImmunoChemistry Technologies (Bloomington, Minn.). All other chemicals were purchased from Sigma (St. Louis, Mo.).

Cell Culture—

Malignant cell lines were cultured at 37° C. in 5% CO$_2$ in RPMI 1640 medium supplemented with 10% heat-inactivated fetal bovine serum, 2 mM L-glutamine, 200 U/ml penicillin and 100 µg/ml streptomycin. Cells from CLL and MCL patients were collected from whole blood by Ficoll-Hypaque separation and grown in RPMI media as described for the cell lines.

Cell Proliferation Assay—

Cells were seeded in 48-well plates ($5 \times 10^4$ cells per well) and incubated with each test article at a final concentration of 0.006 to 100 nM for 4 days. The number of viable cells was then determined using the MTS assay per the manufacturer's protocol, plotted as percent of the untreated, and analyzed by Prism software.

Effector Function Assays—

ADCC was performed as described previously (Rossi et al., 2008, *Cancer Res* 68:8384-8392), using JeKo-1 as the target cell and freshly isolated peripheral blood mononuclear cells as the effector cells. To perform CDC, cells were seeded in black 96-well plates at $5 \times 10^4$ cells in 50 µl per well and incubated with serial dilutions (concentration range $3.3 \times 10^{-8}$ to $2.6 \times 10^{-10}$ M) of test articles in the presence of human complement (1/20 final dilution, Quidel Corp., San Diego, Calif.) for 2 h at 37° C. and 5% CO$_2$. Viable cells were then quantified using the MTS assay. Controls included cells treated with 0.25% Triton X-100 (100% lysis) and cells treated with complement alone (background).

Annexin V Binding Assay—

Cells in 6-well plates ($2 \times 10^5$ cells per well) were treated with each test article at 10 nM for 24 to 48 h, washed, resuspended in 100 µl of annexin-binding buffer (10 mM HEPES, 140 mM NaCl and 2.5 mM CaCl$_2$ in PBS), stained with 5 µl of Annexin V-ALEXA FLUOR® 488 conjugate for 20 min, then with 1 µg/ml of propidium iodide (PI) in 400 µl of annexin binding buffer, and analyzed by flow cytometry (FACSCALIBUR®, Becton Dickinson, San Jose, Calif.). Cells stained positive with annexin V (including both PI-negative and PI-positive) were counted as apoptotic populations. When required, cells were pretreated with the indicated inhibitors for 2 h before adding the test article.

Immunoblot Analysis—

JeKo-1 cells ($6 \times 10^6$ cells in 6 ml) were treated with each test article at 10 nM for a predetermined time. Cells were washed with PBS, centrifuged, and lysed in ice-cold PHOSPHOSAFE™ buffer followed by centrifugation at 13,000×g. Supernatants were collected and protein samples (20 µg) were separated by SDS-PAGE on 4-20% gradient Tris-glycine gels followed by transfer onto nitrocellulose membranes (Bio-Rad, Hercules, Calif.), which were probed with suitable antibodies and developed as described (Rossi et al., 2009, *Blood* 113:6161-6171).

Nuclear Extracts—

JeKo-1 cells ($6 \times 10^6$ cells in 6 ml) were treated with each test article at 10 nM for 72 h. Cells were collected and cytosolic and nuclear extracts were obtained as described (Mayo et al., 2001, *Methods Enzymol* 333:73-87). Equal amounts of nuclear and cytosolic proteins (10 µg) were separated on SDS-PAGE and analyzed for NF-κB protein p65, Brg-1 and β-actin, with the latter two serving as loading controls for nuclear and cytosolic proteins, respectively.

Assessment of $\Delta\psi_m$ and ROS—

Flow cytometry was used to determine $\Delta\psi_m$ and ROS. Briefly, cells in 6-well plates ($2 \times 10^5$ cells per well) were treated with each test article at 10 nM for 48 h, washed, stained for 30 min in the dark at 37° C. with TMRE (50 nM) for $\Delta\psi_m$ or CM-H$_2$DCF-DA (1 µM) for ROS. Samples were then washed with PBS and analyzed.

Assessment of Lysosomal Changes and Cathepsin B Release—

To determine the changes in lysosomal volumes, $2 \times 10^5$ cells per well in 6-well plates were treated with each test article at 10 nM for 48 h. After washing, cells were labeled with LYSOTRACKER® Red DND-99 (75 nM) followed by incubation in the dark at 37° C. for 1 h. Cells were washed with PBS and samples were analyzed by flow cytometry. To evaluate lysosomal membrane permeabilization, JeKo-1 cells were treated with select antibodies at 10 µg/ml for 4 h, labeled with acridine orange, and examined under a fluorescence microscope. To study cathepsin B release, JeKo-1 cells were treated with select antibodies (10 nM) for 48 h, fixed with 4% paraformaldehyde, permeabilized with 0.1% tritonX-100, costained with MAGIC RED™ Cathepsin B and DAPI, and examined under a fluorescence microscope.

Effect on Actin—

Cells were treated with various antibodies or combinations of antibodies as indicated, stained for 30 min with either rhodamine phalloidin and DAPI for actin and nucleus, respectively, or rhodamine phalloidin and FITC-conjugated, Fc fragment-specific, goat anti-human (GAH) antibody (for the location of test antibodies), and visualized under a fluorescence microscope after washing.

Ex Vivo Depletion of JeKo-1 and B Cells from Whole Blood—

JeKo-1 cells ($5 \times 10^4$) were mixed with heparinized whole blood (150 µl) from healthy volunteers and incubated with varying concentrations of each test article for 2 d at 37° C. and 5% CO$_2$. After lysing the red blood cells and washing, the remaining cells were stained with FITC-anti-CD19, PE-anti-CD14 or allophycocyanin (APC)-conjugated mouse IgG$_1$ isotype control, and analyzed by flow cytometry. JeKo-1 cells and monocytes were identified in the monocyte gate as CD19$^+$ and CD14$^+$ populations, respectively. Normal B cells are CD19$^+$ in the lymphocyte gate.

In Vivo Efficacy—

Female 8-week-old SCID mice (Taconic Farms; Germantown, N.Y.) were used. Seven different treatment groups of eight mice each were inoculated i.v. with JeKo-1 ($2.5 \times 10^7$ cells). After seven days, one group received 370 µg of 20-(74)-(74) i.p. twice weekly for two weeks. A second group received 74-(20)-(20) with the same dose and schedule. Two lower doses (37 μg and 3.7 μg) also were examined for each HexAb with the same schedule and injection route. The control group received saline. The mice were observed daily for signs of distress or paralysis, weighed weekly, and killed humanely when they developed hind-limb paralysis, became moribund, or lost more than 20% of initial body weight.

Statistical Analyses—

For in vitro studies, the statistical difference between two populations was determined by Student's t-test. For in vivo studies, statistical differences in survival between treatment groups were analyzed using Kaplan-Meier plots provided by Prism software. P<0.05 was considered statistically significant.

Results

Generation of HexAbs and Demonstration of Direct Cytotoxicity In Vitro—

Figure 1B:
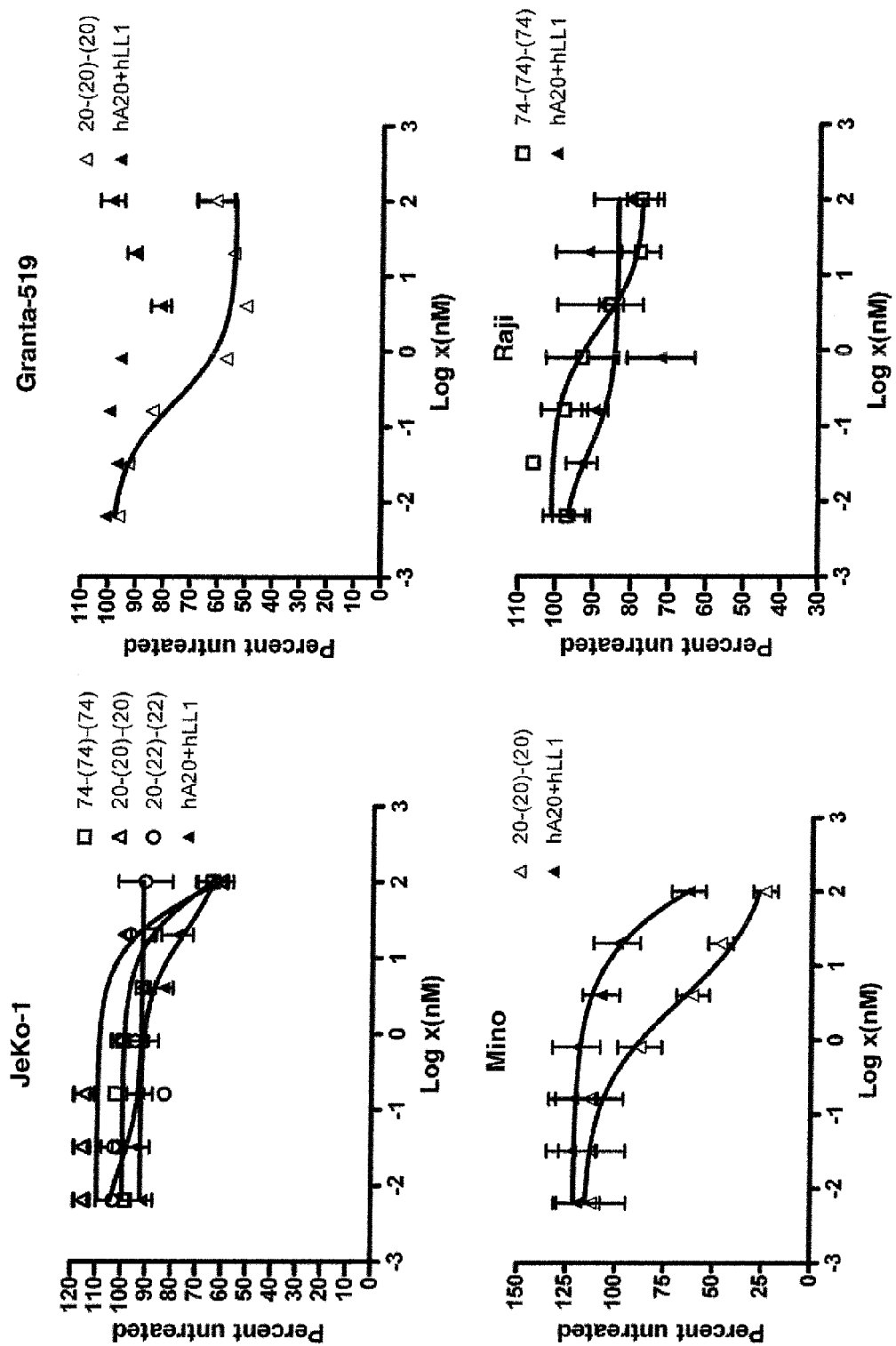
FIG. 1B. Direct cytotoxicity induced by anti-CD20/CD74 HexAbs in NHL cell lines as determined by the MTS assay. Effect of monospecific 20-(20)-(20) on JeKo-1, Granta-519 and Mino; bispecific 20-(22)-(22) on JeKo-1; and monospecific 74-(74)-(74) on Raji.

The generation of monospecific and bispecific HexAbs by the DNL method from the cognate $C_H3$-AD2-IgG-X and $C_H1$-Fab-DDD2-Y, where X and Y can be either hLL1 (milatuzumab) or hA20 (veltuzumab), was performed as described in Examples 9 and 10 above. The HexAbs were purified to near homogeneity, as indicated by SDS-PAGE and SE-HPLC analyses (not shown) for 20-(74)-(74) and 74-(20)-(20). Both also showed stronger binding to three MCL cell lines (JeKo-1, Granta-519 and Mino) than their parental antibodies (data not shown).

range. In comparison, we observed <20% (Granta-519 and Raji) and <50% (Jeko-1 and Mino) growth inhibition when both parental antibodies were combined at the highest concentration tested (100 nM) (FIG. 1A). Additional results shown in FIG. 1B revealed that the anti-proliferative activity of the monospecific 74-(74)-(74) and 20-(20)-(20) HexAbs, as well as the bispecific anti-CD20/CD22 HexAb, 20-(22)-(22), paralleled that of combined hLL1 and hA20 in JeKo-1, and thus was considerably lower in activity than the bispecific anti-CD20/CD74 HexAbs.

Figure 1C:
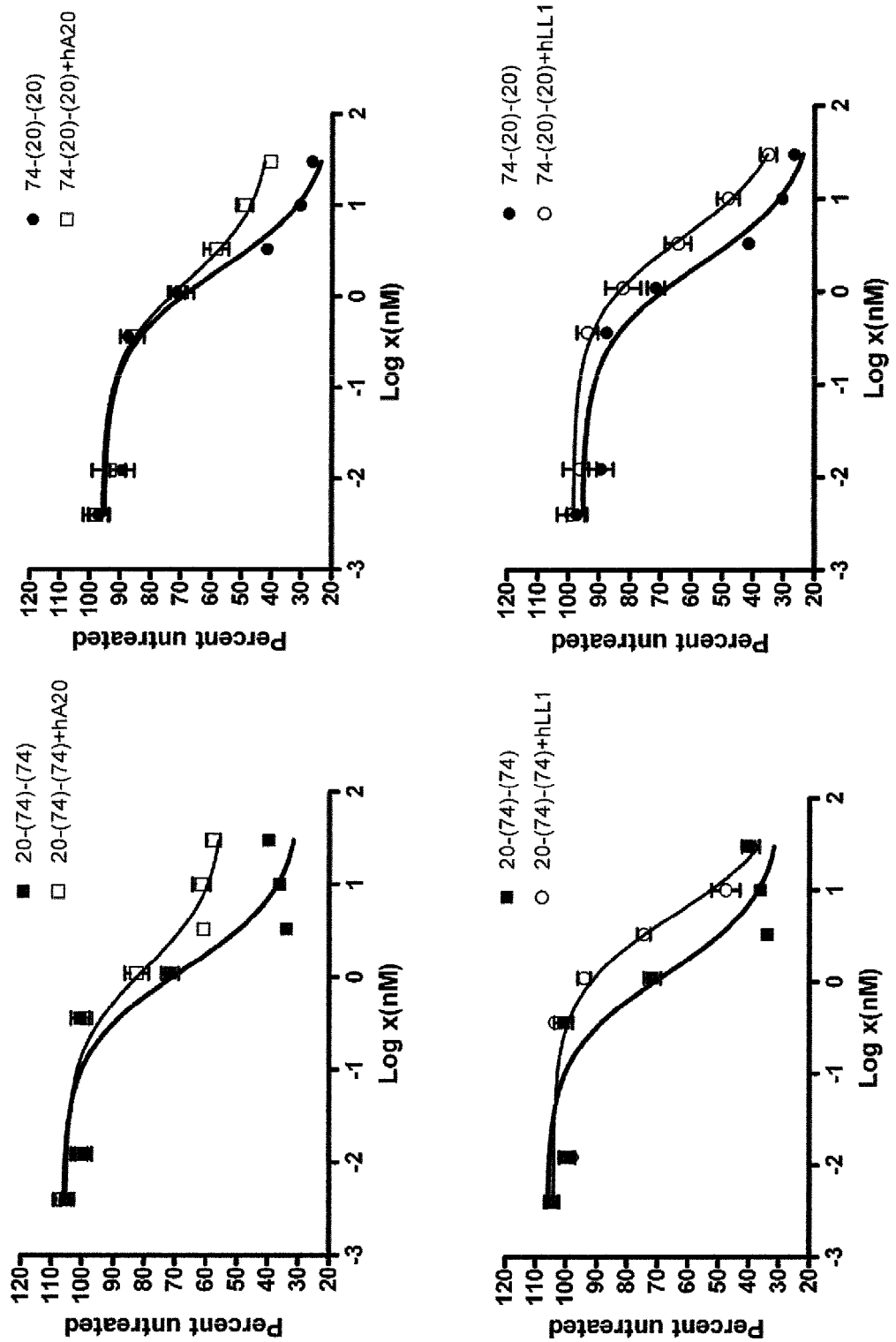
FIG. 1C. Direct cytotoxicity induced by anti-CD20/CD74 HexAbs in NHL cell lines as determined by the MTS assay. Dose-response curves showing partial inhibition of 20-(74)-(74) and 74-(20)-(20) in JeKo-1 by excess hA20 or hLL1 (10 µg/ml).

On the other hand, notable cytotoxicity of 20-(20)-(20) was found in Mino and Granta-519, and an initial survey showed cell lines derived from CLL (WAC and MEC-1), acute lymphocytic leukemia (REH-1 and MN60), and multiple myeloma (CAG, RPMI8266, KMS11, KMS12-BM, and KMS12-PE) were relatively resistant to the HexAbs. For both 20-(74)-(74) and 74-(20)-(20), the addition of either parental antibody at a moderate concentration of 10 μg/mL partially reduced their anti-proliferative effects in JeKo-1 (FIG. 1C). A list of the $EC_{50}$ values (nM), as determined by the MTS assay, is provided in Table 9. Surprisingly, DNL constructs comprising anti-CD74 and anti-CD20 antibodies or fragments thereof were substantially more effective at treating mantle cell lymphoma than anti-CD20/anti-CD22 DNL constructs or either parental antibody administered alone or together.

TABLE 9

$EC_{50}$ values (nM) for HexAbs comprising hA20 and hLL1 in three MCL (JeKo-1, Granta-519, Mino) and 2 Burkitt lymphoma lines (Daudi, Raji). The $EC_{50}$ values as determined by the MTS assay for 20-(74)-(74) and 74-(20)-(20) in two CLL lines (WAC, MEC-1), 2 ALL lines (REH-1, MN60), and 5 MM lines ((CAG, RPMI8226, KMS11, KMS12-BM, KMS12-PE), were all greater than 100 nM. In MM lines, hLL1, hA20, hLL1 + GAH, hA20 + GAH, and hLL1 + hA20 + GAH show no anti-proliferative effect.

| | $EC_{50}$ (nM) | | | | | Percent inhibition (%) at 100 nM | | | |
|---|---|---|---|---|---|---|---|---|---|
| | JeKo-1 | Granta-519 | Mino | Daudi | Raji | JeKo-1 | Granta-519 | Mino | Raji |
| hLL2 | | | | | | | | | |
| hLL1 | | | | | | 0 | 0 | | |
| HA20 | | | | | | 0 | 8 | | |
| Rituximab | | | | | | 0 | 11 | | |
| hLL2 + GAH | | | | | | | | | |
| hLL1 + GAH | | | | | | 36 | 38 | | |
| hA20 + GAH | | | | | | 27 | 37 | | |
| Rituximab + GAH | | | | | | 20 | 45 | | |
| hA20 + hLL1 | >100 | >100 | >100 | | >100 | 0 | 34 | | |
| Rituximab + hLL1 | | | | | | 0 | 40 | | |
| hA20 + hLL1 + GAH | | | | | | 68 | 61 | | |
| Rituximab + hLL1 + GAH | | | | | | 67 | 60 | | |
| 20-(74)-(74) | 3 | 2 | 13.7 | 5.3 | 0.3 | 70 | 55 | 80 | 50 |
| 74-(20)-(20) | 2 | 0.6 | 1.2 | 1.2 | 0.3 | 90 | 65 | 100 | 50 |
| 74-(74)-(74) | >100 | | | | | | | | |
| 20-(20)-(20) | >100 | 0.2 | 3.4 | 5.8 | 8 | | | | |
| 22-(20)-(20) | | | | | | | | | |
| 20-(22)-(22) | >100 | | | | | | | | |

In the cell proliferation assays (FIG. 1A), the two bispecific anti-CD20/CD74 HexAbs demonstrated potent cytotoxicity against JeKo-1, Granta-519, Mino, and Raji, with the half maximal effector concentration ($EC_{50}$) in the low nanomolar Antibody-Dependent Cellular Cytotoxicity (ADCC)—

Figure 6:
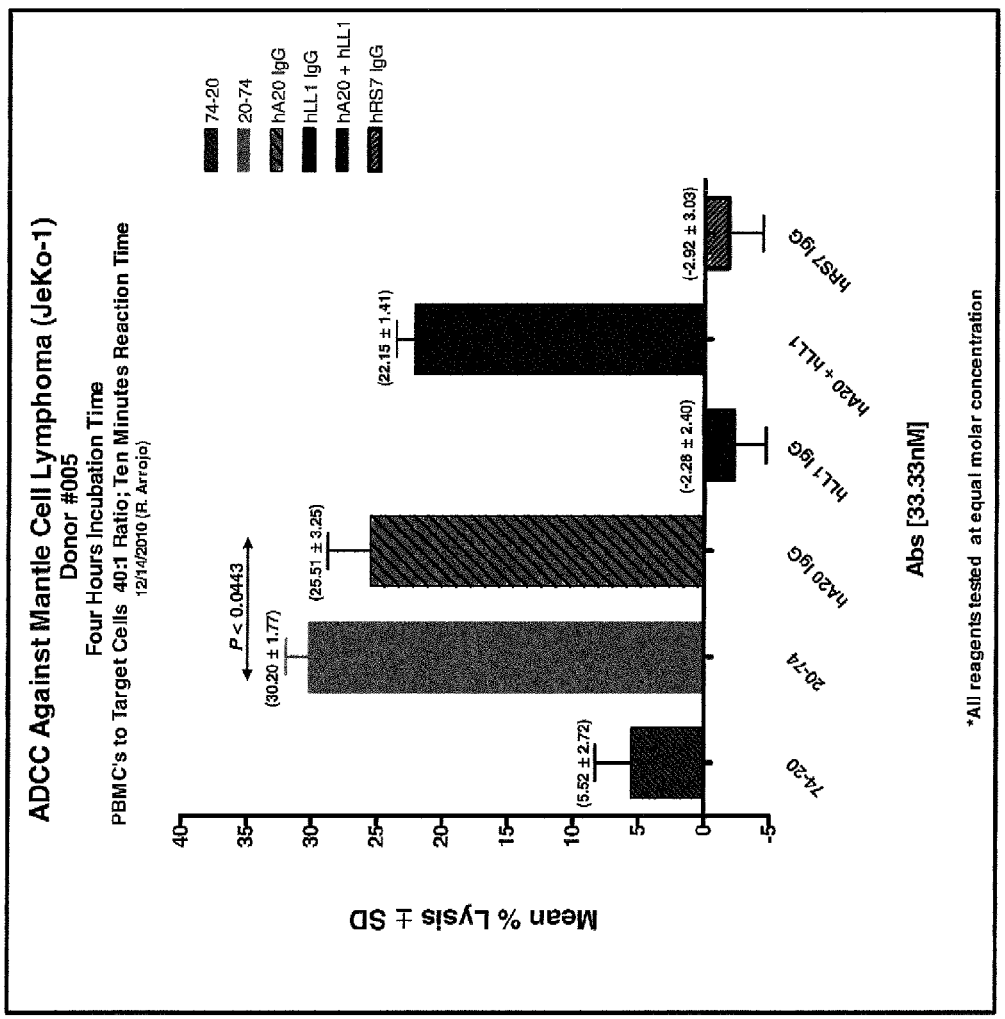
FIG. 6. 20-(74)-(74) Induced potent ADCC in JeKo-1 cells.

HexAbs based on anti-CD20 IgG, i.e., the 20-(X)-(X) series, were expected to display ADCC with a similar potency to hA20 IgG (Rossi et al., 2008, *Cancer Res* 68:8384-8392;

Rossi et al., 2009, *Blood* 113:6161-6171). As shown in FIG. 6, the mean cell lysis obtained in JeKo-1 with 20-(74)-(74) dosed at 33 nM, with a 40 to 1 effector to target cell ratio, was 30.2%, slightly higher but statistically significantly (P<0.0443) more than hA20 IgG (25.5%). Under the same conditions, a much weaker ADCC (5.5% lysis) was observed for 74-(20)-(20), whereas hLL1 IgG or a non-binding control (hRS7 IgG) had no ADCC.

Complement-Dependent Cytotoxicity (CDC)—

The results of CDC were determined for JeKo-1, Granta-519, and Daudi cells. In all three cell lines, 74-(20)-(20) displayed negligible CDC (not shown), whereas 20-(74)-(74) was moderately active in Jeko-1 and Granta-519, but as potent as hA20 IgG in Daudi (not shown).

Apoptosis—

Figure 2A:
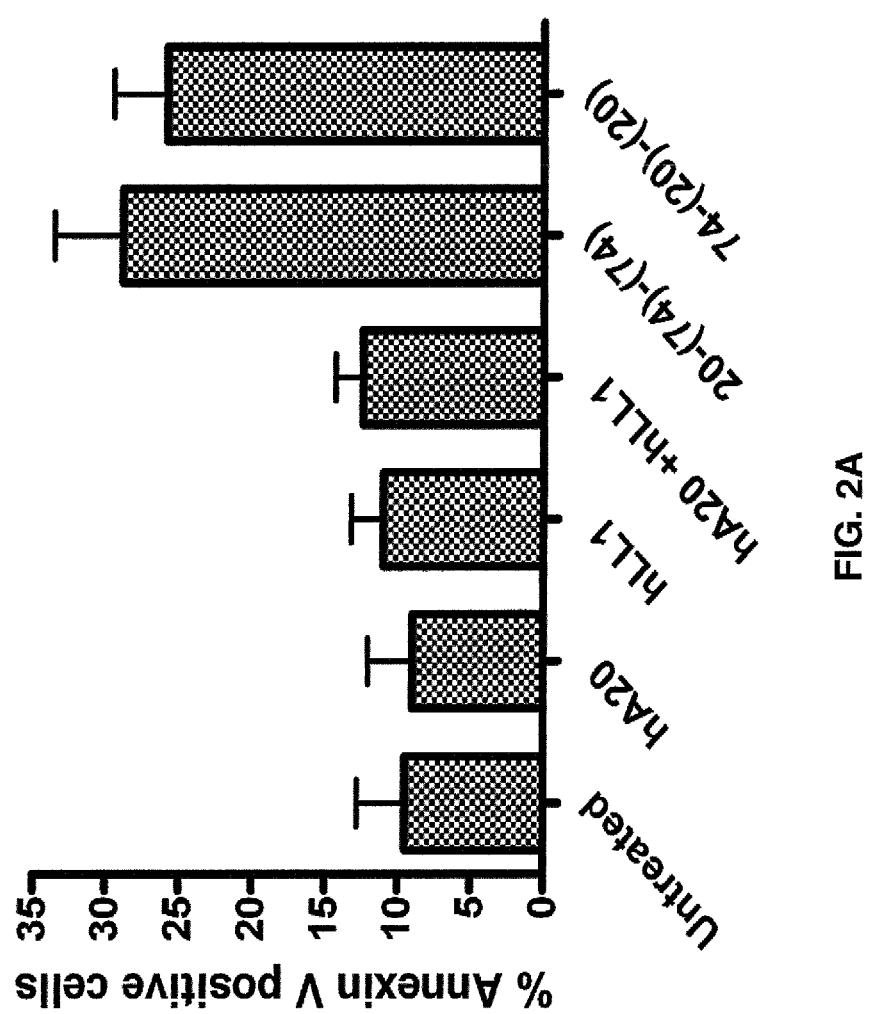
FIG. 2A. Induction of apoptosis by anti-CD20/CD74 HexAbs. JeKo-1 cells ($2 \times 10^5$ cells per well in 6-well plate) were treated with 10 nM of indicated antibodies for 48 h followed by annexin staining analysis. The two bispecific anti-CD20/CD74 HexAbs induced statistically significant apoptosis in JeKo-1 cells compared to cells treated or not treated with parental antibodies, alone or combined ($P<0.033$).
Figure 2B:
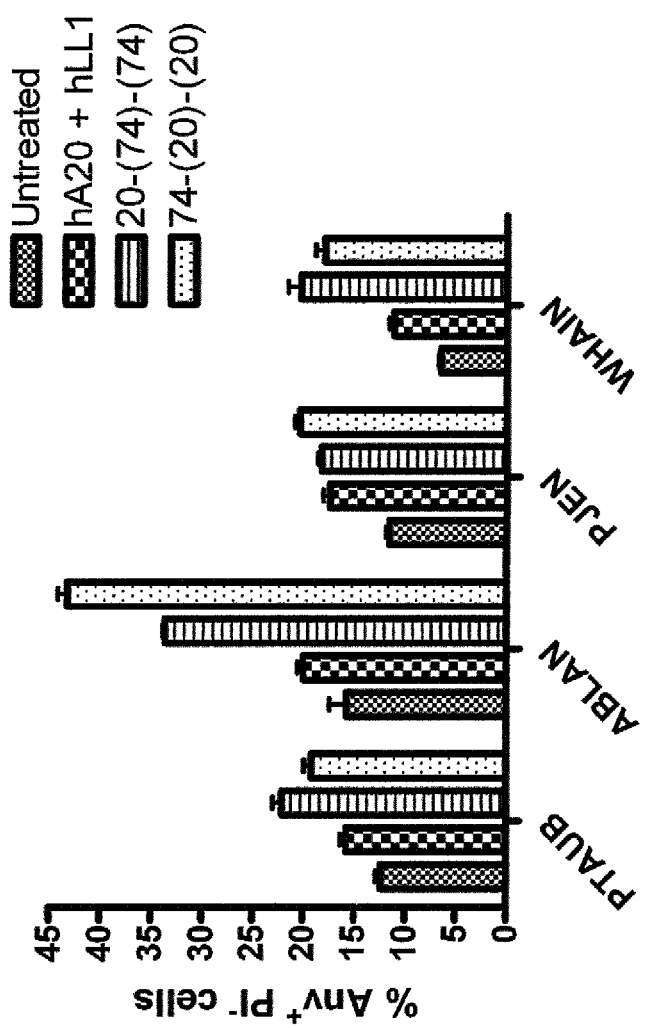
FIG. 2B. Induction of apoptosis by anti-CD20/CD74 HexAbs. Annexin analysis on primary samples from MCL patients treated with indicated antibodies (10 nM) for 24 to 48 h. Data are shown as Annexin$^+$ PI$^-$ cells (early apoptosis). The two anti-CD20/CD74 HexAbs induced statistically significant early apoptosis in MCL ($P<0.008$) compared to the untreated controls.
Figure 2C:
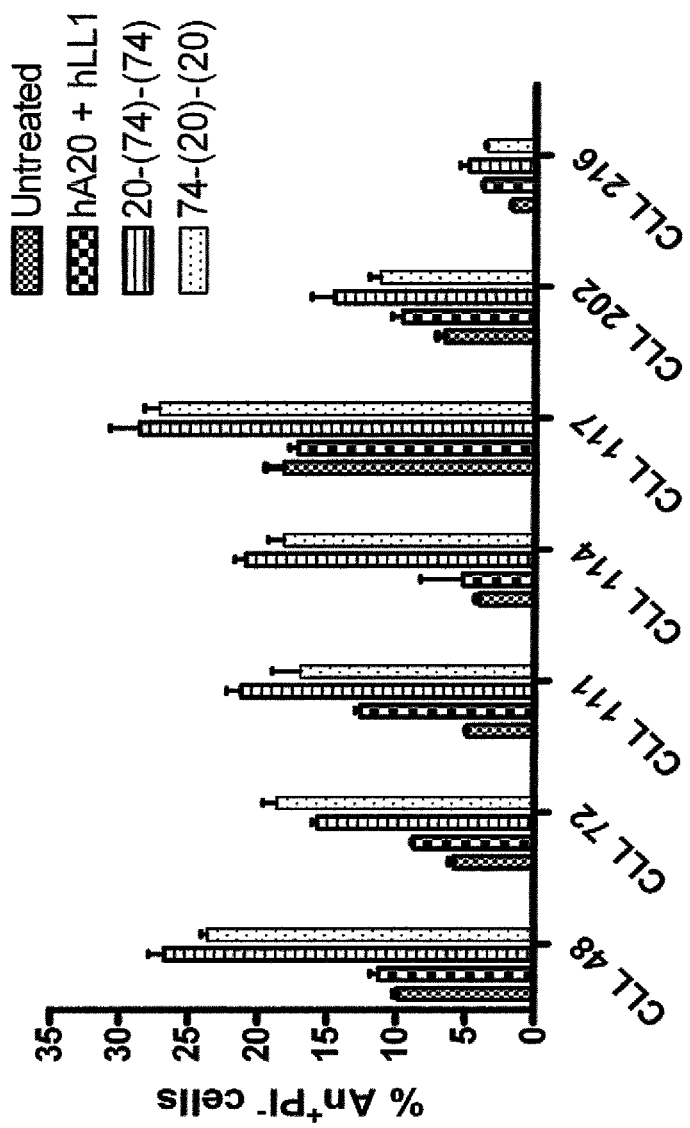
FIG. 2C. Induction of apoptosis by anti-CD20/CD74 HexAbs. Annexin analysis on primary samples from CLL patients treated with indicated antibodies (10 nM) for 24 to 48 h. Data are shown as Annexin$^+$ PI$^-$ cells (early apoptosis). The two anti-CD20/CD74 HexAbs induced statistically significant early apoptosis in CLL ($P<0.03$) compared to the untreated controls. One of the patient samples (CLL 216) did not respond to any treatment.
Figure 2D:
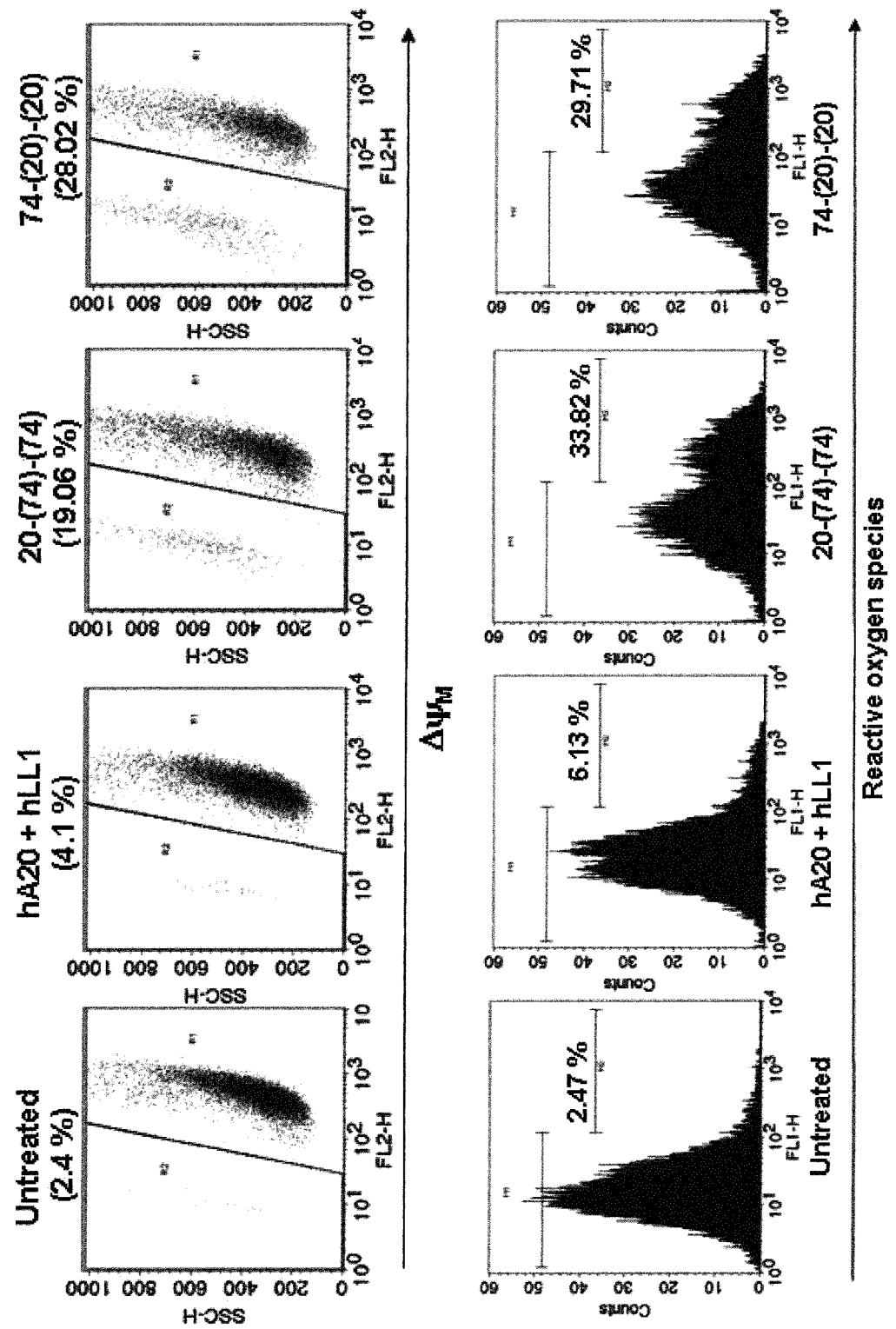
FIG. 2D. Induction of apoptosis by anti-CD20/CD74 HexAbs. Both anti-CD20/CD74 HexAbs induced changes in mitochondrial membrane potential (upper panel) and generated ROS (lower panel) in Granta-519.
Figure 3A:
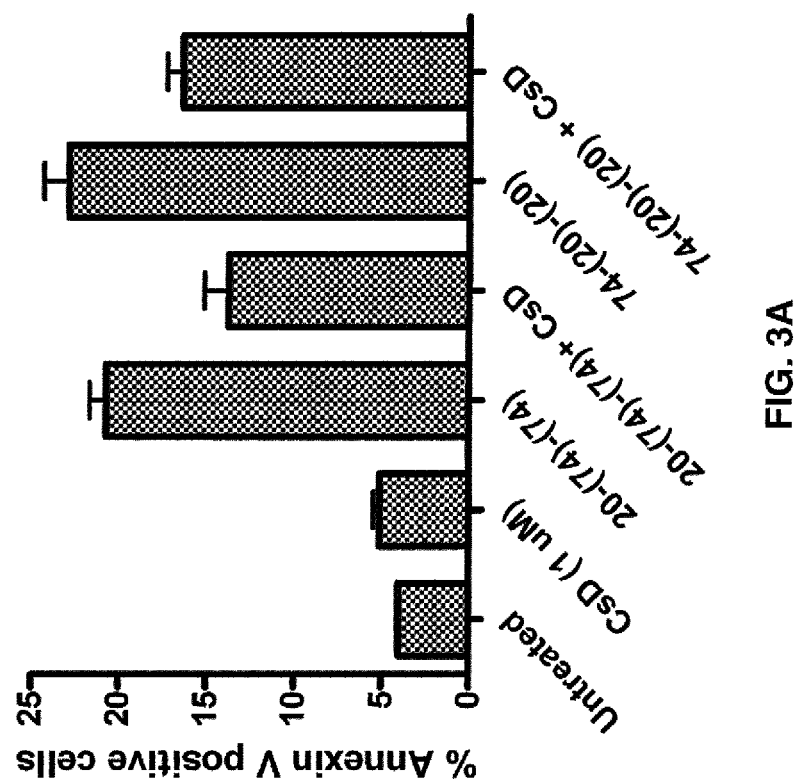
FIG. 3A. Correlation of homotypic adhesion, actin reorganization, and lysosomal involvement to cell death evoked by the bispecific anti-CD20/CD74 HexAbs. Apoptosis induced by HexAbs was reduced significantly ($P<0.025$) in Jeko-1 with 2 µM of cytochalasin D (CsD), another inhibitor of actin polymerization.

The ability of 20-(74)-(74) and 74-(20)-(20) to induce apoptosis was evaluated by flow cytometry using the Annexin V binding assay. In JeKo-1, both bispecific anti-CD20/CD74 HexAbs at 10 nM showed a statistically significant (P<0.033) increase of 10-15% in Annexin V-positive cells over the various controls (FIG. 2A), which included untreated cells, cells treated with either parental antibody, and cells treated with both parental antibodies combined. Statistically significant increases of 10 to 25% in annexin V-positive cells were also observed for all four MCL patient samples (P<0.008; FIG. 2B) and six of seven CLL patient samples (P<0.03, FIG. 2C). Immunoblot results indicated that the treatment of JeKo-1 with the bispecific anti-CD20/CD74 HexAbs had no apparent effect on the expression levels of Bcl-2, Mc1-1, and Bax, but substantially reduced the amount of Bcl-xL (not shown). The lack of appreciable change in the expression level and cleavage of caspase 3, caspase 8, and caspase 9 (not shown) suggest that the bispecific anti-CD20/CD74 mediate a caspase-independent apoptosis, which was associated with 20 to 30% changes in mitochondrial membrane potential ($\Delta\psi_m$) and about 30% increase in ROS in Granta-519 (FIG. 2D), and somewhat less in JeKo-1 (not shown).

Homotypic Adhesion and Actin Reorganization—

The 20-(74)-(74) and 74-(20)-(20) hexavalent DNL constructs, but not the parental antibodies, evoked in JeKo-1 a strong homotypic adhesion (not shown), which was prevented by latrunculin B, an inhibitor of actin polymerization. Similar results were observed for Granta-519, Mino and Raji (data not shown). Significant homotypic adhesion (>40%) also could be induced in Jeko-1, but not in KMS-11 (a CD20-negative multiple myeloma line expressing a high level of CD74), by tositumomab (murine anti-human CD20 $IgG_{2b}$) alone, or by the parental antibodies in the presence of a crosslinking antibody (Table 10). JeKo-1 and KMS-11 cells ($2\times10^6$/mL) were incubated with the indicated treatments for 2 and 24 h at 37° C. The values (%) shown were the mean from three different fields. KMS-11 is a multiple myeloma cell line with low CD20 expression and high CD74. nd, not determined.

Pretreatment of JeKo-1 with cytochalasin D, which is less toxic than latrunculin B and allows a longer period of incubation, decreased the extent of annexin V-positive cells (FIG. 3A) from 21±1% to 13±2% (P<0.02) by 20-(74)-(74) or from 23±2% to 16±1% (P<0.025) by 74-(20)-(20). These results correlate homotypic adhesion and actin reorganization with apoptosis in cell lines sensitive to treatment with the bispecific anti-CD20/CD74 HexAbs. Additional studies in JeKo-1 revealed that treatment with 20-(74)-(74) or 74-(20)-(20) induced actin to cluster at the cell-cell junction (not shown) and similar results could be produced either with B1 in the absence of a crosslinking antibody, or with rituximab, veltuzumab, or milatuzumab in the presence of a crosslinking antibody (not shown). However, neither 20-(74)-(74) nor 74-(20)-(20) appeared to co-localize with actin at the cell-cell junction when cells were co-stained with FITC-conjugated anti-human-Fc (not shown).

TABLE 10

Homotypic adhesion induced in JeKo-1 by various antibodies and combinations of antibodies.

| | | JeKo-1 | | KMS-11 | |
|---|---|---|---|---|---|
| | | 2 h | 24 h | 2 h | 24 h |
| | µg/mL | | | | |
| Untreated | — | 5 ± 2 | <8 | <2 | <4 |
| GAH | 20 | 6 ± 3 | <8 | <3 | <4 |
| hLL2 | 5 | 5 ± 2 | <8 | <2 | <5 |
| hLL1 | 5 | 5 ± 3 | <8 | <3 | <5 |
| hA20 | 5 | 5 ± 3 | <14 | <2 | <4 |
| Rituximab | 5 | 10 ± 4 | <18 | <2 | <5 |
| B1 | 5 | 95 ± 4 | nd | nd | nd |
| hLL2 + GAH | 5 + 20 | 4 ± 2 | <7 | <2 | <8 |
| hLL1 + GAH | 5 + 20 | 8 ± 3 | >95 | <2 | <6 |
| hA20 + GAH | 5 + 20 | 55 ± 10 | >95 | <4 | <4 |
| Rituximab + GAH | 5 + 20 | 42 ± 8 | >95 | <4 | <7 |
| hA20 + hLL1 | 5 + 5 | 10 ± 5 | <18 | <4 | <4 |
| Rituximab + hLL1 | 5 + 5 | 21 ± 5 | <24 | <3 | <8 |
| hA20 + hLL1 + GAH | 5 + 5 + 20 | 60 ± 4 | >95 | <4 | <9 |
| Rituximab + hLL1 + GAH | 5 + 5 + 20 | 56 ± 12 | >95 | <2 | <8 |
| | (nM) | | | | |
| B1 | 10 | 90 ± 5 | >95 | <3 | <9 |
| 20-(74)-(74) | 10 | 90 ± 5 | >95 | <4 | <8 |
| 74-(20)-(20) | 10 | 90 ± 5 | >95 | <2 | <9 |
| 74-(74)-(74) | 10 | nd | nd | nd | nd |
| 20-(20)-(20) | 10 | 16 ± 2 | <21 | <3 | <5 |
| 22-(20)-(20) | 10 | 18 ± 4 | <20 | <3 | <8 |
| 20-(22)-(22) | 10 | 15 ± 4 | <24 | <2 | <6 |

Involvement of Lysosomes—

Figure 3B:
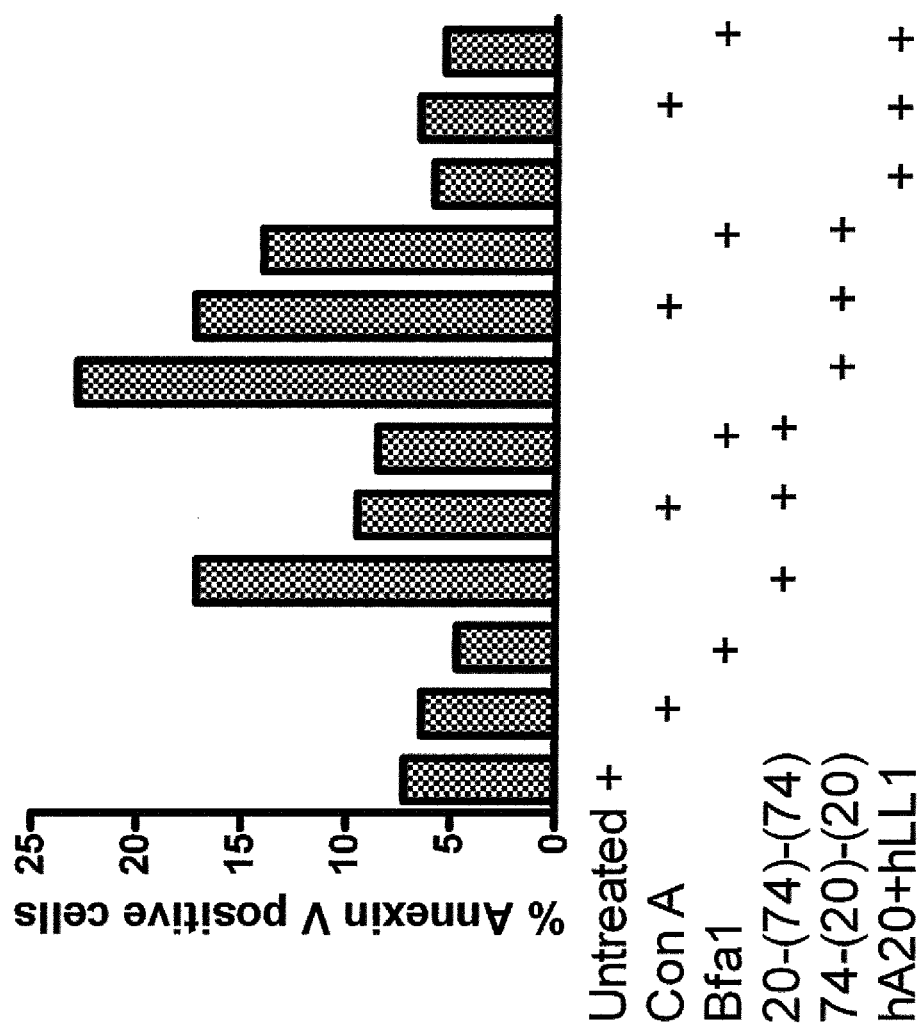
FIG. 3B. Correlation of homotypic adhesion, actin reorganization, and lysosomal involvement to cell death evoked by the bispecific anti-CD20/CD74 HexAbs. Lysosomal V ATPase inhibitors, concanamycin A (Con A) and bafilomycin A1 (Bfa1), inhibited the apoptosis induced by HexAbs in JeKo-1 cells.

HexAb-mediated apoptosis could be reduced effectively with concanamycin A or bafilomycin A1, both functioning by blocking lysosomal acidification through selective inhibition of the V-type ATPase (Drose & Altendorf, 1997, *J Exp Biol* 200:1-8). As shown in FIG. 3B, treatment of JeKo-1 with concanamycin A (10 nM) or bafilomycin A1 (50 nM) before the addition of either 20-(74)-(74) or 74-(20)-(20) largely decreased the extent of annexin V-positive cells. Further, a sizable enlargement of the lysosomal compartments by the two bispecific anti-CD20/CD74 HexAbs was demonstrated using flow cytometry with a fluorescent acidotropic probe, LYSOTRACKER® Red DND-99 (not shown). These results implicate a causal role of lysosomes in cell death, and are supported by fluorescence microscopic evidence of lysosomal membrane permeabilization and release of cathepsin B into the cytosol (not shown).

Effect on MAP Kinases, Src, p65/NF-κB, and Akt—

The bispecific anti-CD20/CD74 HexAbs induced rapid and sustained activation of ERK and JNK kinases in Jeko-1. For 74-(20)-(20) and 20-(74)-(74) phosphorylated ERKs and JNK, respectively, could be detected within 30 min (not shown), which persisted for the next 6 h and returned to basal levels by 24 h (not shown). In contrast, no phosphorylation of ERKs and JNK was observed in those cells incubated with both parental antibodies (not shown). Due to the high expression of the p38 MAP kinase in Jeko-1, we were unable to determine whether its level had changed upon treatment with the bispecific HexAbs.

Select signals upstream and downstream of ERKs and JNK were also found to be modulated by treating JeKo-1 with the bispecific anti-CD20/CD74 HexAbs. Pertinent results include the ability of both HexAbs to induce a larger decrease (~60%) of the upstream phospho-Src than that of the parental hA20 MAb (~30%) (not shown), and the effective inhibition of the downstream p65/NF-κB from nuclear translocation by both HexAbs (not shown). We also observed that the bispecific HexAbs notably reduced the level of constitutively activated Akt in JeKo-1 (not shown).

Ex Vivo Depletion of JeKo-1 and Normal B Cells from Human Whole Blood—

Figure 4A:
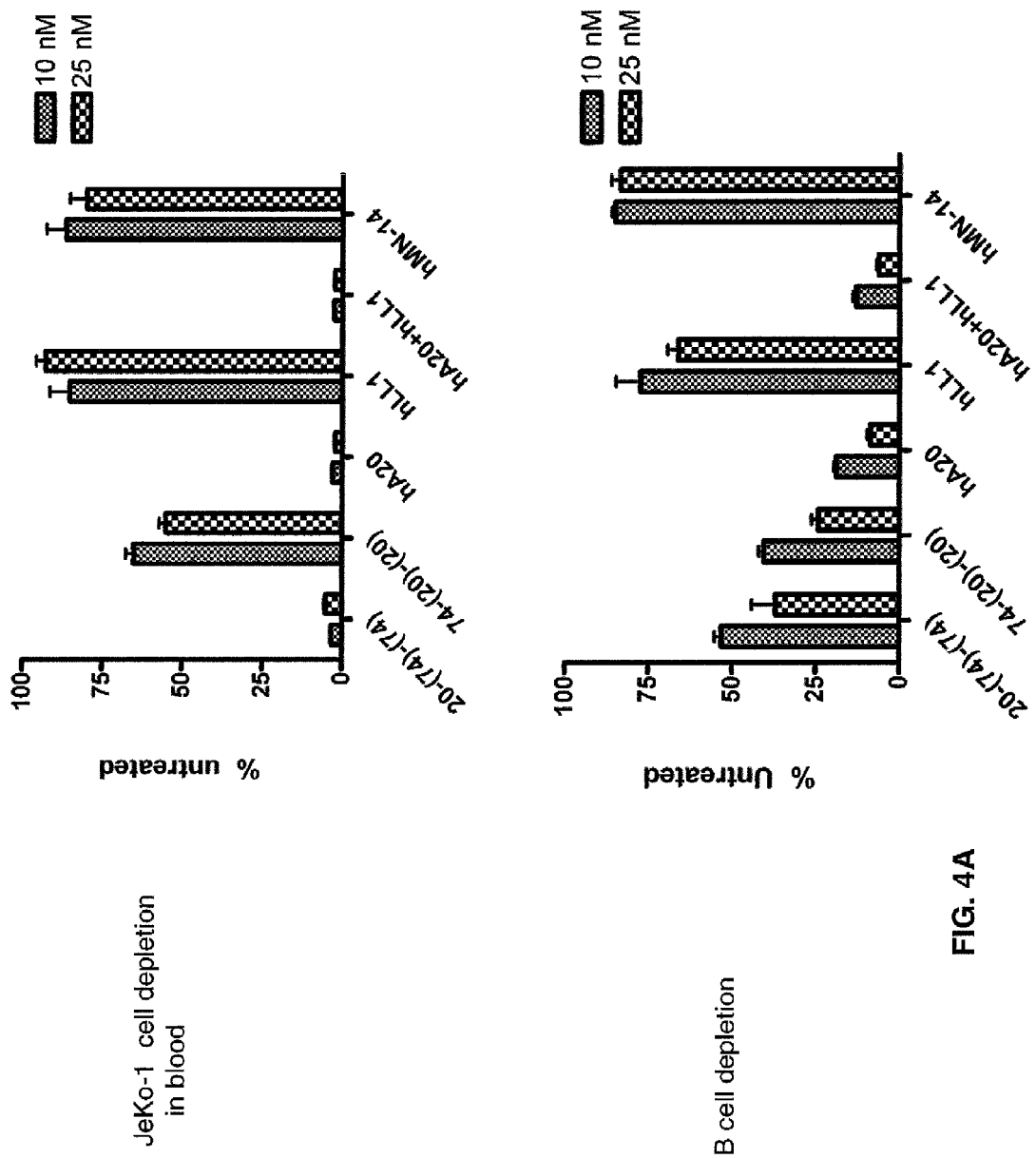
FIG. 4A. Activity of HexAbs in human blood ex vivo. 20-(74)-(74) and 74-(20)-(20), tested at 10 and 25 nM in JeKo-1 (upper panel) and normal B cells (lower panel).
Figure 4B:
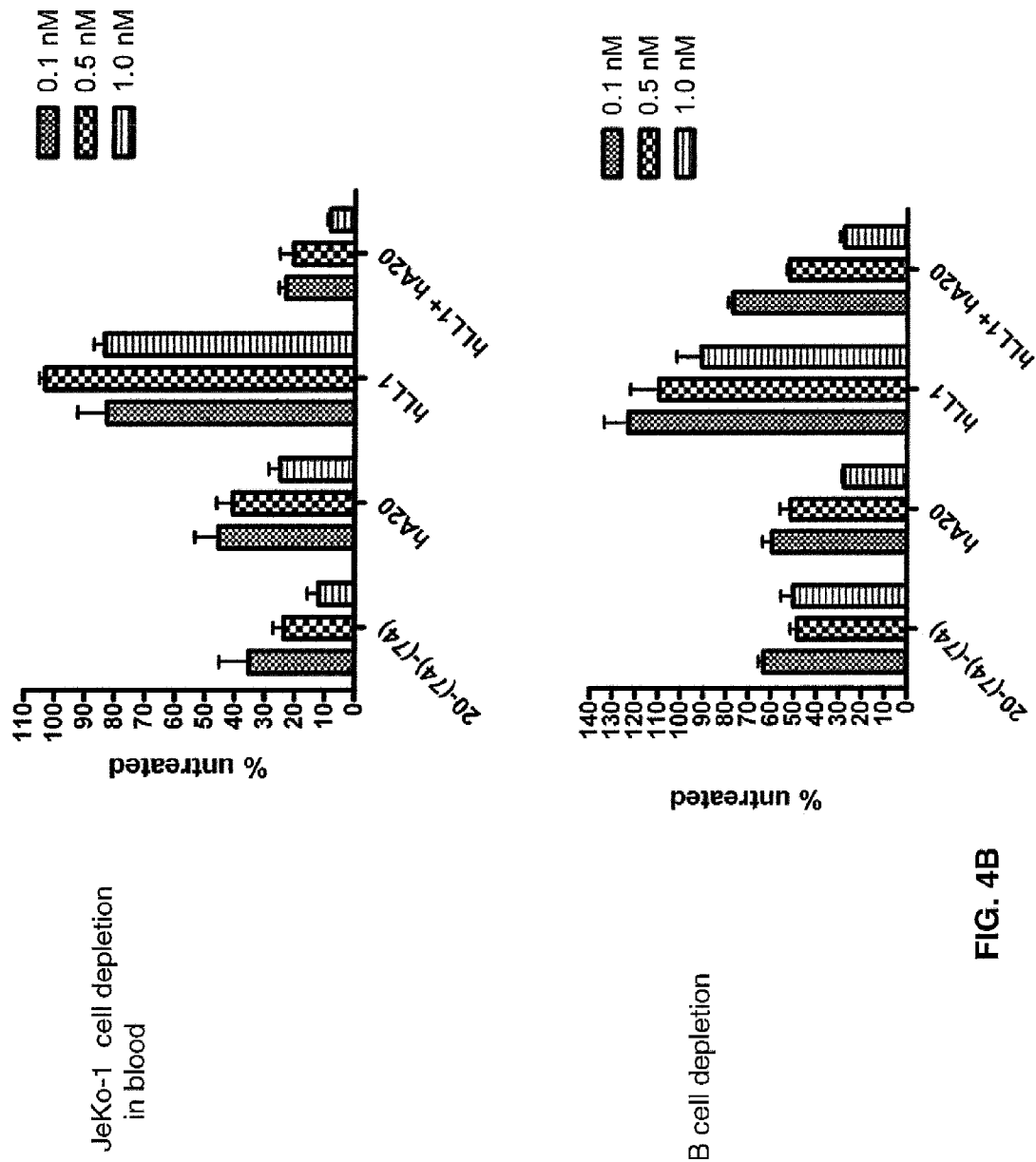
FIG. 4B. Activity of HexAbs in human blood ex vivo. 20-(74)-(74) tested at 0.1, 0.5 and 1 nM in Jeko-1 (upper panel) and normal B cells (lower panel). The effect of the indicated antibodies on the growth of spiked JeKo-1 cells in whole blood from a healthy volunteer was determined after 48 h. JeKo-1 cells were analyzed as CD19+ events in the monocyte gate. B cells were analyzed as CD19+ events in the lymphocyte gate. Error bars represent SD.

When evaluated at high concentrations (10 and 25 nM) in whole blood spiked with JeKo-1 cells, we observed >90% depletion of JeKo-1 cells for 20-(74)-(74), hA20, and hA20+ hLL1, but no more than 50% depletion for 74-(20)-(20), and <20% depletion for hLL1 or the non-targeting hMN-14 (anti-CEACAM5) control antibody (FIG. 4A, upper panel). The depletion of normal B cells, on the other hand, was similar for the two HexAbs, in the range of 50 to 70% for 20-(74)-(74) and 60 to 75% for 74-(20)-(20), with higher depletion (80 to 90%) attained by hA20 or the combination of hA20 and hLL1 (FIG. 4A, lower panel). The apparently higher potency of 20-(74)-(74) as compared to 74-(20)-(20) in depleting JeKo-1 cells from whole blood prompted subsequent studies using three lower concentrations (0.1, 0.5 and 1 nM), and the results shown in FIG. 4B (upper panel) and FIG. 4C (upper panel) confirmed the higher activity of 20-(74)-(74) than 74-(20)-(20) in depleting JeKo-1 cells from whole blood, since 20-(74)-(74) at 0.1 nM was able to deplete 70% of JeKo-1 cells, whereas 74-(20)-(20) at 25 nM could not achieve more than 50% depletion. The high potency of 20-(74)-(74) was also manifested by its ability to deplete 40 to 50% of normal B cells at 0.1 to 1 nM (FIG. 4B, lower panel), a blood concentration that should be easily attainable clinically. Under the same conditions, 74-(20)-(20) at 0.1 to 1 nM depleted 10% or less of normal B cells (FIG. 4C, lower panel). It is noted that the ability of 20-(74)-(74) to deplete either JeKo-1 or normal B cells from whole blood is comparable, not superior, to that of hA20 or the combination of hA20 and hLL1.

In Vivo Studies—

Figure 5:
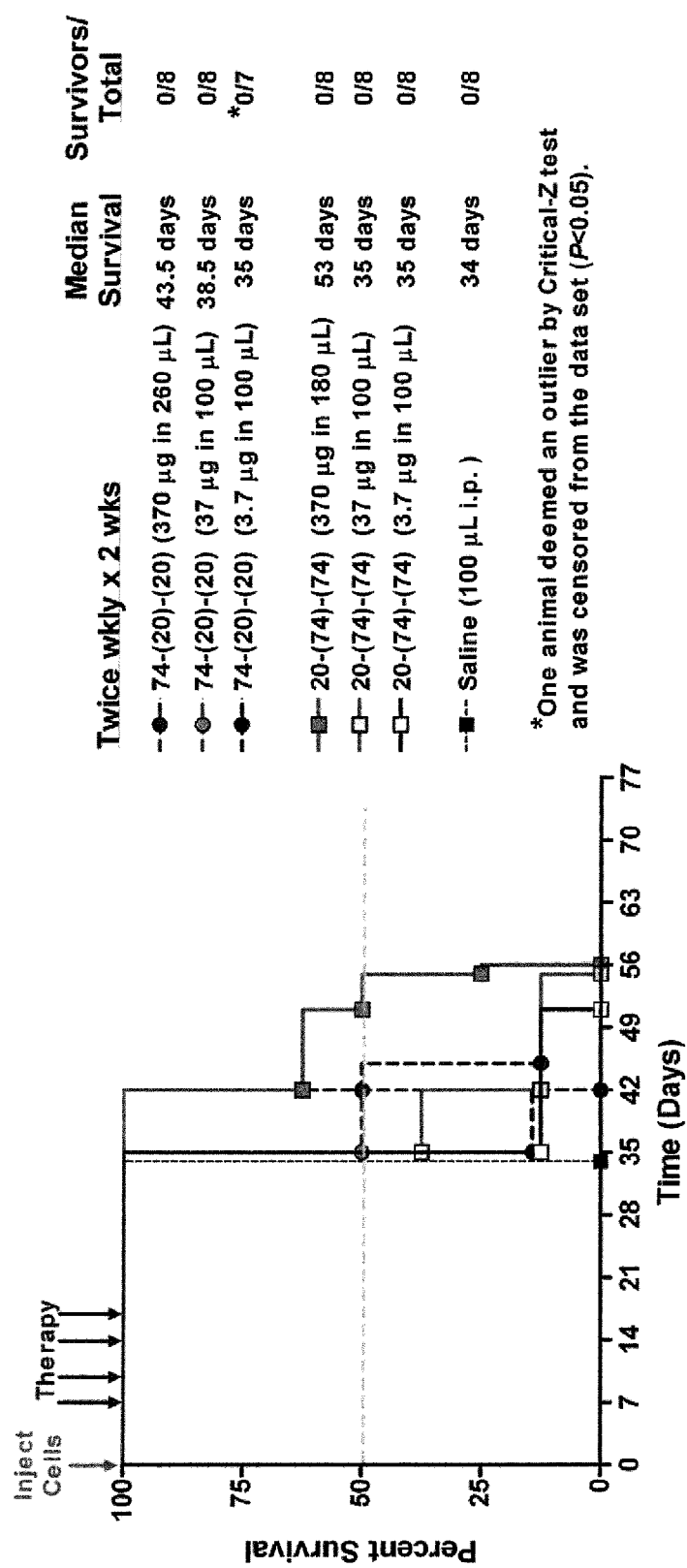
FIG. 5. Therapeutic efficacy of HexAbs in disseminated JeKo-1 xenograft model. Seven groups of 8 mice (8-wk-old female SCID mice) each were inoculated i.v. with JeKo-1 ($2.5 \times 10^7$ cells per animal). After 7 days, three different does (i.e., 370 µg, 37 µg and 3.7 µg) of both HexAbs were administered via i.p. injections twice a week for two weeks. Control mice received saline injections. 74-(20)-(20) and 20-(74)-(74), at the 370 µg dose level, resulted in 30% and 60% increases in median survival compared to saline controls, respectively.

To evaluate the efficacy of HexAbs in vivo, mice bearing disseminated JeKo-1 were treated with increasing doses (3.7, 37, or 370 μg) of either 20-(74)-(74) or 74-(20)-(20) given twice weekly for two weeks. Survival curves for the various treatment groups are shown in FIG. 5. Saline control mice succumbed to disease progression by day 34. Both treatments at all three doses significantly improved survival compared to the control animals (P=0.0001). Mice treated with the highest dose of 74-(20)-(20) had an approximate 30% increase in median survival over saline controls (43.5 days vs. 34 days; P=0.0001). A 60% increase in median survival (MST=53 days) over saline controls was observed in mice treated with 20-(74)-(74) at 370 μg (P=0.0001). Both HexAbs given at 370 μg were more effective than the two lower doses (P<0.0143). However, there were no significant differences between mice treated with 20-(74)-(74) and 74-(20)-(20) at the same dose.

Discussion

CD74 is the cell surface form of the HLA class II-associated invariant chain, which plays a key role as a chaperone protein in antigen presentation by HLA-DR to Th cells (Weenink & Gautam, 1997, *Immunol Cell Biol* 75:69-81). In addition, CD74 mediates macrophage migration inhibitory factor (MIF)-induced signal transduction as its cognate membrane receptor (Leng et al., 2003, *J Exp Med* 197:1467-1476), resulting in activation of ERK1/2 and protection from p53-dependent apoptosis in a process that requires CD44 as a signaling component and involves PKA and c-Src (Shi et al., 2006, *Immunity* 25:595-606). Moreover, the intracellular domain of CD74 (CD74-ICD) released from intramembrane proteolysis in the endocytic compartments can activate NF-κB to induce B-cell maturation (Becker-Herman et al., 2005, *Mol Biol Cell* 16:5061-5069), and this activity is further enhanced by stimulating CD74 with an agonistic antibody or MIF, either of which augments CD74-ICD release, increases Bcl-xL expression, and elevates the phosphorylation of both Akt and Syk (Starlets, 2006, *Blood* 107:4807-4816). In CLL cells (Binsky et al., 2007, *Proc Natl Acad Sci USA* 104:13408-13413) and B-lymphocytes (Gore et al., 2008, *J Biol Chem* 283:2784-2792), binding of CD74 to MIF initiates a signaling cascade that promotes cell survival via activation of NF-κB and secretion of IL-8, which can be inhibited by the antagonistic anti-CD74 MAb, milatuzumab (Binsky et al., 2007, *Proc Natl Acad Sci USA* 104:13408-13413; Shachar & Haran 2011, *Leuk Lymphoma* 52:1446-1454), thus further substantiating the rationale to develop milatuzumab-based therapeutic agents for the treatment of cancer (Stein et al., 2007, *Clin Cancer Res* 13:5556s-5563s) and autoimmune disease (Borghese & Clanchy, 2011, *Exp Opin Ther Targets* 15:237-251) by blocking the CD74/MIF pathway.

The commercial success of rituximab in treating certain B-cell malignancies and autoimmune disorders has stimulated much interest in developing new anti-CD20 antibodies with improved efficacy, as well as elucidating the in vitro and in vivo mechanisms of action for rituximab and its analogues (Lim et al., 2010, *Haematologica* 95:135-143). At present, next-generation anti-CD20 MAbs include human and humanized forms, with some claiming enhanced potency by antibody reengineering (Pawluczkowycz et al., 2009, *J Immunol* 183:749-758; Mossner et al., 2010, *Blood* 115:4393-4402). Although CD20 is a well-validated therapeutic target and despite more than 10 years of clinical use of rituximab and an expansive preclinical literature on the use of anti-CD20 MAbs in lymphoma models in vitro and in vivo, how rituximab or other anti-CD20 MAbs kill lymphoma cells is still being debated (Glennie et al., 2007, *Mol Immunol* 44:3823-3837) among the three principal mechanisms proposed, CDC, ADCC, and direct toxicity induced by signaling. Functional differences, as revealed by a variety of assays such as induction of homotypic adhesion, stimulation of calcium mobilization, association with lipid rafts, capability for effective CDC, ADCC or both, and requirement of hypercrosslinking for direct in vitro cytotoxicity, have been used (Cragg et al., 2003, *Blood* 101:1045-52) to classify anti-CD20 MAbs into type I, represented by rituximab, or type II, represented by tositumomab, with some data indicating that type II MAbs appear to outperform type I in preclinical models (Cardarelli et al., 2002, *Cancer Immunol Immunother* 51:15-24; Beers et al., 2008, *Blood* 112:4170-4177), which awaits confirmation in patients. We have previously noted (Rossi et al., 2008, *Cancer Res* 68:8384-8392) that one effective approach to converting a type I anti-CD20 MAb to a type II can be achieved by making the type I MAb multivalent, as shown by the HexAb generated from the type I veltuzumab, 20-(20)-(20), which exhibits biological properties attributable to both type II (for example, negative for CDC and calcium mobilization; positive for anti-proliferation, apoptosis, and homotypic adhesion) and type I (for example, positive for trafficking to lipid rafts).

The strategy to target both CD20 and CD74 with distinct MAbs was reported recently in a preclinical study using a combination of milatuzumab and rituximab plus a secondary crosslinking Ab in MCL lines and primary tumor cells (Alinari et al., 2011, *Blood* 117:4530-41), which showed that the treatment resulted in rapid cell death, generation of ROS, loss of mitochondria membrane potential, strong homotypic adhesion, and inhibition of p65 nuclear translocation. The observed cell death was attributed to a nonclassical apoptotic mechanism, because it lacks evidence of autophagy and caspase-activation, but requires the participation of actin and lysosomes. In the current study, we evaluated the potential of two anti-CD20/CD74 HexAbs for the therapy of MCL, and observed similar intracellular events to those obtained with milatuzumab and rituximab combined in the presence of a secondary crosslinking Ab, which include generation of ROS, loss of mitochondria membrane potential, inhibition of p65 nuclear translocation, absence of autophagy, and caspase-independence. Surprisingly, the two anti-CD20/CD74 HexAbs, were capable of manifesting direct in vitro cytotoxicity in 3 MCL, 2 NHL, and 2 CLL cell lines, as well as inducing a significantly higher number of annexin V-positive cells in primary tumor samples from MCL and CLL patients, compared to untreated controls.

We also investigated the signaling pathways triggered in JeKo-1 cells by the two anti-CD20/CD74 HexAbs. Our findings suggest that the rapid and sustained activation of ERKs and JNK may contribute to cell death (Zhuang & Schnellmann, 2006, *J Pharmacol Exp Ther* 319:991-997), as shown in Raji and SU-DHL4 treated with tositumomab and radiation (Ivanov et al., 2008, *Clin Cancer Res* 14:4925-4934), in renal epithelial cells during oxidative injury (Di Mari et al., 1999, *Am J Physiol* 277:F195-F203), and in Raji and other B-lymphoma lines (including Jeko-1 and Granta-519) upon ligation to hL243 (anti-HLA-DR) MAb (Stein et al., 2010, *Blood* 115:5180-5190). We also found that both anti-CD20/CD74 HexAbs disrupt the NF-κB pathway by inhibiting the translocation of p65 from cytosol to the nucleus, and downregulate Bcl-xL, which may further promote cell death.

Ligation of various antibodies with receptors such as HLA-DR, CD 19, CD20, CD39, CD40, CD43, and others has been observed to induce homotypic adhesion in a panel of B-cell lymphoma lines (Kansas & Tedder, 1991, *J Immunol* 147: 4094-4102). The anti-CD20/CD74 HexAbs, like the anti-CD20/CD22 HexAbs, also induced strong homotypic adhesion in JeKo-1 cells that was not observed with the parental MAbs alone or in combination. The HexAb-induced homotypic adhesion was blocked by inhibitors of actin polymerization, which also reduced cell death. Similar results have been observed with the combination of rituximab and milatuzumab in the presence of secondary crosslinking antibody in MCL lines (Alinari et al., 2011, *Blood* 117:4530-41). Our studies also indicate that the induction of homotypic adhesion by the anti-CD20/CD74 HexAbs is independent of their susceptibility to internalization, and neither classical apoptosis nor autophagy is involved in cell death, which appeared to closely resemble the actin- and lysosome-dependent cell death evoked by tositumomab and hL243 in Raji and SU-DHL4 (Ivanov et al., 2009, *J Clin Invest* 119:2143-2159).

When examined ex vivo using normal human blood spiked with JeKo-1 cells, 20-(74)-(74) depleted JeKo-1 cells more effectively than the parental MAb hA20, while hLL1 and 74-(20)-(20) did not show much activity. This improved efficacy may result from the fact that 20-(74)-(74), but not 74-(20)-(20), displays effector functions, as determined by ADCC and CDC. Both HexAbs, nevertheless, showed reduced but similar potency in depleting normal B cells, which could be due to a lower expression of CD20 or CD74 antigens, as well as the more mature cell type.

In summary, bispecific anti-CD20/CD74 HexAbs, as represented by 20-(74)-(74) and 74-(20)-(20), were successfully generated and their potential for therapy of MCL evaluated and demonstrated in preclinical studies. The key findings are as follows. (1) Effective inhibition of proliferation requires juxtaposing CD20 and CD74 in close proximity. (2) The observed direct in vitro cytotoxicity is accompanied by extensive homotypic adhesion, relocation of actin to the cell-cell junction, notable lysosomal enlargement, release of cathespin B into the cytosol, loss of mitochondria membrane potential, generation of ROS, deactivation of the PI3K/Akt signaling pathway, as well as rapid and sustained activation of ERK and JNK MAPKs. (3) Homotypic adhesion can be a first indicator for determining whether a certain antibody or combination of antibodies will display toxicity against antigen-expressing hematological cells. (4) Both 20-(74)-(74) and 74-(20)-(20) will be of use in additional B-cell malignancies, in particular CLL, and in autoimmune disease. These compounds constitute a new therapeutic class of anticancer antibodies.

Example 12

Anti-CD74 Antibodies Improve the Efficacy of Standard Treatments for B Cell Malignancies Milatuzumab (humanized anti-CD74 monoclonal antibody) is in clinical evaluation for therapy of multiple myeloma, CLL and NHL (Berkova et al., 2010, Expert Opin Invest Drugs 19:141-49). CD74, the MHC class-II chaperone molecule, also functions as the cellular receptor for the proinflammatory cytokine, macrophage migration-inhibitory factor, and initiates a signaling cascade resulting in proliferation and survival (e.g., Leng et al., 2003, J Exp Med 197:1467-76). Preclinically, milatuzumab demonstrates therapeutic activity against various B-cell malignancies when used alone (Berkova et al., 2010, Expert Opin Invest Drugs 19:141-49), and the therapeutic efficacies of bortezomib, doxorubicin, and dexamethasone are enhanced in multiple myeloma cell lines when given combined with milatuzumab (Stein et al., 2009, Clin Cancer Res 15:2808-17). Milatuzumab acts through distinct mechanisms from rituximab, and exhibits different expression and sensitivity profiles. We examined the effects of milatuzumab given in combination with rituximab or fludarabine in human NHL, CLL, and ALL cell lines.

Methods

Three human NHL (WSU-FSCCL, Raji, and RL); two ALL (MN60 and REH), and two CLL (MEC-1 and WAC) cell lines were tested, with evaluation of therapeutic efficacies of milatuzumab and fludarabine performed in the NHL and CLL cell lines. The cell lines were selected to evaluate a range of different CD74 and CD20 expression levels (Table 11).

TABLE 11

Cell surface expression of CD74 and CD20 (mean fluorescence)

| | Cell line | Isotype control (hMN14, anti-CEA) | CD74 (hLL1, milatuzumab) | CD20 (hA20, veltuzumab) |
|---|---|---|---|---|
| NHL | Raji | 11.6 | 318.6 | 760.4 |
| | RL | 6.2 | 56.0 | 264.5 |
| | WSU-FSCCL | 5.3 | 20.9 | 36.6 |
| ALL | REH | 3.0 | 70.6 | 15.0 |
| | MN60 | 8.4 | 57.0 | 719.4 |
| CLL | MEC-1 | 5.4 | 41.4 | 270.5 |
| | WAC | 5.2 | 17.4 | 210.6 |

Results

Figure 7:
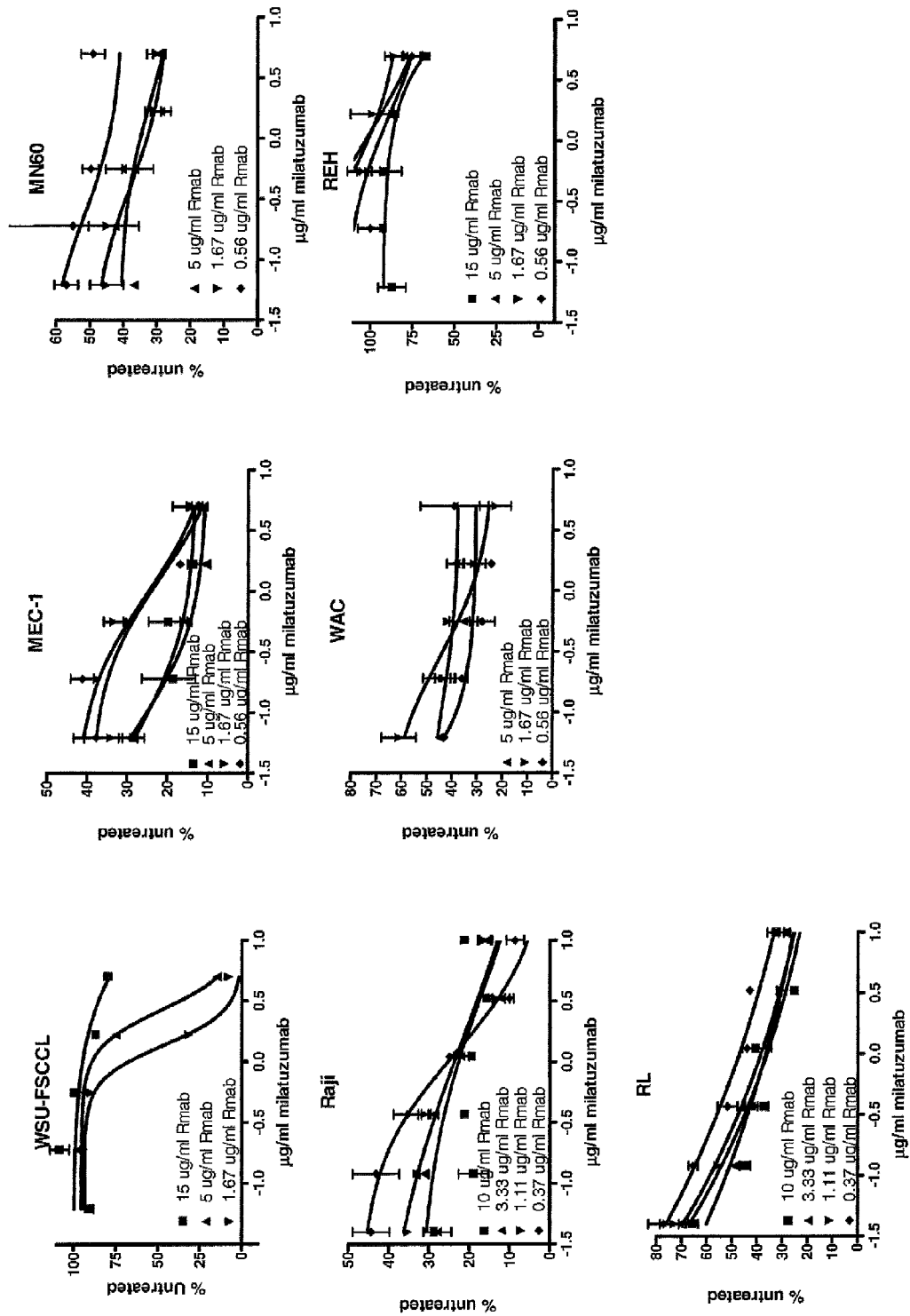
FIG. 7. Anti-CD74 antibody (milatuzumab) increases the cytotoxicity of rituximab. The Figure shows the percent of untreated control values in MTT cytotoxicity assays. Cells were incubated with the antibodies for 4 days in the presence of goat anti-human IgG as a crosslinker. The Figure shows several lines of NHL (left side), CLL (center) and ALL (right side) cell lines.

Anti-proliferative activity was augmented in vitro when milatuzumab and rituximab were combined (FIG. 7). For example in WSU-FSCCL cells, which are relatively insensitive to rituximab, inhibition of proliferation in the presence of 33.3 nM rituximab increased from 12.6±3.7% in the absence of milatuzumab to 85.5±0.0% (P=0.023) in the presence of 33.3 nM milatuzumab (FIG. 7). In Raji, a more sensitive cell line, inhibition of proliferation in the presence of 22.2 nM rituximab increased from 64.8±1.3% without milatuzumab to 86.6±0.9% (P=0.018) with 22.2 nM milatuzumab (FIG. 7). Significant increases in the anti-proliferative activity of rituximab were similarly observed in all but one of the tested NHL, CLL, and ALL cell lines (FIG. 7), with the exception of REH, which was not sensitive to killing by either milatuzumab or rituximab. Unlike rituximab, milatuzumab induced little or no ADCC or CDC (not shown). However, in vitro exposure of cells to milatuzumab did not affect rituximab mediated ADCC or CDC (not shown).

The effects of milatuzumab on mitochondrial membrane potential were examined using an alamar blue assay. Alamar blue (10%) was added to wells 24 h after each period of incubation and changes in alamar blue reduction were measured every fifteen minutes for a total of 4 hours. Rituximab-resistant cell lines were generated from the Raji parental cell lines by exposing cells to an escalating dose of rituximab (0.1 to 128 µg/ml), either without human serum (Raji 2R) or in the presence of human serum (Raji4RH). The combination of milatuzumab and rituximab was observed to result in a more potent decrease in the mitochondrial potential in rituximab-sensitive cell lines, but not in rituximab-resistant cell lines.

Figure 8:
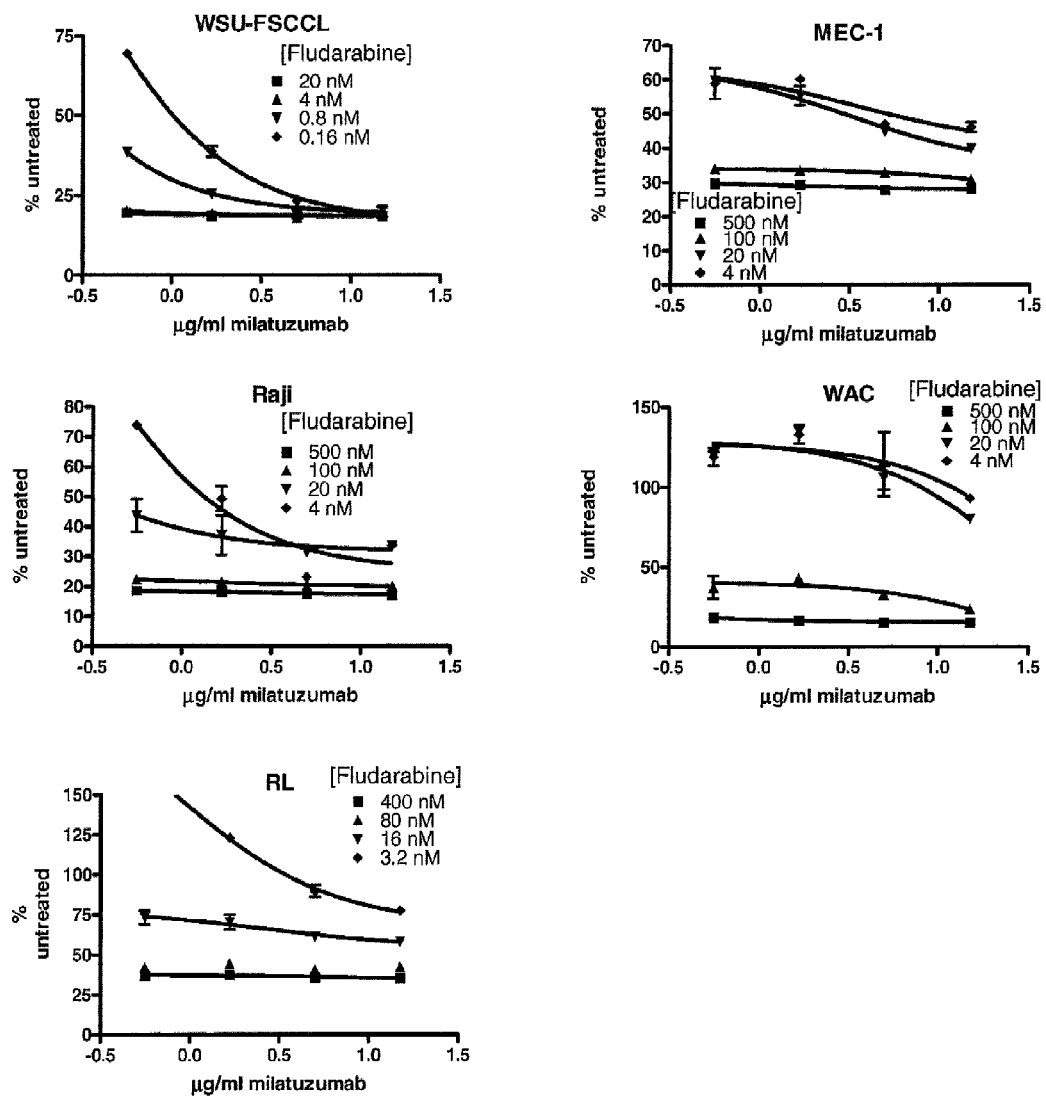
FIG. 8. Anti-CD74 antibody (milatuzumab) increases the cytotoxicity of fludarabine. The Figure shows the percent of untreated control values in MTS cytotoxicity assays. Cells were incubated with fludarabine and milatuzumab for 4 days in the presence of goat anti-human IgG as a crosslinker. The Figure shows the effects on NHL (left side) and CLL (right side) cell lines.

It was found that milatuzumab increased the efficacy of fludarabine-induced cytotoxicity in 3 NHL and 2 CLL cell lines (FIG. 8). For example, in Raji cells, which are relatively insensitive to fludarabine, inhibition of proliferation in the presence of 4 nM fludarabine increased from no inhibition in the absence of milatuzumab to 76.9±0.7% (P=0.009) in the presence of 33.3 nM milatuzumab (FIG. 8). In WSU-FSCCL cells, a more fludarabine-sensitive cell line, inhibition of proliferation in the presence of 0.8 nM fludarabine increased from 41.3±0.3% in the absence of milatuzumab to 79.7±0.1% (P<0.0001) with 33.3 nM milatuzumab (FIG. 8).

CONCLUSIONS

Milatuzumab and other antagonistic anti-CD74 antibodies can significantly add to the efficacy of currently approved therapies, such as fludarabine and rituximab, for B cell diseases, including NHL, CLL and ALL.

It will be readily apparent to one skilled in the art that varying substitutions and modifications may be made to the invention disclosed herein without departing from the scope and spirit of the invention. Thus, such additional embodiments are within the scope of the present invention.

What is claimed is:

1. A method of killing human B cells comprising:

a) obtaining a dock-and-lock (DNL) construct that comprises (i) at least one anti-CD74 antibody or antigen-binding fragment thereof and (ii) at least one anti-CD20 antibody or antigen-binding fragment thereof, wherein the antibodies or fragments thereof bind to human CD20 or CD74, wherein the DNL construct is a hexavalent DNL construct comprising an IgG moiety and four Fab moieties; and b) exposing human B cells to the DNL construct.

2. The method of claim 1, wherein the anti-CD20 antibody is rituximab or hA20.

3. The method of claim 1, wherein the anti-CD74 antibody is hLL1.

4. The method of claim 1, wherein the anti-CD20 and anti-CD74 antibodies are chimeric, humanized or human.

* * * * *

SEQUENCE LISTING

```
<160> NUMBER OF SEQ ID NOS: 151

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Ser Ser Gln Ser Leu Val His Arg Asn Gly Asn Thr Tyr Leu His
1               5                   10                  15

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Thr Val Ser Asn Arg Phe Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ser Gln Ser Ser His Val Pro Pro Thr
1               5

<210> SEQ ID NO 4
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 4

Asn Tyr Gly Val Asn
1               5

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Trp Ile Asn Pro Asn Thr Gly Glu Pro Thr Phe Asp Asp Asp Phe Lys
1               5                   10                  15

Gly

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Arg Gly Lys Asn Glu Ala Trp Phe Ala Tyr
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Ala Ser Ser Ser Val Ser Tyr Ile His
1               5                   10

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Thr Ser Asn Leu Ala Ser
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9
```

Gln Gln Trp Thr Ser Asn Pro Pro Thr
1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Tyr Asn Met His
1               5

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala Ile Tyr Pro Gly Asn Gly Asp Thr Ser Tyr Asn Gln Lys Phe Lys
1               5                   10                  15

Gly

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ser Thr Tyr Tyr Gly Gly Asp Trp Tyr Phe Asp Val
1               5                   10

<210> SEQ ID NO 13
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Lys Ser Ser Gln Ser Val Leu Tyr Ser Ala Asn His Lys Tyr Leu Ala
1               5                   10                  15

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Trp Ala Ser Thr Arg Glu Ser
1               5

<210> SEQ ID NO 15
<211> LENGTH: 9
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 15

His Gln Tyr Leu Ser Ser Trp Thr Phe
1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser Tyr Trp Leu His
1               5

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Tyr Ile Asn Pro Arg Asn Asp Tyr Thr Glu Tyr Asn Gln Asn Phe Lys
1               5                   10                  15

Asp

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Asp Ile Thr Thr Phe Tyr
1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asn Tyr Gly Met Asn
1               5

<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20
```

```
Trp Ile Asn Thr Tyr Thr Arg Glu Pro Thr Tyr Ala Asp Asp Phe Lys
1               5                   10                  15
Gly

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Asp Ile Thr Ala Val Val Pro Thr Gly Phe Asp Tyr
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Ala Ser Glu Asn Ile Tyr Ser Asn Leu Ala
1               5                   10

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ala Ala Ser Asn Leu Ala Asp
1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gln His Phe Trp Thr Thr Pro Trp Ala
1               5

<210> SEQ ID NO 25
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
```

```
                35                  40

<210> SEQ ID NO 26
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Cys Gly His Ile Gln Ile Pro Pro Gly Leu Thr Glu Leu Leu Gln Gly
1               5                   10                  15

Tyr Thr Val Glu Val Leu Arg Gln Gln Pro Pro Asp Leu Val Glu Phe
            20                  25                  30

Ala Val Glu Tyr Phe Thr Arg Leu Arg Glu Ala Arg Ala
        35                  40                  45

<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gln Ile Glu Tyr Leu Ala Lys Gln Ile Val Asp Asn Ala Ile Gln Gln
1               5                   10                  15

Ala

<210> SEQ ID NO 28
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Cys Gly Gln Ile Glu Tyr Leu Ala Lys Gln Ile Val Asp Asn Ala Ile
1               5                   10                  15

Gln Gln Ala Gly Cys
            20

<210> SEQ ID NO 29
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Ser Leu Arg Glu Cys Glu Leu Tyr Val Gln Lys His Asn Ile Gln Ala
1               5                   10                  15

Leu Leu Lys Asp Ser Ile Val Gln Leu Cys Thr Ala Arg Pro Glu Arg
            20                  25                  30

Pro Met Ala Phe Leu Arg Glu Tyr Phe Glu Arg Leu Glu Lys Glu Glu
        35                  40                  45

Ala Lys
    50
```

-continued

<210> SEQ ID NO 30
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Met Ser Cys Gly Gly Ser Leu Arg Glu Cys Glu Leu Tyr Val Gln Lys
1               5                   10                  15

His Asn Ile Gln Ala Leu Leu Lys Asp Ser Ile Val Gln Leu Cys Thr
            20                  25                  30

Ala Arg Pro Glu Arg Pro Met Ala Phe Leu Arg Glu Tyr Phe Glu Arg
        35                  40                  45

Leu Glu Lys Glu Glu Ala Lys
    50                  55

<210> SEQ ID NO 31
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Cys Gly Phe Glu Glu Leu Ala Trp Lys Ile Ala Lys Met Ile Trp Ser
1               5                   10                  15

Asp Val Phe Gln Gln Gly Cys
            20

<210> SEQ ID NO 32
<211> LENGTH: 51
<212> TYPE: PRT
<213> ORGANISM: Homo sapiens

<400> SEQUENCE: 32

Ser Leu Arg Glu Cys Glu Leu Tyr Val Gln Lys His Asn Ile Gln Ala
1               5                   10                  15

Leu Leu Lys Asp Val Ser Ile Val Gln Leu Cys Thr Ala Arg Pro Glu
            20                  25                  30

Arg Pro Met Ala Phe Leu Arg Glu Tyr Phe Glu Lys Leu Glu Lys Glu
        35                  40                  45

Glu Ala Lys
    50

<210> SEQ ID NO 33
<211> LENGTH: 54
<212> TYPE: PRT
<213> ORGANISM: Homo sapiens

<400> SEQUENCE: 33

Ser Leu Lys Gly Cys Glu Leu Tyr Val Gln Leu His Gly Ile Gln Gln
1               5                   10                  15

Val Leu Lys Asp Cys Ile Val His Leu Cys Ile Ser Lys Pro Glu Arg
            20                  25                  30

Pro Met Lys Phe Leu Arg Glu His Phe Glu Lys Leu Glu Lys Glu Glu
        35                  40                  45

Asn Arg Gln Ile Leu Ala
    50

```
<210> SEQ ID NO 34
<211> LENGTH: 44
<212> TYPE: PRT
<213> ORGANISM: Homo sapiens

<400> SEQUENCE: 34

Ser His Ile Gln Ile Pro Pro Gly Leu Thr Glu Leu Leu Gln Gly Tyr
1               5                   10                  15

Thr Val Glu Val Gly Gln Gln Pro Pro Asp Leu Val Asp Phe Ala Val
            20                  25                  30

Glu Tyr Phe Thr Arg Leu Arg Glu Ala Arg Arg Gln
        35                  40

<210> SEQ ID NO 35
<211> LENGTH: 44
<212> TYPE: PRT
<213> ORGANISM: Homo sapiens

<400> SEQUENCE: 35

Ser Ile Glu Ile Pro Ala Gly Leu Thr Glu Leu Leu Gln Gly Phe Thr
1               5                   10                  15

Val Glu Val Leu Arg His Gln Pro Ala Asp Leu Leu Glu Phe Ala Leu
            20                  25                  30

Gln His Phe Thr Arg Leu Gln Gln Glu Asn Glu Arg
        35                  40

<210> SEQ ID NO 36
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Thr His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 37
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Ser Lys Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 38
<211> LENGTH: 44
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 38

Ser Arg Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 39
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Ser His Ile Asn Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 40
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Ser His Ile Gln Ile Pro Pro Ala Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 41
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Ser His Ile Gln Ile Pro Pro Gly Leu Ser Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 42
<211> LENGTH: 44
<212> TYPE: PRT
```

<210> SEQ ID NO 42
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Ser His Ile Gln Ile Pro Pro Gly Leu Thr Asp Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 43
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Ser His Ile Gln Ile Pro Pro Gly Leu Thr Glu Leu Leu Asn Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 44
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Ser His Ile Gln Ile Pro Pro Gly Leu Thr Glu Leu Leu Gln Ala Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 45
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Ser His Ile Gln Ile Pro Pro Gly Leu Thr Glu Leu Leu Gln Gly Tyr
1               5                   10                  15

Ser Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 46
<211> LENGTH: 44

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Ser His Ile Gln Ile Pro Pro Gly Leu Thr Glu Leu Leu Gln Gly Tyr
1               5                   10                  15

Thr Val Asp Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 47
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Ser His Ile Gln Ile Pro Pro Gly Leu Thr Glu Leu Leu Gln Gly Tyr
1               5                   10                  15

Thr Val Glu Val Leu Lys Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 48
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Ser His Ile Gln Ile Pro Pro Gly Leu Thr Glu Leu Leu Gln Gly Tyr
1               5                   10                  15

Thr Val Glu Val Leu Arg Asn Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 49
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Ser His Ile Gln Ile Pro Pro Gly Leu Thr Glu Leu Leu Gln Gly Tyr
1               5                   10                  15

Thr Val Glu Val Leu Arg Gln Asn Pro Pro Asp Leu Val Glu Phe Ala
            20                  25                  30

Val Glu Tyr Phe Thr Arg Leu Arg Glu Ala Arg Ala
        35                  40

<210> SEQ ID NO 50
```

```
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Ser His Ile Gln Ile Pro Pro Gly Leu Thr Glu Leu Leu Gln Gly Tyr
1               5                   10                  15

Thr Val Glu Val Leu Arg Gln Gln Pro Pro Gly Leu Val Glu Phe Ala
            20                  25                  30

Val Glu Tyr Phe Thr Arg Leu Arg Glu Ala Arg Ala
        35                  40

<210> SEQ ID NO 51
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Asp Phe Ala
            20                  25                  30

Val Glu Tyr Phe Thr Arg Leu Arg Glu Ala Arg Ala
        35                  40

<210> SEQ ID NO 52
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Leu
            20                  25                  30

Val Glu Tyr Phe Thr Arg Leu Arg Glu Ala Arg Ala
        35                  40

<210> SEQ ID NO 53
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ile
            20                  25                  30

Val Glu Tyr Phe Thr Arg Leu Arg Glu Ala Arg Ala
        35                  40
```

```
<210> SEQ ID NO 54
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Val
            20                  25                  30

Val Glu Tyr Phe Thr Arg Leu Arg Glu Ala Arg Ala
        35                  40

<210> SEQ ID NO 55
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Asp Tyr Phe Thr Arg Leu Arg Glu Ala Arg Ala
        35                  40

<210> SEQ ID NO 56
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Asn Ile Glu Tyr Leu Ala Lys Gln Ile Val Asp Asn Ala Ile Gln Gln
1               5                   10                  15

Ala

<210> SEQ ID NO 57
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gln Leu Glu Tyr Leu Ala Lys Gln Ile Val Asp Asn Ala Ile Gln Gln
1               5                   10                  15

Ala

<210> SEQ ID NO 58
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 58

Gln Val Glu Tyr Leu Ala Lys Gln Ile Val Asp Asn Ala Ile Gln Gln
1               5                   10                  15

Ala

<210> SEQ ID NO 59
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gln Ile Asp Tyr Leu Ala Lys Gln Ile Val Asp Asn Ala Ile Gln Gln
1               5                   10                  15

Ala

<210> SEQ ID NO 60
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gln Ile Glu Phe Leu Ala Lys Gln Ile Val Asp Asn Ala Ile Gln Gln
1               5                   10                  15

Ala

<210> SEQ ID NO 61
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gln Ile Glu Thr Leu Ala Lys Gln Ile Val Asp Asn Ala Ile Gln Gln
1               5                   10                  15

Ala

<210> SEQ ID NO 62
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gln Ile Glu Ser Leu Ala Lys Gln Ile Val Asp Asn Ala Ile Gln Gln
1               5                   10                  15

Ala

<210> SEQ ID NO 63
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 63

Gln Ile Glu Tyr Ile Ala Lys Gln Ile Val Asp Asn Ala Ile Gln Gln
1               5                   10                  15

Ala

<210> SEQ ID NO 64
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gln Ile Glu Tyr Val Ala Lys Gln Ile Val Asp Asn Ala Ile Gln Gln
1               5                   10                  15

Ala

<210> SEQ ID NO 65
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gln Ile Glu Tyr Leu Ala Arg Gln Ile Val Asp Asn Ala Ile Gln Gln
1               5                   10                  15

Ala

<210> SEQ ID NO 66
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gln Ile Glu Tyr Leu Ala Lys Asn Ile Val Asp Asn Ala Ile Gln Gln
1               5                   10                  15

Ala

<210> SEQ ID NO 67
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gln Ile Glu Tyr Leu Ala Lys Gln Ile Val Glu Asn Ala Ile Gln Gln
1               5                   10                  15

Ala

<210> SEQ ID NO 68
<211> LENGTH: 17
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 68

Gln Ile Glu Tyr Leu Ala Lys Gln Ile Val Asp Gln Ala Ile Gln Gln
1               5                   10                  15

Ala

<210> SEQ ID NO 69
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gln Ile Glu Tyr Leu Ala Lys Gln Ile Val Asp Asn Ala Ile Asn Gln
1               5                   10                  15

Ala

<210> SEQ ID NO 70
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gln Ile Glu Tyr Leu Ala Lys Gln Ile Val Asp Asn Ala Ile Gln Asn
1               5                   10                  15

Ala

<210> SEQ ID NO 71
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gln Ile Glu Tyr Leu Ala Lys Gln Ile Val Asp Asn Ala Ile Gln Gln
1               5                   10                  15

Leu

<210> SEQ ID NO 72
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gln Ile Glu Tyr Leu Ala Lys Gln Ile Val Asp Asn Ala Ile Gln Gln
1               5                   10                  15

Ile

<210> SEQ ID NO 73
<211> LENGTH: 17
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 73

Gln Ile Glu Tyr Leu Ala Lys Gln Ile Val Asp Asn Ala Ile Gln Gln
1               5                   10                  15

Val

<210> SEQ ID NO 74
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gln Ile Glu Tyr Val Ala Lys Gln Ile Val Asp Tyr Ala Ile His Gln
1               5                   10                  15

Ala

<210> SEQ ID NO 75
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gln Ile Glu Tyr Lys Ala Lys Gln Ile Val Asp His Ala Ile His Gln
1               5                   10                  15

Ala

<210> SEQ ID NO 76
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gln Ile Glu Tyr His Ala Lys Gln Ile Val Asp His Ala Ile His Gln
1               5                   10                  15

Ala

<210> SEQ ID NO 77
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gln Ile Glu Tyr Val Ala Lys Gln Ile Val Asp His Ala Ile His Gln
1               5                   10                  15

Ala

<210> SEQ ID NO 78
<211> LENGTH: 18
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 78

Pro Leu Glu Tyr Gln Ala Gly Leu Leu Val Gln Asn Ala Ile Gln Gln
1               5                   10                  15

Ala Ile

<210> SEQ ID NO 79
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Leu Leu Ile Glu Thr Ala Ser Ser Leu Val Lys Asn Ala Ile Gln Leu
1               5                   10                  15

Ser Ile

<210> SEQ ID NO 80
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Leu Ile Glu Glu Ala Ala Ser Arg Ile Val Asp Ala Val Ile Glu Gln
1               5                   10                  15

Val Lys

<210> SEQ ID NO 81
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ala Leu Tyr Gln Phe Ala Asp Arg Phe Ser Glu Leu Val Ile Ser Glu
1               5                   10                  15

Ala Leu

<210> SEQ ID NO 82
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Leu Glu Gln Val Ala Asn Gln Leu Ala Asp Gln Ile Ile Lys Glu Ala
1               5                   10                  15

Thr

<210> SEQ ID NO 83
<211> LENGTH: 17
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Phe Glu Glu Leu Ala Trp Lys Ile Ala Lys Met Ile Trp Ser Asp Val
1               5                   10                  15

Phe

<210> SEQ ID NO 84
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Glu Leu Val Arg Leu Ser Lys Arg Leu Val Glu Asn Ala Val Leu Lys
1               5                   10                  15

Ala Val

<210> SEQ ID NO 85
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Thr Ala Glu Glu Val Ser Ala Arg Ile Val Gln Val Val Thr Ala Glu
1               5                   10                  15

Ala Val

<210> SEQ ID NO 86
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gln Ile Lys Gln Ala Ala Phe Gln Leu Ile Ser Gln Val Ile Leu Glu
1               5                   10                  15

Ala Thr

<210> SEQ ID NO 87
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Leu Ala Trp Lys Ile Ala Lys Met Ile Val Ser Asp Val Met Gln Gln
1               5                   10                  15

<210> SEQ ID NO 88
<211> LENGTH: 24
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 88

Asp Leu Ile Glu Glu Ala Ala Ser Arg Ile Val Asp Ala Val Ile Glu
1               5                   10                  15

Gln Val Lys Ala Ala Gly Ala Tyr
            20

<210> SEQ ID NO 89
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Leu Glu Gln Tyr Ala Asn Gln Leu Ala Asp Gln Ile Ile Lys Glu Ala
1               5                   10                  15

Thr Glu

<210> SEQ ID NO 90
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Phe Glu Glu Leu Ala Trp Lys Ile Ala Lys Met Ile Trp Ser Asp Val
1               5                   10                  15

Phe Gln Gln Cys
            20

<210> SEQ ID NO 91
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gln Ile Glu Tyr Leu Ala Lys Gln Ile Pro Asp Asn Ala Ile Gln Gln
1               5                   10                  15

Ala

<210> SEQ ID NO 92
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Lys Gly Ala Asp Leu Ile Glu Glu Ala Ala Ser Arg Ile Val Asp Ala
1               5                   10                  15

Val Ile Glu Gln Val Lys Ala Ala Gly
            20                  25
```

<210> SEQ ID NO 93
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Lys Gly Ala Asp Leu Ile Glu Glu Ala Ala Ser Arg Ile Pro Asp Ala
1               5                   10                  15

Pro Ile Glu Gln Val Lys Ala Ala Gly
            20                  25

<210> SEQ ID NO 94
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Pro Glu Asp Ala Glu Leu Val Arg Leu Ser Lys Arg Leu Val Glu Asn
1               5                   10                  15

Ala Val Leu Lys Ala Val Gln Gln Tyr
            20                  25

<210> SEQ ID NO 95
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Pro Glu Asp Ala Glu Leu Val Arg Thr Ser Lys Arg Leu Val Glu Asn
1               5                   10                  15

Ala Val Leu Lys Ala Val Gln Gln Tyr
            20                  25

<210> SEQ ID NO 96
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Pro Glu Asp Ala Glu Leu Val Arg Leu Ser Lys Arg Asp Val Glu Asn
1               5                   10                  15

Ala Val Leu Lys Ala Val Gln Gln Tyr
            20                  25

<210> SEQ ID NO 97
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

```
Pro Glu Asp Ala Glu Leu Val Arg Leu Ser Lys Arg Leu Pro Glu Asn
1               5                   10                  15

Ala Val Leu Lys Ala Val Gln Gln Tyr
            20                  25

<210> SEQ ID NO 98
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Pro Glu Asp Ala Glu Leu Val Arg Leu Ser Lys Arg Leu Pro Glu Asn
1               5                   10                  15

Ala Pro Leu Lys Ala Val Gln Gln Tyr
            20                  25

<210> SEQ ID NO 99
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Pro Glu Asp Ala Glu Leu Val Arg Leu Ser Lys Arg Leu Val Glu Asn
1               5                   10                  15

Ala Val Glu Lys Ala Val Gln Gln Tyr
            20                  25

<210> SEQ ID NO 100
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Glu Glu Gly Leu Asp Arg Asn Glu Glu Ile Lys Arg Ala Ala Phe Gln
1               5                   10                  15

Ile Ile Ser Gln Val Ile Ser Glu Ala
            20                  25

<210> SEQ ID NO 101
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Leu Val Asp Asp Pro Leu Glu Tyr Gln Ala Gly Leu Leu Val Gln Asn
1               5                   10                  15

Ala Ile Gln Gln Ala Ile Ala Glu Gln
            20                  25

<210> SEQ ID NO 102
<211> LENGTH: 25
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 102

Gln Tyr Glu Thr Leu Leu Ile Glu Thr Ala Ser Ser Leu Val Lys Asn
1               5                   10                  15

Ala Ile Gln Leu Ser Ile Glu Gln Leu
            20                  25

<210> SEQ ID NO 103
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Leu Glu Lys Gln Tyr Gln Glu Gln Leu Glu Glu Glu Val Ala Lys Val
1               5                   10                  15

Ile Val Ser Met Ser Ile Ala Phe Ala
            20                  25

<210> SEQ ID NO 104
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Asn Thr Asp Glu Ala Gln Glu Glu Leu Ala Trp Lys Ile Ala Lys Met
1               5                   10                  15

Ile Val Ser Asp Ile Met Gln Gln Ala
            20                  25

<210> SEQ ID NO 105
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Val Asn Leu Asp Lys Lys Ala Val Leu Ala Glu Lys Ile Val Ala Glu
1               5                   10                  15

Ala Ile Glu Lys Ala Glu Arg Glu Leu
            20                  25

<210> SEQ ID NO 106
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Asn Gly Ile Leu Glu Leu Glu Thr Lys Ser Ser Lys Leu Val Gln Asn
1               5                   10                  15

Ile Ile Gln Thr Ala Val Asp Gln Phe
            20                  25
```

<210> SEQ ID NO 107
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Thr Gln Asp Lys Asn Tyr Glu Asp Glu Leu Thr Gln Val Ala Leu Ala
1               5                   10                  15

Leu Val Glu Asp Val Ile Asn Tyr Ala
            20                  25

<210> SEQ ID NO 108
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Glu Thr Ser Ala Lys Asp Asn Ile Asn Ile Glu Glu Ala Ala Arg Phe
1               5                   10                  15

Leu Val Glu Lys Ile Leu Val Asn His
            20                  25

<210> SEQ ID NO 109
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 109
aatgcggcgg tggtgacagt a                                          21

<210> SEQ ID NO 110
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 110
aagctcagca cacagaaaga c                                          21

<210> SEQ ID NO 111
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 111
uaaaaucuuc cugcccacct t                                              21

<210> SEQ ID NO 112
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 112
ggaagcuguu ggcugaaaat t                                              21

<210> SEQ ID NO 113
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 113
aagaccagcc ucuuugccca g                                              21

<210> SEQ ID NO 114
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 114
ggaccaggca gaaaacgag                                                 19

<210> SEQ ID NO 115
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 115
cuaucaggau gacgcgg                                                   17

<210> SEQ ID NO 116
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

-continued

<400> SEQUENCE: 116
ugacacaggc aggcuugacu u                                           21

<210> SEQ ID NO 117
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 117
ggtgaagaag ggcgtccaa                                              19

<210> SEQ ID NO 118
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 118
gatccgttgg agctgttggc gtagttcaag agactcgcca acagctccaa cttttggaaa    60

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 119
aggtggtgtt aacagcagag                                             20

<210> SEQ ID NO 120
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 120
aaggtggagc aagcggtgga g                                           21

<210> SEQ ID NO 121
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 121
aaggagttga aggccgacaa a                                              21

<210> SEQ ID NO 122
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 122
uauggagcug cagaggaugt t                                              21

<210> SEQ ID NO 123
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 123
tttgaatatc tgtgctgaga acacagttct cagcacagat attctttt                 49

<210> SEQ ID NO 124
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 124
aatgagaaaa gcaaaaggtg ccctgtctc                                      29

<210> SEQ ID NO 125
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 125
aaucaucauc aagaaagggc a                                              21

<210> SEQ ID NO 126
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<223> OTHER INFORMATION: Description of Combined DNA/RNA Molecule:
      Synthetic oligonucleotide

<400> SEQUENCE: 126
augacuguca ggauguugct t                                              21

<210> SEQ ID NO 127
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 127
gaacgaaucc ugaagacauc u                                              21

<210> SEQ ID NO 128
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 128
aagcctggct acagcaatat gcctgtctc                                      29

<210> SEQ ID NO 129
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 129
ugaccaucac cgaguuuaut t                                              21

<210> SEQ ID NO 130
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 130
aagtcggacg caacagagaa a                                              21

<210> SEQ ID NO 131
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide <220> FEATURE:
<223> OTHER INFORMATION: Description of Combined DNA/RNA Molecule:
      Synthetic oligonucleotide

<400> SEQUENCE: 131
cuaccuuucu acggacgugt t                                              21

<210> SEQ ID NO 132
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 132
ctgcctaagg cggatttgaa t                                              21

<210> SEQ ID NO 133
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 133
ttauuccuuc uucgggaagu c                                              21

<210> SEQ ID NO 134
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 134
aaccttctgg aacccgccca c                                              21

<210> SEQ ID NO 135
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 135
gagcatcttc gagcaagaa                                                 19

<210> SEQ ID NO 136
<211> LENGTH: 19
<212> TYPE: DNA
<213> ORGANISM: Artificial Sequence
<220> FEATURE:
<223> OTHER INFORMATION: Description of Artificial Sequence: Synthetic

```
           oligonucleotide
<220> FEATURE:
<223> OTHER INFORMATION: Description of Combined DNA/RNA Molecule:
      Synthetic oligonucleotide

<400> SEQUENCE: 136
catgtggcac cgtttgcct                                                   19

<210> SEQ ID NO 137
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 137
aactaccaga aaggtatacc t                                                21

<210> SEQ ID NO 138
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 138
ucacaguguc cuuuauguat t                                                21

<210> SEQ ID NO 139
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 139
gcaugaaccg gaggcccaut t                                                21

<210> SEQ ID NO 140
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 140
ccggacagtt ccatgtata                                                   19

<210> SEQ ID NO 141
<211> LENGTH: 44
<212> TYPE: PRT
<213> ORGANISM: Artificial Sequence
<220> FEATURE:
```

```
<223> OTHER INFORMATION: Description of Artificial Sequence: Synthetic
      consensus polypeptide
<220> FEATURE:
<221> NAME/KEY: MOD_RES
<222> LOCATION: (1)..(1)
<223> OTHER INFORMATION: Ser or Thr
<220> FEATURE:
<221> NAME/KEY: MOD_RES
<222> LOCATION: (2)..(2)
<223> OTHER INFORMATION: His, Lys or Arg
<220> FEATURE:
<221> NAME/KEY: MOD_RES
<222> LOCATION: (4)..(4)
<223> OTHER INFORMATION: Gln or Asn
<220> FEATURE:
<221> NAME/KEY: MOD_RES
<222> LOCATION: (8)..(8)
<223> OTHER INFORMATION: Gly or Ala
<220> FEATURE:
<221> NAME/KEY: MOD_RES
<222> LOCATION: (10)..(10)
<223> OTHER INFORMATION: Thr or Ser
<220> FEATURE:
<221> NAME/KEY: MOD_RES
<222> LOCATION: (11)..(11)
<223> OTHER INFORMATION: Glu or Asp
<220> FEATURE:
<221> NAME/KEY: MOD_RES
<222> LOCATION: (14)..(14)
<223> OTHER INFORMATION: Gln or Asn
<220> FEATURE:
<221> NAME/KEY: MOD_RES
<222> LOCATION: (15)..(15)
<223> OTHER INFORMATION: Gly or Ala
<220> FEATURE:
<221> NAME/KEY: MOD_RES
<222> LOCATION: (17)..(17)
<223> OTHER INFORMATION: Thr or Ser
<220> FEATURE:
<221> NAME/KEY: MOD_RES
<222> LOCATION: (19)..(19)
<223> OTHER INFORMATION: Glu or Asp
<220> FEATURE:
<221> NAME/KEY: MOD_RES
<222> LOCATION: (22)..(22)
<223> OTHER INFORMATION: Arg or Lys
<220> FEATURE:
<221> NAME/KEY: MOD_RES
<222> LOCATION: (23)..(24)
<223> OTHER INFORMATION: Gln or Asn
<220> FEATURE:
<221> NAME/KEY: MOD_RES
<222> LOCATION: (27)..(27)
<223> OTHER INFORMATION: Asp or Glu
<220> FEATURE:
<221> NAME/KEY: MOD_RES
<222> LOCATION: (30)..(30)
<223> OTHER INFORMATION: Glu or Asp
<220> FEATURE:
<221> NAME/KEY: MOD_RES
<222> LOCATION: (32)..(32)
<223> OTHER INFORMATION: Ala, Leu, Ile or Val
<220> FEATURE:
<221> NAME/KEY: MOD_RES
<222> LOCATION: (34)..(34)
<223> OTHER INFORMATION: Glu or Asp
<220> FEATURE:
<221> NAME/KEY: MOD_RES
<222> LOCATION: (37)..(37)
<223> OTHER INFORMATION: Thr or Ser
<220> FEATURE:
<221> NAME/KEY: MOD_RES
<222> LOCATION: (38)..(38)
<223> OTHER INFORMATION: Arg or Lys
<220> FEATURE:
<221> NAME/KEY: MOD_RES
<222> LOCATION: (40)..(40)
<223> OTHER INFORMATION: Arg or Lys
<220> FEATURE:
```

```
<221> NAME/KEY: MOD_RES
<222> LOCATION: (41)..(41)
<223> OTHER INFORMATION: Glu or Asp
<220> FEATURE:
<221> NAME/KEY: MOD_RES
<222> LOCATION: (42)..(42)
<223> OTHER INFORMATION: Ala, Leu, Ile or Val
<220> FEATURE:
<221> NAME/KEY: MOD_RES
<222> LOCATION: (43)..(43)
<223> OTHER INFORMATION: Arg or Lys
<220> FEATURE:
<221> NAME/KEY: MOD_RES
<222> LOCATION: (44)..(44)
<223> OTHER INFORMATION: Ala, Leu, Ile or Val

<400> SEQUENCE: 141

Xaa Xaa Ile Xaa Ile Pro Pro Xaa Leu Xaa Xaa Leu Leu Xaa Xaa Tyr
1               5                   10                  15

Xaa Val Xaa Val Leu Xaa Xaa Xaa Pro Pro Xaa Leu Val Xaa Phe Xaa
            20                  25                  30

Val Xaa Tyr Phe Xaa Xaa Leu Xaa Xaa Xaa Xaa Xaa
        35                  40

<210> SEQ ID NO 142
<211> LENGTH: 17
<212> TYPE: PRT
<213> ORGANISM: Artificial Sequence
<220> FEATURE:
<223> OTHER INFORMATION: Description of Artificial Sequence: Synthetic
      consensus peptide
<220> FEATURE:
<221> NAME/KEY: MOD_RES
<222> LOCATION: (1)..(1)
<223> OTHER INFORMATION: Gln or Asn
<220> FEATURE:
<221> NAME/KEY: MOD_RES
<222> LOCATION: (2)..(2)
<223> OTHER INFORMATION: Ile, Leu or Val
<220> FEATURE:
<221> NAME/KEY: MOD_RES
<222> LOCATION: (3)..(3)
<223> OTHER INFORMATION: Glu or Asp
<220> FEATURE:
<221> NAME/KEY: MOD_RES
<222> LOCATION: (4)..(4)
<223> OTHER INFORMATION: Tyr, Phe, Thr or Ser
<220> FEATURE:
<221> NAME/KEY: MOD_RES
<222> LOCATION: (5)..(5)
<223> OTHER INFORMATION: Leu, Ile or Val
<220> FEATURE:
<221> NAME/KEY: MOD_RES
<222> LOCATION: (7)..(7)
<223> OTHER INFORMATION: Lys or Arg
<220> FEATURE:
<221> NAME/KEY: MOD_RES
<222> LOCATION: (8)..(8)
<223> OTHER INFORMATION: Gln or Asn
<220> FEATURE:
<221> NAME/KEY: MOD_RES
<222> LOCATION: (11)..(11)
<223> OTHER INFORMATION: Asp or Glu
<220> FEATURE:
<221> NAME/KEY: MOD_RES
<222> LOCATION: (12)..(12)
<223> OTHER INFORMATION: Asn or Gln
<220> FEATURE:
<221> NAME/KEY: MOD_RES
<222> LOCATION: (15)..(16)
<223> OTHER INFORMATION: Gln or Asn
<220> FEATURE:
<221> NAME/KEY: MOD_RES
<222> LOCATION: (17)..(17)
<223> OTHER INFORMATION: Ala, Leu, Ile or Val
```

-continued

```
<400> SEQUENCE: 142

Xaa Xaa Xaa Xaa Xaa Ala Xaa Xaa Ile Val Xaa Xaa Ala Ile Xaa Xaa
1               5                   10                  15

Xaa

<210> SEQ ID NO 143
<211> LENGTH: 44
<212> TYPE: PRT
<213> ORGANISM: Artificial Sequence
<220> FEATURE:
<223> OTHER INFORMATION: Description of Artificial Sequence: Synthetic
      consensus polypeptide
<220> FEATURE:
<221> NAME/KEY: MOD_RES
<222> LOCATION: (1)..(1)
<223> OTHER INFORMATION: Ser or Thr
<220> FEATURE:
<221> NAME/KEY: MOD_RES
<222> LOCATION: (4)..(4)
<223> OTHER INFORMATION: Gln or Asn
<220> FEATURE:
<221> NAME/KEY: MOD_RES
<222> LOCATION: (10)..(10)
<223> OTHER INFORMATION: Thr or Ser
<220> FEATURE:
<221> NAME/KEY: MOD_RES
<222> LOCATION: (18)..(18)
<223> OTHER INFORMATION: Val, Ile, Leu or Ala
<220> FEATURE:
<221> NAME/KEY: MOD_RES
<222> LOCATION: (23)..(23)
<223> OTHER INFORMATION: Gln or Asn
<220> FEATURE:
<221> NAME/KEY: MOD_RES
<222> LOCATION: (33)..(33)
<223> OTHER INFORMATION: Val, Ile, Leu or Ala
<220> FEATURE:
<221> NAME/KEY: MOD_RES
<222> LOCATION: (34)..(34)
<223> OTHER INFORMATION: Glu or Asp
<220> FEATURE:
<221> NAME/KEY: MOD_RES
<222> LOCATION: (37)..(37)
<223> OTHER INFORMATION: Thr or Ser
<220> FEATURE:
<221> NAME/KEY: MOD_RES
<222> LOCATION: (38)..(38)
<223> OTHER INFORMATION: Arg or Lys
<220> FEATURE:
<221> NAME/KEY: MOD_RES
<222> LOCATION: (40)..(40)
<223> OTHER INFORMATION: Arg or Lys
<220> FEATURE:
<221> NAME/KEY: MOD_RES
<222> LOCATION: (42)..(42)
<223> OTHER INFORMATION: Ala, Leu, Ile or Val
<220> FEATURE:
<221> NAME/KEY: MOD_RES
<222> LOCATION: (44)..(44)
<223> OTHER INFORMATION: Ala, Leu, Ile or Val

<400> SEQUENCE: 143

Xaa His Ile Xaa Ile Pro Pro Gly Leu Thr Glu Leu Leu Gln Gly Tyr
1               5                   10                  15

Thr Xaa Glu Val Leu Arg Xaa Gln Pro Pro Asp Leu Val Glu Phe Ala
            20                  25                  30

Xaa Xaa Tyr Phe Xaa Xaa Leu Xaa Glu Xaa Arg Xaa
                35                  40

<210> SEQ ID NO 144
<211> LENGTH: 330
```

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 144

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 145
<211> LENGTH: 990
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 145

```
gcctccacca agggcccatc ggtcttcccc ctggcaccct cctccaagag cacctctggg    60
ggcacagcgg ccctgggctg cctggtcaag gactacttcc ccgaaccggt gacggtgtcg   120
tggaactcag gcgccctgac cagcggcgtg cacaccttcc cggctgtcct acagtcctca   180
ggactctact ccctcagcag cgtggtgacc gtgccctcca gcagcttggg cacccagacc   240
tacatctgca acgtgaatca caagcccagc aacaccaagg tggacaagag agttgagccc   300
aaatcttgtg acaaaactca cacatgccca ccgtgcccag cacctgaact cctggggga   360
ccgtcagtct tcctcttccc cccaaaaccc aaggacaccc tcatgatctc ccggaccct   420
gaggtcacat gcgtggtggt ggacgtgagc cacgaagacc ctgaggtcaa gttcaactgg   480
tacgtggacg gcgtggaggt gcataatgcc aagacaaagc cgcgggagga gcagtacaac   540
agcacgtacc gggtggtcag cgtcctcacc gtcctgcacc aggactggct gaatggcaag   600
gagtacaagt gcaaggtctc caacaaagcc ctcccagccc ccatcgagaa aaccatctcc   660
aaagccaaag ggcagccccg agaaccacag gtgtacaccc tgcccccatc ccgggaggag   720
atgaccaaga accaggtcag cctgacctgc ctggtcaaag gcttctatcc cagcgacatc   780
gccgtggagt gggagagcaa tgggcagccg gagaacaact acaagaccac gcctcccgtg   840
ctggactccg acggctcctt cttcctctat agcaagctca ccgtggacaa gagcaggtgg   900
cagcagggga acgtcttctc atgctccgtg atgcatgagg ctctgcacaa ccactacacg   960
cagaagagcc tctccctgtc tccgggtaaa                                    990
```

<210> SEQ ID NO 146
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 146

```
Thr Val Ala Ala Pro Ser Val Phe Ile Phe Pro Pro Ser Asp Glu Gln
1               5                  10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

<210> SEQ ID NO 147
<211> LENGTH: 318
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 147

```
actgtggctg caccatctgt cttcatcttc ccgccatctg atgagcagtt gaaatctgga    60
actgcctctg ttgtgtgcct gctgaataac ttctatccca gagaggccaa agtacagtgg   120
aaggtggata cgccctcca atcgggtaac tcccaggaga gtgtcacaga gcaggacagc    180
aaggacagca cctacagcct cagcagcacc ctgacgctga gcaaagcaga ctacgagaaa   240
cacaaagtct acgcctgcga agtcacccat cagggcctga gctcgcccgt cacaaagagc   300
ttcaacaggg gagagtgt                                                  318
```

```
<210> SEQ ID NO 148
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

Gly Ser Gly Gly Gly Gly Ser Gly Gly Gly Ser His Ile Gln Ile
1               5                   10                  15

Pro Pro Gly Leu Thr Glu Leu Leu Gln Gly Tyr Thr Val Glu Val Leu
            20                  25                  30

Arg Gln Gln Pro Pro Asp Leu Val Glu Phe Ala Val Glu Tyr Phe Thr
        35                  40                  45

Arg Leu Arg Glu Ala Arg Ala
    50                  55

<210> SEQ ID NO 149
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Gly Ser Gly Gly Gly Gly Ser Gly Gly Gly Gly Ser Gln Ile Glu Tyr
1               5                   10                  15

Leu Ala Lys Gln Ile Val Asp Asn Ala Ile Gln Gln Ala
            20                  25

<210> SEQ ID NO 150
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Arg Ser Gln Ser Arg Ser Arg Tyr Tyr Arg Gln Arg Gln Arg Ser Arg
1               5                   10                  15

Arg Arg Arg Arg Arg Ser
            20

<210> SEQ ID NO 151
<211> LENGTH: 164
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

```
<221> NAME/KEY: MOD_RES
<222> LOCATION: (1)..(1)
<223> OTHER INFORMATION: Pyroglutamate

<400> SEQUENCE: 151

Gln Asp Trp Leu Thr Phe Gln Lys Lys His Ile Thr Asn Thr Arg Asp
1               5                   10                  15

Val Asp Cys Asp Asn Ile Met Ser Thr Asn Leu Phe His Cys Lys Asp
            20                  25                  30

Lys Asn Thr Phe Ile Tyr Ser Arg Pro Glu Pro Val Lys Ala Ile Cys
            35                  40                  45

Lys Gly Ile Ile Ala Ser Lys Asn Val Leu Thr Thr Ser Glu Phe Tyr
    50                  55                  60

Leu Ser Asp Cys Asn Val Thr Ser Arg Pro Cys Lys Tyr Lys Leu Lys
65                  70                  75                  80

Lys Ser Thr Asn Lys Phe Cys Val Thr Cys Glu Asn Gln Ala Pro Val
                85                  90                  95

His Phe Val Gly Val Gly Ser Cys Gly Gly Gly Ser Leu Glu Cys
            100                 105                 110

Gly His Ile Gln Ile Pro Pro Gly Leu Thr Glu Leu Leu Gln Gly Tyr
            115                 120                 125

Thr Val Glu Val Leu Arg Gln Gln Pro Pro Asp Leu Val Glu Phe Ala
    130                 135                 140

Val Glu Tyr Phe Thr Arg Leu Arg Glu Ala Arg Ala Val Glu His His
145                 150                 155                 160

His His His His
```